United States Patent
Seitz et al.

(10) Patent No.: US 10,589,107 B2
(45) Date of Patent: Mar. 17, 2020

(54) CIRCUIT BOARD MOUNTED FILTERED FEEDTHROUGH ASSEMBLY HAVING A COMPOSITE CONDUCTIVE LEAD FOR AN AIMD

(71) Applicant: Greatbatch Ltd., Clarence, NY (US)

(72) Inventors: Keith W. Seitz, Clarence Center, NY (US); Thomas Marzano, East Amherst, NY (US); Robert A. Stevenson, Canyon Country, CA (US); Christine A. Frysz, Orchard Park, NY (US); Jason Woods, Carson City, NV (US); Richard L. Brendel, Carson City, NV (US); Marc Gregory Martino, Westlake Village, CA (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 16/291,356

(22) Filed: Mar. 4, 2019

(65) Prior Publication Data
US 2019/0192862 A1   Jun. 27, 2019

Related U.S. Application Data

(63) Continuation of application No. 15/603,521, filed on May 24, 2017, now Pat. No. 10,272,252.
(Continued)

(51) Int. Cl.
*A61N 1/375*    (2006.01)
*H01G 4/018*    (2006.01)
(Continued)

(52) U.S. Cl.
CPC .......... *A61N 1/3754* (2013.01); *H01G 4/018* (2013.01); *H01G 4/224* (2013.01); *H01G 4/236* (2013.01);
(Continued)

(58) Field of Classification Search
CPC ...... A61N 1/3754; H01G 4/018; H01G 4/224; H01G 4/236; H01G 4/35; H01G 4/012; H05K 1/181; H02K 2201/10015
See application file for complete search history.

(56) References Cited

U.S. PATENT DOCUMENTS

| 3,681,612 A | 8/1972 | Kinzler et al. |
| 3,745,430 A | 7/1973 | Kerr et al. |

(Continued)

FOREIGN PATENT DOCUMENTS

| EP | 0243573 | 11/1987 |
| EP | 0145430 | 5/1991 |

(Continued)

OTHER PUBLICATIONS

Olenick, "Ultrathin Flexible Ceramics for Electronics Applications", www.ceramicindustry.com—Product Profile, Oct. 2016, pp. 30 and 31.
(Continued)

*Primary Examiner* — Lindsey G Wehrheim
(74) *Attorney, Agent, or Firm* — Michael F. Scalise

(57) ABSTRACT

A feedthrough separates a body fluid side from a device side. A passageway is disposed through the feedthrough. A body fluid side leadwire extends from a first end disposed inside the passageway to a second end on the body fluid side. A device side leadwire extends from a first end disposed inside the passageway to a second end on the device side. The body fluid side leadwire is hermetically sealed to the feedthrough body and is not of the same material as the device side leadwire. A circuit board has an active via hole with a second end of the second leadwire residing therein. The circuit board has an active circuit trace that is electrically connectable to electronic circuits housed in an AIMD, and a circuit board ground metallization. An active electrical path extends from the first leadwire to the second leadwire to an MLCC (Continued)

chip capacitor mounted on the circuit board and to the circuit board active circuit trace, and a ground electrical path extends from the MLCC chip capacitor to the circuit board ground metallization and then to the ferrule.

32 Claims, 88 Drawing Sheets

Related U.S. Application Data

(60) Provisional application No. 62/418,834, filed on Nov. 8, 2016.

(51) Int. Cl.
*H01G 4/224* (2006.01)
*H01G 4/236* (2006.01)
*H01G 4/35* (2006.01)
*H05K 1/18* (2006.01)
*H01G 4/012* (2006.01)
*H01G 4/40* (2006.01)

(52) U.S. Cl.
CPC .................. *H01G 4/35* (2013.01); *H01G 4/40* (2013.01); *H05K 1/181* (2013.01); *H01G 4/012* (2013.01); *H05K 2201/10015* (2013.01)

(56) References Cited

U.S. PATENT DOCUMENTS

| | | |
|---|---|---|
| 3,871,382 A | 3/1975 | Mann |
| 3,961,294 A | 6/1976 | Hollyday |
| 3,968,802 A | 7/1976 | Ballis |
| 3,980,975 A | 9/1976 | Maxon et al. |
| 4,188,598 A | 2/1980 | Hunt |
| 4,236,127 A | 11/1980 | Scherba |
| 4,295,467 A | 10/1981 | Mann et al. |
| 4,320,763 A | 3/1982 | Money |
| 4,424,551 A | 1/1984 | Stevenson et al. |
| 4,431,005 A | 2/1984 | McCormick |
| 4,437,474 A | 3/1984 | Peers-Trevarton et al. |
| 4,445,501 A | 5/1984 | Bresler |
| 4,572,198 A | 2/1986 | Codrington |
| 4,585,001 A | 4/1986 | Belt |
| 4,633,181 A | 12/1986 | Murphy-Boesch et al. |
| 4,643,186 A | 2/1987 | Rosen et al. |
| 4,654,880 A | 3/1987 | Sontag |
| 4,672,972 A | 6/1987 | Berke |
| 4,689,621 A | 8/1987 | Kleinberg |
| 4,712,555 A | 12/1987 | Thornander et al. |
| 4,746,864 A | 5/1988 | Satoh et al. |
| 4,754,752 A | 7/1988 | Ginsburg et al. |
| 4,757,820 A | 7/1988 | Itoh |
| 4,766,381 A | 8/1988 | Conturo et al. |
| 4,788,980 A | 12/1988 | Mann et al. |
| 4,799,499 A | 1/1989 | Bisping |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,858,064 A | 8/1989 | Segawa et al. |
| 4,858,623 A | 8/1989 | Bradshaw et al. |
| 4,859,950 A | 8/1989 | Keren |
| 4,932,411 A | 6/1990 | Fritschy et al. |
| 4,940,052 A | 7/1990 | Mann et al. |
| 4,944,298 A | 7/1990 | Sholder |
| 4,960,106 A | 10/1990 | Kubokawa et al. |
| 4,989,608 A | 2/1991 | Ratner |
| 4,991,580 A | 2/1991 | Moore |
| 5,019,075 A | 5/1991 | Spears et al. |
| 5,039,965 A | 8/1991 | Higgins |
| 5,044,375 A | 9/1991 | Bach et al. |
| 5,052,404 A | 10/1991 | Hodgson et al. |
| 5,063,348 A | 11/1991 | Kuhara et al. |
| 5,095,911 A | 3/1992 | Pomeranz |
| 5,099,208 A | 3/1992 | Fitzpatrick et al. |
| 5,167,233 A | 12/1992 | Eberle et al. |
| 5,178,618 A | 1/1993 | Kandarpa |
| 5,190,046 A | 3/1993 | Shturman |
| 5,197,468 A | 3/1993 | Proctor et al. |
| 5,209,233 A | 5/1993 | Holland et al. |
| 5,211,165 A | 5/1993 | Dumoulin et al. |
| 5,217,010 A | 6/1993 | Tsitlik et al. |
| 5,222,506 A | 6/1993 | Patrick et al. |
| 5,246,438 A | 9/1993 | Langberg |
| 5,251,120 A | 10/1993 | Smith |
| 5,268,810 A | 12/1993 | Dimarco et al. |
| 5,271,400 A | 12/1993 | Dumoulin et al. |
| 5,300,108 A | 4/1994 | Rebell et al. |
| 5,306,291 A | 4/1994 | Kroll et al. |
| 5,307,808 A | 5/1994 | Dumoulin et al. |
| 5,307,814 A | 5/1994 | Kressel et al. |
| 5,318,025 A | 6/1994 | Dumoulin et al. |
| 5,323,776 A | 6/1994 | Blakeley et al. |
| 5,323,778 A | 6/1994 | Kandarpa et al. |
| 5,331,505 A | 7/1994 | Wilheim |
| 5,333,095 A | 7/1994 | Stevenson et al. |
| 5,334,045 A | 8/1994 | Cappa et al. |
| 5,334,193 A | 8/1994 | Nardella |
| 5,348,010 A | 9/1994 | Schnall et al. |
| 5,352,979 A | 10/1994 | Conturo |
| 5,358,515 A | 10/1994 | Hurter et al. |
| 5,363,845 A | 11/1994 | Chowdhury et al. |
| 5,365,928 A | 11/1994 | Rhinehart et al. |
| 5,370,644 A | 12/1994 | Langberg |
| 5,398,683 A | 3/1995 | Edwards et al. |
| 5,400,787 A | 3/1995 | Marandos |
| 5,404,880 A | 4/1995 | Throne |
| 5,413,104 A | 5/1995 | Buijs et al. |
| 5,419,325 A | 5/1995 | Dumoulin et al. |
| 5,428,337 A | 6/1995 | Vinclarelli et al. |
| 5,433,717 A | 7/1995 | Rubinsky et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,450,090 A | 9/1995 | Gels et al. |
| 5,451,232 A | 9/1995 | Rhinehart et al. |
| 5,462,055 A | 10/1995 | Casey et al. |
| 5,466,254 A | 11/1995 | Helland |
| 5,476,095 A | 12/1995 | Schnall et al. |
| 5,476,483 A | 12/1995 | Bornzin et al. |
| 5,491,300 A | 2/1996 | Huppenthal et al. |
| 5,493,259 A | 2/1996 | Blalock et al. |
| 5,498,261 A | 3/1996 | Strul |
| 5,507,743 A | 4/1996 | Edwards et al. |
| 5,512,825 A | 4/1996 | Atalar et al. |
| 5,514,173 A | 5/1996 | Rebell et al. |
| 5,540,679 A | 7/1996 | Fram et al. |
| 5,545,201 A | 8/1996 | Helland et al. |
| 5,558,093 A | 9/1996 | Pomeranz |
| 5,578,008 A | 11/1996 | Hara |
| 5,588,432 A | 12/1996 | Crowley |
| 5,590,657 A | 1/1997 | Cain et al. |
| 5,591,218 A | 1/1997 | Jacobson |
| 5,620,476 A | 4/1997 | Truex et al. |
| 5,623,241 A | 4/1997 | Minkoff |
| 5,623,724 A | 4/1997 | Gurkovich et al. |
| 5,629,622 A | 5/1997 | Scampini |
| 5,650,759 A | 7/1997 | Hittman et al. |
| 5,662,108 A | 9/1997 | Budd et al. |
| 5,682,897 A | 11/1997 | Pomeranz |
| 5,683,435 A | 11/1997 | Truex et al. |
| 5,685,878 A | 11/1997 | Falwell et al. |
| 5,697,958 A | 12/1997 | Paul et al. |
| 5,699,801 A | 12/1997 | Atalar et al. |
| 5,700,548 A | 12/1997 | Warnier et al. |
| 5,706,810 A | 1/1998 | Rubinsky et al. |
| 5,715,825 A | 2/1998 | Crowley |
| 5,716,390 A | 2/1998 | Li |
| 5,722,998 A | 3/1998 | Prutchi et al. |
| 5,735,884 A | 4/1998 | Thompson et al. |
| 5,735,887 A | 4/1998 | Barreras et al. |
| 5,741,321 A | 4/1998 | Brennen |

(56) References Cited

U.S. PATENT DOCUMENTS

| | | |
|---|---|---|
| 5,751,539 A | 5/1998 | Stevenson et al. |
| 5,757,252 A | 5/1998 | Cho et al. |
| 5,759,202 A | 6/1998 | Schroeppel |
| 5,765,779 A | 6/1998 | Hancock et al. |
| 5,769,800 A | 6/1998 | Gelfand et al. |
| 5,772,693 A | 6/1998 | Brownlee |
| 5,775,338 A | 7/1998 | Hastings |
| 5,779,669 A | 7/1998 | Haissaguerre et al. |
| 5,782,891 A | 7/1998 | Hassler et al. |
| 5,792,055 A | 8/1998 | McKinnon |
| 5,800,467 A | 9/1998 | Park et al. |
| 5,822,174 A | 10/1998 | Yamate et al. |
| 5,824,026 A | 10/1998 | Diaz et al. |
| 5,824,029 A | 10/1998 | Weijand et al. |
| 5,833,608 A | 11/1998 | Acker |
| 5,836,992 A | 11/1998 | Thompson et al. |
| 5,840,031 A | 11/1998 | Crowley |
| 5,851,226 A | 12/1998 | Skubitz et al. |
| 5,855,995 A | 1/1999 | Haq et al. |
| 5,864,234 A | 1/1999 | Luedeke |
| 5,867,361 A | 2/1999 | Seifried et al. |
| 5,868,674 A | 2/1999 | Glowinski et al. |
| 5,879,347 A | 3/1999 | Saadat |
| 5,891,134 A | 4/1999 | Goble et al. |
| 5,896,267 A | 4/1999 | Hittman et al. |
| 5,905,627 A | 5/1999 | Brendel et al. |
| 5,916,162 A | 6/1999 | Snelten et al. |
| 5,928,145 A | 7/1999 | Ocali et al. |
| 5,928,159 A | 7/1999 | Eggers et al. |
| 5,929,729 A | 7/1999 | Swarup |
| 5,938,609 A | 8/1999 | Pomeranz |
| 5,938,692 A | 8/1999 | Rudie |
| 5,959,336 A | 9/1999 | Barsan |
| 5,959,829 A | 9/1999 | Stevenson et al. |
| 5,964,705 A | 10/1999 | Truwit et al. |
| 5,973,906 A | 10/1999 | Stevenson et al. |
| 5,973,907 A | 10/1999 | Reed |
| 5,978,204 A | 11/1999 | Stevenson |
| 6,004,269 A | 12/1999 | Crowley et al. |
| 6,008,980 A | 12/1999 | Stevenson et al. |
| 6,011,995 A | 1/2000 | Guglielmi et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,031,710 A | 2/2000 | Wolf et al. |
| 6,041,496 A | 3/2000 | Haq et al. |
| 6,045,532 A | 4/2000 | Eggers et al. |
| 6,052,614 A | 4/2000 | Morris et al. |
| 6,055,457 A | 4/2000 | Bonner |
| 6,066,136 A | 5/2000 | Geistert |
| 6,099,524 A | 8/2000 | Lipson et al. |
| 6,101,417 A | 8/2000 | Vogel et al. |
| 6,128,522 A | 10/2000 | Acker et al. |
| 6,129,670 A | 10/2000 | Burdette et al. |
| 6,137,161 A | 10/2000 | Gilliland et al. |
| 6,141,594 A | 10/2000 | Flynn et al. |
| 6,146,743 A | 11/2000 | Haq et al. |
| 6,159,560 A | 12/2000 | Stevenson et al. |
| 6,171,240 B1 | 1/2001 | Young et al. |
| 6,171,241 B1 | 1/2001 | McVeigh et al. |
| 6,188,219 B1 | 2/2001 | Reeder et al. |
| 6,198,972 B1 | 3/2001 | Hartlaub et al. |
| 6,209,764 B1 | 4/2001 | Hartlaub et al. |
| 6,226,545 B1 | 5/2001 | Gilderdale |
| 6,236,205 B1 | 5/2001 | Lüdeke et al. |
| 6,238,390 B1 | 5/2001 | Tu et al. |
| 6,252,761 B1 | 6/2001 | Branchevsky |
| 6,263,229 B1 | 7/2001 | Atalar et al. |
| 6,272,370 B1 | 8/2001 | Gillies et al. |
| 6,275,369 B1 | 8/2001 | Stevenson et al. |
| 6,275,379 B1 | 8/2001 | Sleboda et al. |
| 6,280,385 B1 | 8/2001 | Melzer et al. |
| 6,284,080 B1 | 9/2001 | Haq et al. |
| 6,284,971 B1 | 9/2001 | Atalar et al. |
| 6,332,089 B1 | 12/2001 | Acker et al. |
| 6,370,427 B1 | 4/2002 | Alt et al. |
| 6,373,673 B1 | 4/2002 | Anthony |
| 6,390,996 B1 | 5/2002 | Halperin et al. |
| 6,395,637 B1 | 5/2002 | Park et al. |
| 6,408,202 B1 | 6/2002 | Lima et al. |
| 6,414,835 B1 | 7/2002 | Wolf et al. |
| 6,424,234 B1 | 7/2002 | Stevenson |
| 6,428,537 B1 | 8/2002 | Swanson et al. |
| 6,433,653 B1 | 8/2002 | Matsumura et al. |
| 6,456,481 B1 | 9/2002 | Stevenson |
| 6,459,935 B1 | 10/2002 | Piersma |
| 6,470,545 B1 | 10/2002 | Branchevsky |
| 6,473,291 B1 | 10/2002 | Stevenson |
| 6,473,314 B1 | 10/2002 | Custer et al. |
| 6,486,529 B2 | 11/2002 | Chi et al. |
| 6,493,591 B1 | 12/2002 | Stokes |
| 6,512,666 B1 | 1/2003 | Duva |
| 6,529,103 B1 | 3/2003 | Brendel et al. |
| 6,535,766 B1 | 3/2003 | Thompson et al. |
| 6,539,253 B2 | 3/2003 | Thompson et al. |
| 6,539,261 B2 | 3/2003 | Dal Molin |
| 6,549,800 B1 | 4/2003 | Atalar et al. |
| 6,556,009 B2 | 4/2003 | Kellman et al. |
| 6,566,978 B2 | 5/2003 | Stevenson et al. |
| 6,567,259 B2 | 5/2003 | Stevenson et al. |
| 6,567,703 B1 | 5/2003 | Thompson et al. |
| 6,593,884 B1 | 7/2003 | Gilboa et al. |
| 6,606,513 B2 | 8/2003 | Lardo et al. |
| 6,615,483 B2 | 9/2003 | Lindegren |
| 6,628,980 B2 | 9/2003 | Atalar et al. |
| 6,633,780 B1 | 10/2003 | Berger |
| 6,643,903 B2 | 11/2003 | Stevenson et al. |
| 6,654,628 B1 | 11/2003 | Silber et al. |
| 6,660,116 B2 | 12/2003 | Wolf |
| 6,675,033 B1 | 1/2004 | Lardo et al. |
| 6,675,036 B2 | 1/2004 | Kreger et al. |
| 6,675,779 B2 | 1/2004 | King et al. |
| 6,675,780 B1 | 1/2004 | Wendels et al. |
| 6,687,550 B1 | 2/2004 | Doan |
| 6,690,963 B2 | 2/2004 | Ben-Haim et al. |
| 6,694,583 B2 | 2/2004 | Branchevsky |
| 6,697,675 B1 | 2/2004 | Safarevich et al. |
| 6,701,176 B1 | 3/2004 | Halperin et al. |
| 6,714,809 B2 | 3/2004 | Lee et al. |
| 6,728,575 B2 | 4/2004 | Hedberg |
| 6,728,579 B1 | 4/2004 | Lindgren et al. |
| 6,759,388 B1 | 7/2004 | Marchant et al. |
| 6,765,779 B2 | 7/2004 | Stevenson et al. |
| 6,765,780 B2 | 7/2004 | Brendel et al. |
| 6,768,630 B2 | 7/2004 | Togashi |
| 6,771,067 B2 | 8/2004 | Kellman et al. |
| 6,795,730 B2 | 9/2004 | Connelly et al. |
| 6,806,806 B2 | 10/2004 | Anthony |
| 6,823,215 B2 | 11/2004 | Obel et al. |
| 6,829,509 B1 | 12/2004 | MacDonald et al. |
| 6,847,837 B1 | 1/2005 | Melzer et al. |
| 6,868,288 B2 | 3/2005 | Thompson |
| 6,871,091 B2 | 3/2005 | Wilkinson et al. |
| 6,876,885 B2 | 4/2005 | Swoyer et al. |
| 6,882,248 B2 | 4/2005 | Stevenson et al. |
| 6,888,715 B2 | 5/2005 | Stevenson et al. |
| 6,898,454 B2 | 5/2005 | Atalar et al. |
| 6,901,292 B2 | 5/2005 | Hrdlicka et al. |
| 6,904,307 B2 | 6/2005 | Karmarkar et al. |
| 6,925,328 B2 | 8/2005 | Foster et al. |
| 6,930,242 B1 | 8/2005 | Helfer et al. |
| 6,931,283 B1 | 8/2005 | Magnusson |
| 6,931,286 B2 | 8/2005 | Sigg et al. |
| 6,934,588 B1 | 8/2005 | Brand et al. |
| 6,944,489 B2 | 9/2005 | Zeijlemaker et al. |
| 6,944,507 B2 | 9/2005 | Fröberg et al. |
| 6,949,929 B2 | 9/2005 | Gray et al. |
| 6,950,696 B2 | 9/2005 | Björling et al. |
| 6,952,613 B2 | 10/2005 | Swoyer et al. |
| 6,971,391 B1 | 12/2005 | Wang et al. |
| 6,985,347 B2 | 1/2006 | Stevenson et al. |
| 6,985,775 B2 | 1/2006 | Reinke et al. |
| 6,987,660 B2 | 1/2006 | Stevenson et al. |
| 6,999,818 B2 | 2/2006 | Stevenson et al. |

(56) References Cited

U.S. PATENT DOCUMENTS

| | | |
|---|---|---|
| 7,012,192 B2 | 3/2006 | Stevenson et al. |
| 7,013,180 B2 | 3/2006 | Dougherty et al. |
| 7,015,393 B2 | 3/2006 | Weiner et al. |
| 7,035,076 B1 | 4/2006 | Stevenson |
| 7,038,900 B2 | 5/2006 | Stevenson et al. |
| 7,039,455 B1 | 5/2006 | Brosovich et al. |
| 7,046,499 B1 | 5/2006 | Imani et al. |
| 7,047,073 B2 | 5/2006 | Höijer et al. |
| 7,050,855 B2 | 5/2006 | Zeijlemaker et al. |
| 7,068,491 B1 | 6/2006 | Burdon et al. |
| 7,091,412 B2 | 8/2006 | Wang et al. |
| 7,092,766 B1 | 8/2006 | Salys et al. |
| 7,110,227 B2 | 9/2006 | Anthony et al. |
| 7,113,387 B2 | 9/2006 | Stevenson et al. |
| 7,123,013 B2 | 10/2006 | Gray |
| 7,127,294 B1 | 10/2006 | Wang et al. |
| 7,136,273 B2 | 11/2006 | Stevenson et al. |
| 7,148,783 B2 | 12/2006 | Parsche et al. |
| 7,149,578 B2 | 12/2006 | Edvardsson |
| 7,149,773 B2 | 12/2006 | Haller et al. |
| 7,155,271 B2 | 12/2006 | Halperin et al. |
| 7,162,302 B2 | 1/2007 | Wang et al. |
| 7,164,572 B1 | 1/2007 | Burdon et al. |
| 7,164,950 B2 | 1/2007 | Kroll et al. |
| 7,174,219 B2 | 2/2007 | Wahlstrand et al. |
| 7,174,223 B2 | 2/2007 | Money et al. |
| 7,199,995 B2 | 4/2007 | Stevenson |
| 7,211,103 B2 | 5/2007 | Greenberg et al. |
| 7,236,816 B2 | 6/2007 | Kumar et al. |
| 7,236,834 B2 | 6/2007 | Christopherson et al. |
| 7,276,474 B2 | 10/2007 | Marchant et al. |
| 7,301,748 B2 | 11/2007 | Anthony et al. |
| 7,310,216 B2 | 12/2007 | Stevenson et al. |
| 7,319,905 B1 | 1/2008 | Morgan et al. |
| 7,322,832 B2 | 1/2008 | Kronich et al. |
| 7,327,553 B2 | 2/2008 | Brendel |
| 7,363,090 B2 | 4/2008 | Halperin et al. |
| 7,369,898 B1 | 5/2008 | Kroll et al. |
| 7,387,928 B2 | 6/2008 | Cheung |
| 7,388,378 B2 | 6/2008 | Gray et al. |
| 7,422,568 B2 | 9/2008 | Yang et al. |
| 7,423,860 B2 | 9/2008 | Anthony et al. |
| 7,428,136 B2 | 9/2008 | Barnett |
| 7,433,168 B2 | 10/2008 | Anthony |
| 7,436,672 B2 | 10/2008 | Ushijima et al. |
| 7,439,449 B1 | 10/2008 | Kumar et al. |
| 7,446,996 B2 | 11/2008 | Togashi |
| 7,450,396 B2 | 11/2008 | Ye et al. |
| 7,480,988 B2 | 1/2009 | Ok et al. |
| 7,489,495 B2 | 2/2009 | Stevenson |
| 7,495,884 B2 | 2/2009 | Togashi |
| 7,517,769 B2 | 4/2009 | Van Schuylenbergh et al. |
| 7,529,590 B2 | 5/2009 | MacDonald |
| 7,535,693 B2 | 5/2009 | Stevenson et al. |
| 7,551,963 B2 | 6/2009 | Rusin et al. |
| 7,561,906 B2 | 7/2009 | Atalar et al. |
| 7,586,728 B2 | 9/2009 | Anthony |
| 7,593,208 B2 | 9/2009 | Anthony et al. |
| 7,623,335 B2 | 11/2009 | Stevenson et al. |
| 7,675,729 B2 | 3/2010 | Anthony et al. |
| 7,679,926 B2 | 3/2010 | Hsu et al. |
| 7,689,288 B2 | 3/2010 | Stevenson et al. |
| 7,693,576 B1 | 4/2010 | Lavie et al. |
| 7,702,387 B2 | 4/2010 | Stevenson et al. |
| 7,719,854 B2 | 5/2010 | Youker et al. |
| 7,729,770 B2 | 6/2010 | Cabelka et al. |
| 7,733,621 B2 | 6/2010 | Anthony et al. |
| 7,797,048 B2 | 9/2010 | Stevenson et al. |
| 7,812,691 B1 | 10/2010 | Fisk et al. |
| 7,839,146 B2 | 11/2010 | Gray |
| 7,844,319 B2 | 11/2010 | Susil et al. |
| 7,844,343 B2 | 11/2010 | Wahlstrand et al. |
| 7,853,324 B2 | 12/2010 | Stevenson et al. |
| 7,899,551 B2 | 3/2011 | Westlund et al. |
| 7,901,761 B1 | 3/2011 | Jiang et al. |
| 7,957,806 B2 | 6/2011 | Stevenson et al. |
| 7,989,080 B2 | 8/2011 | Greenberg et al. |
| 8,000,804 B1 | 8/2011 | Wessendorf et al. |
| 8,043,454 B1 | 10/2011 | Jiang et al. |
| 8,095,224 B2 | 1/2012 | Truex et al. |
| 8,131,376 B1 | 3/2012 | Greenberg et al. |
| 8,163,397 B2 | 4/2012 | Ok et al. |
| 8,179,658 B2 | 5/2012 | Stevenson et al. |
| 8,219,208 B2 | 7/2012 | Stevenson et al. |
| 8,301,249 B2 | 10/2012 | Min |
| 8,494,635 B2 | 7/2013 | Guebler et al. |
| 8,528,201 B2 | 9/2013 | Guebler et al. |
| 8,588,916 B2 | 11/2013 | Satou et al. |
| 8,604,341 B2 | 12/2013 | Barry et al. |
| 8,653,384 B2 | 2/2014 | Tang et al. |
| 8,659,870 B2 | 2/2014 | Brendel et al. |
| 8,670,829 B2 | 3/2014 | Satou et al. |
| 8,755,887 B2 | 6/2014 | Troetzschel et al. |
| 8,763,245 B1 | 7/2014 | Lucisano et al. |
| 8,841,558 B2 | 9/2014 | Satou et al. |
| 8,855,768 B1 | 10/2014 | Dabney et al. |
| 8,872,035 B2 | 10/2014 | Satou et al. |
| 8,874,206 B2 | 10/2014 | Malinowski et al. |
| 8,886,320 B2 | 11/2014 | Wollenberg et al. |
| 8,927,862 B2 | 1/2015 | Barry et al. |
| 8,929,987 B2 | 1/2015 | Troetzschel et al. |
| 8,938,309 B2 | 1/2015 | Marzano et al. |
| 9,008,779 B2 | 4/2015 | Satou et al. |
| 9,032,614 B2 | 5/2015 | Specht |
| 9,108,066 B2 | 8/2015 | Woods et al. |
| 9,233,253 B2 | 1/2016 | Stevenson et al. |
| 9,407,076 B2 | 8/2016 | Troetzschel et al. |
| 9,418,778 B2 | 8/2016 | Makino et al. |
| 9,427,596 B2 | 8/2016 | Brendel et al. |
| 9,431,814 B2 | 8/2016 | Blilie et al. |
| 9,480,168 B2 | 10/2016 | Troetzschel et al. |
| 9,492,659 B2 | 11/2016 | Brendel et al. |
| 9,552,899 B2 | 1/2017 | Glynn et al. |
| 2002/0055678 A1 | 5/2002 | Scott et al. |
| 2002/0095197 A1 | 7/2002 | Lardo et al. |
| 2002/0177771 A1 | 11/2002 | Guttman et al. |
| 2002/0192688 A1 | 12/2002 | Yang et al. |
| 2003/0013928 A1 | 1/2003 | Saruwatari |
| 2003/0013948 A1 | 1/2003 | Russell |
| 2003/0028094 A1 | 2/2003 | Kumar et al. |
| 2003/0028095 A1 | 2/2003 | Tulley et al. |
| 2003/0050557 A1 | 3/2003 | Susil et al. |
| 2003/0053284 A1 | 3/2003 | Stevenson et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0171792 A1 | 9/2003 | Zarinetchi et al. |
| 2003/0179536 A1 | 9/2003 | Stevenson et al. |
| 2003/0204217 A1 | 10/2003 | Greatbatch |
| 2003/0208252 A1 | 11/2003 | O'Boyle et al. |
| 2003/0212373 A1 | 11/2003 | Hall et al. |
| 2003/0213605 A1 | 11/2003 | Brendel et al. |
| 2004/0015079 A1 | 1/2004 | Berger et al. |
| 2004/0034338 A1 | 2/2004 | Thierfelder et al. |
| 2004/0088012 A1 | 5/2004 | Kroll et al. |
| 2004/0167392 A1 | 8/2004 | Halperin et al. |
| 2004/0210289 A1 | 10/2004 | Wang et al. |
| 2004/0230271 A1 | 11/2004 | Wang et al. |
| 2004/0249428 A1 | 12/2004 | Wang et al. |
| 2004/0263173 A1 | 12/2004 | Gray |
| 2004/0263174 A1 | 12/2004 | Gray et al. |
| 2005/0007718 A1 | 1/2005 | Stevenson et al. |
| 2005/0070972 A1 | 3/2005 | Wahlstrand et al. |
| 2005/0113669 A1 | 5/2005 | Helfer et al. |
| 2005/0113676 A1 | 5/2005 | Weiner et al. |

(56) References Cited

U.S. PATENT DOCUMENTS

| | | |
|---|---|---|
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0197677 A1 | 9/2005 | Stevenson |
| 2005/0201039 A1 | 9/2005 | Stevenson et al. |
| 2005/0215914 A1 | 9/2005 | Bornzin et al. |
| 2005/0222642 A1 | 10/2005 | Przybyszewski et al. |
| 2005/0222647 A1 | 10/2005 | Wahlstrand et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0247472 A1 | 11/2005 | Helfer et al. |
| 2005/0248340 A1 | 11/2005 | Berkcan et al. |
| 2005/0248907 A1 | 11/2005 | Stevenson et al. |
| 2006/0009819 A1 | 1/2006 | Przybyszewski |
| 2006/0025820 A1 | 2/2006 | Phillips et al. |
| 2006/0028784 A1 | 2/2006 | Brendel |
| 2006/0030774 A1 | 2/2006 | Gray et al. |
| 2006/0032665 A1 | 2/2006 | Ice |
| 2006/0041294 A1 | 2/2006 | Gray |
| 2006/0085043 A1 | 4/2006 | Stevenson |
| 2006/0100506 A1 | 5/2006 | Halperin et al. |
| 2006/0119361 A1 | 6/2006 | Karmarkar et al. |
| 2006/0200218 A1 | 9/2006 | Wahlstrand |
| 2006/0211979 A1 | 9/2006 | Smith et al. |
| 2006/0212096 A1 | 9/2006 | Stevenson |
| 2006/0221543 A1 | 10/2006 | Stevenson et al. |
| 2006/0229693 A1 | 10/2006 | Bauer et al. |
| 2006/0247684 A1 | 11/2006 | Halperin et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0259093 A1 | 11/2006 | Stevenson et al. |
| 2006/0271138 A1 | 11/2006 | MacDonald |
| 2007/0035910 A1 | 2/2007 | Stevenson |
| 2007/0043399 A1 | 2/2007 | Stevenson et al. |
| 2007/0083244 A1 | 4/2007 | Stevenson et al. |
| 2007/0088416 A1 | 4/2007 | Atalar et al. |
| 2007/0093142 A1 | 4/2007 | MacDonald et al. |
| 2007/0106332 A1 | 5/2007 | Denker et al. |
| 2007/0112398 A1 | 5/2007 | Stevenson et al. |
| 2007/0123949 A1 | 5/2007 | Dabney et al. |
| 2007/0167867 A1 | 7/2007 | Wolf |
| 2007/0168005 A1 | 7/2007 | Gray |
| 2007/0168006 A1 | 7/2007 | Gray |
| 2007/0179554 A1 | 8/2007 | Lyer et al. |
| 2007/0179577 A1 | 8/2007 | Marshall et al. |
| 2007/0203529 A1 | 8/2007 | Iyer et al. |
| 2007/0208383 A1 | 9/2007 | Williams |
| 2007/0250143 A1 | 10/2007 | Sommer et al. |
| 2007/0255332 A1 | 11/2007 | Cabelka et al. |
| 2007/0255377 A1 | 11/2007 | Marshall et al. |
| 2007/0288058 A1 | 12/2007 | Halperin et al. |
| 2007/0299490 A1 | 12/2007 | Yang et al. |
| 2008/0004670 A1 | 1/2008 | McVenes et al. |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0049410 A1 | 2/2008 | Kawaguchi et al. |
| 2008/0051854 A1 | 2/2008 | Bulkes et al. |
| 2008/0071313 A1 | 3/2008 | Stevenson et al. |
| 2008/0116997 A1 | 5/2008 | Dabney et al. |
| 2008/0132986 A1 | 6/2008 | Gray et al. |
| 2008/0132987 A1 | 6/2008 | Westlund et al. |
| 2008/0140149 A1 | 6/2008 | John et al. |
| 2008/0158746 A1 | 7/2008 | Anthony et al. |
| 2008/0161886 A1 | 7/2008 | Stevenson et al. |
| 2008/0195180 A1 | 8/2008 | Stevenson et al. |
| 2008/0195186 A1 | 8/2008 | Li et al. |
| 2008/0195187 A1 | 8/2008 | Li et al. |
| 2008/0221638 A1 | 9/2008 | Wedan et al. |
| 2008/0239622 A1 | 10/2008 | Hsu et al. |
| 2008/0243218 A1 | 10/2008 | Bottomley et al. |
| 2008/0247111 A1 | 10/2008 | Anthony et al. |
| 2008/0247116 A1 | 10/2008 | Kawano et al. |
| 2008/0247117 A1 | 10/2008 | Elam et al. |
| 2008/0262584 A1 | 10/2008 | Bottomley et al. |
| 2008/0262592 A1 | 10/2008 | Jordan et al. |
| 2008/0264685 A1 | 10/2008 | Park et al. |
| 2008/0269591 A1 | 10/2008 | Halperin et al. |
| 2008/0277153 A1 | 11/2008 | Teshome et al. |
| 2009/0036944 A1 | 2/2009 | Fonte |
| 2009/0097219 A1 | 4/2009 | Cho et al. |
| 2009/0099440 A1 | 4/2009 | Viohl |
| 2009/0099555 A1 | 4/2009 | Viohl et al. |
| 2009/0107717 A1 | 4/2009 | Hsu et al. |
| 2009/0116167 A1 | 5/2009 | Stevenson et al. |
| 2009/0128976 A1 | 5/2009 | Anthony |
| 2009/0139760 A1 | 6/2009 | Tanaka |
| 2009/0163974 A1 | 6/2009 | Taylor et al. |
| 2009/0163980 A1 | 6/2009 | Stevenson |
| 2009/0180237 A1 | 7/2009 | Hou et al. |
| 2009/0187229 A1 | 7/2009 | Lavie |
| 2009/0236141 A1 | 9/2009 | Kim et al. |
| 2009/0243756 A1 | 10/2009 | Stevenson et al. |
| 2009/0270948 A1 | 10/2009 | Nghiem et al. |
| 2009/0281592 A1 | 11/2009 | Vase |
| 2009/0312835 A1 | 12/2009 | Stevenson |
| 2010/0010602 A1 | 1/2010 | Wedan et al. |
| 2010/0016936 A1 | 1/2010 | Stevenson et al. |
| 2010/0023000 A1 | 1/2010 | Stevenson et al. |
| 2010/0023095 A1 | 1/2010 | Stevenson et al. |
| 2010/0046135 A1 | 2/2010 | Niki et al. |
| 2010/0046137 A1 | 2/2010 | Adachi |
| 2010/0076538 A1 | 3/2010 | Desai et al. |
| 2010/0109958 A1 | 5/2010 | Haubrich et al. |
| 2010/0109966 A1 | 5/2010 | Mateychuk et al. |
| 2010/0114246 A1 | 5/2010 | Hill et al. |
| 2010/0114276 A1 | 5/2010 | Min et al. |
| 2010/0114277 A1 | 5/2010 | Zhao et al. |
| 2010/0138192 A1 | 6/2010 | Min |
| 2010/0149042 A1 | 6/2010 | Utsi et al. |
| 2010/0151113 A1 | 6/2010 | Shelton |
| 2010/0160989 A1 | 6/2010 | Legay |
| 2010/0174348 A1 | 7/2010 | Bulkes et al. |
| 2010/0174349 A1 | 7/2010 | Stevenson et al. |
| 2010/0198312 A1 | 8/2010 | Stevenson et al. |
| 2010/0217262 A1 | 8/2010 | Stevenson et al. |
| 2010/0217264 A1 | 8/2010 | Odom et al. |
| 2010/0217341 A1 | 8/2010 | John et al. |
| 2010/0234907 A1 | 9/2010 | Dobak |
| 2010/0241206 A1 | 9/2010 | Truex et al. |
| 2011/0043297 A1 | 2/2011 | Stevenson et al. |
| 2011/0248184 A1 | 10/2011 | Shah |
| 2012/0006576 A1 | 1/2012 | Barry et al. |
| 2012/0197335 A1 | 8/2012 | Reisinger |
| 2013/0032378 A1 | 2/2013 | Morioka et al. |
| 2013/0058003 A1 | 3/2013 | Iyer et al. |
| 2013/0138186 A1 | 5/2013 | Iyer et al. |
| 2013/0184796 A1 | 7/2013 | Marzano et al. |
| 2014/0151114 A1 | 6/2014 | Morioka et al. |
| 2014/0168850 A1 | 6/2014 | Stevenson et al. |
| 2014/0168917 A1 | 6/2014 | Marzano et al. |
| 2014/0243944 A1 | 8/2014 | Stevenson et al. |
| 2015/0004359 A1 | 1/2015 | Shahbazi et al. |
| 2015/0217111 A1 | 8/2015 | Stevenson et al. |
| 2015/0245468 A1 | 8/2015 | Barry et al. |
| 2015/0283374 A1 | 10/2015 | Kronmueller et al. |
| 2015/0314131 A1 | 11/2015 | Marzano et al. |
| 2015/0343224 A1 | 12/2015 | Woods et al. |
| 2016/0151635 A1 | 6/2016 | Frysz et al. |
| 2016/0263384 A1 | 9/2016 | Stevenson et al. |
| 2016/0287883 A1 | 10/2016 | Barry et al. |
| 2018/0126175 A1 | 5/2018 | Seitz et al. |

FOREIGN PATENT DOCUMENTS

| | | |
|---|---|---|
| EP | 0466424 | 1/1992 |
| EP | 0557127 | 8/1993 |
| EP | 0673621 | 9/1995 |
| EP | 0498996 | 3/1997 |
| EP | 1021730 | 4/2003 |
| EP | 0930509 | 3/2004 |

(56) References Cited

FOREIGN PATENT DOCUMENTS

| | | |
|---|---|---|
| EP | 1469910 | 12/2006 |
| EP | 1883449 | 1/2009 |
| EP | 2025361 | 2/2009 |
| EP | 2617461 A1 | 7/2013 |
| EP | 2617461 B1 | 12/2018 |
| FR | 2811900 | 2/2003 |
| JP | 60141034 | 7/1985 |
| JP | 61181925 | 8/1986 |
| JP | 62233905 | 10/1987 |
| JP | 4071536 | 3/1992 |
| JP | 6054823 | 3/1994 |
| JP | 06070902 | 3/1994 |
| JP | 6176962 | 6/1994 |
| JP | 7272975 | 10/1995 |
| JP | 9094238 | 4/1997 |
| JP | 11239572 | 9/1999 |
| JP | 2004254257 | 9/2004 |
| JP | 2004289760 | 10/2004 |
| JP | 2005117606 | 4/2005 |
| JP | 2007129565 | 5/2007 |
| WO | 8704080 | 7/1987 |
| WO | 9210213 | 6/1992 |
| WO | 9423782 | 10/1994 |
| WO | 9740396 | 10/1997 |
| WO | 9852461 | 11/1998 |
| WO | 9919739 | 4/1999 |
| WO | 0010456 | 3/2000 |
| WO | 0025672 | 5/2000 |
| WO | 02083016 | 10/2002 |
| WO | 2003037424 | 5/2003 |
| WO | 2003063946 | 8/2003 |
| WO | 2003063952 | 8/2003 |
| WO | 2003063953 | 8/2003 |
| WO | 2003063955 | 8/2003 |
| WO | 2003063956 | 8/2003 |
| WO | 2003063957 | 8/2003 |
| WO | 2005081784 | 9/2005 |
| WO | 2005102445 | 11/2005 |
| WO | 2005102446 | 11/2005 |
| WO | 2005102447 | 11/2005 |
| WO | 2005115531 | 12/2005 |
| WO | 2006093685 | 9/2006 |
| WO | 2007047966 | 4/2007 |
| WO | 2007089988 | 8/2007 |
| WO | 2007102893 | 9/2007 |
| WO | 2007145671 | 12/2007 |
| WO | 2008077037 | 6/2008 |
| WO | 2008111986 | 9/2008 |
| WO | 2010008833 | 1/2010 |
| WO | 2013/158552 | 10/2013 |

OTHER PUBLICATIONS

Roguin, et al., "Modem Pacemaker and Implantable Cardioverter/Defibrillator systems Can Be Magnetic Resonance Imaging Safe", Journal of the American Heart Association, Aug. 4, 2004, 475-482.
Sakabe, et al., "High Frequency Performance of Multilayer Ceramic Capacitors", Electronic Components and Technology Confrerence, 1995, Proceedings 45th, May 21, 1995, 234-240.
Sarda, et al., "Ceramic EMI Filters—A Review", American Ceramic Society Bulletin; vol. 67, No. 4, 1988, 737-746.
Shellock, et al., "Comparative Analyses of MR-Induced Distal Heating in Novel Filtered Cardiac Pacing Leads UsingTwo Geometric Configurations", 17th Scientific Meeting & Exhibition of the International Society for Magnetic Resonance in Medicine, Honolulu, Hawaii, Apr. 2009, 3014.
Shellock, "MRI Issues for Neuromodulation Devices", Institute for Magnetic Resonance Safety Education, and Research (IMRSER).
Susil, et al., "Multifunctional Interventional Devices for MRI: A Combined Electrophysiology/MRI Catheter", 2002, 594-600.
Susil, et al., "U.S. Appl. No. 60/283,725", Multifunctional Interventional Devices for Use in MRI, Apr. 13, 2001.
Weiner, et al., "U.S. Appl. No. 60/269,817", Electromagnetic Interference immune Cardiac Assist System, Feb. 20, 2001.
Wilk, et al., "High-K Gate Dielectrics: Current Status and Materials Properties Considerations", Journal of Applied Physi s, vol. 89, No. 10, May 15, 2001, 5243-5275.
European search, Application No. 10167031.3, dated Sep. 19, 2012.
Gabriel, et al., "The Dielectric Properties of Biological Tissues: II.", Measurements in the Frequency Range 10 Hz to 20 GHz, Apr. 2, 1996, 2251-2269.
Gabriel, et al., "The Dielectric Properties of Biological Tissues: Parametric Models for the Dielectric Spectrum of Tissues", Parametric Models for the Dielectric Spectrum of Tissues Phys. Med. Bio. 41, 1996, 2271-2293.
Johnson, et al., "Characterization of the Relationship between MR-Induced Distal Tip Heating in Cardiac Pacing Leads and Electrical Performance of Novel Filtered Tip Assemblies", 17th Scientific Meeting & Exhibition of the International Society for Magnetic Resonance in Medicine, Honolulu, Hawaii, Apr. 2009, 307.
Karbasi, "Developing a High Density PT/Alumina Hermetic Feedthrough", Florida International University, FIU Digital Commons, FIU Electronic Theses and Dissertations, University Graduate School, Published May 15, 2012.
Kingery, et al., "Atom Mobility in Introduction to Ceramics, 2nd Edition", Published in New York, Wiley, copyright 1976, pp. 217-263.
Kingery, et al., "Surfaces, Interfaces, and Grain Boundaries in Introduction to Ceramics", 2nd Edition, Publiched in New York, Wiley, copyright 1976, pp. 177-215.
Konings, et al., "Heating Around Intravascular Guidewires by Resonating RF Waves", Journal of Magnetic Resonance Imaging, 2000, 79-85.
Lamouri, et al., "Control of the y-alumina to a-alumina phase transformation for an optimized alumina densification", Boletin de la Sociedad Espanola De Ceramica Y Vidrio 56 (2017) pp. 47-54.
Luchinger, "Safety Aspects of Cardiac Pacemakers in Magnetic Resonance Imaging", A dissertation submitted to the Swiss Federal Institute of Technology Zurich, Switzerland, 2002.
Extended European Search Report, Application No. 19164185.1, dated Jul. 8, 2019.
European Search Report, Application No. 15165863.0, dated Sep. 12, 2016.
European Search Report, Application No. 18150642.9, dated Jun. 6, 2018.
European Search Report, Application No. 12157697.9, dated Jul. 5, 2012.
Extended European Search Report, Application No.17201160.3 dated Apr. 16, 2018.
Extended European Search Report, Application No. 17197151.8, dated Apr. 26, 2018.
Extended European Search Report, Application No. 16175505.3, dated Nov. 15, 2016.
Exteneded European Search Report, Application No. 18177098.3, dated Aug. 8, 2018.
Holy Stone Enterprise, Ceramic Capacitor Catalog 2008-2009, May 2008.
Wikipedia article, EIA Class 1 dielectric., Sep. 13, 2006.
Balanis, "Advanced Engineering Electromagnetics", 1989.
Becker, "Die Keimbildung Bei Der Ausscheidung in Metallischen Mischkristallen", Published Annalen der Physik, Issue 5, vol. 32, 1938, pp. 128-140.
Boser, et al., "High Frequency Behavior of Ceramic Multilayer Capacitors", IEEE Transactions on Components, Hybrids, and Manufacturing Technology, vol. CHMT-10, No. 3, Sep. 1987, pp. 437-439.
Clement, et al., "Estimation of Effective Lead Loop Area for Implantable Pulse Generators and Cardioverter/Defibrillators for Determination of Susceptibility to Radiated Electromagnetic Interference", AAMI EMC Task Force, Apr. 12, 2004, 10 pages.
Ennis, et al., "Cautions About the Use of Equivalent Series Resistance (ESR) in Specifying Capacitors", Mar. 8, 1993, 58-64.
European Search Report, Application No. 10167031.3, dated Sep. 19, 2012.

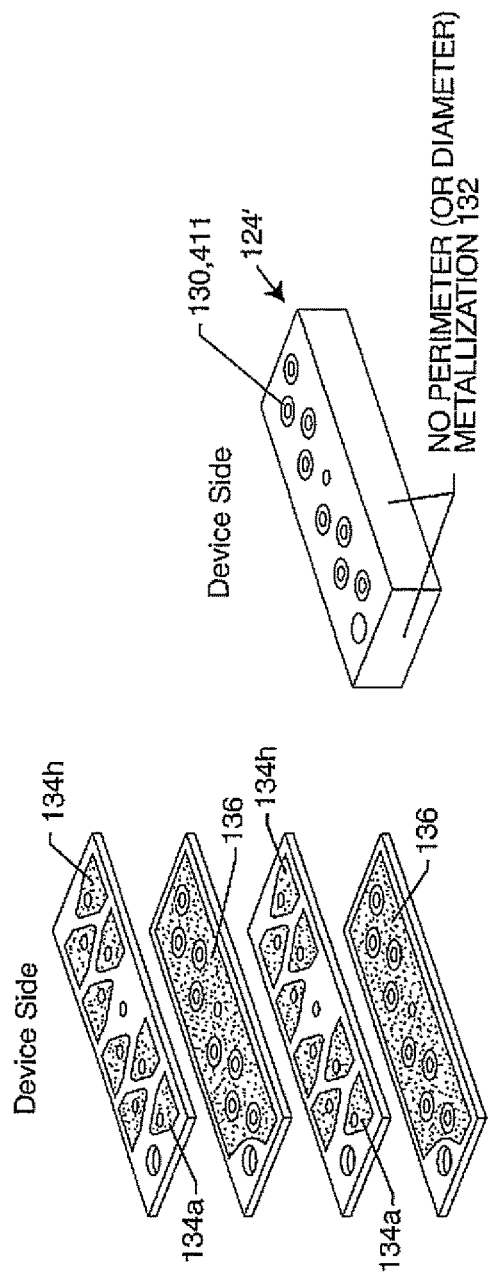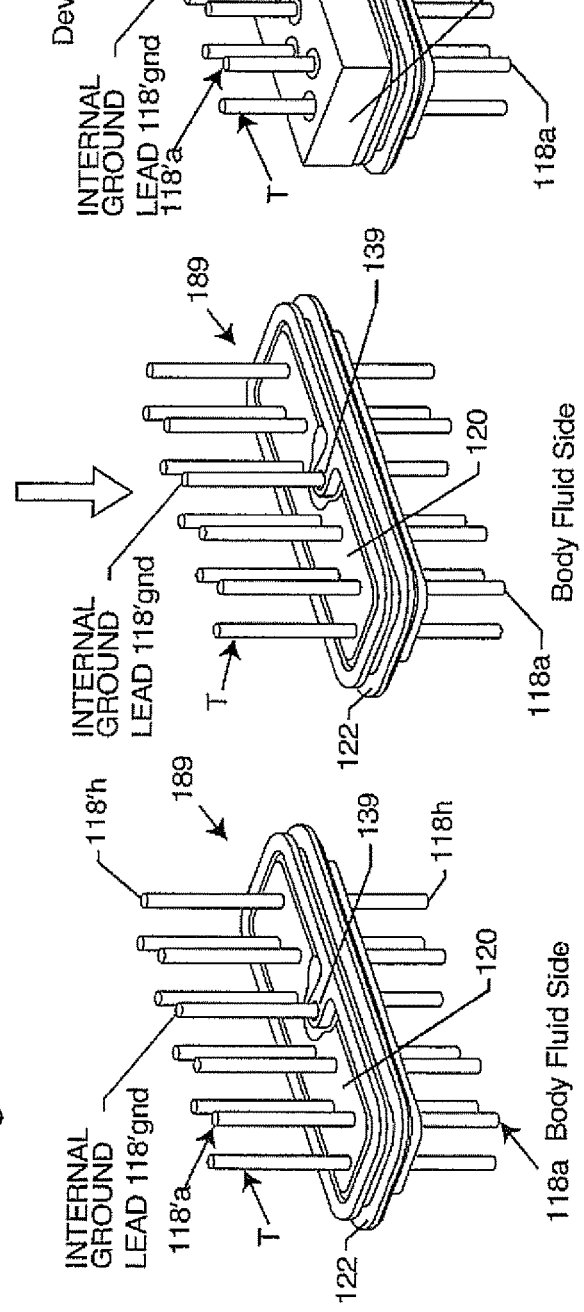
FIG. 5 PRIOR ART
FIG. 6 PRIOR ART
FIG. 7 PRIOR ART

DEVICE SIDE

DEVICE SIDE

BODY FLUID SIDE (TOP VIEW OF DEVICE SIDE)

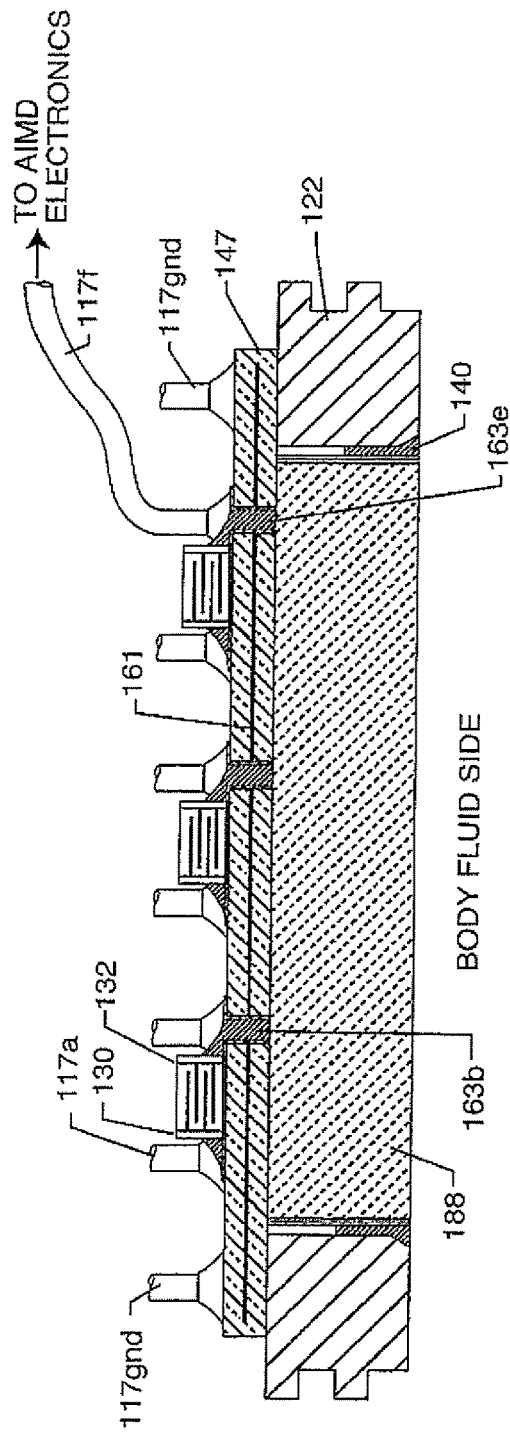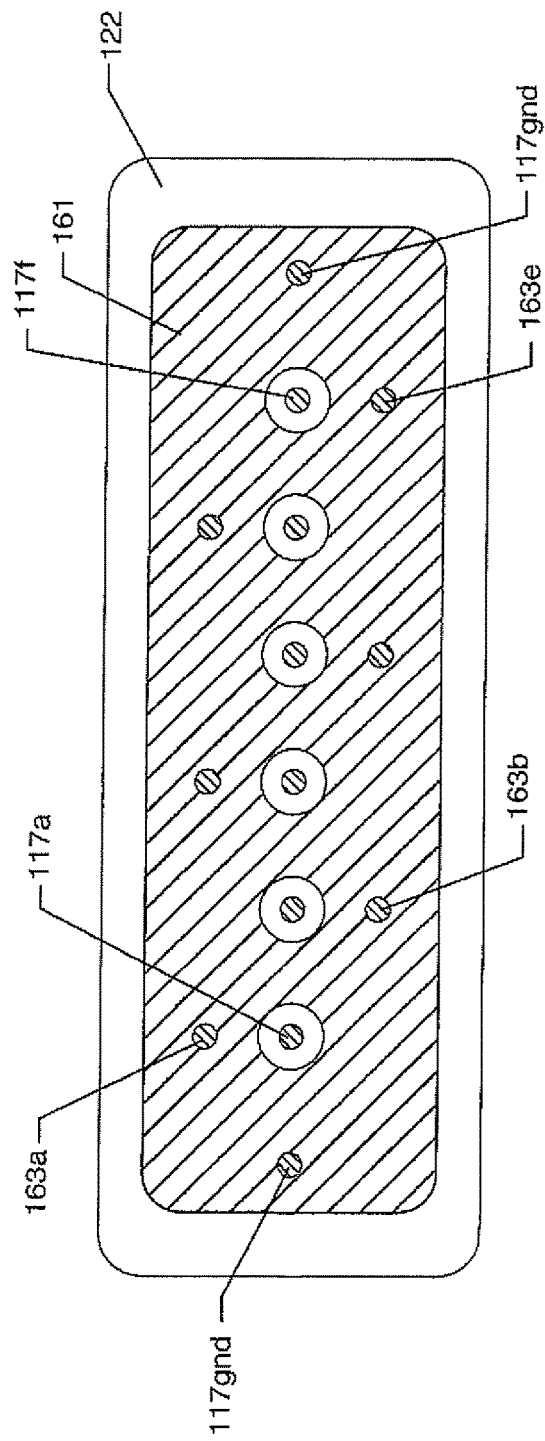
FIG. 53
FIG. 53A

FIG. 58    TO CIRCUIT BOARD OR AIMD ELECTRODE

| Composition | M.P. °C S/L | Eutectic | Sn | Pb | Ag | Cu | Sb | Bi | In | Zn | Cd | Au | oth. |
|---|---|---|---|---|---|---|---|---|---|---|---|---|---|
| Au₈Ir₁₈ | 451/485 | no | | | | | | | | | | 82 | |
| Au₇₈.₅Si₂₁.₅ | 370/363 | yes | | | | | | | | | | 96.8 | Si₃.₂ |
| Au₉₈Si₂ | 370/800 | yes | | | | | | | | | | 98 | Si₂ |
| Au₈₇.₅Ge₁₂.₅ | 361/356 | yes | | | | | | | | | | 87.5 | Ge₁₂.₅ |
| Cd₉₅Ag₅ | 338/393 | no | | | 5 | | | | | | 95 | | |
| Pb₉₂Cd₈ | 310 | | | 92 | | | | | | | 8 | | |
| Pb₉₇.₅Ag₁.₅Sn₁ | 309 | yes | 1 | 97.5 | 1.5 | | | | | | | | |
| Pb₉₅Ag₅ | 305/364 | no | | 95 | 5 | | | | | | | | |
| Pb₉₄.₅Ag₅.₅ | 304/343 | no | | 94.5 | 5.5 | | | | | | | | |
| Pb₉₇.₅Ag₂.₅ | 304/579 | yes | | 97.5 | 2.5 | | | | | | | | |
| Pb₉₂.₅Ag₂.₅Sn₅ | 300/310 | no | 5 | 92.5 | 2.5 | | | | | | | | |
| Pb₉₂.₅In₅Au₂.₅ | 300/310 | no | | 92.5 | | | | | 5 | | | 2.5 | |
| Pb₉₅.₅Ag₂.₅Sn₂ | 299/304 | no | 2 | 95.5 | 2.5 | | | | | | | | |
| Pb₉₃.₅Ag₁.₅Sn₅ | 296/301 | no | 5 | 93.5 | 1.5 | | | | | | | | |
| Pb₉₀Sn₅Ag₅ | 292 | yes | 5 | 90 | 5 | | | | | | | | |
| Pb₉₀Sn₅Ag₅ | 290/310 | no | 5 | 90 | 5 | | | | | | | | |
| Pb₉₂.₅Sn₅Ag₂.₅ | 287/296 | no | 5 | 92.5 | 2.5 | | | | | | | | |
| Pb₉₂Sn₅.₅Ag₂.₅ | 285/301 | no | 5.5 | 92 | 2.5 | | | | | | | | |
| Pb₈₁In₁₉ | 260/275 | no | | 81 | | | | | 19 | | | | |
| Pb₉₀Sn₁₀ | 268/302 | no | 10 | 90 | | | | | | | | | |
| Pb₈₈Sn₁₀Ag₂ | 268/290 | no | 10 | 88 | 2 | | | | | | | | |
| Cd₈₂.₅Zn₁₇.₅ | 265 | yes | | | | | | | | 17.5 | 82.5 | | |
| Zn₉₀Cd₁₀ | 265/399 | no | | | | | | | | 90 | 10 | | |
| Zn₆₀Cd₄₀ | 266/335 | no | | | | | | | | 60 | 40 | | |
| Cd₆₀Zn₄₀ | 255/316 | no | | | | | | | | 40 | 60 | | |
| Cd₇₀Zn₃₀ | 255/303 | no | | | | | | | | 30 | 70 | | |
| Pb₈₆Sn₁₂Ag₂ | 254/296 | no | 12 | 86 | 2 | | | | | | | | |
| Pb₉₆Sn₂Ag₂ | 252/395 | no | 2 | 96 | 2 | | | | | | | | |
| Pb₈₀Sn₁₅Ag₅ | 252/260 | no | 15 | 80 | 5 | | | | | | | | |
| Pb₇₅In₂₅ | 240/260 | no | | 75 | | | | | 25 | | | | |
| Cd₅₇Zn₁₇In₃₀ | 249/316 | no | | | | | | | 30 | 17 | 70 | | |
| Pb₇₀Sn₁₈ | 245/260 | no | 18 | 70 | | | | | | | | | |
| Pb₈₅Sn₁₅ | 227/288 | no | 15 | 85 | | | | | | | | | |

FIG. 78

CIRCUIT BOARD MOUNTED FILTERED FEEDTHROUGH ASSEMBLY HAVING A COMPOSITE CONDUCTIVE LEAD FOR AN AIMD

CROSS-REFERENCE TO RELATED APPLICATIONS

This application is a continuation of U.S. patent application Ser. No. 15/603,521, filed on May 24, 2017, now U.S. Pat. No. 10,272,252, which claims priority to U.S. provisional application Ser. No. 62/418,834, filed on Nov. 8, 2016, the entire contents of which are fully incorporated herein with these references.

FIELD OF THE INVENTION

The present invention generally relates to implantable medical devices and hermetic terminal subassemblies. More particularly, the present invention relates a hermetic terminal having a composite conductive lead brazed into an insulator body.

BACKGROUND OF THE INVENTION

A wide assortment of active implantable medical devices (AIMDs) are presently known and in commercial use. Such devices include cardiac pacemakers, cardiac defibrillators, cardioverters, neurostimulators, and other devices for delivering and/or receiving electrical signals to/from a portion of the body. Sensing and/or stimulating leads extend from the associated implantable medical device to a distal tip electrode or electrodes in contact with body tissue.

The hermetic terminal or feedthrough of these implantable devices is considered critical. Hermetic terminals or feedthroughs are generally well-known in the art for connecting electrical signals through the housing or case of an AIMD. For example, in implantable medical devices such as cardiac pacemakers, implantable cardioverter defibrillators, and the like, a hermetic terminal comprises one or more conductive pathways which may include conductive terminal pins, conductive filled vias, leadwires and the like supported by an insulative structure for feedthrough passage from the exterior to the interior of an AIMD electromagnetic shield housing. Hermetic terminals or feedthroughs for AIMDs must be biocompatible as well as resistant to degradation under applied bias current or voltage (biostable). Hermeticity of the feedthrough is imparted by judicious material selection and carefully prescribed manufacturing processing. Sustainable hermeticity of the feedthrough over the lifetime of these implantable devices is critical because the hermetic terminal intentionally isolates the internal circuitry and components of the device (AIMD) from the external body fluid environment to which the component is exposed. In particular, the hermetic terminal isolates the internal circuitry, connections, power sources and other components in the device from ingress of body fluids. Ingress of body fluids into an implantable medical device is known to be a contributing factor to device malfunction and may contribute to the compromise or failure of electrical circuitry, connections, power sources and other components within an implantable medical device that are necessary for consistent and reliable device therapy delivery to a patient. Furthermore, ingress of body fluids may compromise an implantable medical device's functionality which may constitute electrical shorting, element or joint corrosion, metal migration or other such harmful consequences affecting consistent and reliable device therapy delivery.

In addition to concerns relative to sustained terminal or feedthrough hermeticity, other potentially compromising conditions must be addressed, particularly when a hermetic terminal or feedthrough is incorporated within an implantable medical device. For example, the hermetic terminal or feedthrough pins are typically connected to one or more lead conductors of implantable therapy delivery leads. These implantable therapy delivery leads can effectively act as antennas that receive electromagnetic interference (EMI) signals. Therefore, when these electromagnetic signals enter within the interior space of a hermetic implantable medical device, facilitated by the therapy delivery leads, they can negatively impact the intended function of the medical device and as a result, negatively impact therapy delivery intended for a patient by that device. EMI engineers commonly refer to this as the "genie in the bottle" effect. In other words, once the genie (i.e., EMI) is inside the hermetic housing of the device, it can wreak havoc with electronic circuit functions by cross-coupling and re-radiating within the device.

Another particularly problematic condition associated with implanted therapy delivery leads occurs when a patient is in an MRI environment. In this case, the MRI RF electrical currents imposed on the implanted therapy delivery leads can cause the leads to heat to the point where tissue damage is likely. Moreover, MRI induced RF currents (electromagnetic interference—EMI) may be coupled to implanted therapy delivery leads resulting in undesirable electrical currents which can enter the AIMD and can disrupt or damage the sensitive electronics within the implantable medical device.

Therefore, materials selection and fabrication processing parameters are of utmost importance in creating a hermetic terminal (or feedthrough) or a structure embodying a hermetic terminal (or feedthrough), that can survive anticipated and possibly catastrophically damaging environmental conditions and that can be practically and cost effectively manufactured.

In general, hermetic terminal subassemblies for AIMDs comprise a titanium ferrule and a gold brazed alumina insulator. Alternatively, hermetic terminals may comprise a ferrule and a compression or fusion glass seal. Hermetic terminals or feedthrough assemblies utilizing ceramic dielectric materials may fail in a brittle manner. A brittle failure typically occurs when the ceramic structure is deformed elastically up to an intolerable stress, at which point the ceramic fails catastrophically. Most brittle failures occur by crack propagation in a tensile stress field. Even microcracking caused by sufficiently high tensile stress concentrations may result in a catastrophic failure including loss of hermeticity identified as critical in hermetic terminals for implantable medical devices. Loss of hermeticity may be a result of design aspects such as a sharp corner which creates a stress riser, mating materials with a difference of coefficient of thermal expansions (CTE) that generate tensile stresses that ultimately result in loss of hermeticity of the feedthrough or interconnect structure.

In the specific case of hermetic terminal or feedthrough designs, a tensile stress limit for a given ceramic based hermetic design structure cannot be specified because failure stress in these structures is not a constant. As indicated above, variables affecting stress levels include the design itself, the materials selection, symmetry of the feedthrough, and the bonding characteristics of mating surfaces within the feedthrough. Hence, length, width and height of the overall ceramic structure matters as do the number, spacing, length and diameter of the conductive pathways (vias, terminal pins, leadwires, etc.) in that structure. The selection of the mating materials, that is, the material that fills the vias (or leadwire) and the material that forms the base ceramic, are important. Finally, the fabrication processing parameters, particularly at binder burnout, sintering and cool down, make a difference. When high reliability is required in an application such as indicated with hermetic terminals or feedthroughs for AIMDs, to provide insurance for a very low probability of failure it is necessary to design a hermetic terminal assembly or feedthrough structure so that stresses imparted by design, materials and/or processing are limited to a smaller level of an average possible failure stress. Further, to provide insurance for a very low probability of failure in a critical ceramic based assembly or subassembly having sustainable hermetic requirements, it is also necessary to design structures embodying a hermetic terminal or feedthrough such that stresses in the final assembly or subassembly are limited to a smaller level of an average possible failure stress for the entire assembly or subassembly. In hermetic terminals and structures comprising hermetic terminals for AIMDs wherein the demand for biocompatibility exists, this task becomes even more difficult.

The most critical feature of a feedthrough design or any terminal subassembly is the metal/ceramic interface within the feedthrough that establishes the hermetic seal. One embodiment of the present invention therefore provides where a hermetic feedthrough comprising a monolithic alumina insulator substrate within which a platinum, palladium or the like conductive pathway or via resides or wherein a metallic leadwire (terminal pin) resides. More specifically in the case of a filled via, the present invention provides a hermetic feedthrough in which the hermetic seal is created through the intimate bonding of a CERMET (ceramic metal) or a platinum metal residing within the alumina substrate.

A traditional ceramic-to-metal hermetic terminal is an assembly of three components: electrical conductors (leadwires, pins, terminal pins, filled vias) that conduct electrical current, a ceramic insulator, and a metal housing, which is referred to as the flange or the ferrule (or even the AIMD housing itself). Brazed joints typically hermetically seal the metal leadwires and the flange or ferrule to the ceramic insulator. For a braze-bonded joint, the braze material is generally intended to deform in a ductile manner in order to compensate for perturbations that stress the bond between the mating materials as the braze material may provide ductile strain relief when the thermal expansion mismatch between the ceramic and metal is large. Thus, mating materials with large mismatches in CTE can be coupled through braze materials whose high creep rate and low yield strength reduce the stresses generated by the differential contraction existing between these mating materials. Glass seals are also known in the art, which form a hermetic seal to the ferrule and one or more leadwires passing through the glass seal.

Regarding EMI, a terminal or feedthrough capacitor EMI filter may be disposed at, near or within a hermetic terminal or feedthrough resulting in a feedthrough filter capacitor which diverts high frequency electrical signals from lead conductors to the housing or case of an AIMD. Many different insulator structures and related mounting methods are known in the art for use of feedthrough capacitor EMI filters in AIMDs, wherein the insulative structure also provides a hermetic terminal or feedthrough to prevent entry of body fluids into the housing of an AIMD. In the prior art devices, the hermetic terminal subassembly has been combined in various ways with a ceramic feedthrough filter EMI capacitor to decouple interference signals to the housing of the medical device.

In a typical prior art unipolar construction (as described in U.S. Pat. No. 5,333,095 and herein incorporated by reference), a round/discoidal (or rectangular) ceramic feedthrough EMI filter capacitor is combined with a hermetic terminal pin assembly to suppress and decouple undesired interference or noise transmission along a terminal pin. The feedthrough capacitor is coaxial having two sets of electrode plates embedded in spaced relation within an insulative dielectric substrate or base, formed typically as a ceramic monolithic structure. One set of the electrode plates are electrically connected at an inner diameter cylindrical surface of the coaxial capacitor structure to the conductive terminal pin utilized to pass the desired electrical signal or signals. The other or second set of electrode plates are coupled at an outer diameter surface of the round/discoidal capacitor to a cylindrical ferrule of conductive material, wherein the ferrule is electrically connected in turn to the conductive housing of the electronic device. The number and dielectric thickness spacing of the electrode plate sets varies in accordance with the capacitance value and the voltage rating of the coaxial capacitor. The outer feedthrough capacitor electrode plate sets (or "ground" plates) are coupled in parallel together by a metalized layer which is fired, sputtered or plated onto the ceramic capacitor. This metalized band, in turn, is coupled to the ferrule by conductive adhesive, soldering, brazing, welding, or the like. The inner feedthrough capacitor electrode plate sets (or "active" plates) are coupled in parallel together by a metalized layer which is either glass frit fired or plated onto the ceramic capacitor. This metalized band, in turn, is mechanically and electrically coupled to the lead wire(s) by conductive adhesive, soldering, or the like. In operation, the coaxial capacitor permits passage of relatively low frequency biologic signals along the terminal pin, while shielding and decoupling/attenuating undesired interference signals of typically high frequency to the AIMD conductive housing. Feedthrough capacitors of this general type are available in unipolar (one), bipolar (two), tripolar (three), quadpolar (four), pentapolar (five), hexpolar (6) and additional lead configurations. The feedthrough capacitors (in both discoidal and rectangular configurations) of this general type are commonly employed in implantable cardiac pacemakers and defibrillators and the like, wherein the pacemaker housing is constructed from a biocompatible metal such as titanium alloy, which is electrically and mechanically coupled to the ferrule of the hermetic terminal pin assembly which is in turn electrically coupled to the coaxial feedthrough filter capacitor. As a result, the filter capacitor and terminal pin assembly prevents entrance of interference signals to the interior of the pacemaker housing, wherein such interference signals could otherwise adversely affect the desired cardiac pacing or defibrillation function.

Therefore, it is very common in the prior art to construct a hermetic terminal subassembly with a feedthrough capacitor attached near the inside of the AIMD housing on the device side. The feedthrough capacitor does not have to be made from biocompatible materials because it is located on the device side inside the AIMD housing. The hermetic terminal subassembly includes conductive pathways (leadwires, pins, terminal pins, filled vias, etc.) to hermetically pass through the insulator in non-conductive relation with the ferrule or the AIMD housing. The conductive pathways also pass through the feedthrough hole of the capacitor to electronic circuits disposed inside of the AIMD housing. These leadwires are typically electrically continuous and, on the body fluid side, must be biocompatible and non-toxic. Generally, these conductive pathways are constructed of platinum or platinum-iridium, palladium or palladium-iridium, niobium pins or filled vias with conductive powders, ceramics, gradient materials or the like. Platinum-iridium is an ideal choice because it is biocompatible, non-toxic and is also mechanically very strong. The iridium is added to enhance material stiffness and to enable the hermetic terminal subassembly leadwire to sustain bending stresses. An issue with the use of platinum for leadwires is that platinum has become extremely expensive and may be subject to premature fracture under rigorous processing such as ultrasonic cleaning or application use/misuse, possibly unintentional damaging forces resulting from Twiddler's Syndrome. Twiddler's Syndrome is a situation documented in the literature where a patient will unconsciously or knowingly twist the implantable device to the point where attached leads may even fracture.

Accordingly, what is needed is a is a hermetic seal subassembly which has a biocompatible and non-toxic lead or leadwire on the body fluid side, which is co-joined within the hermetic seal insulator to a lower cost device side lead, which may be routed to AIMD internal electronic circuits. The present invention does not change the way the prior art leadwires are generally connected to a body fluid side header block or implantable lead. The present invention also does not change the way that leadwires may be routed inside the device and connected directly to an AIMD electronic circuit board or to an intermediate flex cable or the like. Accordingly, what is needed is a way to provide a body fluid side biocompatible leadwire, which is joined within the hermetic seal insulator to a lower cost leadwire or pin. As will be seen, this not only saves a much lower cost hermetic seal subassembly, but also facilitates automation; for example, to add a feedthrough capacitor filter or a circuit board type of EMI filter.

SUMMARY OF THE INVENTION

In an exemplary embodiment of the present invention a hermetically sealed feedthrough subassembly is attachable to an active implantable medical device (AIMD), the feedthrough subassembly comprising: (a) an insulator substrate assembly, comprising: i) an insulator body defined as having a first insulator side opposite a second insulator side, the first insulator side and second insulator side separated and connected by at least one outside surface; ii) at least one via hole disposed through the insulator body extending from the first insulator side to the second insulator side; iii) an internal metallization formed at least partially on an inside of the at least one via hole; iv) a first conductive leadwire having a first conductive leadwire first end at least partially disposed within the at least one via hole and having a first conductive leadwire second end disposed past the first insulator side; v) a second conductive leadwire having a second conductive leadwire first end at least partially disposed within the at least one via hole and having a second conductive leadwire second end disposed past the second insulator side; vi) wherein the first conductive leadwire first end is disposed near, at or adjacent to the second conductive leadwire first end; vii) wherein the first conductive leadwire is not the same material as the second conductive leadwire; viii) a first braze at least partially between the first conductive leadwire first end, the second conductive leadwire first end and the internal metallization, the first braze forming a first hermetic seal separating the first insulator side from the second insulator side; and ix) an external metallization disposed at least partially on the at least one outside surface of the insulator body; and (b) a ferrule, comprising: i) a conductive ferrule body defined as having a first ferrule side opposite a second ferrule side and defining a ferrule opening between and through the first and second ferrule sides, wherein the insulator body is at least partially disposed within the ferrule opening; ii) a second braze at least partially between the external metallization of the insulator body and the conductive ferrule body, the second braze forming a second hermetic seal hermetically sealing the ferrule opening.

Other exemplary embodiments may include a feedthrough filter capacitor disposed on the second insulator side, the feedthrough filter capacitor comprising: i) at least one active electrode plate disposed parallel and spaced from at least one ground electrode plate, wherein the plates are disposed within a capacitor dielectric substrate; ii) a first passageway disposed through the capacitor dielectric substrate and disposed perpendicular to the plates; iii) a capacitor internal metallization disposed within the first passageway electrically connected to the at least one active electrode plate and in non-conductive relation with the at least one ground electrode plate; iv) a capacitor external metallization disposed on an outside surface of the capacitor dielectric substrate and electrically connected to the at least one ground electrode plate and in non-conductive relation with the at least one active electrode plate.

Other exemplary embodiments may include a third conductive leadwire having a third conductive leadwire first end at least partially disposed within the first passageway of the feedthrough filter capacitor and having a third conductive leadwire second end disposed past the feedthrough filter capacitor configured to be connectable to electronics internal to the AIMD, wherein the second conductive leadwire second end is at least partially disposed within the first passageway of the feedthrough filter capacitor, wherein the second conductive leadwire second end is at, near or adjacent to the third conductive leadwire first end.

Other exemplary embodiments may include a first electrically conductive material forming at least a three-way electrical connection electrically connecting the second conductive leadwire second end, the third conductive leadwire first end and the capacitor internal metallization.

The first electrically conductive material may be selected from the group consisting of a solder, a solder BGA, a solder paste, an epoxy, and a polyimide.

Other exemplary embodiments may include a second electrically conductive material electrically connecting the capacitor external metallization to the ferrule and/or to the second braze.

Other exemplary embodiments may include at least one internal ground plate disposed within the insulator body electrically connecting the internal metallization formed at least partially on the inside of the at least one via hole to the external metallization disposed at least partially on the at least one outside surface of the insulator body.

The first braze and second braze may be formed at the same time and are connected by a braze channel.

A conductive clip may be electrically coupled between and to the second conductive leadwire and the ferrule.

The ferrule may include a conductive peninsula extending at least partially into the ferrule opening, wherein the second conductive leadwire is electrically coupled to the conductive peninsula with the first braze.

Other exemplary embodiments may include a chip capacitor disposed on the second insulator side, the chip capacitor comprising: i) at least one active electrode plate disposed parallel and spaced from at least one ground electrode plate, wherein the plates are disposed within a capacitor dielectric substrate; ii) a first capacitor metallization disposed on one end of the chip capacitor and electrically connected to the at least one active electrode plate and in non-conductive relation with the at least one ground electrode plate; iii) a second capacitor metallization disposed on another end of the chip capacitor and electrically connected to the at least one ground electrode plate and in non-conductive relation with the at least one active electrode plate.

Other exemplary embodiments may include a first electrically conductive material electrically coupling the first capacitor metallization to the second conductive leadwire.

Other exemplary embodiments may include a second electrically conductive material electrically coupling the second capacitor metallization to the ferrule and/or the second gold braze.

The chip capacitor may be attached to the insulator body. Alternatively, the chip capacitor may be attached to a circuit board, wherein the circuit board is attached to the insulator body.

Other exemplary embodiments may include an oxide-resistant metal addition, wherein a second electrically conductive material electrically couples the second capacitor metallization to the oxide resistant metal addition, and wherein a third electrically conductive material electrically connects the oxide-resistant metal addition to the ferrule or wherein the oxide-resistant metal addition is welded to the ferrule.

The second conductive leadwire may comprise platinum or palladium.

The first conductive leadwire may comprise niobium or tantalum.

The first braze and second braze may each comprise a gold braze. The first braze may be disposed at or near the second insulator side and does not extend to at or near the first insulator side. The first braze may be disposed at or near the first insulator side and may not extend to at or near the second insulator side.

The third conductive leadwire first end may be pre-tinned.

The first and second hermetic seals may have a leak rate no greater than $1 \times 10^{-7}$ std cc He/sec.

The external metallization may be disposed at least partially on the at least one outside surface of the insulator body comprises an adhesion metallization and a wetting metallization, wherein the adhesion metallization may be disposed at least partially on the at least one outside surface of the insulator body and wherein the wetting metallization may be disposed on the adhesion metallization.

Other exemplary embodiments may include an insulative washer which may be disposed between the insulator substrate assembly and the feedthrough filter capacitor.

The ferrule may be configured to be joined to an AIMD housing by a laser weld or braze.

The ferrule may be formed from and as a continuous part of an AIMD housing.

The first insulator side may be a body fluid side and the second insulator side may be a device side.

In another exemplary embodiment of the present invention, an insulative feedthrough attachable to an active implantable medical device, comprises: a feedthrough body comprising a material which is both electrically insulative and biocompatible, wherein the feedthrough body is configured to be hermetically installed within the active implantable medical device separating a body fluid side from a device side; a passageway disposed through the feedthrough body extending from the body fluid side to the device side; a composite conductor disposed within the passageway, the composite conductor comprising a body fluid side metallic wire electrically conductive to a device side metallic wire;

wherein the body fluid side metallic wire extends from a first end disposed inside the passageway to a second end on the body fluid side; wherein the device side metallic wire extends from a first end disposed inside the passageway to a second end on the device side; wherein the body fluid side metallic wire is hermetically sealed to the feedthrough body; wherein the body fluid side metallic wire is biocompatible; and wherein the body fluid side metallic wire is not the same material as the device side metallic wire.

The ferrule may be made from an electrically conductive material, the ferrule configured to be hermetically sealed to a housing of the implantable medical device, wherein the ferrule defines a ferrule opening and the feedthrough body is hermetically sealed to the ferrule closing the ferrule opening. The ferrule may comprise titanium.

An adhesion layer may be disposed on an outside surface of the feedthrough body, a wetting layer may be disposed on the adhesion layer, and a gold braze may be hermetically sealing the wetting layer to the ferrule.

The ferrule opening may define an inner ferrule surface, wherein the feedthrough body is at least partially disposed within ferrule opening and hermetically sealed by the gold braze to the ferrule inner surface.

The device side metallic wire may not biocompatible. The device side metallic wire may be platinum. The device side metallic wire comprising platinum may not include iridium.

The second end of the body fluid side metallic wire may extend past the feedthrough body on the body fluid side. The second end of the device side metallic wire may extend past the feedthrough body on the device side.

The second end of the body fluid side metallic wire may be aligned with a body fluid side surface of the feedthrough body. The second end of the device side metallic wire may be aligned with a device side surface of the feedthrough body.

The second end of the body fluid side metallic wire may be recessed from a body fluid side surface of the feedthrough body. The second end of the device side metallic wire may be recessed from a device side surface of the feedthrough body.

The first end of the body fluid side metallic wire may be soldered or welded to the first end of the device side metallic wire.

An adhesion layer may be disposed on an inside surface of the passageway, a wetting layer may be disposed on the adhesion layer, and a gold braze may hermetically seal the wetting layer to the body fluid side metallic wire.

The gold braze may be connected to the device side metallic wire.

A capacitor may be disposed on the device side of the feedthrough body, wherein the capacitor comprises at least one active electrode plate and at least one ground electrode plate disposed within a capacitor dielectric, wherein an active end metallization is electrically connected to the at least one active electrode plate and a ground end metallization is electrically connected to the at least one ground electrode plate. The active end metallization may be in electrical communication with the device side metallic wire, and wherein the ground end metallization may be in electrical communication with the ferrule.

The capacitor may be a chip capacitor. The chip capacitor may be mounted to the feedthrough body. The chip capacitor may be mounted to a circuit board, wherein the circuit board is mounted to the feedthrough body.

The capacitor may be a feedthrough capacitor. The capacitor may be mounted to an adhesive washer and the adhesive washer is mounted to the feedthrough body.

The second end of the device side metallic wire may extend past the feedthrough body on the device side and is disposed within a metallized via formed through the feedthrough capacitor, wherein the metallization of the metallized via comprises the active end metallization.

A third wire may be disposed on the device side and extending at least partially into the metallized via.

A conductive material may be electrically connected to the second end of the device side metallic wire, to the third wire and to the active end metallization of the capacitor.

An internally grounded capacitor may be disposed on the device side of the feedthrough body, wherein the capacitor comprises at least one active electrode plate and at least one ground electrode plate disposed within a capacitor dielectric, wherein an active end metallization is electrically connected to the at least one active electrode plate and a ground end metallization is electrically connected to the at least one ground electrode plate, wherein the active end metallization is formed within an active via disposed through the capacitor dielectric and the ground end metallization is formed within a ground via disposed through the capacitor, wherein the capacitor does not have an external metallization on an outside surface of the capacitor dielectric.

The feedthrough body may comprise a conductive pathway in electrical communication with the ferrule on one end of the conductive pathway and in electrical communication with the ground end metallization on the other end of the electrical pathway. The conductive pathway may comprise a gold braze. The gold braze may also hermetically seals the feedthrough body to the ferrule.

The conductive pathway may comprise at least one conductive grounding layer disposed with the feedthrough body.

A conductive pin may be in electrical communication to the ground end metallization on one end of the conductive pin and in electrical communication with the conductive pathway on the other end of the conductive pin.

A ferrule may be made from a conductive material, the ferrule configured to be hermetically sealed to a housing of the implantable medical device, wherein the ferrule defines a ferrule opening and the feedthrough body is hermetically sealed to the ferrule closing the ferrule opening; including a feedthrough capacitor disposed on the device side of the feedthrough body, wherein the capacitor comprises at least one active electrode plate and at least one ground electrode plate disposed within a capacitor dielectric, wherein an active end metallization is electrically connected to the at least one active electrode plate and a ground end metallization is electrically connected to the at least one ground electrode plate; including a gold braze attached to the ferrule on the device side; and including an electrically conductive fill connecting the ground end metallization to the gold braze.

The feedthrough body may comprise a glass insulator, wherein the hermetic seal between the feedthrough body and the ferrule is formed at the same time as the hermetic seal between the composite conductor and the feedthrough body. An alumina washer disposed over the feedthrough body on the body fluid side.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 5 illustrates an exploded perspective view of an internally grounded prior art feedthrough capacitor;

FIG. 6 illustrates the structure of FIG. 5 where now the capacitor is formed as a monolithic structure;

FIG. 7 illustrates the structure of FIG. 6 fully assembled into a feedthrough filtered hermetic terminal;

FIG. 53 is a sectional view taken along lines 53-53 from FIG. 51;

FIG. 53A is a sectional view taken along lines 53A-53A from FIG. 52;

FIG. 70A is a perspective view of new embodiment of pin used in the present invention;

FIG. 70B is the side view of the structure of FIG. 70A;

FIG. 71A is a perspective view of new embodiment of pin used in the present invention;

FIG. 71B is the side view of the structure of FIG. 71A;

FIG. 72A is a perspective view of new embodiment of pin used in the present invention;

FIG. 72B is the side view of the structure of FIG. 72A;

FIG. 73 illustrates that the present invention, shown on the left side embodying body fluid side pin or leadwire and device side were co-joined or co-brazed, may comprise a hybrid structure wherein, one or more of the conductive pathways or conductive vias through the hermetic seal insulator, has been co-fired forming a conductive via;

FIG. 74 illustrates that a co-fired or co-sintered pin that is co-fired with via fill material can be combined with the present invention;

FIG. 75 is very similar to FIG. 12, except that an eyelet is used in place of leadwire and its insulation;

FIG. 76 is taken generally from section 76-76 of FIG. 75 and illustrates that the capacitor inside diameter or via hole metallization may extend onto the device side of the feedthrough capacitor forming a white-wall tire configuration, as previously described in FIG. 12;

FIG. 77 is a sectional view illustrating two and three part pins in accordance with the present invention now used within a hermetic structure that is both the insulator and the capacitor; and FIG. 78 is a chart that details various solder compositions that may be used when manufacturing the present invention.

DETAILED DESCRIPTION OF THE PREFERRED EMBODIMENTS

Figure 1:
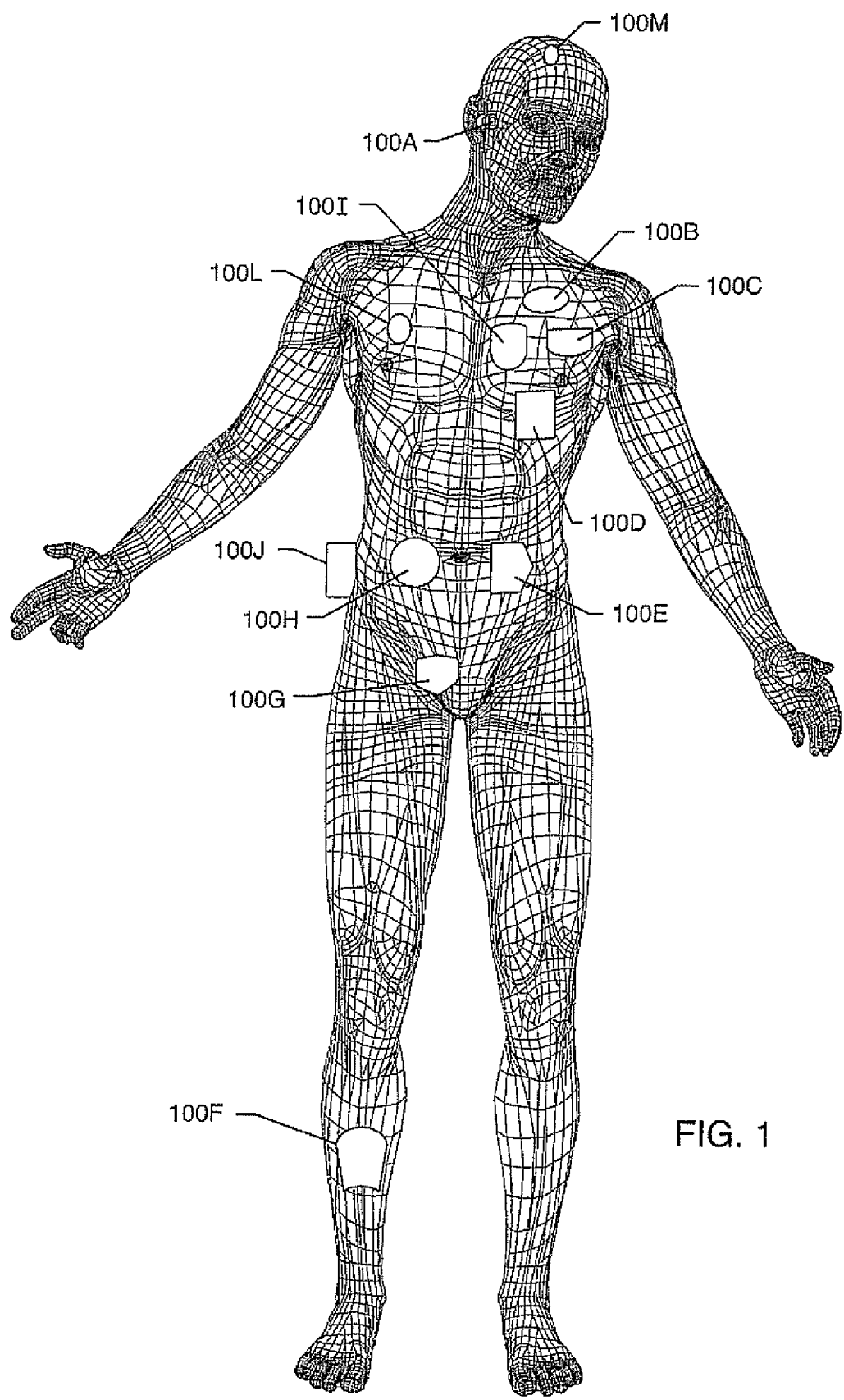
FIG. 1 is a wire-formed diagram of a generic human body showing a number of exemplary implantable medical devices.

FIG. 1 illustrates various types of active implantable and external medical devices 100 that are currently in use. FIG. 1 is a wire formed diagram of a generic human body showing a number of implanted medical devices. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of a seizure and also providing electrical stimulation to brain tissue to prevent the seizure from actually happening. The lead wires that come from a deep brain stimulator are often placed using real time imaging. Most commonly such lead wires are placed during real time MRI. 100C shows a cardiac pacemaker, which is well-known in the art, may have endocardial or epicardial leads. 100D includes the family of left ventricular assist devices (LVAD's) and artificial hearts. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of external or implantable bone growth stimulators for rapid healing of fractures. 100O includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator, a Holter monitor with skin electrodes or even a ventricular assist device power pack. Referring once again to element 100C, the cardiac pacemaker could also be any type of biologic data recording device. This would include loop recorders or the like. Referring once again to FIG. 1, 100I is described as an implantable defibrillator. It should be noted that these could be defibrillators with either endocardial or epicardial leads. This also includes a new family of subcutaneous defibrillators. In summary, as used herein, the term AIMD includes any device implanted in the human body that has at least one electronic component.

Figure 2:
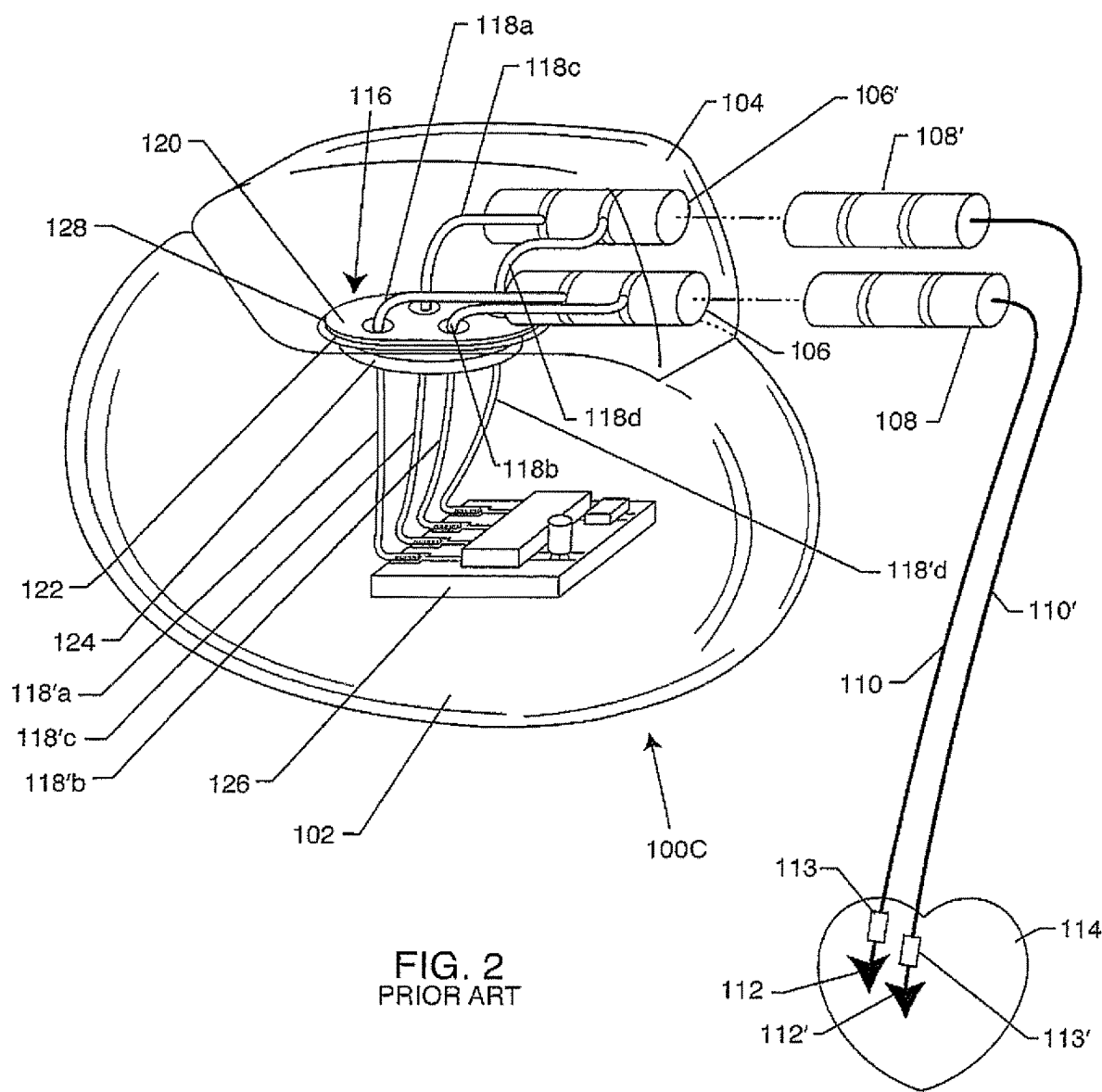
FIG. 2 is a side view of a prior art cardiac pacemaker.

FIG. 2 illustrates a prior art cardiac pacemaker 100C showing a side view. The pacemaker electronics are housed in a hermetically sealed and conductive electromagnetic shield 102 (typically titanium). There is a header block assembly 104 generally made of thermal-setting non-conductive plastic, such as Tecothane®. This header block assembly 104 houses one or more connector assemblies generally in accordance with ISO Standards IS-1, IS-2, or more modern standards, such as IS4 or DF4. These header block connector port assemblies are shown as 106 and 106'. Implantable leadwires 110, 110' have proximal plugs 108, 108' and are designed to insert into and mate with these header block connector cavities 106 and 106', or, in devices that do not have header block assemblies built directly into the pulse generator itself.

As used herein, the term "lead" refers to an implantable lead containing a lead body and one or more internal lead conductors. A "lead conductor" refers to the conductor that is inside of an implanted lead body. The term "leadwire" or "lead wire" refers to wiring that is either inside of the active implantable medical device (AIMD) housing or inside of the AIMD header block assembly or both. Furthermore, as used herein, in general, the terms lead, leadwire and pin are all used interchangeably. Importantly, they are all electrical conductors. This is why, in the broad sense of the term, lead, leadwire or pin can all be used interchangeably since they are all conductors. The term "conductive pathway" can also be used to be synonymous with lead conductor, lead, leadwire or pin o even circuit trace. Additionally, AIMD, as defined herein, includes electronic circuits disposed within the human body that have a primary or secondary battery, or have an alternative energy source, such as energy induced by motion, thermal or chemical effects or through external induction. As used herein, the term "header block" is the biocompatible material that attaches between the AIMD housing and the lead. The term "header block connector assembly" refers to the header block including the connector ports for the leads and the wiring connecting the lead connector ports to the hermetic terminal subassemblies which allow electrical connections to hermetically pass inside the device housing. It is also understood by those skilled in the art that the present invention can be applicable to active implantable medical devices that do not have a header block or header block connector assemblies such as pulse generators.

Figure 3A:
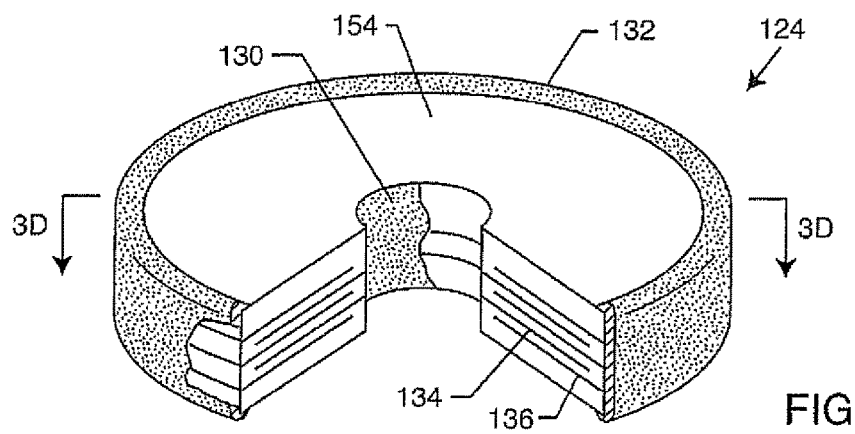
FIG. 3A is a perspective partial cutaway view of a unipolar capacitor.

FIG. 3A illustrates an isometric cut away view of a unipolar feedthrough capacitor. Shown, in cut away view, are active electrode plates 134 and ground electrode plates 136 both disposed within a capacitor dielectric 171. There is a feedthrough hole (passageway) 176, including metallization 130. There is also an outside diameter metallization 132.

Figure 3B:
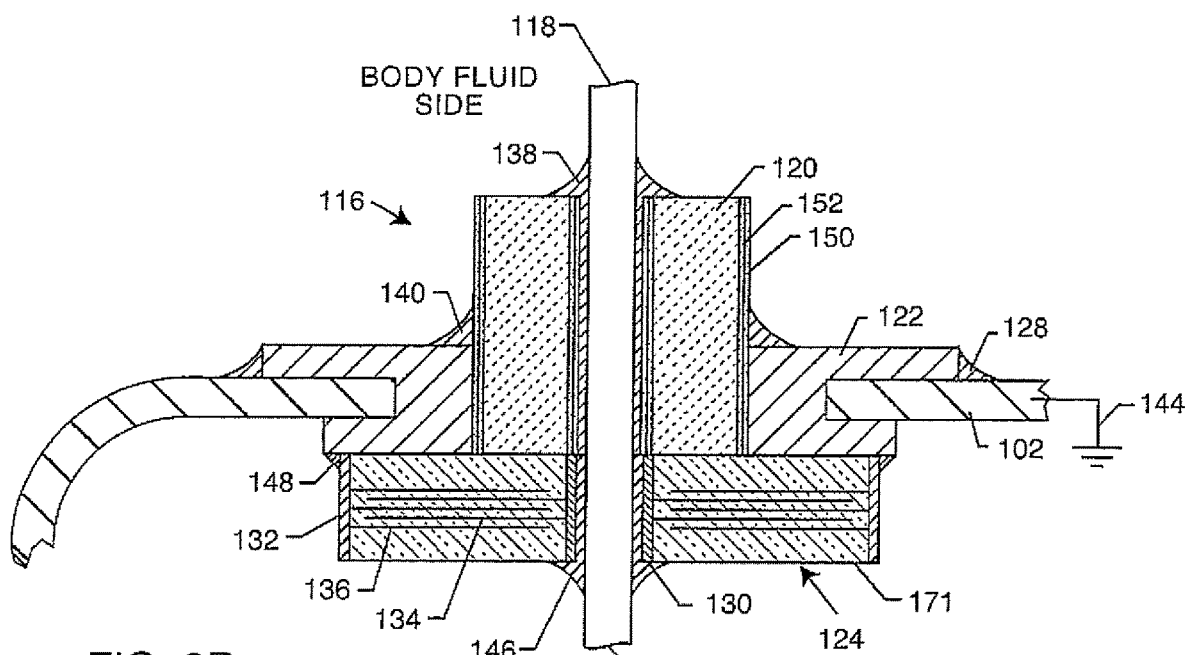
FIG. 3B is a side sectional view of a similar unipolar capacitor of FIG. 3A now mounted to a hermetic feedthrough for an active implantable medical device.

FIG. 3B shows the unipolar capacitor of FIG. 3A in section, mounted to the ferrule 122 of a hermetic seal subassembly 116 for an active implantable medical device. As shown, the ferrule 122 is configured to be laser welded 128 into an opening of an AIMD housing previously illustrated in FIG. 2 as element 102. The AIMD housing is generally of titanium or other biocompatible conductive material and forms an overall electromagnetic shield to help protect AIMD electronics from electromagnetic interference emitters, such as cell phones and the like. Accordingly, referring back to FIG. 3B, we see the ground symbol 144 representing that EMI signals that may be coupled onto the body side of the lead 118, can be decoupled or diverted through the feedthrough capacitor 124 to the equipotential shield. When high frequency electromagnetic signals are diverted from lead 118 to the AIMD housing 102, they circulate around the shield and are converted into meaningless heat (just a few milli or microwatts).

Figure 3C:
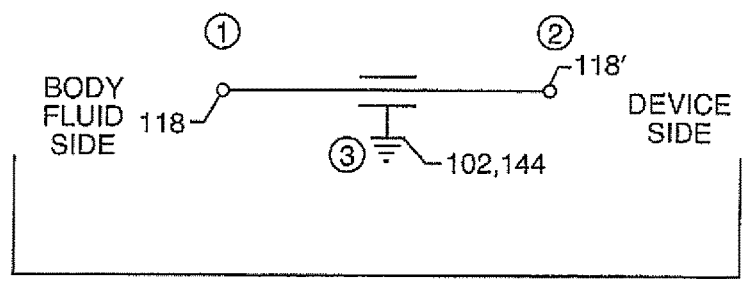
FIG. 3C is an electrical schematic representation of the unipolar filtered feedthrough assembly previously illustrated in FIG. 3B.
Figure 3D:
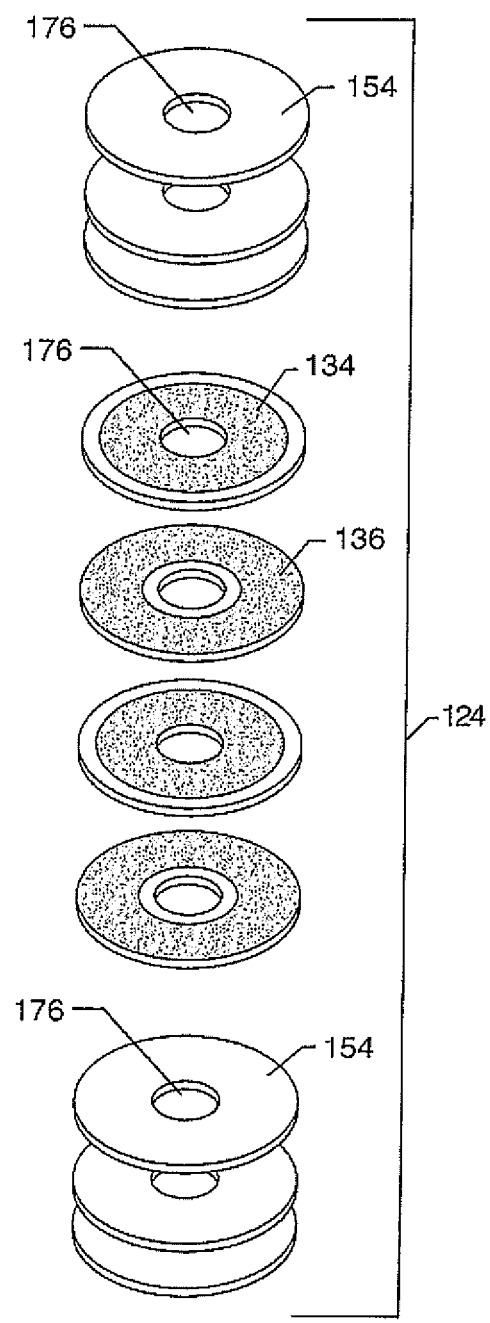
FIG. 3D is generally taken along lines 3D-3D from FIG. 3A and is an exploded perspective view of the electrode layer stack up.

FIG. 3C is the schematic diagram for the feedthrough capacitor of FIGS. 3A and 3B. One can see that this is known as a three-terminal device and that there is significant high frequency attenuation along the length of the leadwire between 118 and 118'. Accordingly, the first terminal is on the body fluid side 118 and the second terminal is on the device side 118', the third terminal being the ground 102, 144, where undesirable electromagnetic interference is diverted to the AIMD housing. It is known in the art that three-terminal feedthrough capacitors have very little to no parasitic series inductance and are therefore, very broadband low pass filters. This means that low frequency signals, such as therapeutic pacing pulses or biologic signals pass along from the body fluid side of the lead conductor 118 to the device side 118' without degradation or attenuation. However, at high frequencies, the capacitive reactance drops to a very low number and ideally, high frequency signals are selectively shorted out from the lead conductor 118, 118' to the ferrule 122 and in turn, to the conductive housing 102. FIG. 3D is an exploded view of the unipolar capacitor of FIG. 3A showing that it has ceramic cover plates 154, active electrode plates that are interleaved with ground electrode plates 136 and one or more cover sheets disposed on the other end 154. In ceramic engineering, the ceramic dielectrics would typically be of BX or X7R having a dielectric constant of approximately 2000 or higher. It will also be appreciated that NP0, which is generally a low k dielectric with a dielectric constant below 200, could also be used, as taught in U.S. Pat. No. 8,855,768, the contents of which are fully incorporated herein by reference.

Figure 4A:
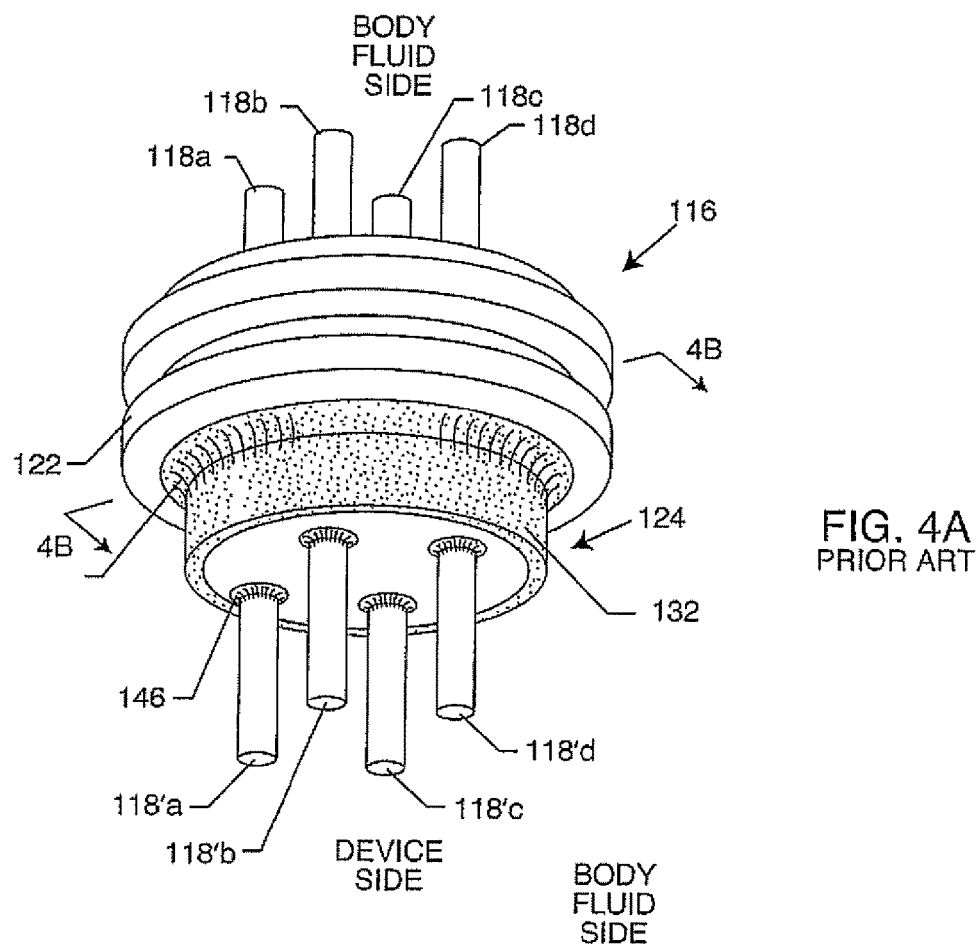
FIG. 4A is a perspective view of a quadpolar feedthrough capacitor and hermetic terminal assembly.

FIG. 4A illustrates a quadpolar feedthrough capacitor and hermetic terminal subassembly 116 where it has four leadwires 118a-118d and four feedthrough holes (quadpolar). It has a metallic ferrule 122 generally of titanium which is ready for laser welding 128 into the AIMD housing 102 (not shown).

Figure 4B:
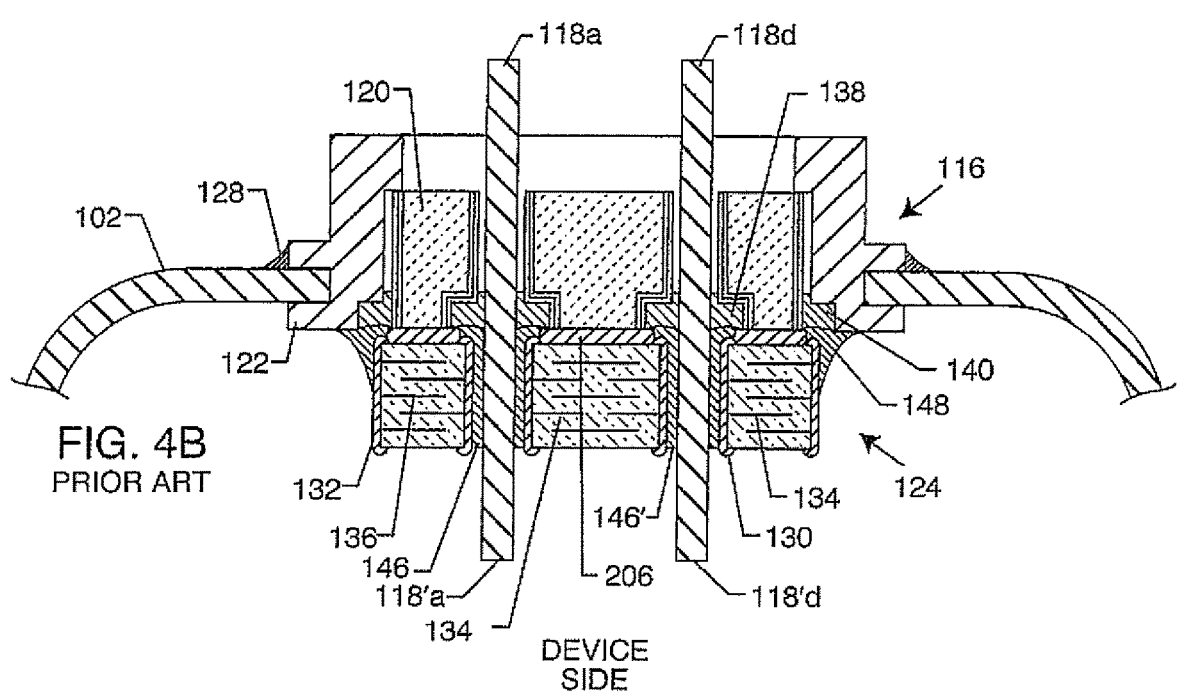
FIG. 4B is a sectional view of the feedthrough and hermetic terminal assembly of FIG. 4A taken along lines 4B-4B.

FIG. 4B is a prior art sectional view taken generally from section 4B-4B from FIG. 4A. This illustrates the hermetic terminal subassembly leadwires 118a-d passing through the hermetic terminal subassembly insulator 120 in non-conductive relationship and also through the feedthrough capacitor 124 wherein the active electrode plates 134 are electrically connected 146 to the hermetic terminal subassembly leadwire 118 and wherein the feedthrough capacitor ground electrode plates 136 are electrically connected 148 to the hermetic terminal subassembly ferrule 122 and gold braze 140. Referring once again to FIGS. 4A and 4B, in each case it is seen that the hermetic terminal subassembly leadwires 118a-d pass all the way through the entire structure, namely, the hermetic terminal subassembly 116 and the feedthrough capacitor 124. In general, these hermetic terminal subassembly leadwires 118a-d are electrically and mechanically continuous (single material) and pass through from the body fluid side to the inside of the device 100 housing 102. Because the hermetic terminal subassembly leadwires 118a-d pass through from the body fluid side to the inside of the device housing by way of header block connector assembly 104 or the like, it is very important that these hermetic terminal subassembly leadwire 118 materials be both biocompatible, biostable and non-toxic. Generally, in the prior art, these hermetic terminal subassembly leadwires are constructed of platinum or platinum-iridium, palladium or palladium-iridium, niobium or the like. Platinum-iridium is an ideal choice because it is biocompatible, non-toxic and is also mechanically very strong. The iridium is added to enhance material ductility and to enable the hermetic terminal subassembly leadwire to sustain bending stresses.

Figure 4C:
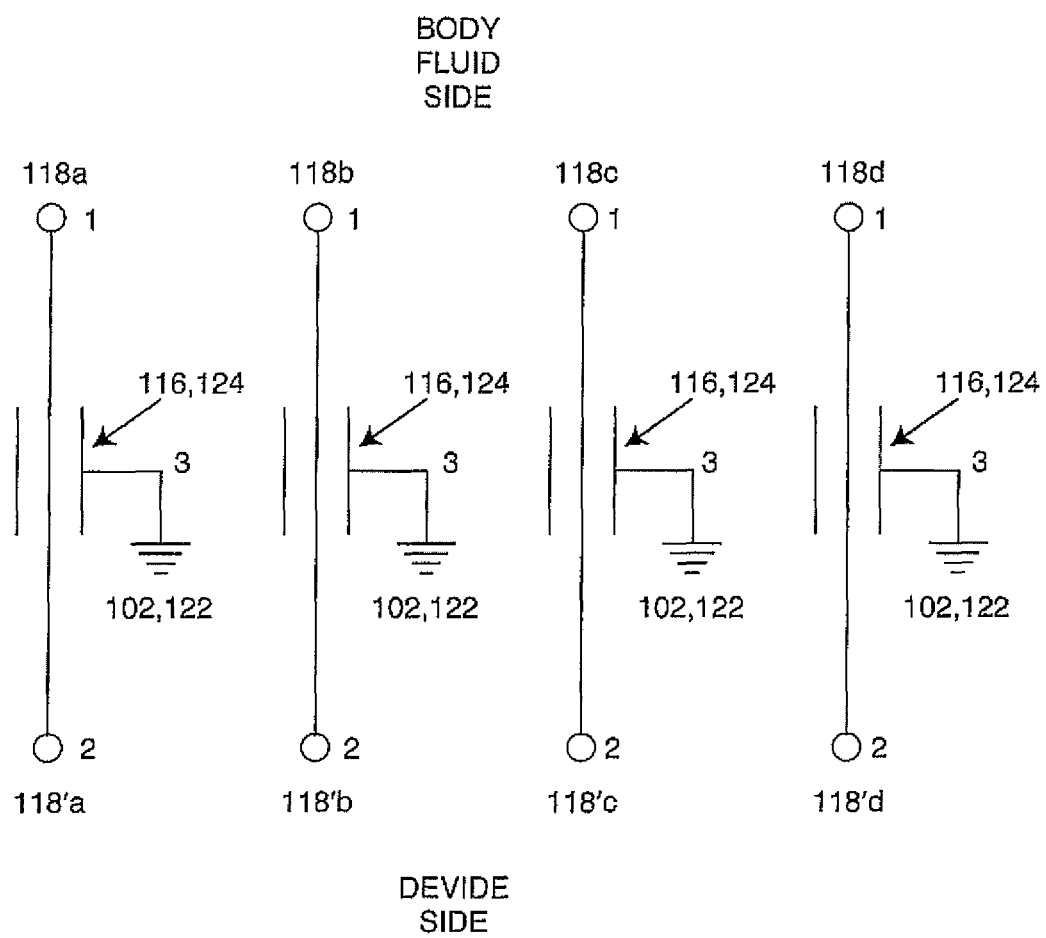
FIG. 4C is an electrical schematic representation of the quadpolar filtered feedthrough assembly as previously illustrated in FIGS. 4A and 4B.

FIG. 4C is an electrical schematic representation of the quadpolar filtered feedthrough assembly 116, 124, as previously illustrated in FIGS. 4A and 4B. Referring once again to FIG. 4C, one can see that these are feedthrough capacitors and are three-terminal devices. For example, feedthrough capacitor 116, 124 has a first terminal 118a, a second active terminal 118'a and a ground terminal 102, 122. In the art, feedthrough capacitors are known as broadband low pass filters. They have practically zero series inductance and are desirable in that, they work over a very wide range of frequencies. In general, feedthrough capacitors and their internal electrode geometries are well known in the prior art. In this case, the feedthrough capacitor is a diverter element, in that, it diverts RF signals on all four leads to the AIMD housing as previously described. This is important for the capacitance reactance formula. At very low frequencies, such as biologic sensing frequencies or biologic therapy frequencies, the capacitor impedance is extremely high and the capacitor acts like it's not present. However, at very high frequencies, such as frequencies around the area of a cell phone (950 MHz), the capacitor tends to look more like a short circuit and diverts those undesirable signals to the AIMD housing. One is referred to U.S. Pat. Nos. 4,424,551; 5,333,095; 5,978,204; 6,643,903; 6,765,779 all of which are incorporated herein by reference.

Figure 4D:
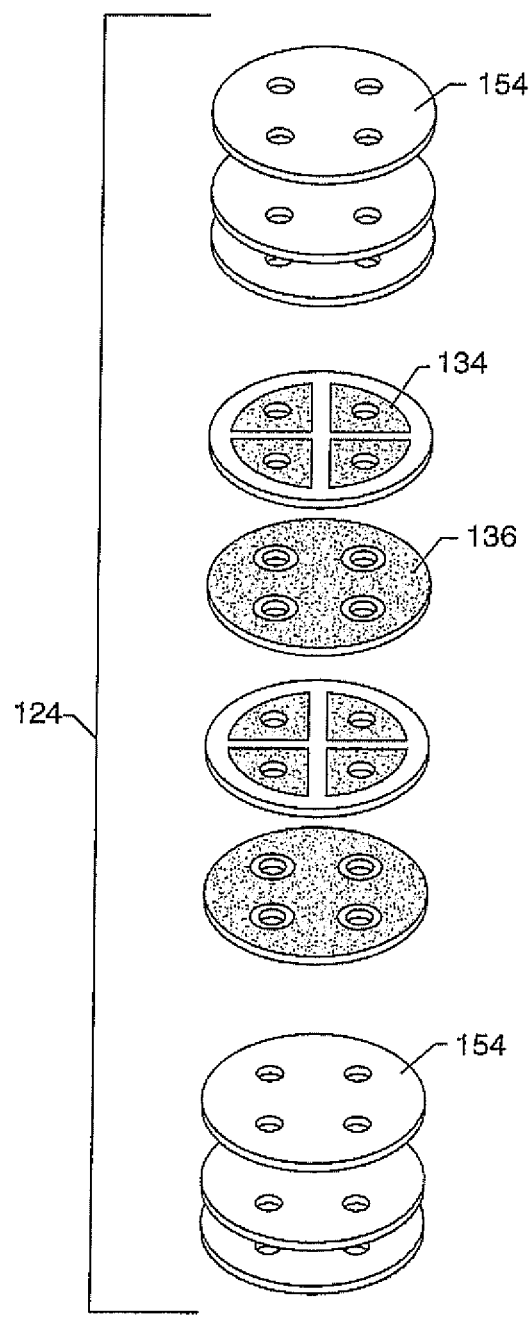
FIG. 4D is an exploded perspective view of the electrode layer stack up of the structure of FIGS. 4A and 4B.

FIG. 4D is an exploded view of the quad polar capacitor 132 of FIG. 4A. In the exploded view, you can see that there are four active electrode plates 134 and one ground plate 136. The effective capacitance area comes from the overlap of the active electrode 134 with the ground electrode 136. The greater this overlap area is, the higher the capacitance of the feedthrough capacitor becomes. One can also say that it is a multilayer structure. In FIG. 4D, there are two active and ground plates shown. This has the effect of increasing the capacitor's effective capacitance area. It will be appreciated that as many as 400 or more ground and active layers could be used.

FIGS. 5, 6 and 7 illustrate an internally grounded prior art feedthrough capacitor. In general, internally grounded feedthrough capacitors are known in the prior art with reference to U.S. Pat. Nos. 5,905,627; 6,529,103; 6,765,780 and the like, all of which are incorporated herein by reference. Referring once again to FIG. 5, one can see an internally grounded feedthrough capacitor, which is octapolar (eight active leads). The eight active leads are labeled 118a through 118h on the body fluid side and on the inside of the AIMD housing they are labeled 118'a through 118'h. The ferrule 122 has a peninsula structure 139, which is connected to an internal ground pin 118gnd. Referring now to the octapolar feedthrough capacitor active electrode plates 134, they are designed to overlay in a sandwich fashion the ground electrode plates 136. One skilled in the art will realize that one can stack up as many of these interleaved layers as is required in order to achieve the required capacitance value and other design factors. The internal ground lead 118gnd is electrically connected to the ground electrode plate layers 136. The active electrodes 134a through 134h are each electrically connected through their respective leadwires 118'a through 118'h. The overlap between the active electrodes 134 and the ground electrodes 136 create what is known as effective capacitance area (or ECA). The active and ground electrode layers may be interleaved with additional ceramic layers to build up the dielectric thickness (not shown). In general, the monolithic ceramic feedthrough capacitor 124, as shown in FIG. 6 as element 124, is a result of laminating the various electrode layers together and then sintering them at a high temperature to form a rigid monolithic ceramic block. This is known as a single feedthrough capacitor that is multipolar (in this case these are octapolar or eight active filtered circuits). One can see that there is a perimeter metallization 132 on the outside of the round capacitor from FIGS. 3A and 4A whereas, in this case in FIG. 6, there is no perimeter metallization 132 at all.

There are several major advantages to internal grounding and removal of the perimeter or diameter metallization 132. This is best understood by referring back to FIGS. 3A through 4B. In contrast to FIG. 3B, with internal grounding there is no longer a need to apply a diameter metallization 132 as shown in FIGS. 5, 6 and 7. In addition, the electrical connection 148 has been entirely eliminated between the capacitor diameter metallization 132 and the gold braze 140 and ferrule 122. The elimination of this electrical connection 148 also makes the capacitor structure 124' much more resistant to mechanical damage caused by subsequent laser welding 128 of the hermetic seal assembly 116 into the AIMD housing 102. A significant amount of heat is produced by laser welding 128 and there is also a mismatch in thermal coefficient of expansion materials. By elimination of the electrical connection material 148, the capacitor 124' is free to float and is therefore, much more resistant to such stresses. Referring once again to FIG. 6, one can see that the internal ground lead 118'gnd makes a low impedance connection from the capacitor's internal electrode plates 136 to the ferrule 122. This is what eliminates the need for the electrical connection material 148, as previously illustrated in FIG. 4. It will be appreciated that only one ground pin is shown in FIG. 6, but some designs may require a multiplicity of ground pins spaced apart such that, there is a very low impedance connection effectively grounding the capacitor internal electrodes 136 at multiple points.

Referring once again to FIG. 6, one can see the ceramic capacitor subassembly 124' ready to be installed onto the hermetic terminal subassembly 189. These are shown joined together in FIG. 7 resulting in a hermetically sealed feedthrough capacitor filter assembly 116.

Referring back to FIG. 6, it is important to clarify some confusion as terms of art. The feedthrough capacitor 124' can also be described as a three-terminal feedthrough capacitor with multiple via holes or feedthrough holes. In a confusing manner, the hermetic terminal subassembly 189 is often referred to in the art as a hermetic feedthrough, Therefore, we have the term feedthrough applying both to the feedthrough capacitor and to the hermetic terminal assembly. As used herein, these are two separate and distinct subassemblies, which are joined together in FIG. 7 to become a feedthrough filter hermetic terminal assembly 116 ready for installation into an opening of an AIMD housing. Referring once again to FIGS. 5 and 6, one will appreciate that leadwires or lead conductors 118', 118 are continuous leadwire. In other words, on the body fluid side, the leadwire is of the same material as on the device side. This is typical in the prior art. Referring once again to FIG. 6, one can see that the internal ground lead 118'gnd does not extend through to the body fluid side of the hermetic terminal feedthrough subassembly 189. It will be appreciated that it could be easily and readily extended to the body fluid side, but in most embodiments, it is not necessary.

An issue with the use of platinum for hermetic terminal subassembly leadwires 118a-d is that platinum has become extremely expensive and may be subject to premature fracture under rigorous processing such as ultrasonic cleaning or application use/misuse, possibly unintentional damaging forces resulting from Twiddler's Syndrome. Accordingly, what is needed is a filtered structure like a feedthrough capacitor assembly 116 which eliminates these high-priced, platinum, platinum-iridium or equivalent noble metal hermetic terminal subassembly leadwires 118. For additional examples of hermetic terminal subassemblies with feedthrough capacitors that employ leadwires 118, one is referred to U.S. Pat. Nos. 5,333,095, 5,896,267, 5,751,539, 5,905,627, 5,959,829, 5,973,906, 6,008,980, 6,159,560, 6,275,379, 6,456,481, 6,529,103, 6,566,978, 6,567,259, 6,643,903, 6,765,779, 6,765,780, 6,888,715, 6,985,347, 6,987,660, 6,999,818, 7,012,192, 7,035,076, 7,038,900, 7,113,387, 7,136,273, 7,199,995. 7,310,216, 7,327,553, 7,489,495, 7,535,693, 7,551,963, 7,623,335, 7,797,048, 7,957,806, 8,095,224, 8,179,658 the contents of all of which are incorporated herein by reference.

Figure 7A:
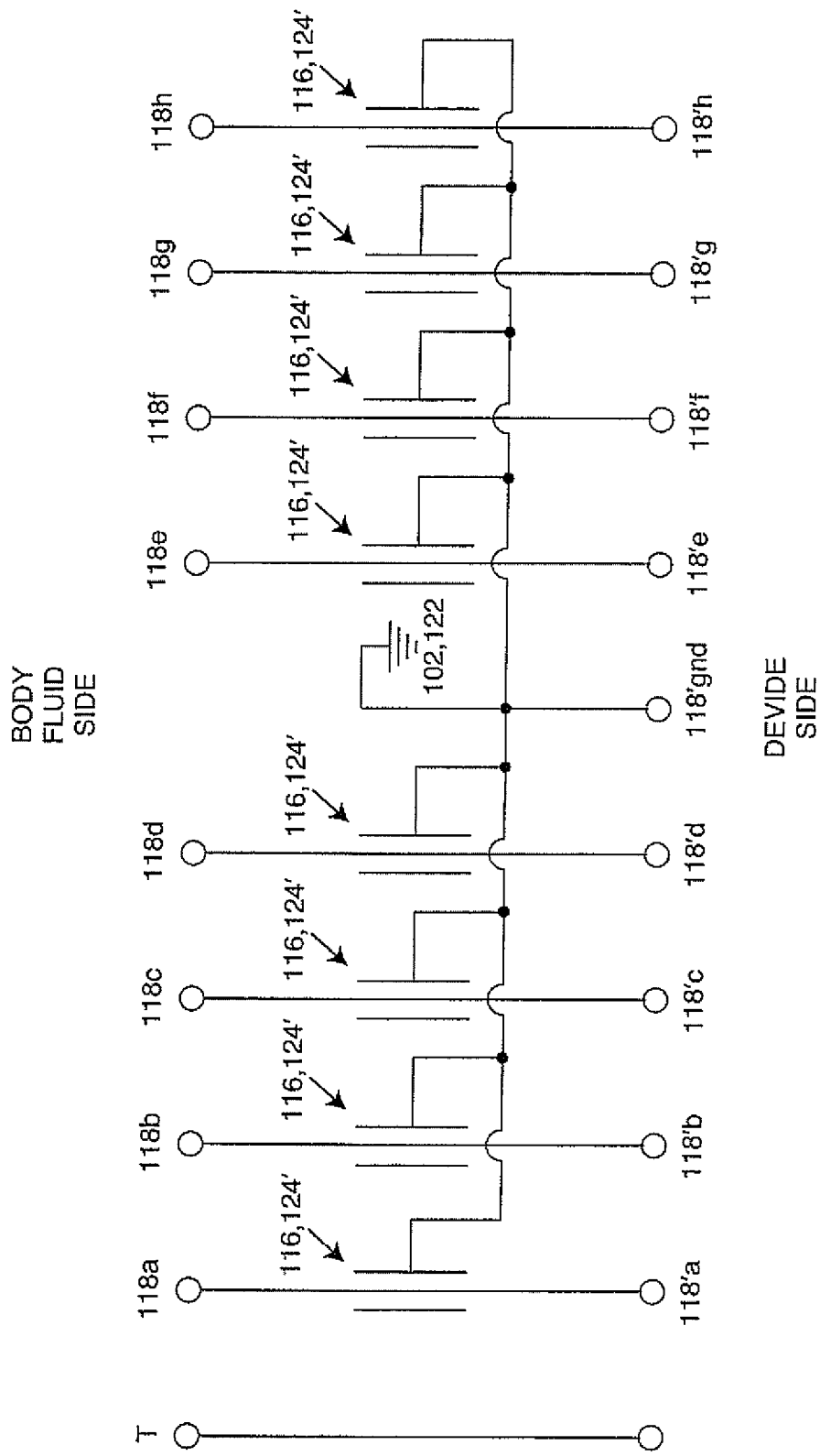
FIG. 7A is the electrical schematic for the feedthrough filtered hermetic terminal previously described in FIGS. 5, 6 and 7.

FIG. 7A is the electrical schematic for the feedthrough filtered hermetic terminal 116 previously described in FIGS. 5, 6 and 7. Referring once again to FIG. 7A, one can see the telemetry pin T, which passes through the filtered hermetic terminal assembly 116 without any appreciable capacitance to ground. In other words, it would be undesirable to have any high frequency filtering of the telemetry terminal since this would preclude the ability to recover stored information or program the AIMD device remotely. Leadwires 118a through 118h all have feedthrough capacitor hermetic terminal assemblies 116, 124 as shown. The internal ground pin 118gnd is shown only on the device side of the hermetic terminal subassembly 189. Referring once again to FIGS. 5, 6, 7 and 7A, it will be noted that the feedthrough filter hermetic seal subassembly has been inverted with reference to FIGS. 2, 3 and 4. It should also be noted that the capacitor 124 is still on the device side; it's just drawn inverted.

Figure 8:
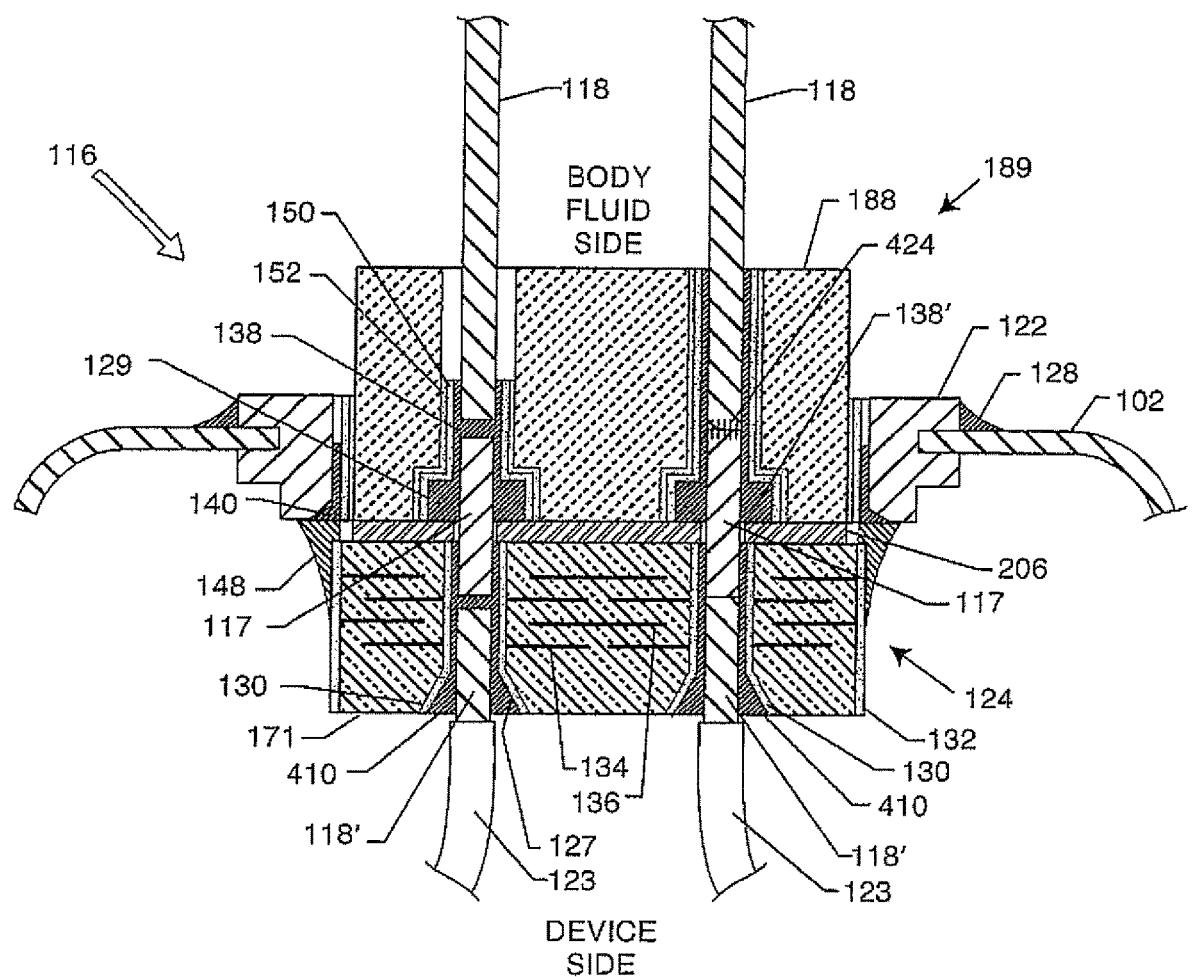
FIG. 8 is a sectional view of an exemplary filtered feedthrough of the present invention now showing an additional leadwire portion connected in shear between both the insulator of the hermetic feedthrough and the internal metallized hole of the capacitor.

FIG. 8 illustrates the present invention where leadwires 118 on the body fluid side could be directed to a connector block cavity 104, 106 or directly to lead conductors (see FIG. 2). In general, body fluid side leadwires 118 must be of biocompatible, non-toxic and biostable materials. This limits the materials to platinum, palladium, niobium, tantalum, titanium and equivalents or combinations thereof. Leadwires 118 are co-brazed 138, co-welded 424 or both to short platinum (palladium or the like) pins (leadwires) 117, as illustrated. When the gold braze 138 flows, it forms a strong mechanical and hermetic seal both to the high cost leadwire 118, to the short platinum pin 117 and to the sputtering 150, 152 of the insulator 188. Referring to the left-hand hermetic braze 138, one can see that it is disposed towards the device side of the hermetic seal insulator 188. On the right side, the gold braze 138' extends all the way to the right side of the body fluid side. In another embodiment, not shown, it will be appreciated that the left-hand side of hermetic seal 138 could be moved and disposed on the body fluid side. In this case, the platinum or equivalent solderable pin 117 would have to be extended in length. Most AIMD manufacturers avoid using pure platinum or palladium leadwires because it has been shown that after repeated bending, they fracture. Accordingly, iridium is typically added to long leadwires in AIMDs because a low percentage of iridium makes the leadwire much more resistant to bending fractures. However, as illustrated in FIG. 8, these short leadwire segments 117 will never be exposed to bending forces, therefore, pure platinum can be used. Using pure platinum for this segment of leadwires is an enormous advantage because pure platinum is very noble and does not form surface oxides readily. The problem with platinum-iridium leads or palladium-iridium leads is the iridium, at the surface, tends to oxidize making properly wetting these leads with solder (or a thermal-setting conductive adhesive) a problem. Referring back to FIG. 8, it is desirable that the short pin 117 not only be very noble (in other words, not oxidize), but also have a very high melting point. This is so it will maintain its structural integrity while the gold braze preform 138 is reflowed in a gold brazing furnace operation. The melting point of pure gold is 1064° C. The melting point of platinum is 1768° C. The melting point of palladium is 1555° C.

Referring once again to FIG. 8, one can see that there is an adhesion layer 152 and a wetting layer 150 that have been applied to the inside diameter and outside diameter (or perimeter) of the alumina ceramic insulator 188. These are required because gold preforms generally will not wet or adhere to bare alumina insulators. The alumina insulator shown in FIG. 8 has been manufactured in a separate manufacturing operation and sintered and fired (as hard as a rock). Through sputtering processes, an adhesion layer 152 is first laid down and then over that, a wetting layer 150 is laid down. This can also be done by some manufacturers in a single process, which combines wetting and adhesion properties into one (such as niobium). Other processes use a molybdenum adhesion layer and then a sputtered titanium layer to which gold braze will readily wet to. In summary, in order for the gold braze preforms 138 and 140 to properly flow and wet to the insulator 188, there must first be layers sputtered onto the ceramic insulator, which will perform both adhesion and wetting characteristics. This will not be further described throughout this invention, but it will be appreciated that every time a gold braze is shown, that the adhesion/wetting layer is present. It will also be noted that on the outside diameter (when necessary) and inside diameter holes of the feedthrough capacitor 124, that there is a metallization 130. This can be a multilayer process, such as a copper and tin or copper and silver during an electroplating. The embodiment shown throughout this invention would be one of applying a silver or palladium-silver bearing glass frit, which is fired on as a single layer 130. It will be appreciated that the metallization 130 or capacitor 124 outside diameter or perimeter metallization 132 be shown throughout this invention as a single layer (but as previously mentioned, it could consist of several different layers). It will also be appreciated that ceramic feedthrough capacitor metallizations 130, 132 can be a metal bearing glass frit or be plated on when the plating operation may consist of selectively plating on one or more under-layers and then a final layer, which would be solderable or receptive through a thermal-setting conductive adhesive 148.

It will be appreciated that the machined ferrule 122, illustrated in FIG. 8, could also be replaced by a stamped ferrule or even a two-piece ferrule, as taught in U.S. Pat. Nos. 8,927,862; 9,431,814; and 8,604,341; and U.S. Patent Publications 2015/0245468 and 2016/0287883, the contents of all of which are incorporated herein by reference. Referring once again to FIG. 8, the machined ferrule 122 is relatively expensive, not just because of the machining process, but because the machining starts with a solid block of titanium and there is a great deal of scrap produced. A stamped metal ferrule or a two-piece stamped ferrule thereby, significantly reduces the machining costs and also results in a material savings, as shown later in FIG. 22. It will be understood that any of the machined ferrule in this teaching could be replaced with stamped ferrules in accordance with the referenced patents and publications.

Referring once again to FIG. 8, it will be appreciated that the device side leadwire 118' can now be of very low cost materials, including copper, tin, or the like. This leadwire 118' could be a solid wire, can be a stranded wire, can be a braided wire and the like. It will be appreciated that, in the prior art, a high cost platinum-iridium or palladium wire would be in a single piece all the way to the device side to the body fluid side. These one piece leadwires were previously described as 118, 118' in FIG. 3B, also in FIGS. 4A and 4B, and FIGS. 5, 6 and 7. The novel two part co-welded or co-brazed leadwires of the present invention, allow one to then use very low cost leadwires 118' on the inside of the device or the device side, which route a filter feedthrough assembly 116 to device electronics circuits, including a circuit board 126, as previously illustrated in FIG. 2. The advantage of stranded wires or braided wires is they are generally more resistant to shock and vibration load. Stranded or braided wires are also more flexible and more easily routed to internal circuit boards (not shown). Referring once again to FIG. 8, it will be appreciated that the short pins 117 could also comprise nickel, in that, nickel has a very high melting point and could accept gold braze 138.

In general, two-part pins as described in FIG. 8 have never been described in any prior art that the inventors are aware of. The closest prior art is U.S. Pat. No. 5,867,361 to Wolf, et al., herein referred to as the Wolf patent. Wolf FIG. 1, on the bottom, shows a leadwire/lead conductor 30, which would be routed to an implantable lead conductive in distal electrodes (not shown). This lead is co-brazed 65 to a hermetic seal insulator 90 as shown. There is a feedthrough capacitor 50 illustrated and a nail head structure 60 that also forms a wire bond pad. There is an electrical conductive material 75, which could comprise, for example, a solder or a thermal-setting conductive adhesive that connects between the nail head pin structure 60 and the gold braze 65, which is also gold brazed to the body fluid side pin 30. To high reliability engineers, such as in the military and space business, this puts a series type electrical connection 75 in the system. Such a series connection can readily compromise the reliability of the overall system if there is shrinkage of the electrical conductive material 65, vibration fractures, micro-cracks or separation of these series elements. The present invention is very different from the Wolf patent, in that, the body fluid side lead 118 is co-welded or co-joined to the device side pin 117. As described in FIG. 8, the body fluid side leadwire 118 and the device side pin 118 are co-joined by extremely reliable welding or brazing processes. These form a very strong metallurgically reliable bond as well as a very low resistance low impedance electrical connection. In summary, the present invention overcomes the difficulties as described in the Wolf patent.

Accordingly, it is the electrical connection material 148 that connects between the capacitor outside diameter metallization 132 to the gold braze 140 that makes the low impedance (very low resistance) RF diverting circuit to the ferrule 122. One can also see that there is a non-conductive polymer, such as an epoxy or a polyimide covering 147 disposed over the feedthrough capacitor. This material 147 helps in binding to the low cost leadwires 118 and improves their pull strength. In addition, the non-conductive epoxy or fill 147 provides a pleasing cosmetic appearance.

Figure 8A:
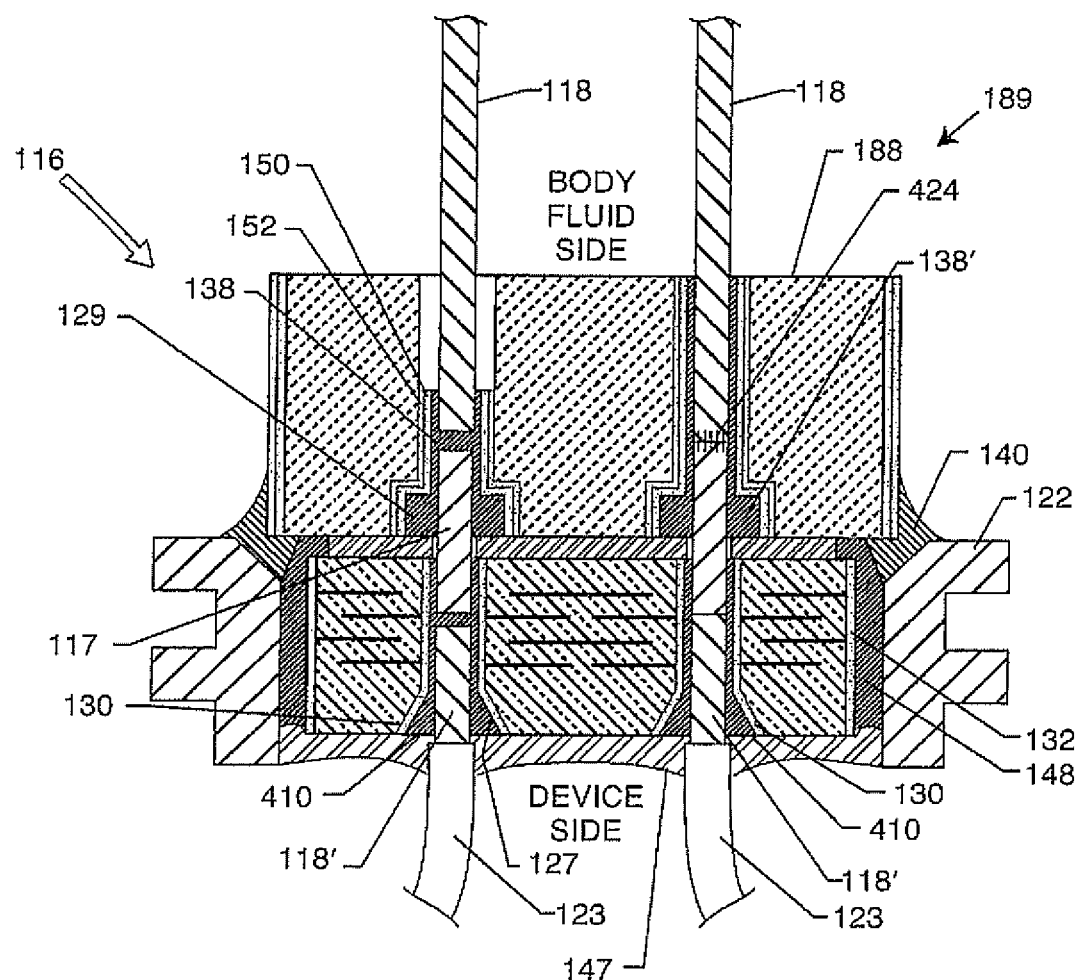
FIG. 8A is similar to FIG. 8 now showing the capacitor captured with the ferrule and a polyimide covering disposed over the capacitor on the device side.

FIG. 8A is very similar to FIG. 8, except that in this case, the insulator 188 sits on top of the ferrule structure 122. The gold braze 140 has been wetted between the alumina insulator 188 and the ferrule. As previously taught, there is an electrical connection material 148 that connects the feedthrough capacitor outside diameter or perimeter metallization 132 to the gold braze 140, which in turns makes a non-oxidized electrical connection to the ferrule 122. As previously taught, a direct connection to titanium is generally undesirable due to the build-up of titanium oxides, which can be resistive or even semi-conductive.

Figure 8B:
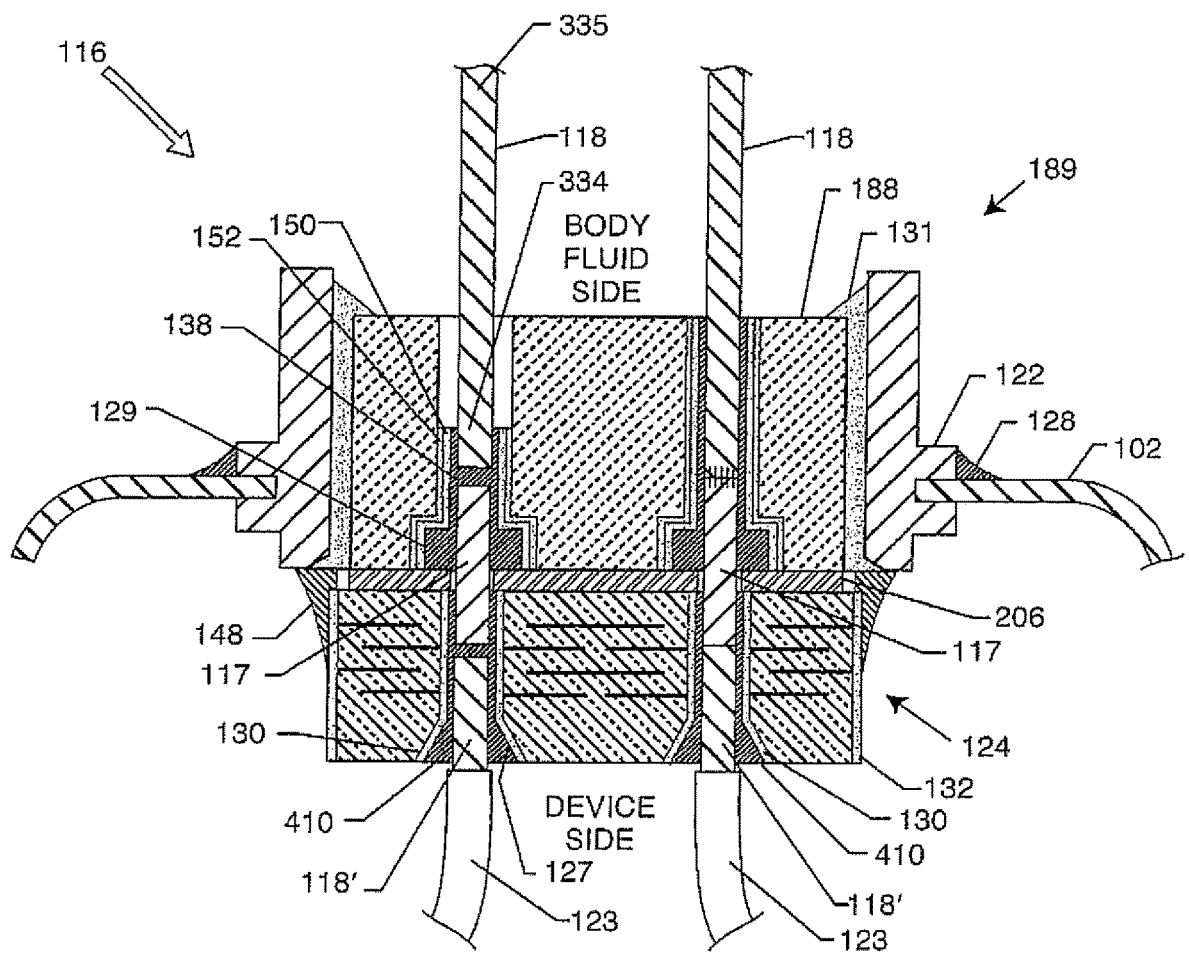
FIG. 8B is similar to FIG. 8 now showing the insulator captured within the ferrule by a cermet.

FIG. 8B is very similar to FIG. 8, except that in this case, there is no gold braze between the insulator 188 and the ferrule 122. In this case, there is a CERMET material 131, which is co-sintered into the ferrule 122 and forms a strong mechanical and hermetic seal between insulator 188 and ferrule 122. A CERMET in the art, is known as ceramic metal paste, which is then sintered at high temperature and is, after sintering, highly conductive. Accordingly, as one can see, the capacitor electrical connection material 148 connects between the capacitor outside diameter or perimeter metallization 132 to at least part of the CERMET 131 so that we do not have a problem with direct contact, only to the titanium ferrule surface 122. Conductive via fill materials of alumina/platinum or pure platinum are described, but other materials including Cermets may be used. For example, it will be known to those skilled in the art from this teaching that other nonlimiting ceramics, glass ceramics, and/or glass oxides may be added to the metal-containing inks/pastes to customize TCE matching/transition pending core material and/or insulator material selections. Palladium may be used instead of platinum. Other nonlimiting biocompatible metals and alloys that may be used in place of platinum include niobium, platinum/palladium, stainless steels, and titanium. Furthermore any of the following list of materials may be used alone or combination with any of the materials already discussed or within this list: Gold (Au), silver (Ag), iridium (Ir), rhenium (Re), rhodium (Rh), titanium (Ti), tantalum (Ta), tungsten (W), zirconium (Zr), and vanadium (V), Cobalt Chromium Molybdenum Alloy, Cobalt Chromium Nickel Iron Molybdenum Manganese Alloy, Cobalt Chromium Tungsten Nickel Iron Manganese Foil, Cobalt Nickel Chromium Iron Molybdenum Titanium Alloy, Cobalt Nickel Chromium Iron Molybdenum Tungsten Titanium Alloy, Cobalt Nickel Chromium Molybdenum Alloy, Copper Aluminum Nickel Alloy, Copper Zinc Alloy, Copper Zinc Aluminum Nickel Alloy, Copper Zinc Silver Alloy, Gold Platinum Palladium Silver Indium Alloy, Iron Chromium Alloy, Iron Chromium Nickel Alloy, Iron Chromium Nickel Aluminum Alloy, Iron Chromium Nickel Copper Alloy, Iron Chromium Nickel Copper Molybdenum Niobium Alloy, Iron Chromium Nickel Copper Niobium Alloy, Iron Chromium Nickel Copper Titanium Niobium Alloy, Iron Chromium Nickel Manganese Molybdenum Alloy, Iron Chromium Nickel Molybdenum Alloy, Iron Chromium Nickel Molybdenum Aluminum Alloy, Iron Chromium Nickel Titanium Molybdenum Alloy, Iron Manganese Chromium Molybdenum Nitrogen Alloy, Nickel Platinum Alloy, Nitinol, Nickel Titanium Alloy, Nickel Titanium Aluminum Alloy, Niobium-Titanium Alloy, Platinum Iridium Alloy, Platinum Palladium Gold Alloy, Titanium Aluminum Vanadium Alloy, Titanium Based Aluminum Iron Alloy, Titanium Based Aluminum Molybdenum Zirconium Alloy, Titanium Based Molybdenum Niobium Alloy, Titanium Based Molybdenum Zirconium Iron Alloy, Titanium based Niobium Zirconium Alloy, Titanium based Niobium Zirconium Tantalum Alloy, Titanium Molybdenum Alloy, Titanium Niobium Alloy, Titanium Platinum Alloy, Titanium-based Molybdenum Zirconium Tin Alloy.

Examples of some PAC, Cermet, CRMC ceramic/metal pairings include, but are not limited to:

1. Alumina (Al2O3) or zirconia (ZrO2) including various stabilized or partially stabilized zirconia like zirconia toughened alumina (ZTA) and alumina toughened zirconia (ATZ) with platinum (Pt) or palladium (Pd)

2. Alumina (Al2O3) or zirconia (ZrO2) with iridium, rhenium, rhodium, various Pt alloys (e.g., Pt—Ir, Pt—Pd, Pt—Rh, Pt—Re, Pt—Au, Pt—Ag etc.), Pd alloys (e.g., Pd—Ir, Pd—Re, Pd—Rh, Pd—Ag, Pd—Au, Pd—Pt, Pd—Nb, etc.), Au alloys (e.g., Au—Nb, Au—Ti, etc.), Au alloys (e.g., Au—Nb, Au—Ti, etc.), and Ti alloys (e.g., Ti—Al—V, Ti—Pt, Ti—Nb, etc.)

Any combination of the ceramics and metals is theoretically suitable for a Cermet used as disclosed herein.

It will also be obvious to one skilled in the art that more than one metal/ceramic, metal/glass oxide, or metal/ceramic/glass oxide formulation may be used to surround the core conductive material of ink/paste, wire, or combinations of both, to create a layering effect about the core material(s) along the longitudinal axis of the via to achieve optimal transition for CTE matching at the respective mating material interface(s).

Figure 8C:
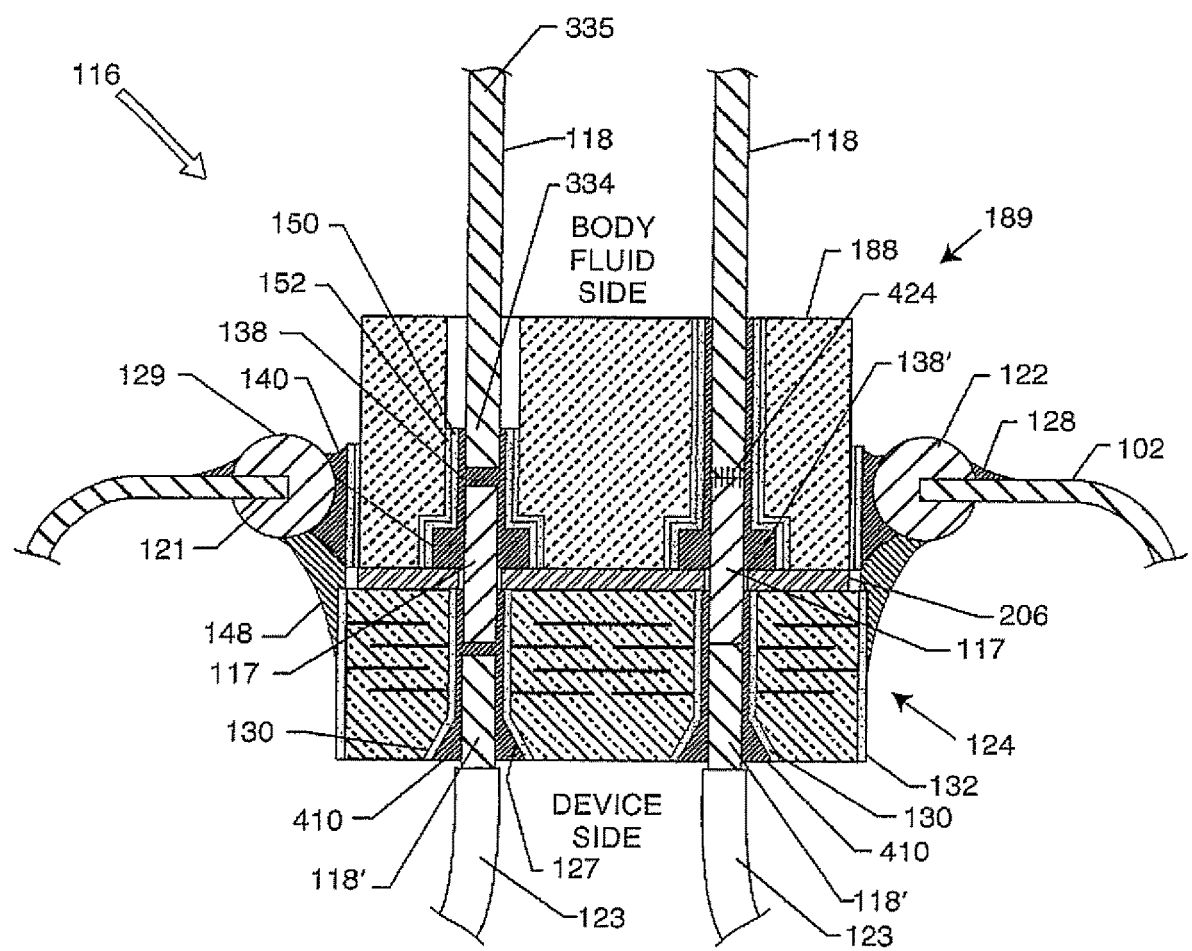
FIG. 8C is similar to FIG. 8 now showing a toroidal-shaped ferrule.

FIG. 8C is very similar to FIGS. 8, 8A and 8B, except in this case, the ferrule 122 is round. It has a notch 121 for capturing the AIMD housing 102 where a convenient laser weld 128 may be formed. When using the word "round" we are referring to the cross-sectional area of the ferrule, which, of course, can be of many other shapes, including oval, elliptical and the like. The cross-section shown in FIG. 8C could be round, as previously illustrated in FIGS. 3A and 4A; however, it will also be appreciated that the ferrule of FIG. 8C could also be of more of a rectangular shape, as previously illustrated in FIGS. 5, 6 and 7. Referring once again to FIG. 8C, this shows a round cross-section of the ferrule and if the feedthrough capacitor is also round, then generally the ferrule 122 would form a toroidal or donut shape.

Figure 8D:
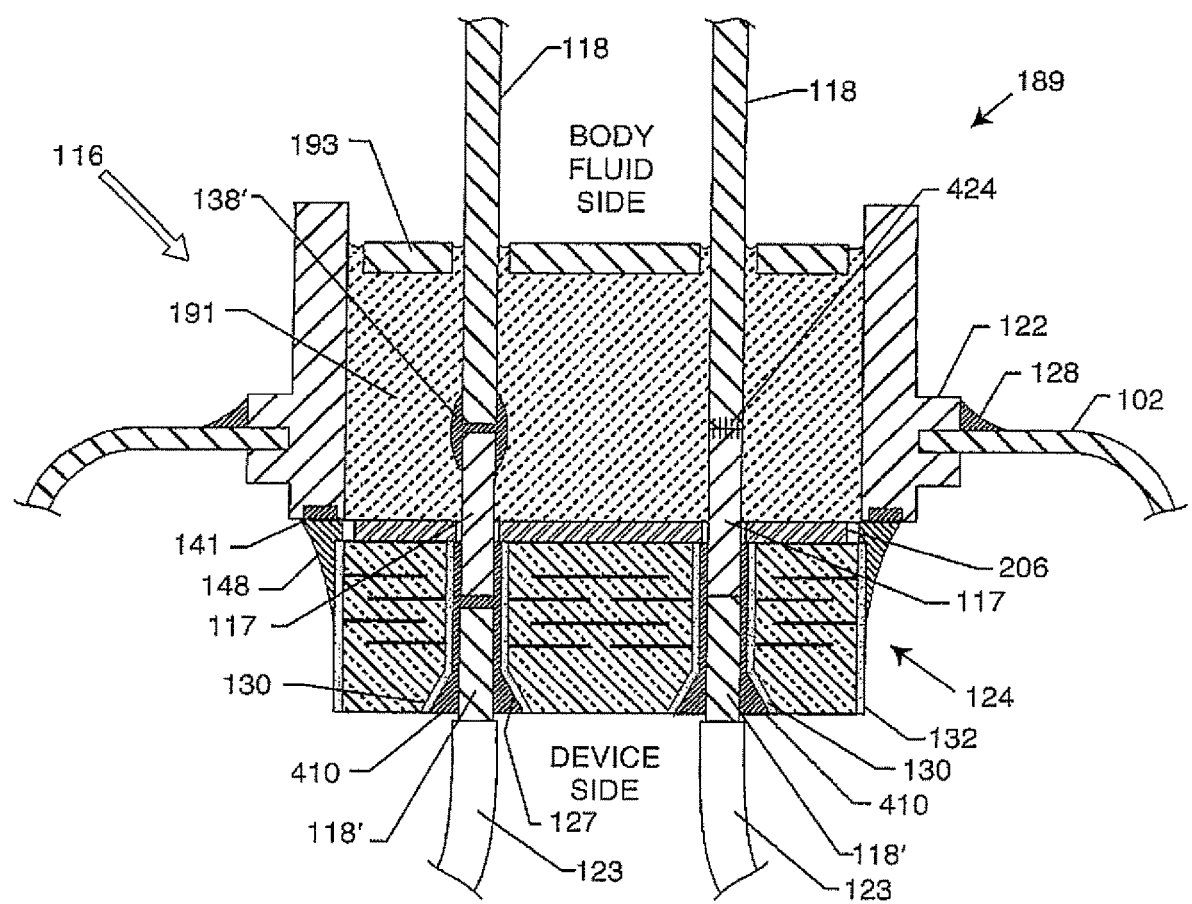
FIG. 8D is similar to FIG. 8 now showing the insulator as a glass which is hermetically sealed to the lead wires and ferrule at the same time.

FIG. 8D is very similar to FIG. 8 through 8C, except that in this case, the alumina ceramic 188 has been replaced with a glass seal 191. This may be a compression glass or a fusion glass, which are well known in the art. In this case, the novel two-part pin of the present invention has been pre-welded 424 (it will also be appreciated that the leads could be pre-co-brazed 138' together before the glass sealing operation instead of welded) so it can be placed into the glass sealing fixture as the glass wets to both the leads and the inside of the ferrule at once forming a mechanical and hermetic seal. An optional alumina ceramic or equivalent insulator sheet 193 is shown. This insulator 193 would be placed on top of the glass pre-form prior to the glass sealing process. When the glass 191 becomes molten, the advantage of having an alumina or equivalent ceramic sheet 193 disposed towards the body fluid side, is that very little of the glass 191 ends up being exposed to body fluids, which can act as solvents. In other words, the alumina sheet 193 makes the assembly of FIG. 8D more stable over the long life of an active implantable medical device.

Referring once again to FIG. 8D, since there are no gold brazes, there are no required metallization layers 150,152.

Figure 8E:
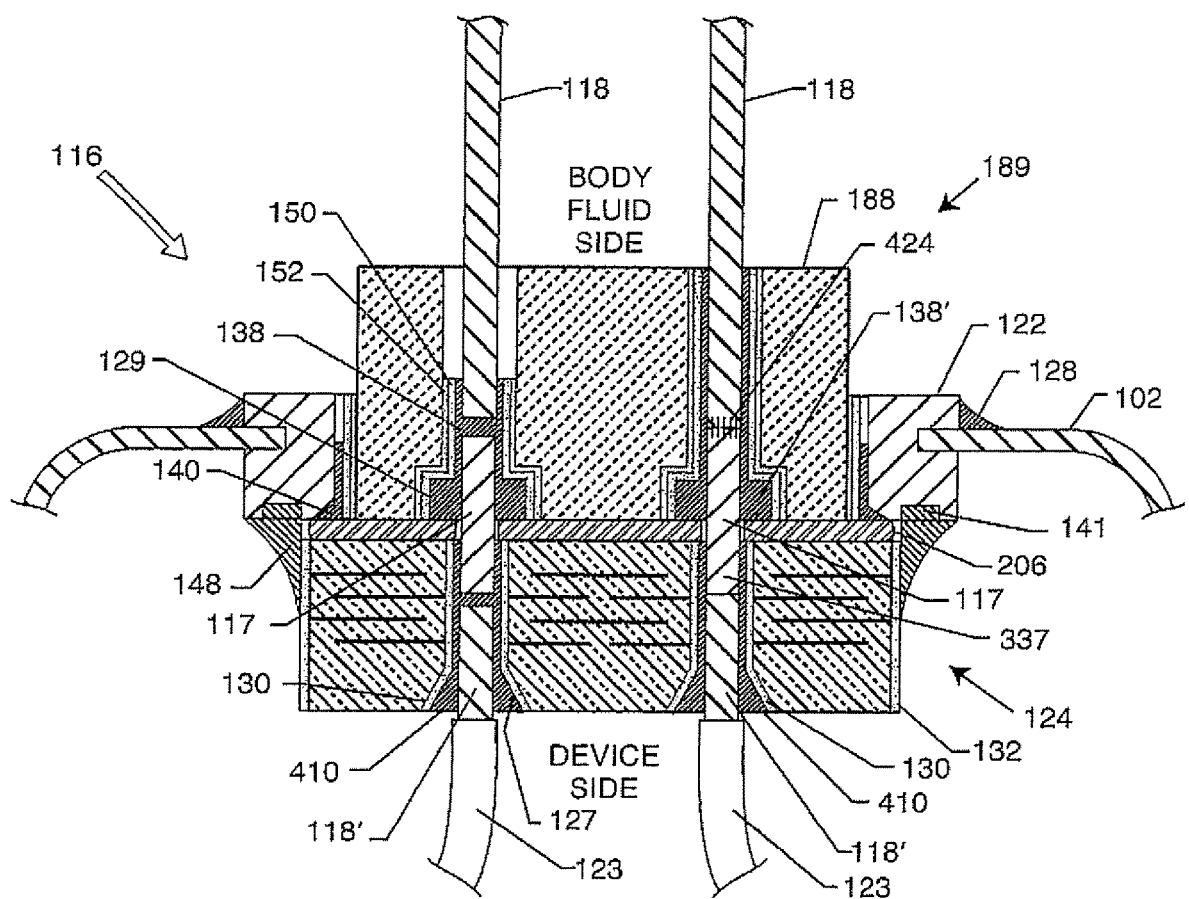
FIG. 8E is similar to FIG. 8 now showing the capacitor outside metallization electrically coupled to the ferrule through a second gold braze separate from the gold braze hermetically sealing the insulator to the ferrule.

FIG. 8E is similar to FIG. 8, except that in this case, the diameter or perimeter of a feedthrough capacitor 124 is enlarged. This is often required for high voltage implantable cardiofibrillator devices where the dielectric thickness has to be quite high so the capacitor has a high voltage rating. Accordingly, in order to increase the feedthrough capacitor's effective capacitance area (ECA), it is required to make the capacitor larger in either its length, width or outside diameter. This creates a problem, in that, the capacitor outside diameter metallization 132 no longer aligns with gold braze 140. In this case, a small or separate round or square or other shape gold pad has been co-brazed, which is not part of the hermetic seal 140. This small area of gold braze 141 allows for the capacitor metallization 132 to be electrically connected 148 to a non-oxidized surface and therefore, provide a very low resistivity path to the ferrule 122 to the AIMD electromagnetic shield housing 102.

Figure 8F:
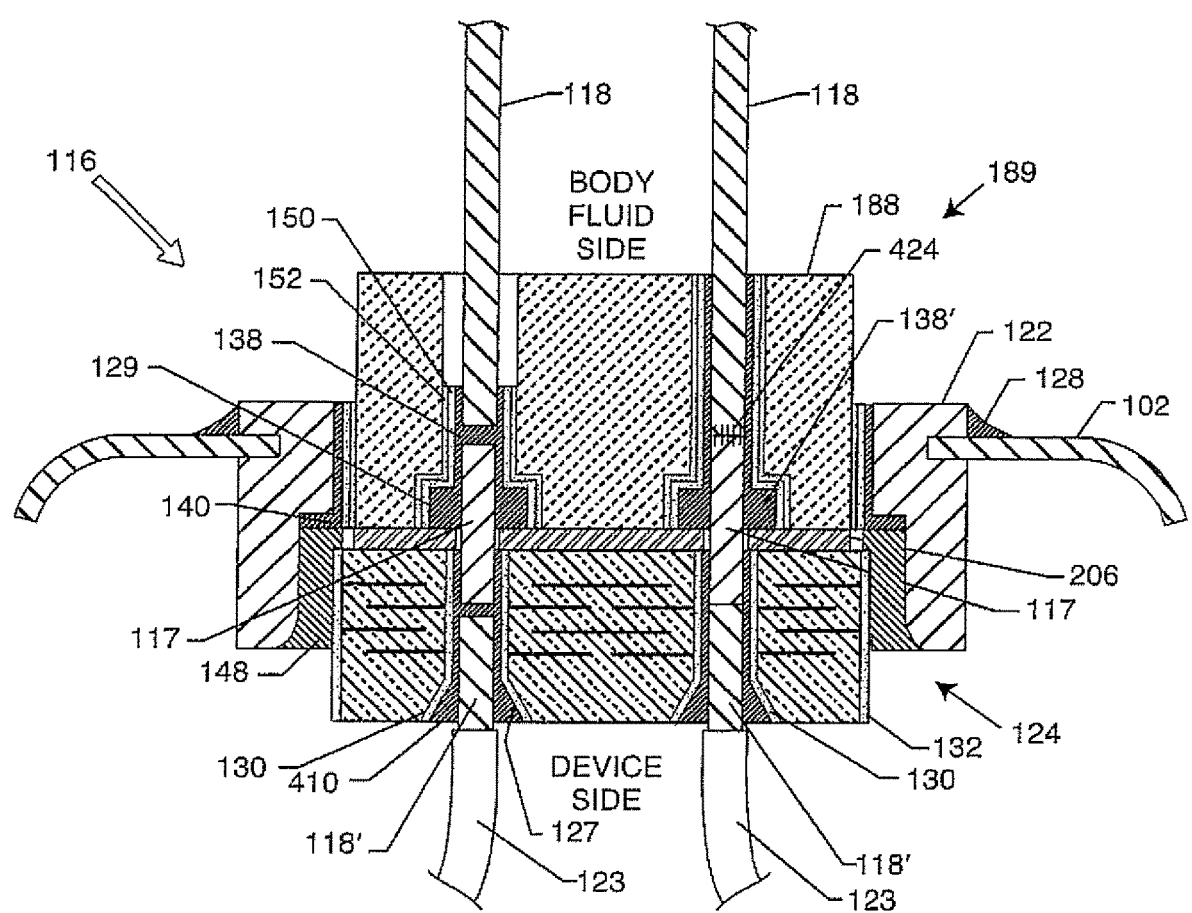
FIG. 8F is similar to FIG. 8 now showing both the insulator and the ferrule are centered by at least partially disposing them within the ferrule.

FIG. 8F is similar to FIG. 8, except that the ferrule structure 122 has been modified such that the capacitor 124 fits partially down into the ferrule. Electrical attachment material 148 comprises a thermal-setting conductive adhesive, such as a conductive epoxy or a conductive polyimide or a solder or the like. It makes an electrical connection between the capacitor metallization 132 and gold braze 140 as illustrated. Having the capacitor sit down part way into the ferrule allows automatic assembly by dispensing of thermal-setting conductive epoxy or solders by robots. One is referred to U.S. Pat. No. 6,643,903, the contents of which are fully incorporated herein by reference.

Figure 9:
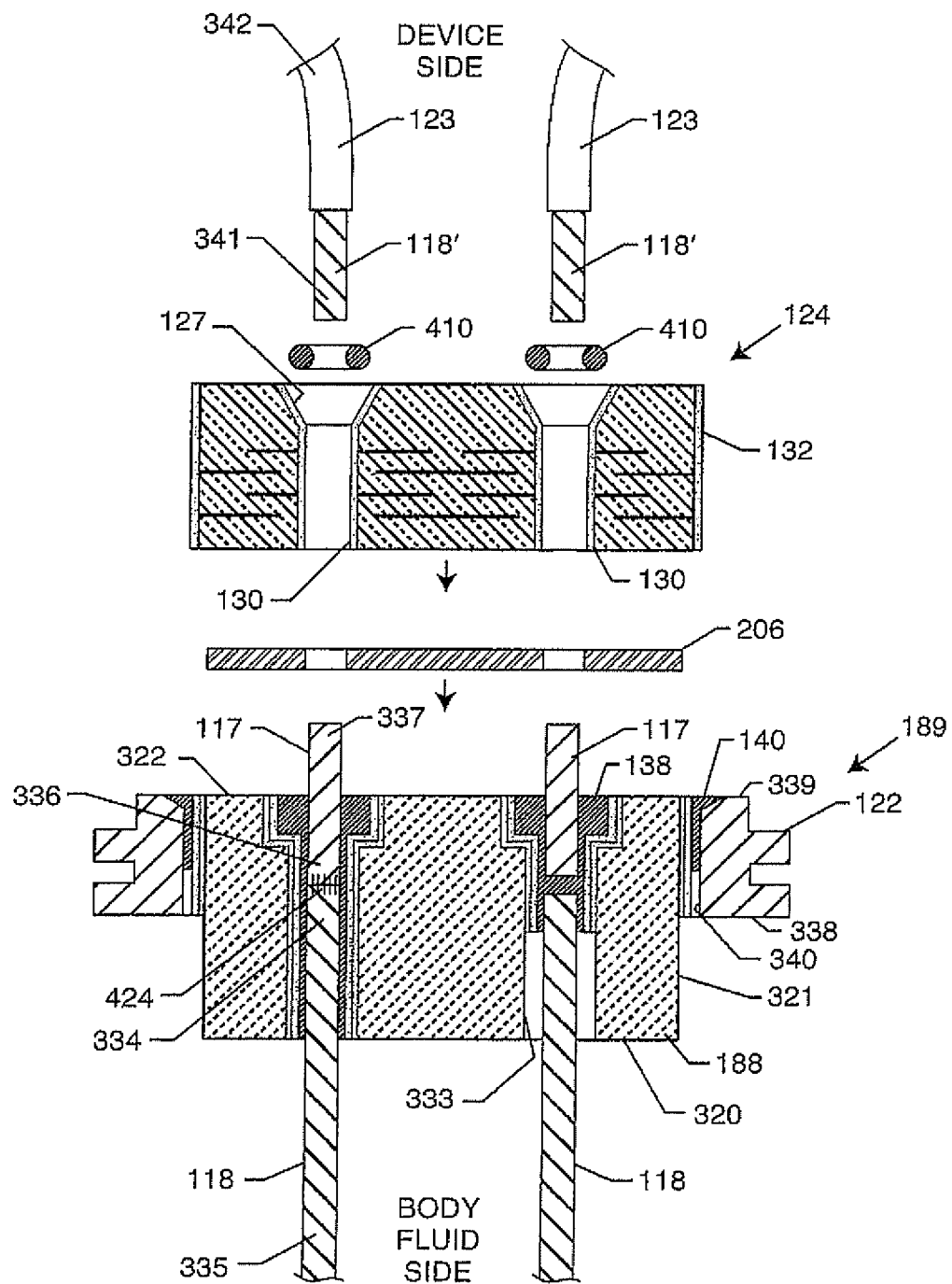
FIG. 9 is an exploded sectional view of the structure of FIG. 8 now shown upside-down for better understanding of the manufacturing steps.

Referring now to FIG. 9, after the hermetic seal subassembly 189 is formed from FIG. 8, the capacitor 124 is subsequently added. First, the insulator assembly 189 is inverted and an optional adhesive insulative washer 206 is placed against it as shown. The capacitor 124 is disposed on top of the adhesive washer, which is then cured in an elevated temperature. This not only firmly and mechanically attaches the feedthrough capacitor 124 to the hermetic seal subassembly 189, but it also confines the area around the platinum, palladium or alloys thereof pins 117, such that a subsequent soldering operation 410 cannot flow between the capacitor and the insulator, thereby, shorting out from lead to lead or lead to ferrule (ground). Referring back to FIG. 9, it will also be appreciated that the electrical connection material 410 could also comprise a thermal-setting conductive adhesive, such as a conductive polyimide or conductive epoxy. It's extremely important in the case of use of thermal-setting conductive adhesives, that an insulating washer 206 be used, such that the conductive material, such as silver particles, in the thermal-setting conductive adhesives, do not migrate or short out from pin to pin or from pin to ferrule or from pin to ferrule gold braze 140. A low cost insulated (insulation 123 is optional) lead 118' is placed along with a solder preform 410, This is best illustrated in FIG. 9 where the hermetic seal subassembly 189 has been inverted and one can see the two platinum, palladium or alloys thereof pins 117 sticking up. The insulative washer 206 is then disposed over the pins 117 and the feedthrough capacitor 124 is placed adjacent the insulating adhesive washer 206. This is then pre-cured so they are firmly adhered and mechanically bonded together. During the curing of adhesive washer 206, it is usually required that a weighting or a spring fixture (not shown) be placed on the top (device side) of the feedthrough capacitor 124. This pushes the feedthrough capacitor firmly against the adhesive washer 206 and the surface of the insulator 188 so that they all bond together. Then, a solder preform 410 is placed into a counter-bore or counter-sink 127 in the device side surface of the feedthrough capacitor. Next, a low cost leadwire, which is typically a tinned-copper leadwire 118', is placed through the solder preform 410. The length of the conductive part of this leadwire 118' is chosen so that the low cost tin-copper leadwire will either touch or become very close to the platinum, palladium or alloys thereof pins 117 of the hermetic insulator.

Figure 10:
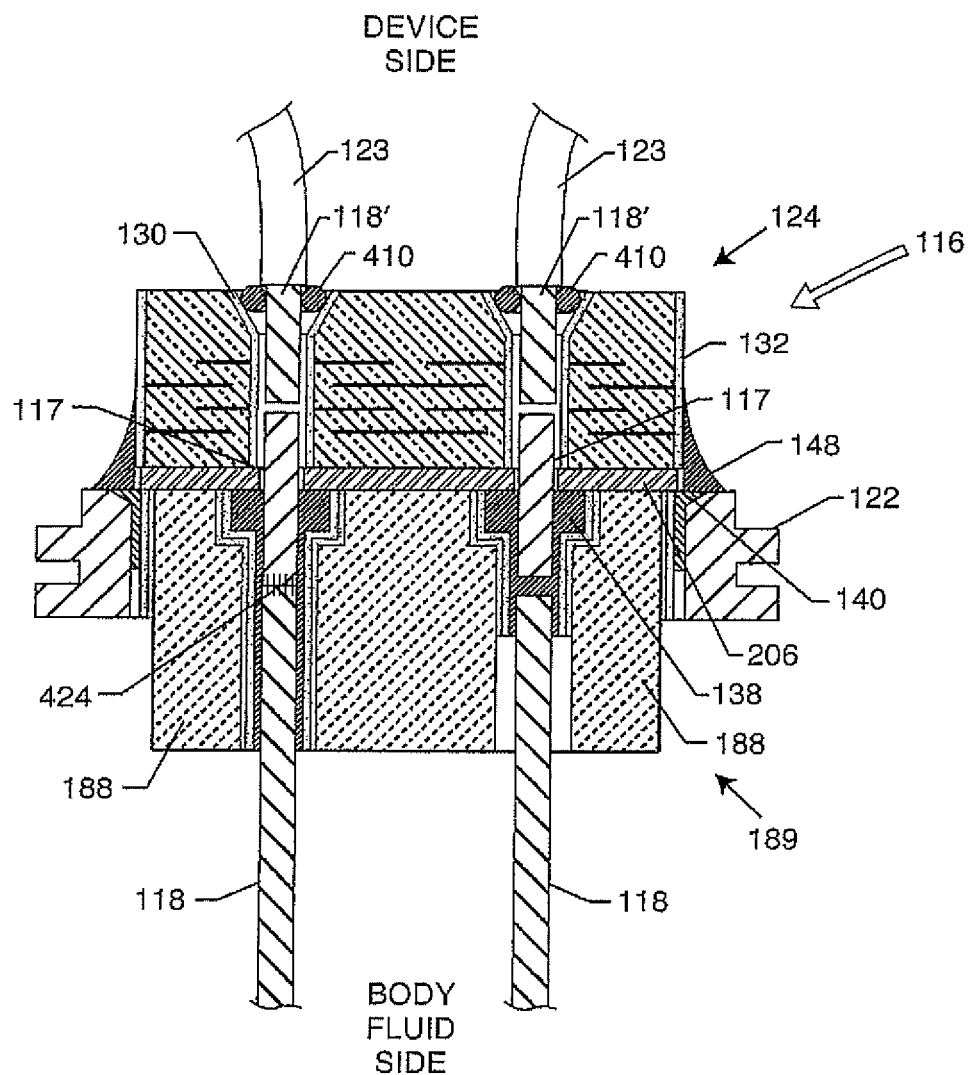
FIG. 10 illustrates the completed assembly of FIG. 9 prior to reflowing the solder preform.

FIG. 10 illustrates the completed assembly prior to reflowing the solder preform 410.

Referring now back to FIG. 8, one can see that the assembly 116 has been inverted in comparison to FIG. 10, but the solder preform 410 has reflowed and is fully flowed around the tin-copper portion 118' of the low cost device side leadwire and also around the short platinum, palladium or alloys thereof pins 117 from the hermetic seal subassembly 189. FIG. 8 increases the reliability of the wiring to the device side of the electronics through lead 118' with its optional insulation 123. As one can see, the reflow solder connection 410 not only forms a butt joint between the low cost leadwire 118' and pin 117, but also the solder 410 flows all about both leads 118' and 117, thereby making the electrical connection not only a butt connection, but also a shear connection. It will be known to reliability engineers that solder joints that embody shear stresses will be more resistant to shock vibration, reflow and the like. Shear forces are also set up between the solder 410 and the inside diameter of the capacitor feedthrough hole metallization 130. This double shear increases the mechanical strength of the attachment of the low cost leadwire 118' and also increases its pull strength force. It will also be appreciated that instead of a solder preform 410, one could use a thermal-setting conductive adhesive, such as a conductive epoxy or a conductive polyimide.

Referring back to FIG. 8, one can see that the solder (or equivalent material) 410 has flowed all about the exposed end portion of the platinum/palladium pin 117 and the low cost leadwire (tin/copper) 118'. As one can see, there is both a butt joint and a sheer joint formed by solder flowing all around the outside diameters of both pin 117 and leadwire 118'. The choice of solders for making connection 410 are somewhat limited in that, they need to have a relatively high melting temperature. This is because of the subsequent laser welding operation 128 wherein, the ferrule 122 is joined mechanically and hermetically to the AIMD housing 102. The laser welding operation 128 elevates the entire structure to a fairly high temperature (approximately 260° C.). This rules out the use of low temperature solders 410, which would have melting points below 260° C. There is another property of the overall assembly 116 that is imposed by the medical implant industry. This property is known as leadwire pull strength. During qualification, customers require leadwire pull strengths ranging anywhere from two to four, or even five pounds in range. This generally is done in a pull strength tester where the leads are put in tension. The inventors tested the assembly of FIG. 8 with two different high temperature solders 410. One, embodying SN10 and the other was using AG1.5. Both of these solders have reflow temperatures in the range of 290° C. The inventors performed various pull strengths and found that the pull strengths always exceeded two pounds and in many cases, depending on process control, exceeded seven pounds. Worse case experiments were run with the pins 117 and leadwires 118' not inside of a feedthrough capacitor. In other words, the two ends were joined just with solder and a certain amount of solder spread over the side walls. It was encouraging to note that in no case did the pull strength of these worse case assemblies, fall below two pounds. Subsequent testing in the inside diameter feedthrough capacitors generally showed pull strengths in the range of six to seven pounds. Accordingly, the inventors are satisfied that the novel arrangement as shown in FIG. 8, will meet both the high temperature, pull strength, the shock and vibration, and the high temperature resistance requirements of the active implantable medical implant industry. Generally, the pull testing conducted by the experimenters placed a tensile load on leadwires 118' until the point of failure.

It is also desired that the solders contain less than 20-25% Sn as the inventors have found that solders with a higher Sn content become brittle and can induce cracks in the ceramic capacitor body when thermally shocked. Such cracks can result in latent electrical field failures. Two example solders would be AG1.5 or SN10. AG1.5 is 97.5% Pb, 1% Sn, and 1.5% Ag with the balance being lead and it has a very high melting point, close to 300° C. SN10 is a composition comprising tin and lead and also has a very high melting point. SN10 is 88% Pb, 10% Sn and 2% Ag. Solders that contain silver are desirable to prevent leaching of the terminations from the ceramic capacitor. The chart shown as FIG. 78 details various solder compositions that may be used by one skilled in the art when manufacturing the present invention. This list is not meant to be a full and complete list, but rather shows some of the solder compositions that could be used.

Referring once again to FIG. 8, one can see that the body fluid side, low cost leadwire 118 can have a gap between it and the short platinum, palladium or alloys thereof pin 117. This gap is shown on the left-hand side of FIG. 8. Referring again to FIG. 8, on the right-hand side, one can see that the body side leadwire 118 has been pre-welded 424 to the pin 117. This pre-welding 424 guarantees that the mechanical and electrical connection be very robust, but it also facilitates manufacturing and assembly just prior to the gold brazing operation 138. It is much easier for an operator to drop in a single lead into a carbon boat before it goes into the gold brazing furnace, then two pieces shown as the left-hand side 117, 118 of this figure. It will also be appreciated that between the device side leadwire 118', there may be a small gap with the short pin 117, as shown on the left, or the two may be butted directly against each other, as shown on the right. It should also be noted that the melted solder preform 410 picks up additional strength, not only because it is in sheer around the circumference of pin 117 and leadwire 118', but it is also wetted to the inside feedthrough capacitor diameter metallization 130. Accordingly, the solder preform 410 not only mates around pin 117 and 118', but it also wets completely to the ceramic capacitor 124 inside diameter of feedthrough hole metallization 130. This creates additional sheer strength. This goes to facilitate the requirement in the industry that the device side leadwire have a very high pull strength. In general, pull strengths are specified generally between the range of 2 lbs. to 5 lbs. This is equally applicable to the body fluid side leads 118 and the device side leadwires 118'. Accordingly, it is very important that process controls ensure that the solder preform 410 flows very evenly around both pins 117 and leadwire 118' and also properly wets the metallization 130 (without having it dissolve into the solder, a situation known in the industry as leaching). Ideally, it would preferable to be able to flow the solder preform 410 without the use of fluxes. If one uses a flux, then one must perform cleaning steps to remove the flux. Accordingly, the assembly as illustrated in FIG. 8, is best accomplished either in a conveyor-type curtain soldering furnace or as a bulk process in a device called a DAP sealer. In both cases, the soldering can be accomplished by either reducing or inert gases, thereby eliminating the need for fluxes and also a temperature profile could be created where the relatively fragile ceramic capacitor 124 can be slowly heated up and the solder 410 molten stage can be held to a relatively short amount of time and then the entire assembly is then slowly cooled down. It is desirable not to have the high temperature solder 410 be molten for too long as the capacitor termination material 130 can actually dissolve or leach undesirably into solder 410.

Referring once again to FIG. 8, one can see that on the device side, the ceramic capacitor has counter-sinks 127 to facilitate placement of the solder preform 410. This counter-sink is best viewed in FIG. 9, as element 127. It will also be appreciated that the counter-sink could be replaced by a counter-bore or even a straight through hole as will be further described. Referring once again to FIG. 8, one can see that there are counter-bores 129 placed in the insulator 188 of the hermetic terminal subassembly 189. These allow for convenient placement of gold braze preforms (not shown).

Referring back to FIG. 8D, it is very similar to FIG. 8, except that the hermetic seal 191 is now a glass-fused or compression glass seal. Referring once again to FIG. 8, the hermetic seal 188 is typically of alumina, which is gold brazed to the ferrule 122; thereby, forming a hermetic seal 140. There are also gold brazes 138 and 138', as previously described in FIG. 8, which also form a hermetic seal between the alumina or ceramic insulator 188 and both body fluid side leads 118 and device side leads, short lead pins 117. FIG. 8D is a similar structure, except the hermetic seal to the ferrule 122 is accomplished by the sealing glass 191. There is also a hermetic seal formed to the two-part leads 118 and 117, again, either by a fusion or a compression sealing of the glass. In FIG. 8D, it is not possible to have the body fluid side lead 118 have a gap between it and the short lead pin 117. Accordingly, as previously described in FIG. 8, there is a welding or joining operation 424, which is first performed before the glass seal can be accomplished. It will be understood by those skilled in the art, that any of the embodiments shown throughout this invention that show a brazed ceramic type seal, could be replaced by the glass seal, as shown in FIG. 8D. Referring once again to FIG. 8B, it will be appreciated that the insulating washer 206 could be replaced by a thin ceramic, such as an alumina washer. There could also be an alumina washer 193 disposed on top of the glass seal 191. The reason for the alumina washer 193 is that, the glass seal would bond very tightly to it; thereby, adding to the overall strength and hermeticity of the package. It will also be appreciated that instead of a fusion or a compression glass 191, there could also be a number of ceramic glasses that could be used. Referring once again to FIG. 8D, one will see that there is a gold braze area 141 that can be continuous or discontinuous or only in spots on top or on the device side of the ferrule 122. This provides an oxide-free electrical connection surface to which electrical connection material 148 forms a low impedance connection between the ferrule and the outside diameter or perimeter metallization 132 of the feedthrough capacitor 124. Problems associated with this are described by U.S. Pat. Nos. 6,765,779; 9,108,066; 9,427, 596 (oxide-free metal addition), the contents of all of which are incorporated herein by reference. In a preferred embodiment, the oxide-free material 141 would be a gold braze. However, the reference patents also show that a number of other oxide resistant materials could be used to perfect a low impedance electrical connection between the capacitor outside diameter perimeter metallization 132 and ferrule 122.

Now referring to FIG. 9, by focusing only on the bottom portion 189, which is the hermetic terminal subassembly, one can see that when the gold braze 138 is placed through gravitational and capillary action in the gold braze furnace, it will flow down and form the gold braze hermetic seal joint 138. It is important that this hermetic seal joint 138 encapsulate both the short pin 117 and the body fluid side leadwire 118. Referring now to FIG. 8, the hermetic seal subassembly 189 has been inverted. Since the gold braze joints 138 and 140 have been formed at very high temperature, they will not be disturbed nor will they reflow during the subsequent capacitor 124 soldering operation 410. It is important to realize that in a typical manufacturing operation, the hermetic terminal subassembly 189 is manufactured in an entirely different manufacturing line with a different set of controls, including braze furnaces and the like. It is equally important to note that the feedthrough capacitor assembly 124 is generally performed in an entirely different manufacturing line (usually in Class 10,000 or better clean rooms). It is a monolithic device consisting of alternating layers of ground and active electrodes, which goes through a number of binder bake-out and then sintering operations. Subsequent to that, metallization layers 130 and outside diameter metallization layer 132 are applied, either by electroplating, by applying conductive glass frits (and firing) and the like. In the final operation shown in FIG. 9, the capacitor subassembly 124 is adhered 206 to the hermetic terminal subassembly 189 and at the same time, device-side leadwires 118' are co-joined.

Referring once again to FIG. 9, one can see that after the solder preform 410 is reflowed, one still needs to make the electrical connection from the capacitor outside diameter perimeter metallization 132 to the gold braze 140 of the ferrule 122 using electrical attachment material 148 as shown in FIG. 8. This attachment 148 could be performed prior to the solder reflow 410 or after. In one embodiment, the electrical attachment material would be a thermally-conductive polyimide, which is cured around 290 to 300° C., but can withstand short-term temperatures up to 500° C. So in this case, the capacitor diameter or perimeter electrical connection 148 would first be formed and then the solder preform 410 would subsequently be reflowed at around 300° C.

Referring once again to FIG. 9, at the bottom is the hermetic seal subassembly 189. This also appears inverted in FIG. 8 with the capacitor 124 attached to it. The short pins 117 could, of course, be of platinum or palladium as described, but also could be of a variety of other materials. It should be noted that these short pins 117 are never exposed directly to body fluid and therefore, they do not need to be biocompatible or non-toxic. For example, pins 117 could be of nickel. If the pins were of nickel, they could still be co-gold brazed 138 to the body fluid side leadwires 118. In order to facilitate ready soldering to the capacitor inside diameter metallization 130 and the low cost leadwire 118', it would be preferred if nickel leadwires or the like were either tinned, solder, flowed or electro-plated etched and then tin-dipped or electroplated, for example, with gold or a gold flash to facilitate solderability. This could easily be achieved in a subsequent operation after building the hermetic seal subassembly as illustrated as 189. Another option would be to sputter a layer of gold, for example, or platinum onto the exposed ends of the pins 117 to facilitate solderability.

It is noted that the body fluid side leadwires 118' have a first end 341 that will at least be partially disposed within the passageway of the feedthrough filter capacitor while the second end 342 will be disposed past the feedthrough filter capacitor configured to be connectable to electronics internal to the AIMD.

FIG. 10 illustrates the capacitor 124 co-joined to the hermetic seal subassembly 189 by adhesive washer 206. The device side leads 118' have been placed through their solder preforms 410. FIG. 10 illustrates the entire assembly 116 just prior to reflow of the solder preform 410. After the solder preform 410 is reflowed at an elevated temperature, it will result in the structure 189, as illustrated in FIG. 8 (inverted). As can be seen, the solder preform 410 flows all around the two pins 117, 118'.

Figure 11:
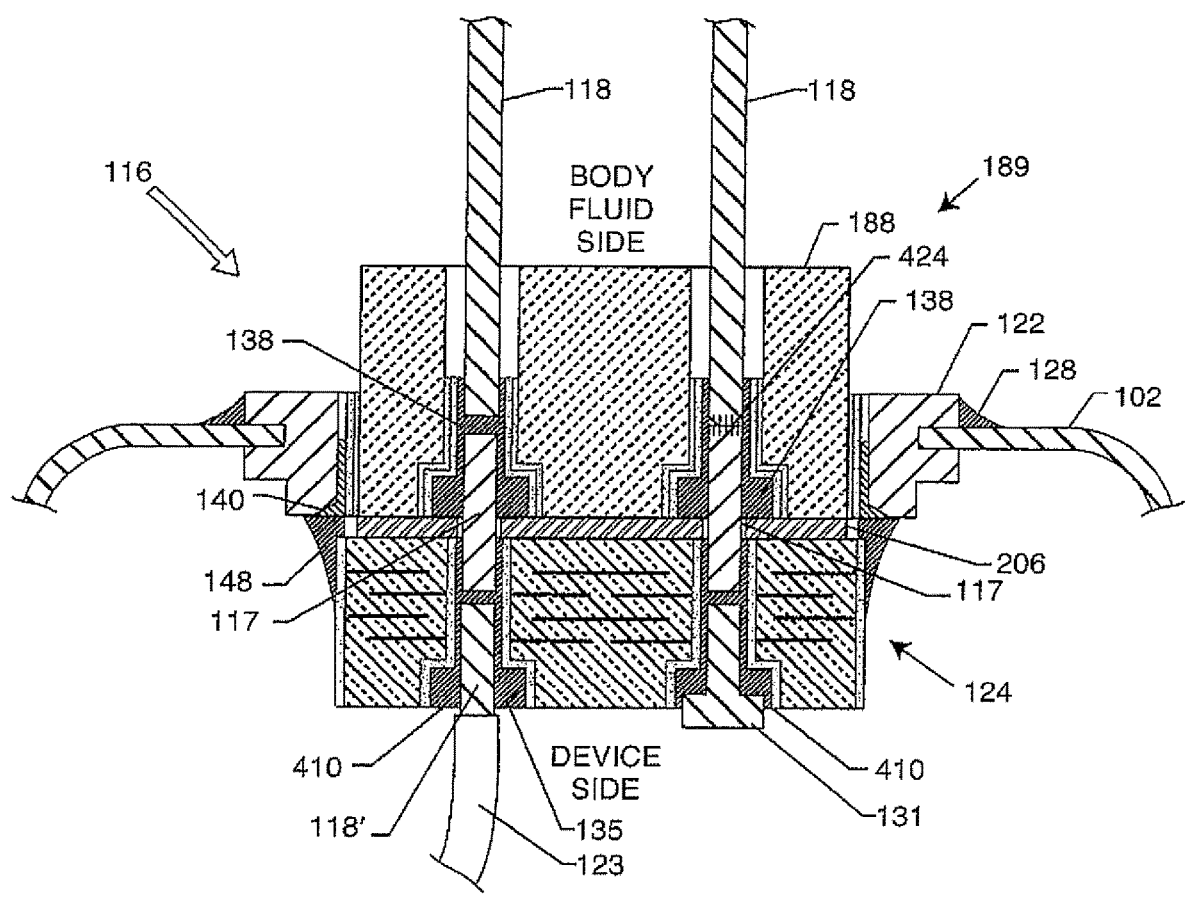
FIG. 11 is very similar to FIG. 8 except on the capacitor device side counter-bores are shown instead of counter-sinks.

FIG. 11 is very similar to FIG. 8 except on the capacitor device side, counter-bores 135 are shown instead of counter-sinks 127. The right side of the device now has a wire bond pad 131 which may be proud of the feedthrough capacitor 124. This nail head 131 may be proud of the device side surface of the feedthrough capacitor 124 (as shown) or it may be flush with the surface (not shown), or it may be reduced below the surface (not shown).

Figure 12:
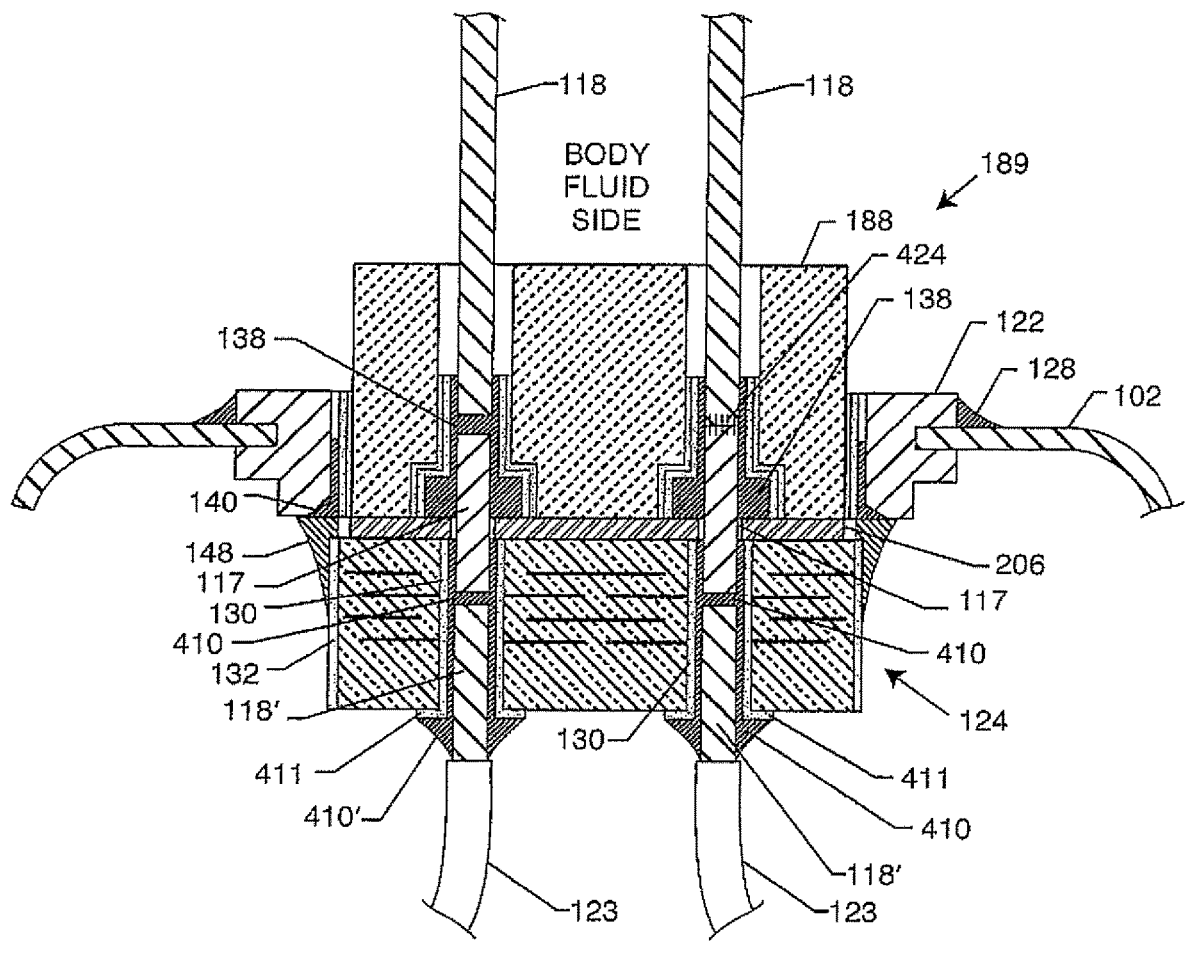
FIG. 12 is very similar to FIG. 8, except that the countersinks have been eliminated on both the right and the left side of the device side of the feedthrough capacitor.

FIG. 12 is very similar to FIG. 8, except that the counter-sinks 127 have been eliminated on both the right and the left side of the device side of the feedthrough capacitor 124. This will make it more difficult to place a solder preform 410 and have it reflow properly. However, it will be understood by one skilled in the art that counter-bores, counter-sinks or combination and variations thereof can be used, or alternatively, as shown in FIG. 12 no such structures are used to help locate and place the solder preform 410.

Referring back to FIG. 12, one can see that the feedthrough capacitor inside diameter (or via hole) metallization 130 has been extended 411 onto the device side of the feedthrough capacitor 124 such that it forms a circular portion, which is also known in the industry as a white-wall tire shape. As previously described, this metallization 130, 411 can be mechanically and electrically adhered to the capacitor electrode plates by firing a silver or palladium-silver glass frit, electroplating or the like. In all cases, the metallization 130, 411 firmly adheres to the body of the feedthrough capacitor 124. The presence of the white-wall tire metallization 411 allows for the solder 410 to form a fillet 410' between the lead conductor 118' and metallization band 411. This forms a solid fillet, which is known in the industry to have very high pull and bending strength. In other words, the white-wall tire metallization 411 and corresponding solder (or thermal-setting conductive adhesive) fillet 410' adds greatly to the pull strength of the lead 118', 123.

Figure 13:
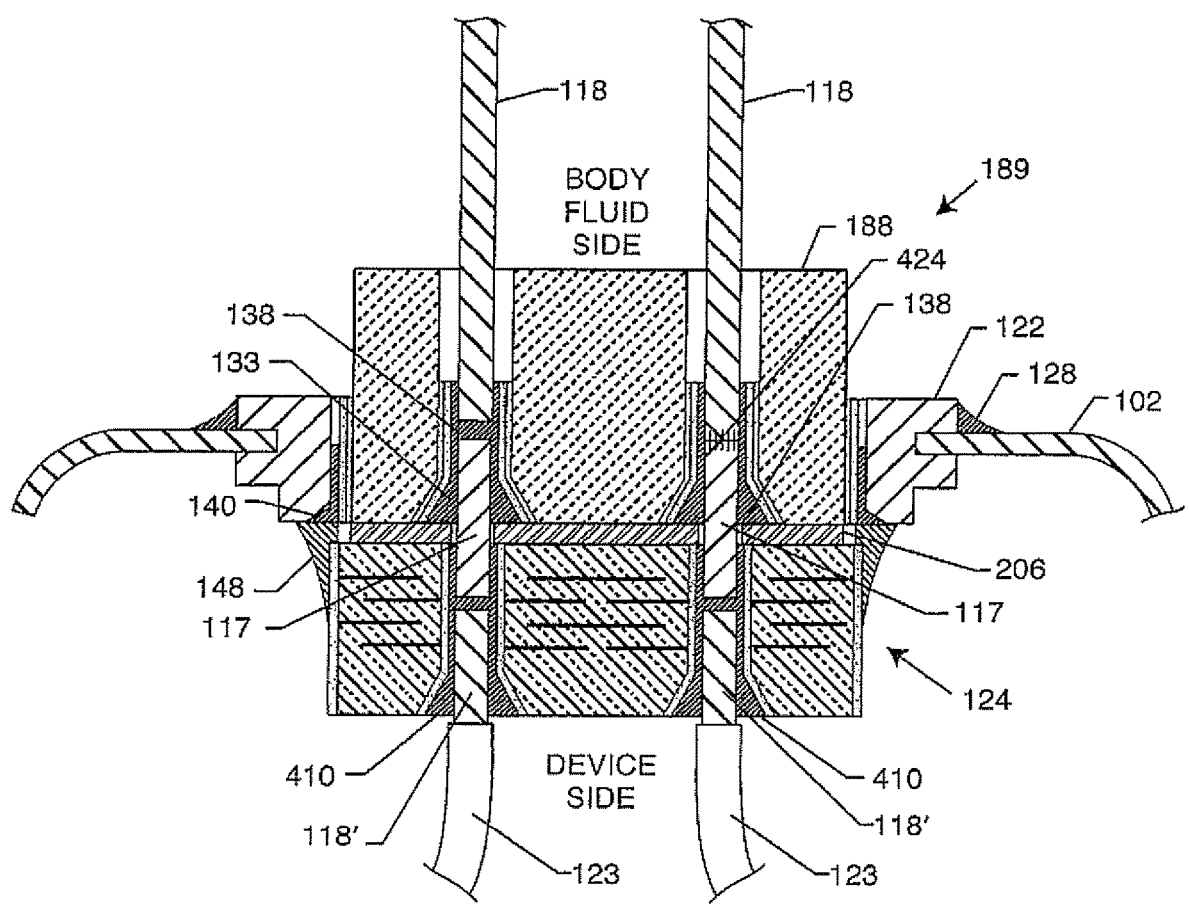
FIG. 13 is very similar to FIG. 8, except that in this case the counter-bores on the device side of the hermetic insulator have been replaced by counter-sinks.

FIG. 13 is very similar to FIG. 8, except that in this case, the counter-bores on the device side of the hermetic insulator 188 have been replaced by counter-sinks 133.

Figure 14:
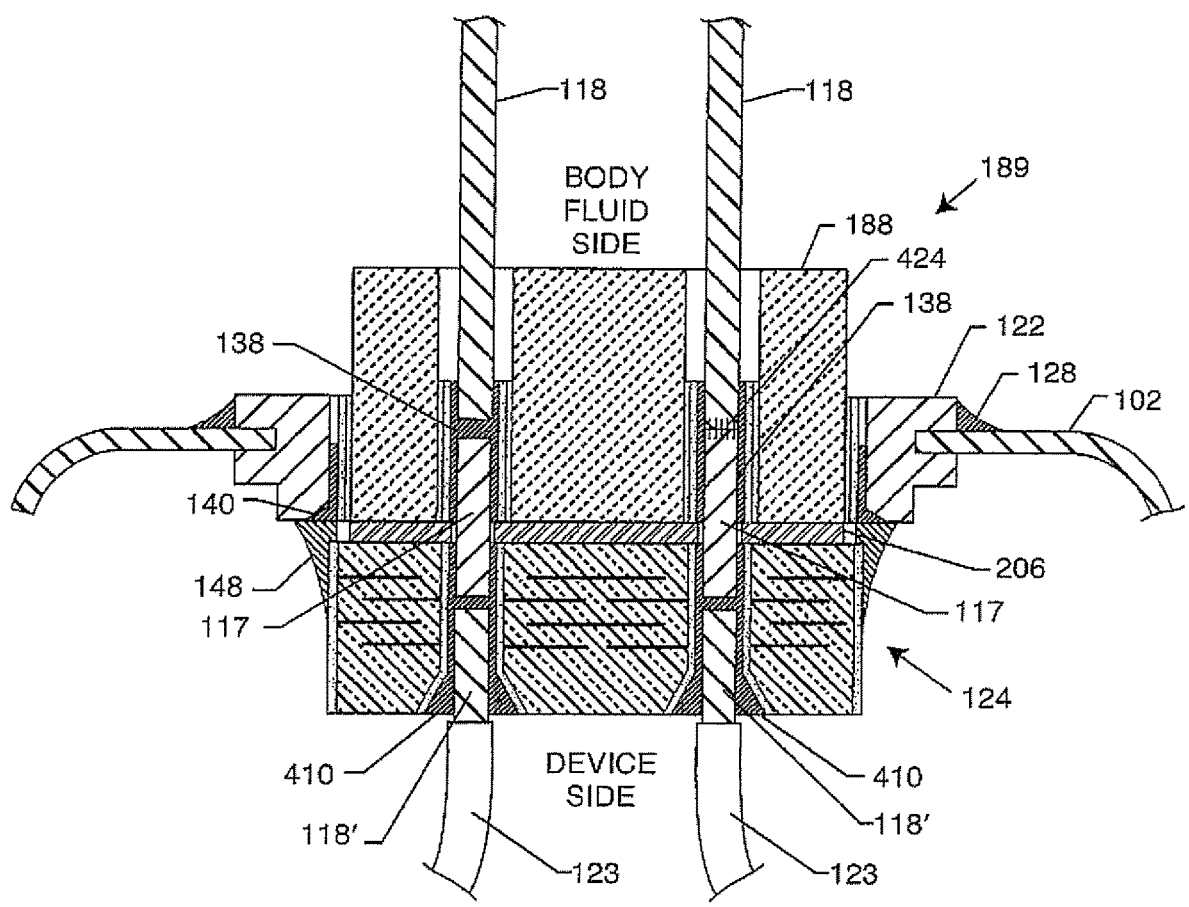
FIG. 14 is very similar to FIG. 8, except that the counter-bores in the alumina ceramic insulator 188 have been removed.

FIG. 14 is very similar to FIG. 8, except that the counter-bores 129 in the alumina ceramic insulator 188 have been removed. This will make it more difficult to place gold brazed preforms 138 (not shown before brazing). Again, it will be understood by one skilled in the art that counter-bores, counter-sinks or combination and variations thereof can be used, or alternatively, as shown in FIG. 14 no such structures are used in the insulator 188 to help locate and place the gold brazed preforms 138 (not shown before brazing).

Figure 15:
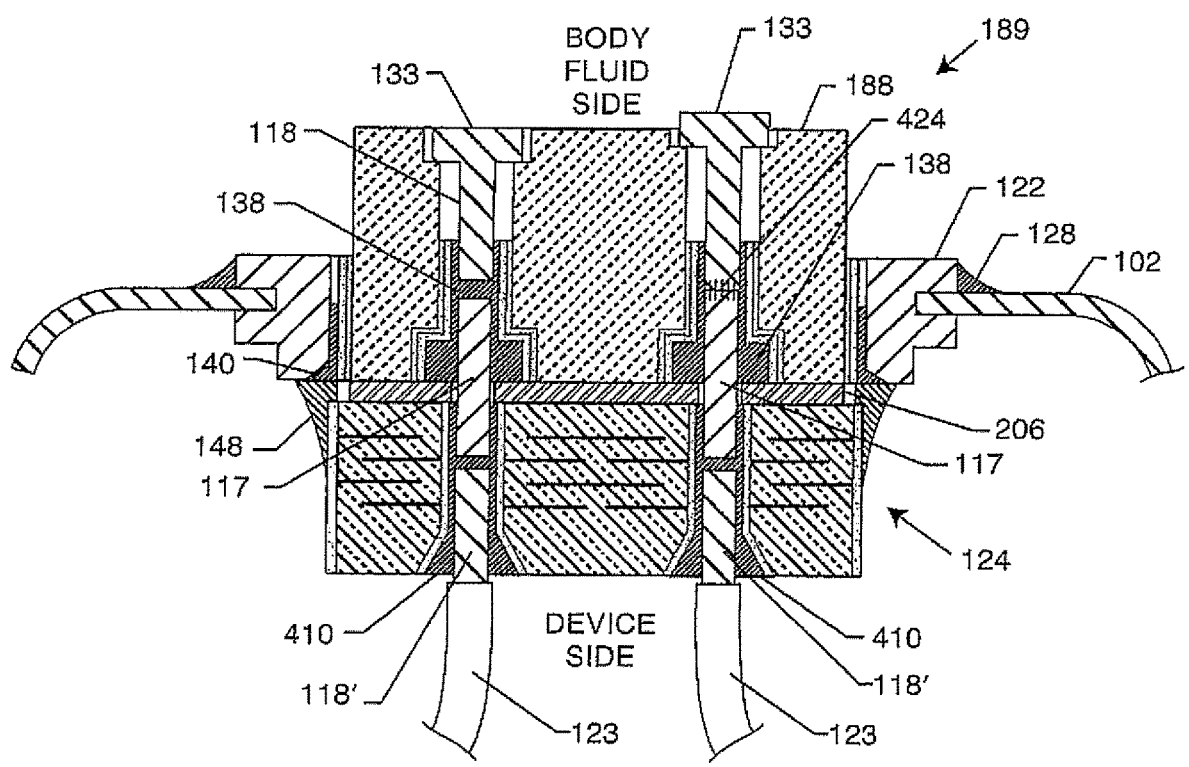
FIG. 15 is very similar to FIG. 8, except that the body fluid side leadwires have been replaced by biostable and biocompatible wire bond pads.

FIG. 15 is very similar to FIG. 8, except that the body fluid side leadwires 118 have been replaced by biostable and biocompatible wire bond pads 133. In a preferred embodiment, these pads are drawn from a single piece of wire 118, which extends down into the gold braze 138.

Figure 16:
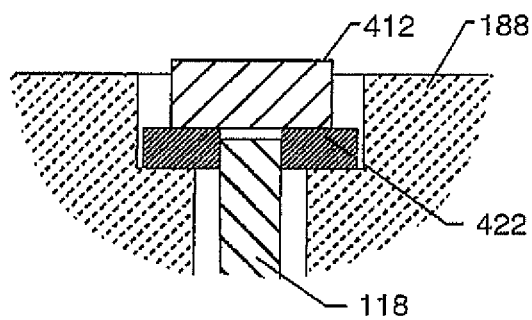
FIG. 16 illustrates an alternate method of manufacturing a nail-headed lead as previously described in FIG. 15.

FIG. 16 illustrates an alternate method of manufacturing a nail-headed lead 118 as previously described in FIG. 15. Instead of continuously drawing the nail head 133 as a continuous piece of the leadwire 118, FIG. 16 illustrates that the nail head 412 may be machined as a separate structure and then gold brazed 422 to the lead 118. Gold braze 422 would typically be a co-brazing operation at the same time gold brazes 138 and 140 are formed. As previously described, sputter layers 150,152 are not shown for simplicity.

Figure 17:
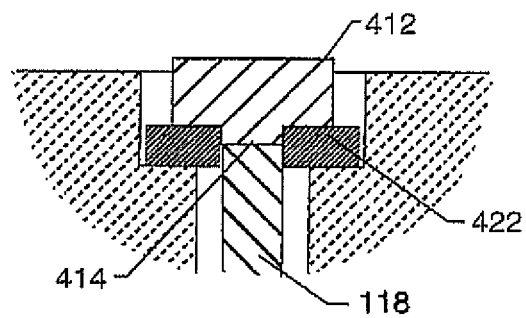
FIG. 17 illustrates that the nail head may be modified to have an elongated piece that engages the gold braze preform.

FIG. 17 illustrates that the nail head 410 may be modified to have an elongated piece that engages the gold braze preform. This aids in centering and aligning the nail head 412 with the lead 118.

Figure 18:
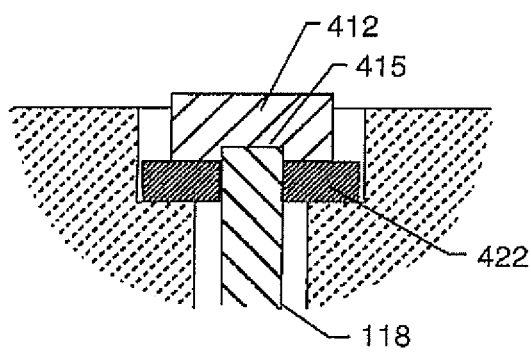
FIG. 18 illustrates that a counter-bore may be included within the machine nail head into which the lead protrudes.

In FIG. 18, one can see that a counter-bore may be included within the machine nail head 412 into which the lead 118 protrudes. Again, this helps with alignment during the gold braze flowing operation 422.

Figure 19:
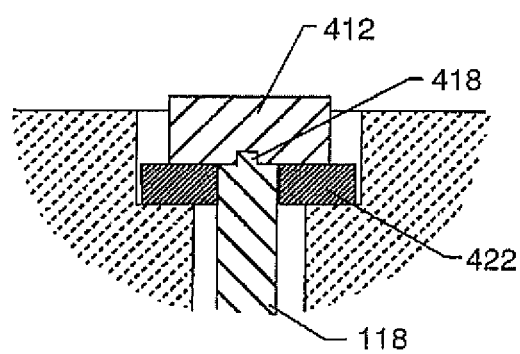
FIG. 19 is very similar to FIG. 18, except that in this case, the counter-bore and nail head is smaller and that a protrusion or extension is formed on the end of lead to engage counter-bore.

FIG. 19 is very similar to FIG. 18, except that in this case, the counter-bore and nail head 412 is smaller and that a protrusion or extension is formed on the end of lead 118 to engage counter-bore 418. Again, this is to help with maintaining alignment during the gold braze reflow operation 422.

Figure 20:
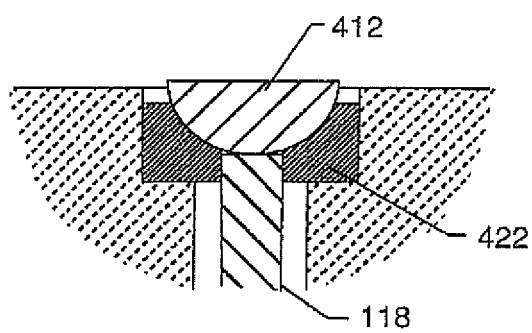
FIG. 20 illustrates that the nail head may have a semi-circular (or other) shape.
Figure 21:
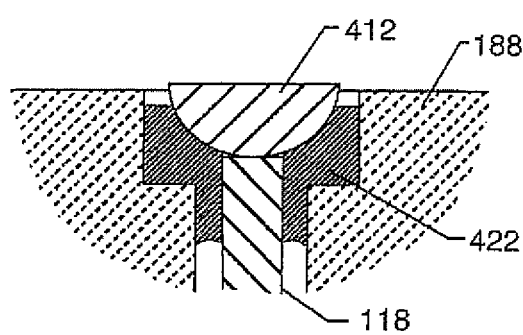
FIG. 21 illustrates that the contact area can be further increased by using a larger gold preform in comparison to FIG. 20.

FIG. 20 illustrates that the nail head 412 may have a semi-circular (or other) shape. The advantage of the semi-circular shape is that this increases the wetting and sheer area to the gold braze 422 and also increases the gold braze contact area to the lead 118. This contact area can be further increased by using a larger gold preform 422, as illustrated in FIG. 21. Referring back to FIGS. 16 through 21, it will be appreciated that a weighting fixture (not shown) may be applied to the top of any of the nail heads or even an alignment fixture so that they are properly held in place during the gold braze reflow 422.

Figure 22:
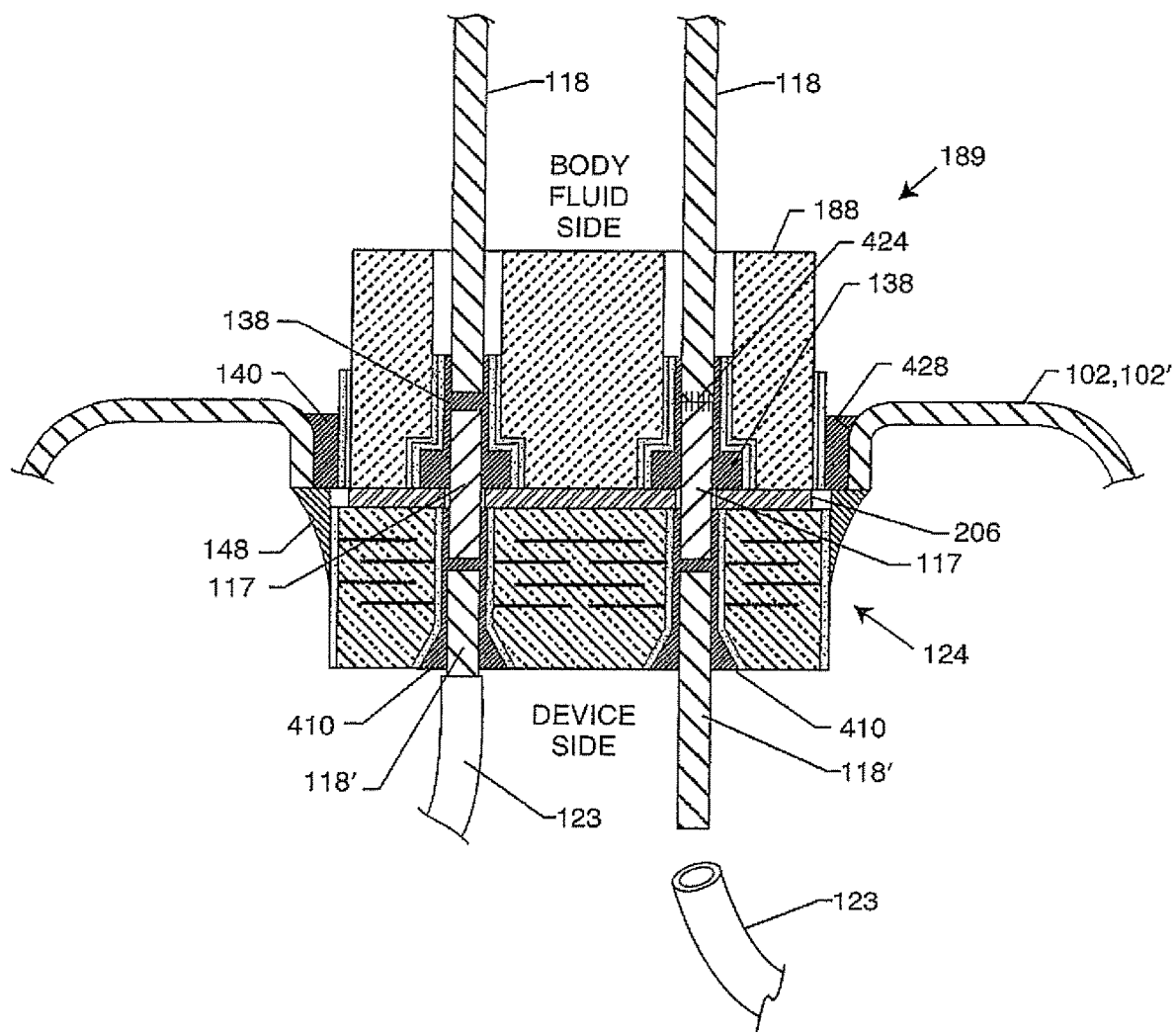
FIG. 22 is very similar to FIG. 8, except now the insulator is hermetically sealed to the active implantable medical device housing thereby eliminating the ferrule.

FIG. 22 is very similar to FIG. 8, except that the ferrule structure 122 has been completely eliminated. By eliminating the ferrule, one eliminates a significant amount of cost. Typically, these titanium ferrules are machined out of a solid piece of titanium, which entails a substantial amount of machining time, labor and scrap. Referring to FIG. 22, one can see that the AIMD housing 102 has been bent down to form an aperture 428 into which the hermetic seal insulator 188 is aligned. The insulator 188 is then gold brazed 140 directly to the AIMD housing 102. This is actually co-brazed along with gold braze 138 as previously described. It will be appreciated that instead of gold brazing directly to the entire AIMD housing 102, the gold braze 140 may be done to a lid or a shield assembly, which is subsequently laser welded into the AIMD housing 102 (not shown). Referring once again to FIG. 22, one can see that on the left side, a low cost insulated leadwire 118' has been co-soldered 410 on the inside diameter of the feedthrough capacitor to pin 117. On the right-hand side of FIG. 22, towards the device side, one can see an alternative low cost leadwire 118' wherein, the insulation 123 can be added later. It will be appreciated that the length of leadwire 118' can be of any suitable length to reach a circuit board or even provide for a stress-relieving or strain-relieving loop. The insulation 123 on the right side of FIG. 22 can be an insulation sleeve, an insulation tubing or even a heat-shrink tubing, which is added later. A preferred material would be an insulative tubing consisting of KAPTON.

Figure 23:
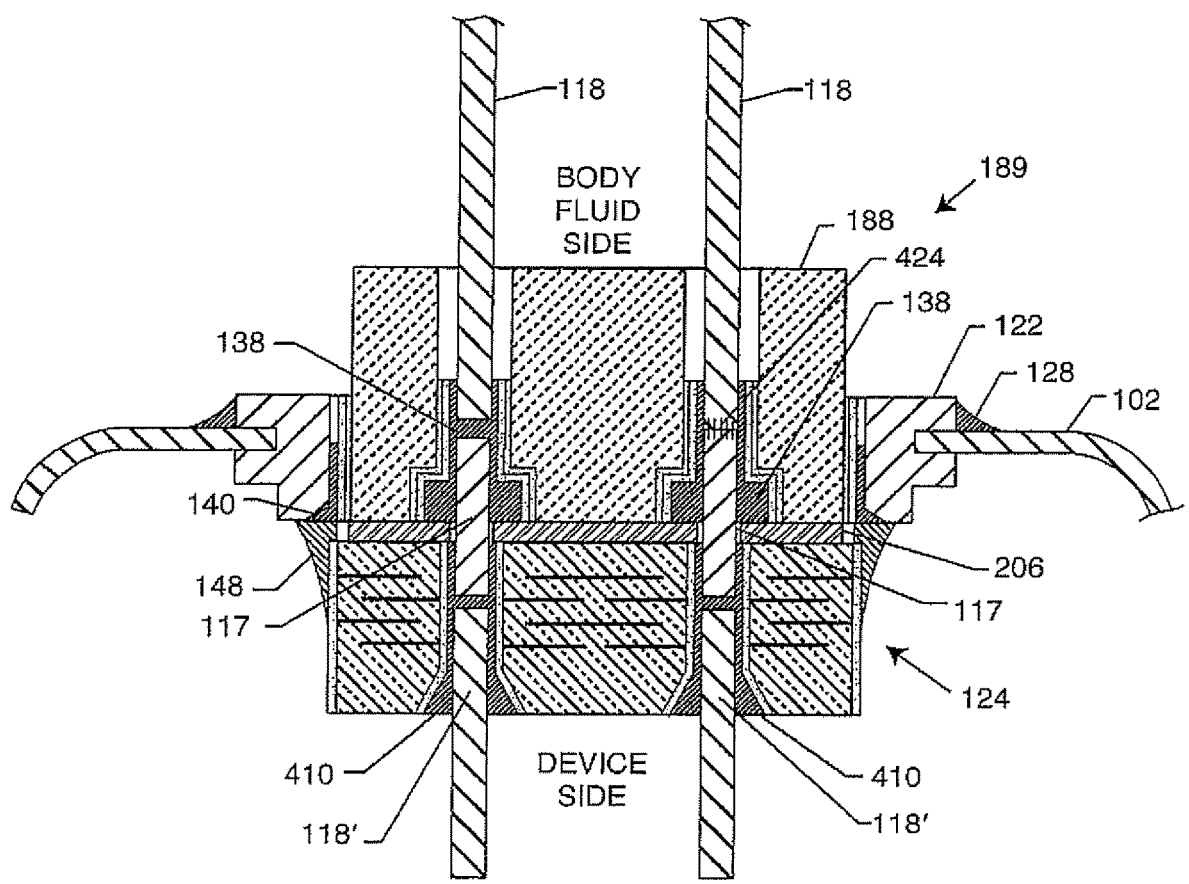
FIG. 23 is the same as FIG. 8, except that the low cost leadwires, instead of being stranded, are solid wire stubs.

FIG. 23 is the same as FIG. 8, except that the low cost leadwires 118', instead of being stranded, are solid wire stubs. The lengths of these leadwire stubs 118' vary in length below the feedthrough capacitor 124 in accordance with the application. For example, if the customer was going to install a very thin flex cable to make the connection between leadwires 118' and a circuit board 126 (not shown), then the leadwires 118' need not stick out very far. However, if a circuit board was being placed adjacent the feedthrough capacitor 124 with via holes (not shown), then it might be necessary to make the leadwire stubs 118' a little longer.

Figure 24:
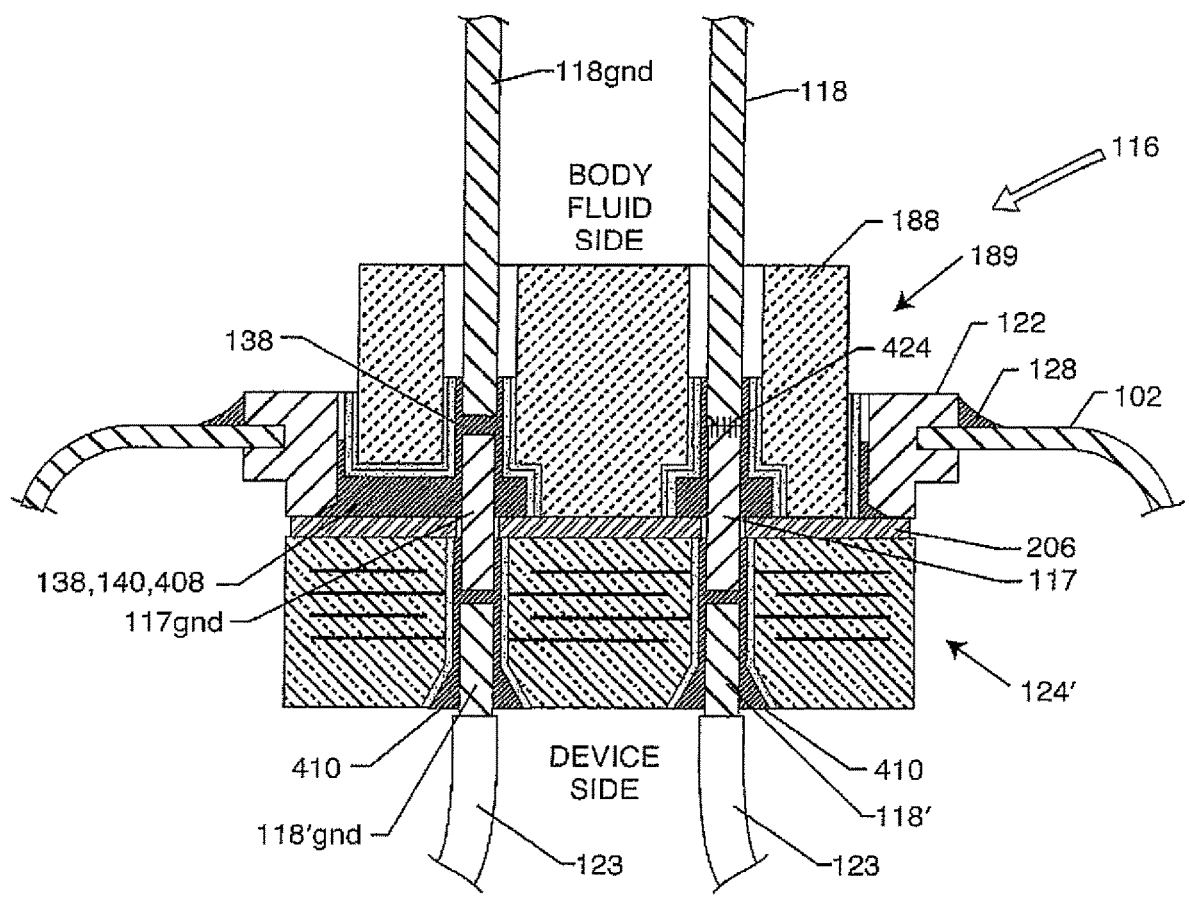
FIG. 24 is similar to FIG. 8, but now shows a gold braze moat electrically coupling the internal ground pin and the ferrule.

FIG. 24 seems similar to FIG. 8, but it also incorporates all the important advantages previously described for internally grounded capacitors shown in FIGS. 5, 6, 7 and 7A. Referring back to FIG. 6, one can see that an internal ground pin 118gnd was provided by co-brazing it into a peninsula 139 of ferrule 122. Instead of machining a peninsula 139 out of the titanium ferrule, a gold braze moat 138, 140, 408 is provided, wherein the brazes 138 and 140 are connected by the braze moat 408. One will appreciate that when viewed isometrically, this gold braze moat could have the very same appearance as a peninsula 139 as previously described in FIG. 6. One will appreciate that this peninsula could have rounded or square edges or the like. (In other words, it need not look identical to that previously illustrated in FIG. 6). Also, there could be a number of these peninsulas, particularly for a long, rectangular part in order to provide a low impedance connection to the feedthrough capacitor internal ground electrode plates. It will also be appreciated that these peninsulas could alternate along the left and right sides of a long rectangular internally grounded feedthrough capacitor. Again, this is in order to make sure that the impedance of the internal ground electrode plate are kept low, such that a high level of filter performance known as insertion loss can be achieved for each active pin. Referring back to FIG. 24, one will see that leadwire 118gnd has been extended into the body fluid side. As previously noted, typically it is not necessary to provide a grounded lead on the body fluid side. However, for certain AIMD abandoned lead port applications, for magnetic resonance imaging, a ground lead provided to the header block could be a very convenient way of dissipating energy from an abandoned lead or a defective lead. For a more thorough explanation, one is referred to U.S. Patent Publication 2014/024,3944, entitled HEADER BLOCK FOR AN AIMD WITH AN ABANDONED LEAD CONNECTOR CAVITY, the contents of which are incorporated herein by reference. The feedthrough capacitor 124 of FIG. 24 is internally grounded, as previously described in FIGS. 5, 6 and 7. It also has all of the intended advantages previously described in FIGS. 5, 6 and 7. Referring to FIG. 8, one can see that the capacitor outside diameter metallization 132 has been completely eliminated. The capacitor outside diameter or perimeter electrical connection 148 to the ferrule has also been completely eliminated. As previously described, not only does this reduce many expensive manufacturing operations and eliminate expensive materials, but it also allows the capacitor body 124 to mechanically float from the ferrule 122. This is important during subsequent customer laser welding 128 of the filtered feedthrough subassembly 189 into the AIMD housing 102 as illustrated in FIG. 8. The capacitor 124 will be much less sensitive to the heat pulse (thermal shock) created by this laser welding 128 since it is not thermally isolated and also mechanically isolated. In other words, there are mismatches in the thermal coefficient of expansion of the ferrule 122 and the ceramic dielectric 124 itself. The insulative washer 206 is preferably a thin washer, which is somewhat flexible; thereby, mechanically isolating the capacitor even further. In an embodiment, the insulative washer 206 would comprise an adhesive washer of polyimide. Polyimides form ring molecules, which are very stress absorbing as opposed to epoxies, which form very long chain molecules. Accordingly, a polyimide washer 206 would be very stress absorbing. On the device side, as shown in FIG. 24, one can see a low cost ground leadwire 118'gnd, which is routed to a circuit board (not shown). This ground wire 118'gnd is optional, but does provide a very convenient way of providing an AIMD housing ground 102 for the circuit board electronics. This is important where the can is to be used as an electrode, perhaps an implantable defibrillator application. In the case where the hermetic seal terminal subassembly 189 and the corresponding internally grounded feedthrough capacitor are long and rectangular (for example, a 12-pin device), then multiple ground pins 117gnd would be required. This would result in multiple peninsulas 138, 140, 408 that accomplish a low impedance electrical grounding of pin 117gnd to ferrule 122. Each one of these multiple locations could be associated with a device side low cost ground lead 118'gnd, however, typically, only one such wire 118'gnd is required to connect to a circuit board ground trace (not shown). In other words, if there were multiple ground pins 117gnd, typically, in only one location would there be a ground leadwire 118'gnd connected to the circuit board and the other feedthrough capacitor grounded via holes would simply be filled with solder without any leadwire directed to the device side at all.

Referring once again to FIG. 24, in comparing it to the prior art, as illustrated in FIG. 2, one can see that there are many advantages. Some of these advantages include: 1) elimination of the expensive platinum or palladium leadwires 118' that extend from the circuit board 126 to the device side of the feedthrough capacitor 124 with replacement low cost leadwires, such as tin-copper or insulated tin-copper; 2) elimination of the relatively expensive electrical connection material 148 shown in FIG. 4B, which in the prior art generally is a thermal-setting conductive polyimide; 3) elimination of the outside capacitor metallization 132. By replacing the rather lengthy leadwires 118 with the short pins 117, one has also designed the device of FIG. 24 for robotic assembly (automation). A robot can place the adhesive washer 206 over the short pins 117 and a robot can also place the feedthrough capacitor 124. The solder preforms 410 could either be threaded by robot or by hand over leadwires 118' or then inserted into the feedthrough capacitor via holes as shown. Then either a conveyor belt or a batch process is used to reflow the solder preform without the need for repetitive processes. It has been found through experimentation that the manufacturing yield of the product, as illustrated in FIG. 24, is in the high 99% range. This is an increase in manufacturing yield of greater than 5% compared to the prior art technology illustrated in FIGS. 4A and 4B. Another important advantage that is not really apparent from FIG. 24 is that it is completely and easily reworkable. The most expensive subcomponent in FIG. 24 is the hermetic seal subassembly 189. It has gold brazes, which are expensive; sputtering, which is expensive: and an alumina insulator, which is expensive. In addition, the ferrule itself 122 tends to be very expensive. It is common practice after the subassembly 116 is formed to do extensive thermal, mechanical and electrical testing before this subassembly 116 is shipped to a customer for installation into an AIMD housing 102. This includes elevated temperature voltage application otherwise known as burn-in and the like. There is usually some infant mortality in the capacitor population 124', meaning that there is a yield associated with this high reliability electrical and mechanical pre-screening. If the capacitor 124 does fail electrically or fails one of its insulation resistance tests, it is easily removable by simply heating it up. In other words, all one has to do is reflow the solder preform 410 and then remove the capacitor from the insulative washer 206 and simply install a new feedthrough capacitor and reuse the hermetic seal subassembly. This is an enormous advantage of the present invention.

Figure 24A:
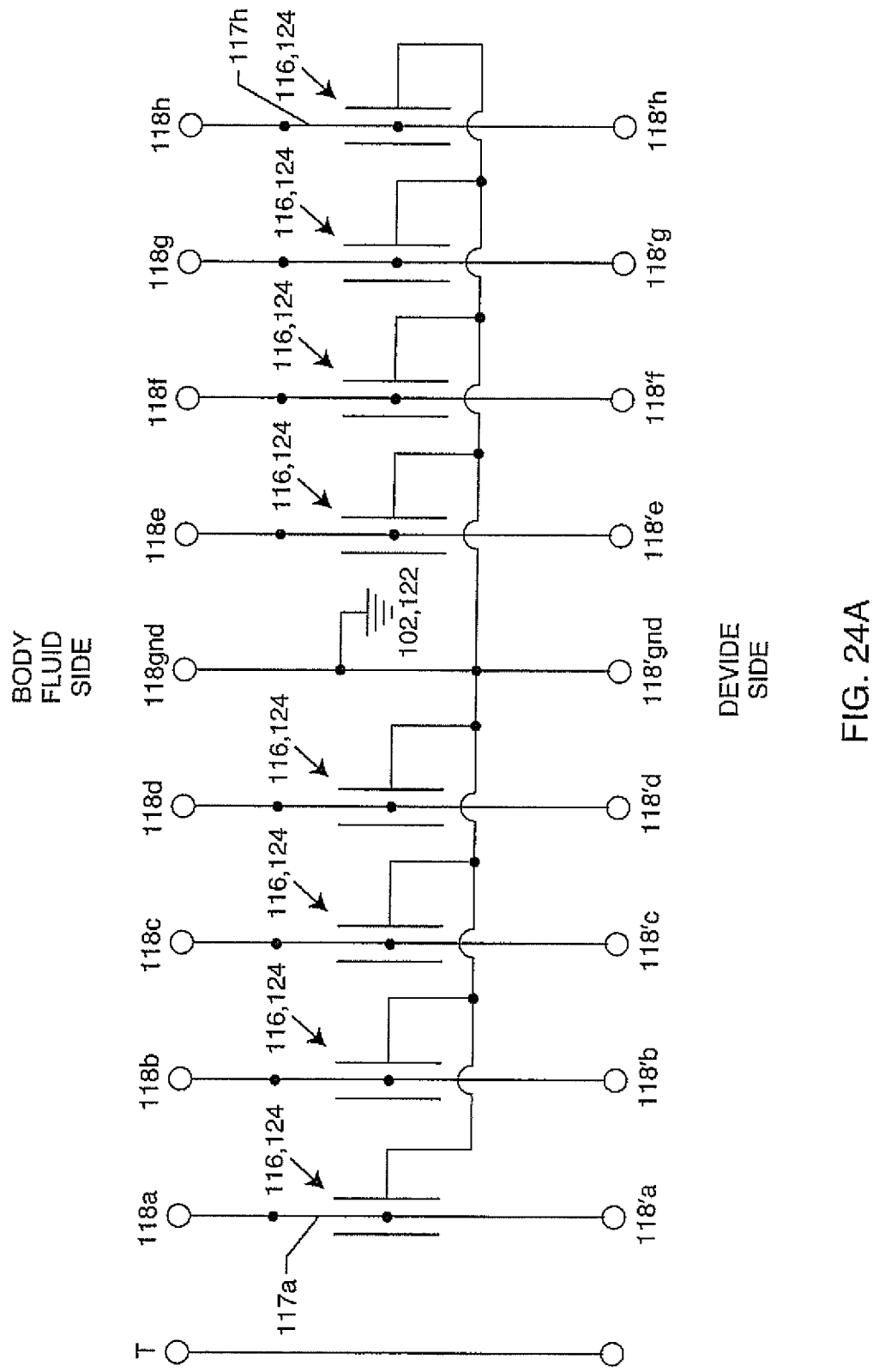
FIG. 24A is one possible schematic diagram of the filtered feedthrough assembly of FIG. 24.

Referring once again to FIG. 2 and the length of device side leadwires 118', one can appreciate why it has never been possible to automate the placement onto the hermetic seal subassembly 189, the feedthrough capacitor insulation washer 206 and the feedthrough capacitor 124 itself. It is because the device side leadwires are so long that they are not rigid and it is literally impossible to keep the tolerance such that they will point perfectly straight. On the other hand, referring to FIG. 24, one can see that the relatively short pins 117 are also pointing straight and rigid. Accordingly, one can appreciate that the assembly of FIG. 24 is readily built by robots and is completely designed for automation. It is only the last step, which involves placement of low cost leadwires 118' that a human hand may be required FIG. 24A is one possible schematic diagram of the filtered feedthrough assembly 116 of FIG. 24. Referring to FIG. 24A, one can see that the ground pin 118'gnd extends from the body fluid side all the way to the device side. One will also appreciate that any number of active leadwires 118' are possible from monopolar to bipolar to tripolar . . . all the way to "n" number of active leads. One will also appreciate that the telemetry pin T is optional or may even embody a multiplicity of RF telemetry pins T. In general, the telemetry pin or telemetry pins are not associated with a feedthrough capacitor active electrode 116, 124.

Figure 24B:
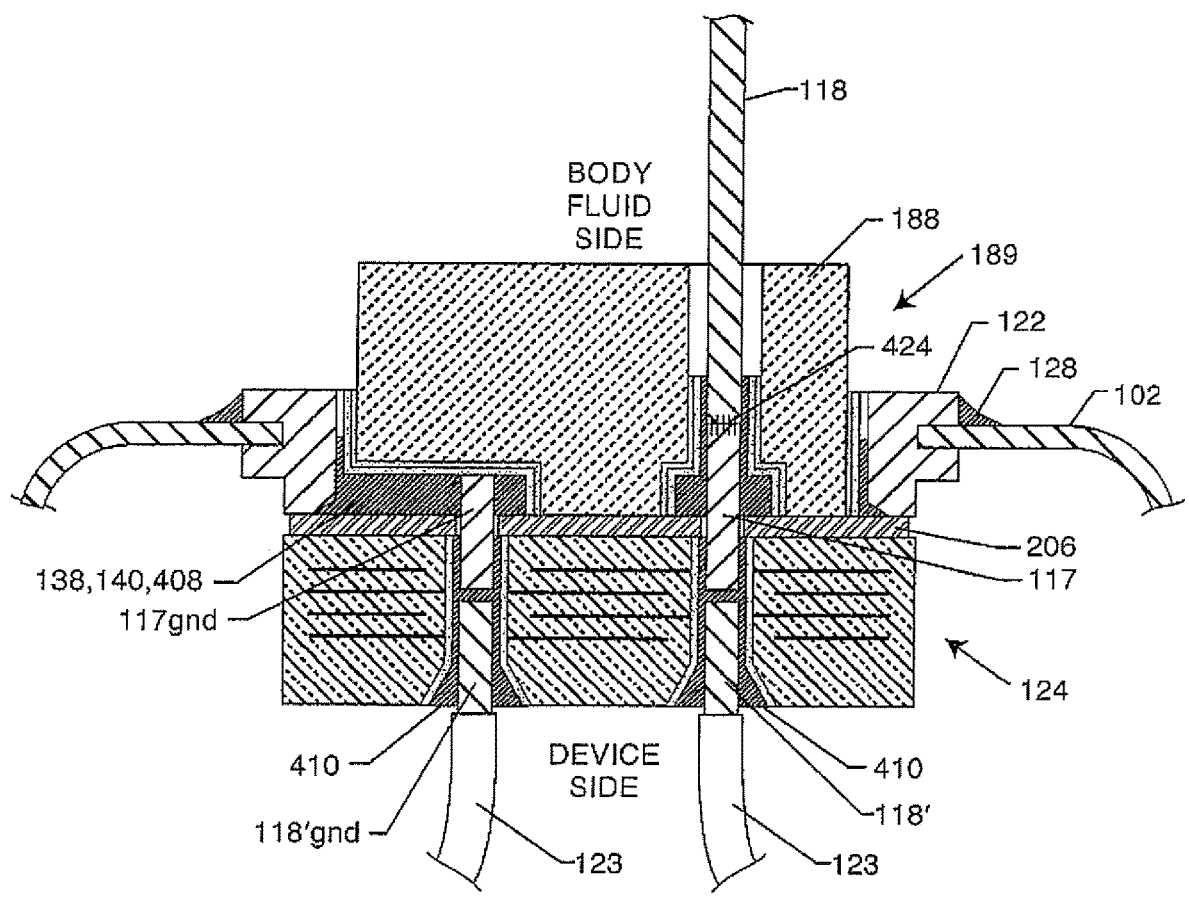
FIG. 24B is almost the same as FIG. 24, except the body fluid side ground lead has been eliminated.

FIG. 24B is almost the same as FIG. 24, except the body fluid side ground lead 118gnd has been eliminated. In most AIMD applications, it is not necessary to provide an implanted lead conductor that has the same potential as the AIMD housing 102. Referring once again to FIG. 24B, one can see that the gold braze preform 138, 140, 408 has covered the top on the body fluid side of the short lead pin 117gnd. Referring once again to FIG. 24B, one can see that the schematic previously described in FIG. 7A could apply. Referring to FIG. 7A, one notes that the device side ground pin 118gnd does not extend to the body fluid side. Again, any number of active pins are possible and the telemetry pin is optional.

Figure 24C:
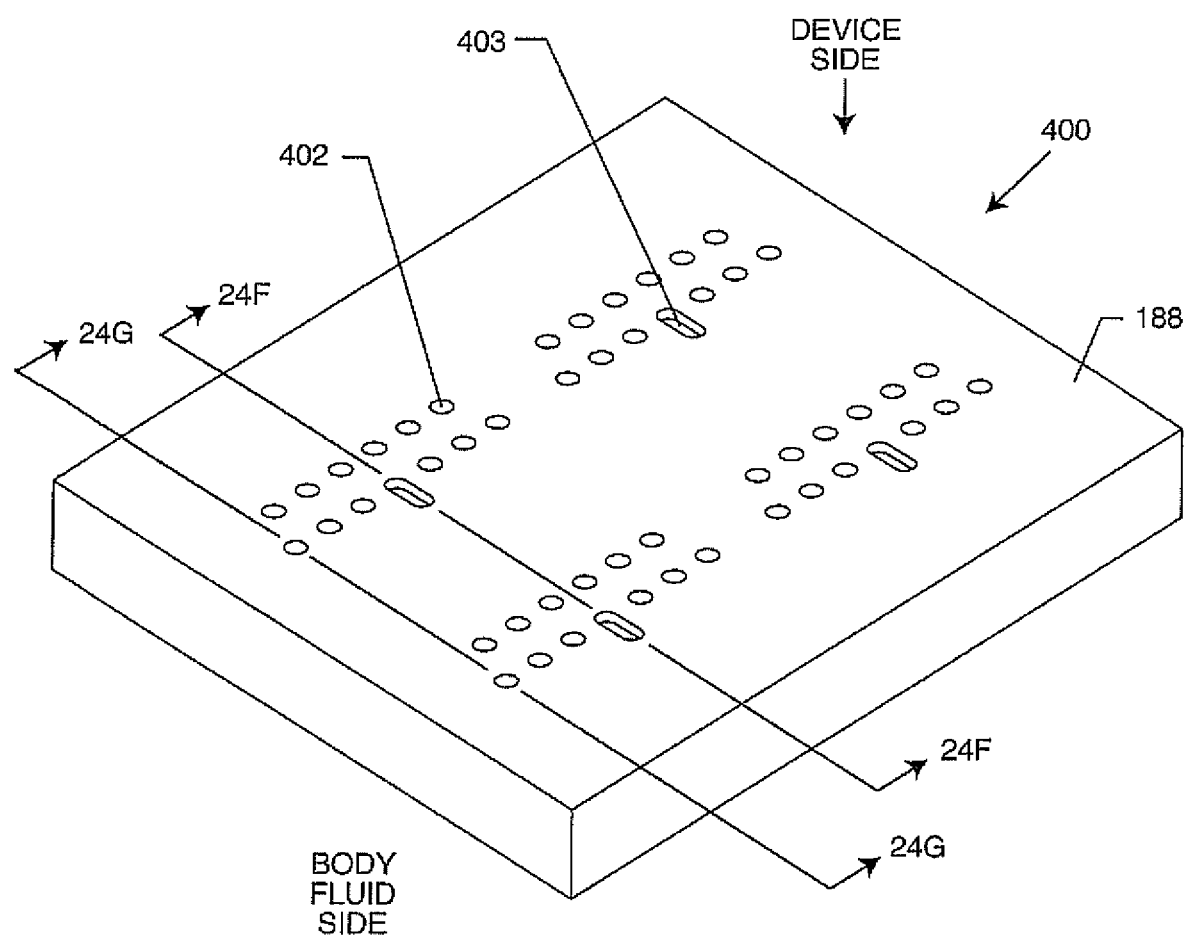
FIG. 24C is a perspective view of a green ceramic bar illustrating that four hermetic insulators are disposed on the bar.

FIG. 24C illustrates a green ceramic bar 188 illustrating that four hermetic insulators are disposed on the bar. It will be appreciated that larger bars may include many more insulators, such as 10, 100 or "n" insulators. Referring once again to FIG. 24C, one can see that in the green bar there are holes 402 that are formed by drilling, punching or equipment operations. There is also a mil-slot 403 as indicated. It should be stated that a green bar includes the alumina ceramic and binders and solvents. The green bar is easily handled, molded, machined, etc. If one were to grasp the bar of FIG. 24C, one could flex it back and forth somewhat. Prior to sintering, it's important to remove the four separate insulator structures, as will be further explained.

Figure 24D:
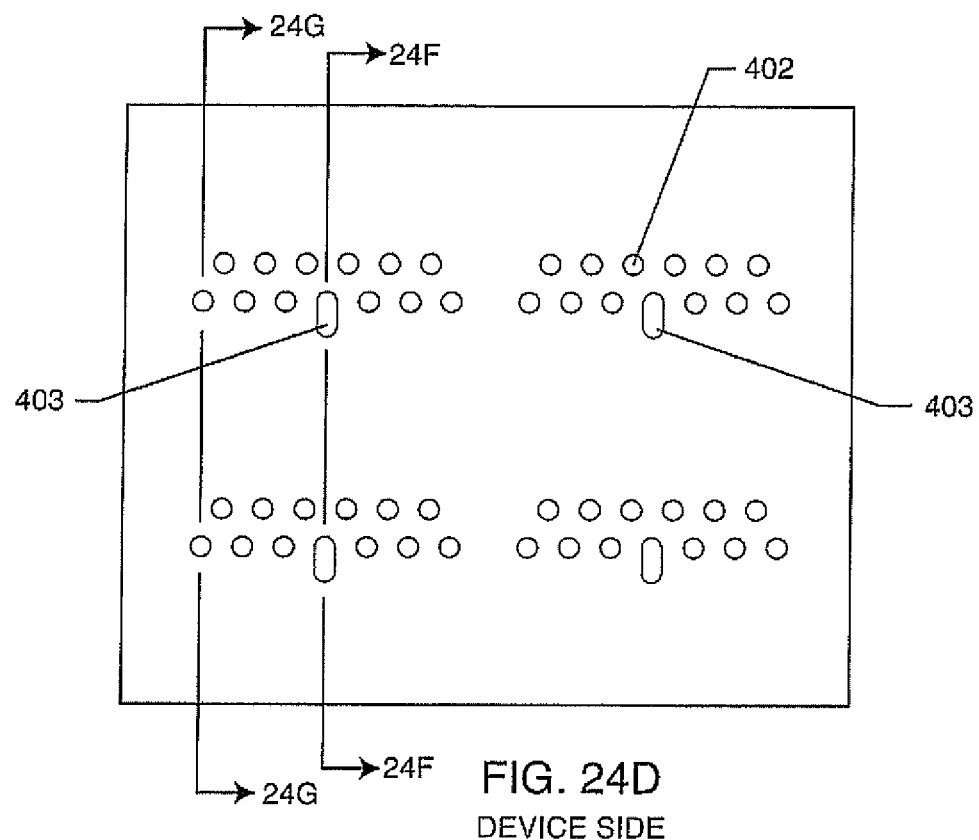
FIG. 24D is a top view of the device side of the green ceramic bar of FIG. 24C.

FIG. 24D illustrates the top view of the device side of the bar of FIG. 24C.

Figure 24E:
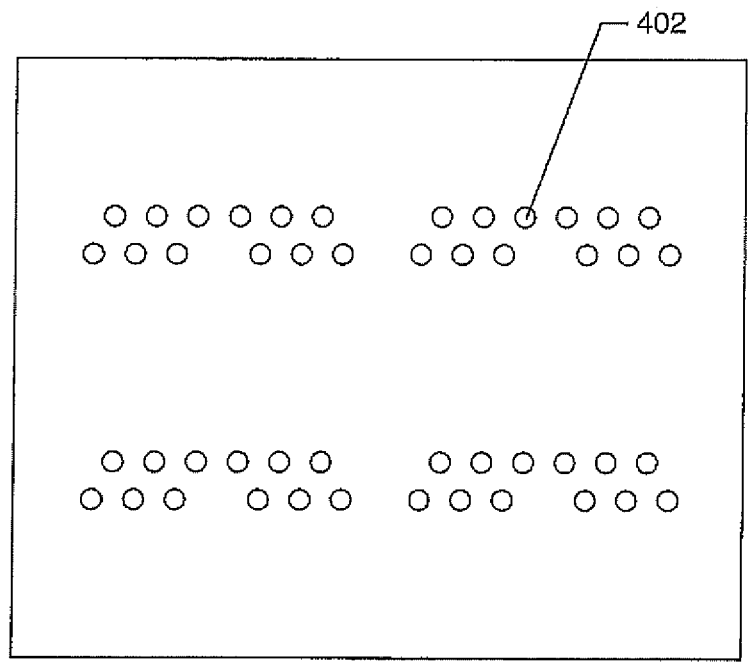
FIG. 24E is a top view of the body fluid side of the green ceramic bar of FIG. 24C.

FIG. 24E illustrates the opposite side of the green bar of FIG. 24C. The shallow slots 403 do not appear on the body fluid side.

Figure 24F:
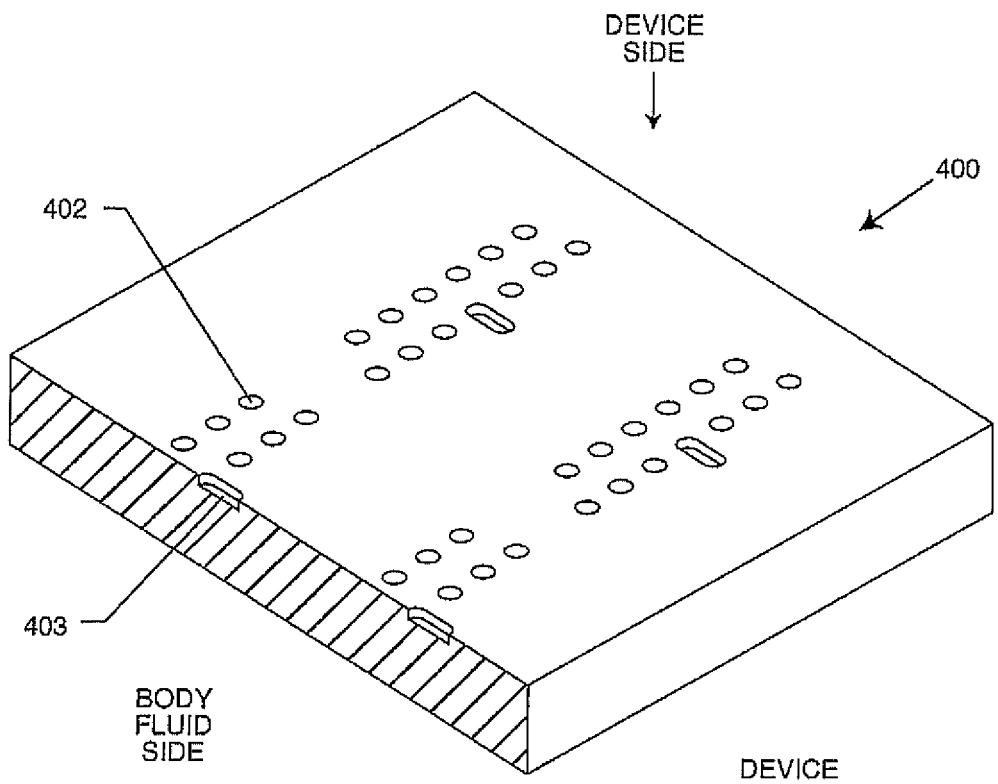
FIG. 24F is a perspective sectional view taken along lines 24F-24F of FIG. 24D.

FIG. 24F is taken from section 24F-24F from FIG. 24D illustrating the slot 403 in cross-section. As will be further explained, the slot 403 becomes a very important and low cost way of providing for internal ground connection to an internally grounded feedthrough capacitor.

Figure 24G:
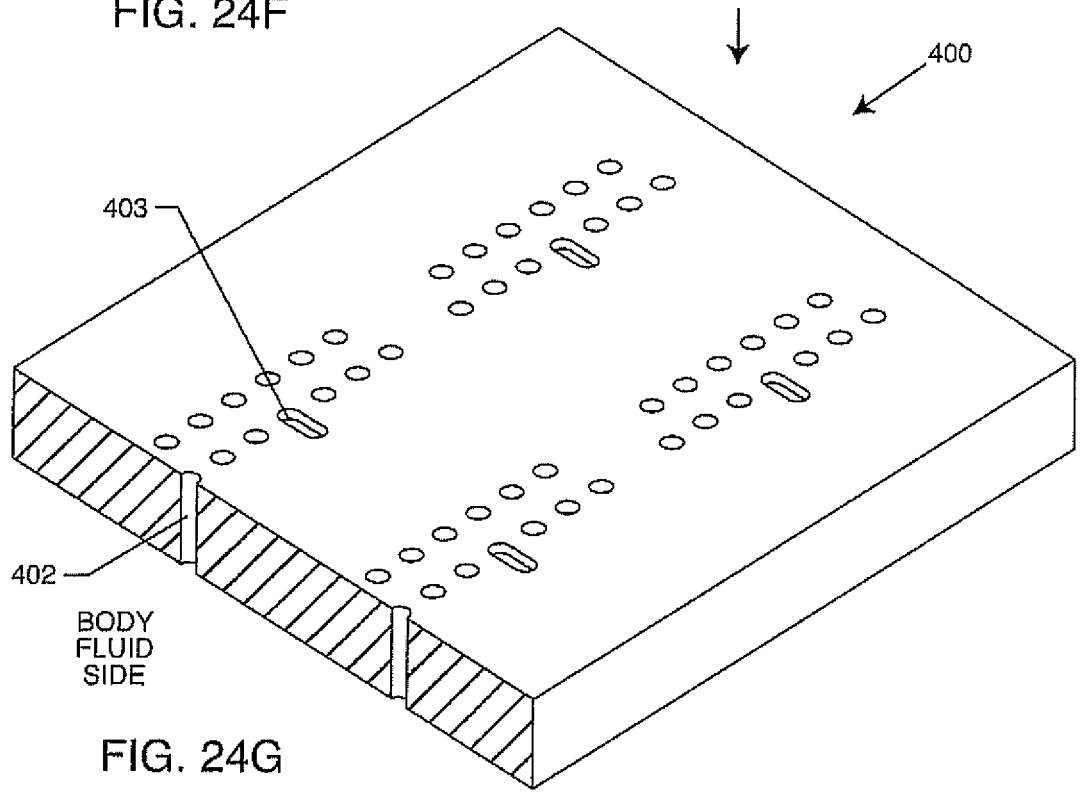
FIG. 24G is a perspective sectional view taken along lines 24G-24G of FIG. 24D.

FIG. 24G is taken from section 24G-24G from FIG. 24D illustrating the cross-section of one of the holes 402.

Figure 24H:
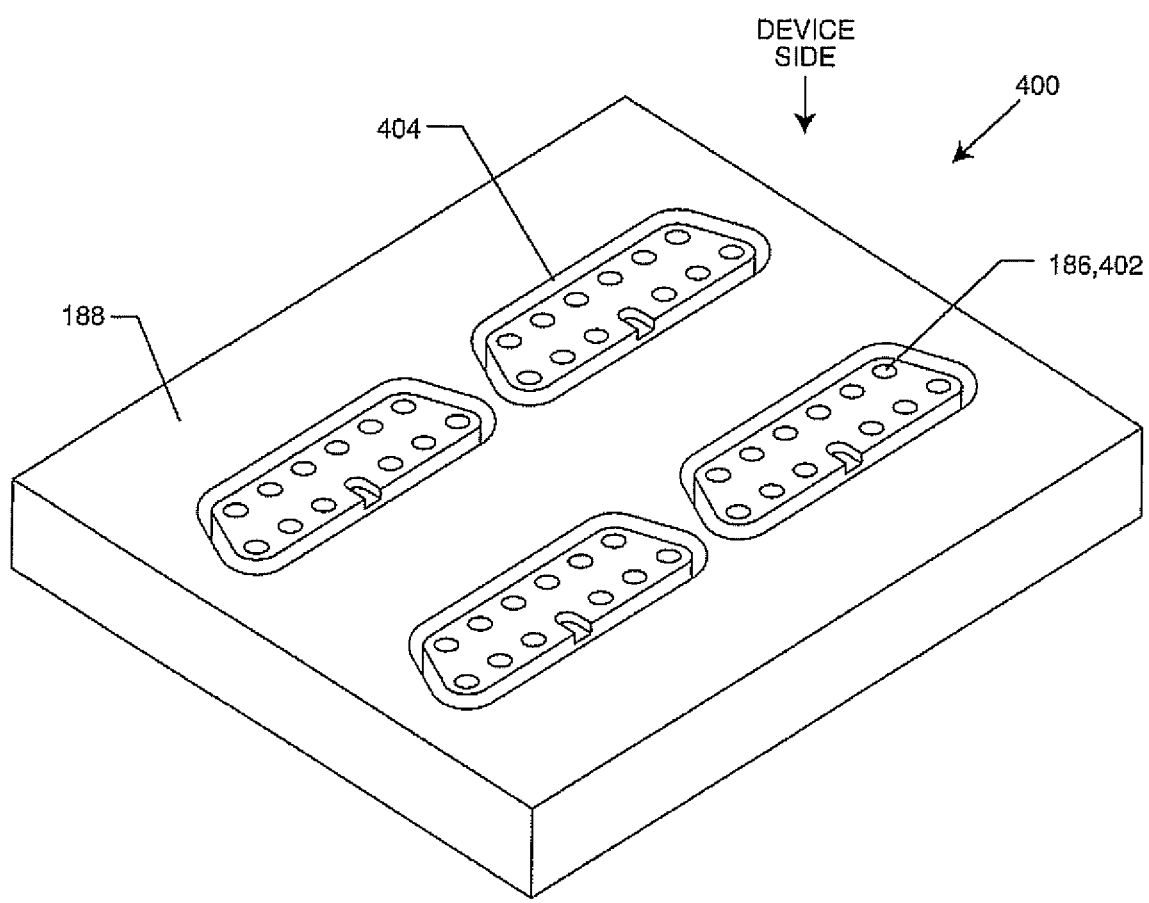
FIG. 24H is a perspective similar to FIG. 24C now showing the four hermetic insulators being partially cut from the bar.

FIG. 24H illustrates the green bar of FIG. 24C with a mil-punched or cut braceway 404. This shows each one of the four hermetic seal insulators about to be cut out of the overall green bar 400. After the operation of FIG. 24H is completed, we now have four separate individual insulators that are ready for sintering. In general, sintering of these alumina ceramic insulators would be accomplished by a binder bake-out in which the temperatures are fully raised until solvents and binders are released and then the sintering process causes the green alumina ceramic to become fired into a hard, monolithic structure. In general, alumina ceramic insulators for human implant applications have to be of very high purity so that they can withstand exposure on the body fluid side. Purities of >99% alumina are typical in the industry. Referring back to FIG. 24H, the four insulators are shown for illustration purposes only. It will be appreciated that the bars 400 can be of any size and contain any number of insulators.

Figure 24I:
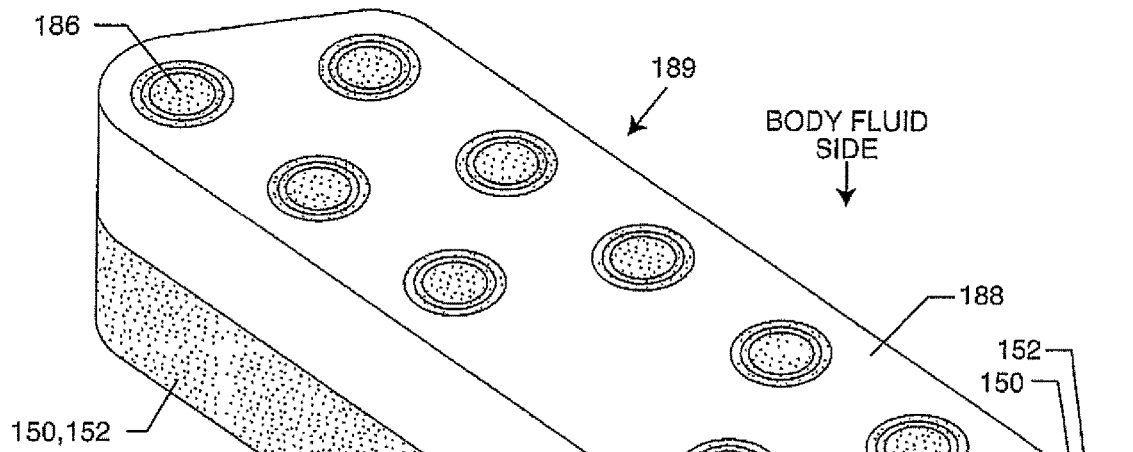
FIG. 24I is a perspective view of the body fluid side of an insulator of the present invention.

FIG. 24I illustrates one of the four insulators of FIG. 24H after it's been sintered and sputtered. Sputter layers 150 and 152 include a wetting and an adhesion layer such that the alumina insulator 188 will accept a gold braze. The inside of the twelve through-holes 186 have also been metallized. Referring back to FIG. 24I, the body fluid side is directed upward.

Figure 24J:
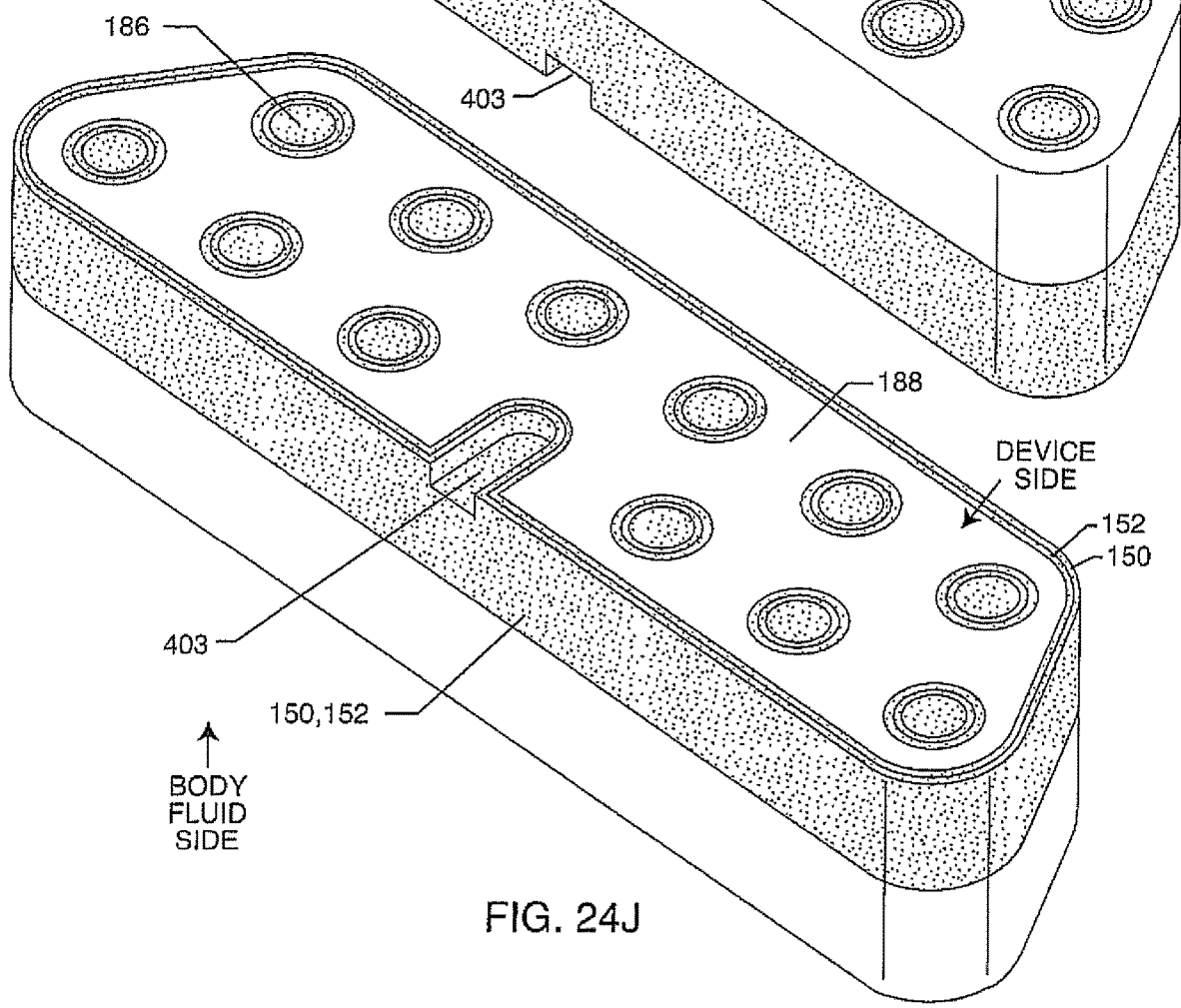
FIG. 24J is a perspective view of the device side of the insulator of FIG. 24I.

FIG. 24J illustrates the same insulator as FIG. 24I, except in this case, the device side is oriented upward. Importantly, one can see that the slot 403 has also been sputtered or metallized with wetting and adhesion layers 150,152.

Figure 24K:
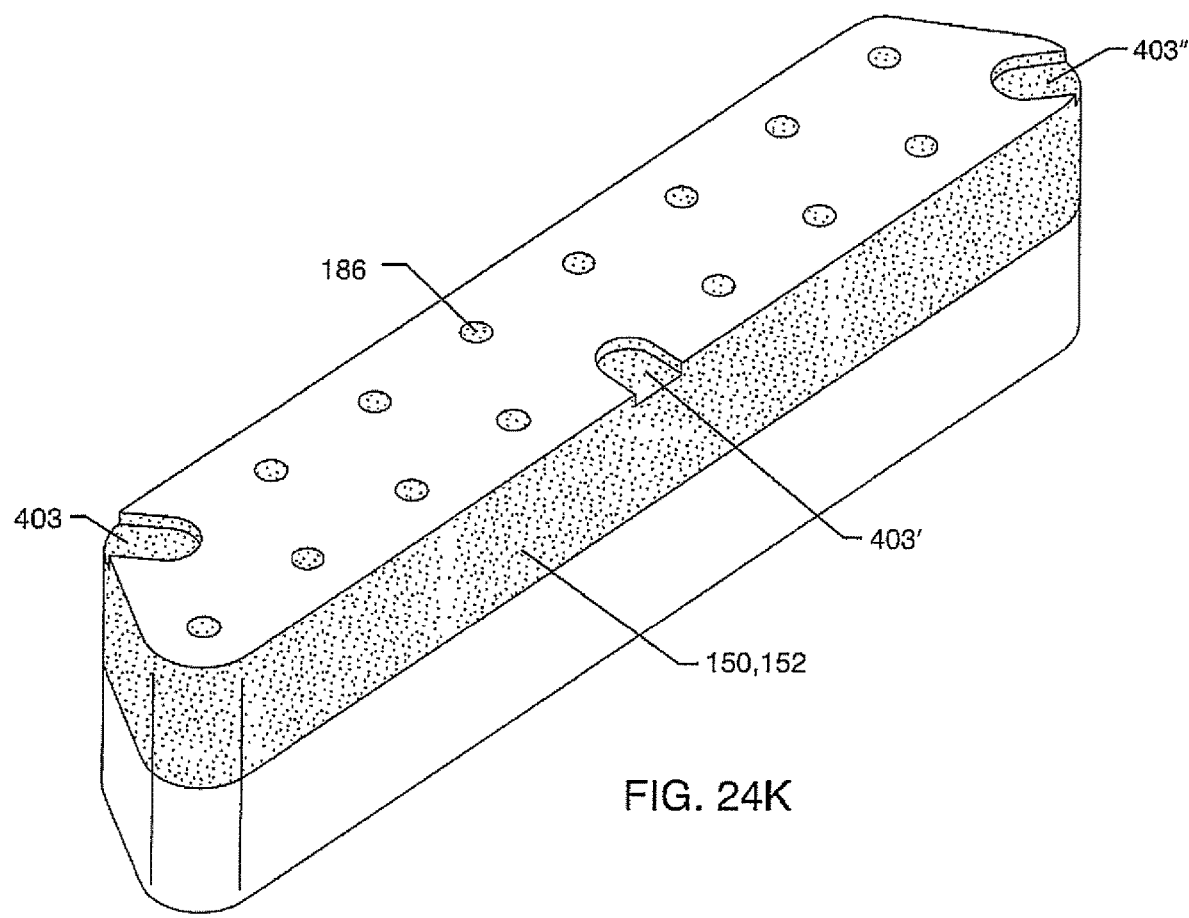
FIG. 24K is very similar to FIG. 24J, but illustrates that more than one slot can be used.

FIG. 24K is very similar to FIG. 24J, but illustrates that more than one slot can be used. In the example shown in FIG. 24K, there are three novel sputter slots 403, 403' and 403". Filter design engineers familiar with internally grounded capacitors will appreciate that it is important to have a ground location relatively close to the active pins or active via holes 186. If one of these holes gets too far from ground, the insertion loss with filter performance will be compromised. Accordingly, it will be appreciated that any number of ground points 403 or ground slots 403 can be provided up to "n" number of ground points.

Figure 24L:
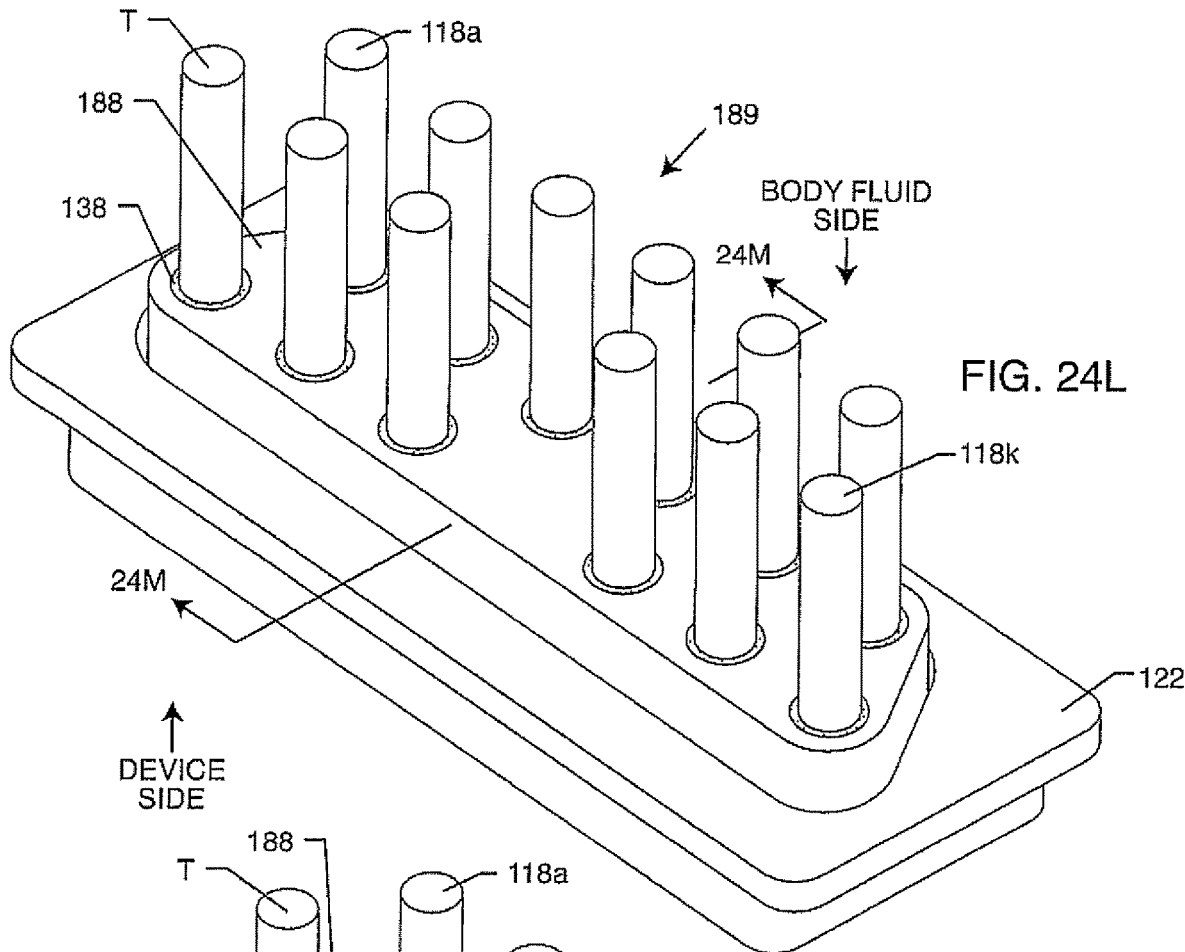
FIG. 24L illustrates the insulator structure of FIG. 24I and FIG. 24J, partially placed into, within or onto a ferrule.

FIG. 24L illustrates the insulator structures illustrated in FIG. 24I and FIG. 24J, placed into, partially within or onto a ferrule 122. A gold braze pre-form 140, 140s is added around the perimeter of the insulator and gold braze preforms 148 are also placed around each of the body fluid side leadwires T and 118A through 118K. In this case, there is a telemetry pin T that will not be filtered and all of the active leadwires 118A through 118K will be filtered.

Figure 24M:
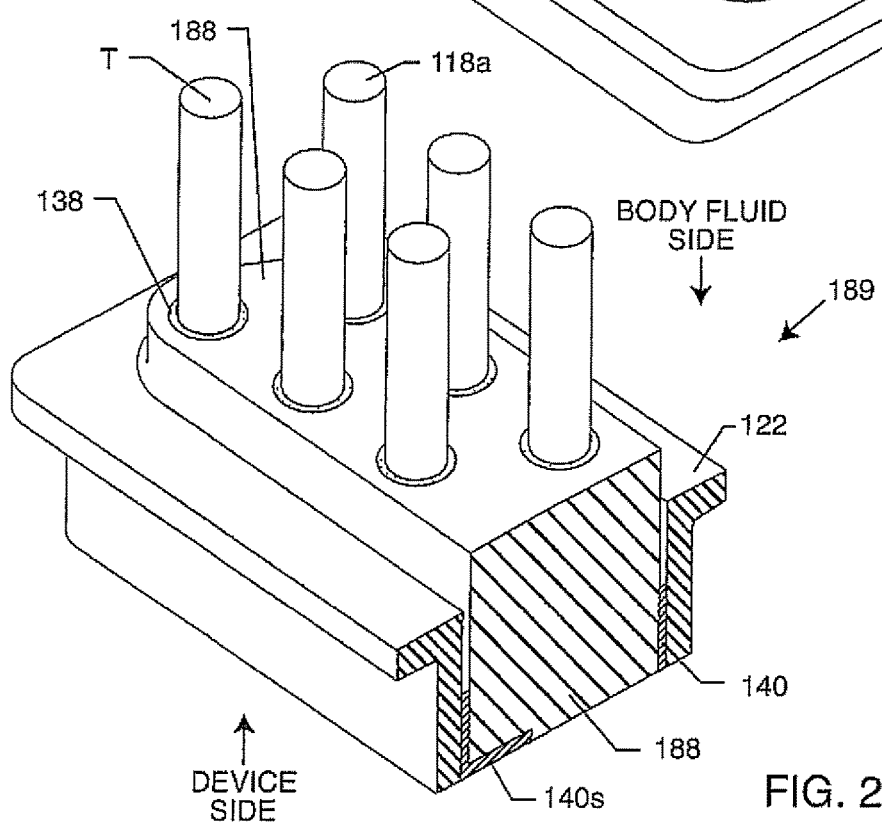
FIG. 24M is a sectional view taken from section 24M-24M from FIG. 24L illustrating the grounding slot in cross-section which comprises a gold braze.

FIG. 24M is a sectional view taken from section 24M-24M from FIG. 24L illustrating the grounding slot 140s in cross-section which comprises a gold braze. As can also be seen, the rest of the insulator perimeter gold braze is formed to ferrule 122. Sputter layers 150 and 152 have been omitted for clarity, but will be appreciated that they would be present. This gold braze 140, 140s forms relatively mechanically robust and hermetic seal between the ferrule and the insulator 188. At the same time, gold braze pre-form 138 around each of the leads form a strong mechanical and hermetic seal between the insulator 188 and each of the leads T,118.

Figure 24N:
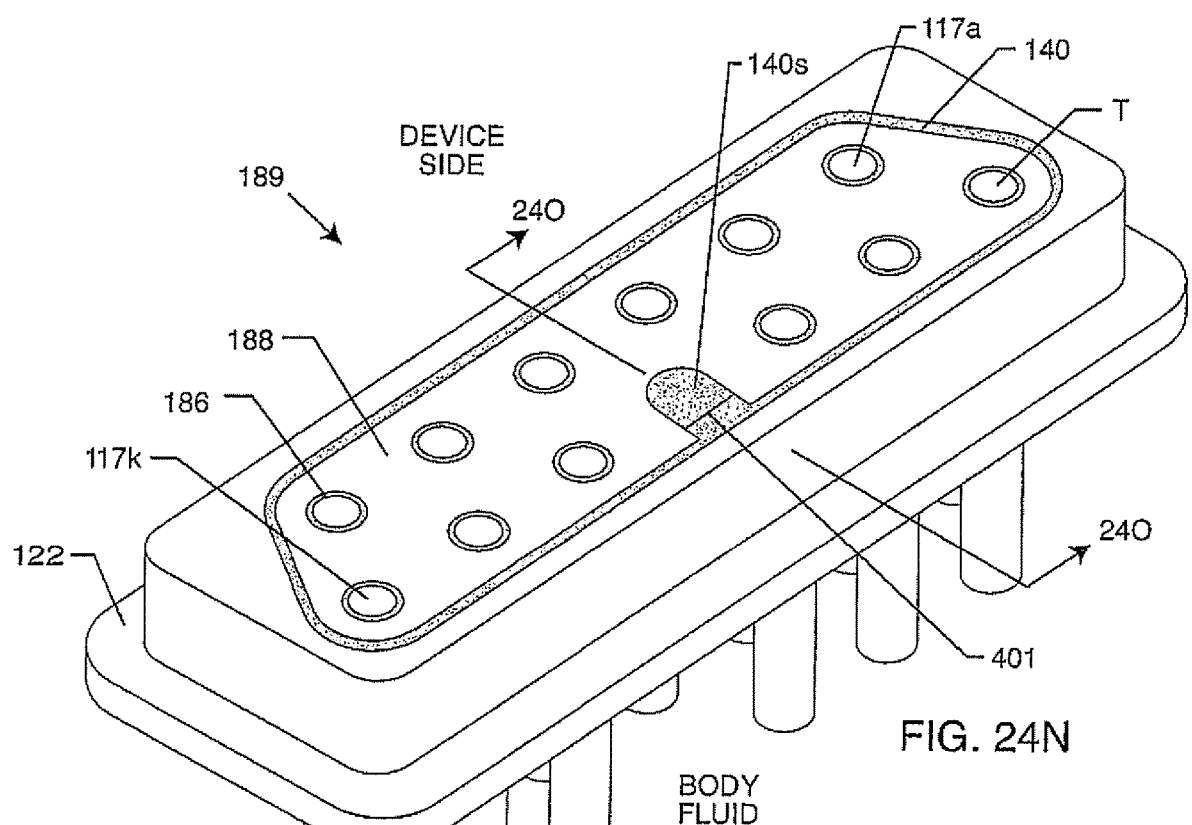
FIG. 24N illustrates the hermetic seal subassembly of FIG. 24 inverted and rotated.

FIG. 24N illustrates the hermetic seal subassembly 189 of FIG. 24 inverted and rotated. In this case, one can see that there are two-part pins in accordance with the present invention, illustrated as 117a through 117k. The telemetry pin can also optionally be a two-part pin in accordance with the present invention. Referring once again to FIG. 24N, one can see the top view of the gold braze pedestal slot 140s. Referring back to FIG. 6, one can see the prior art machined pedestal 139 for convenient attachment of an internally grounded capacitor 124. As will be further described, the gold brazed slot 140s will contact the internally grounded capacitor internal electrode plates. The novel gold braze slot provides a much lower cost convenient alternative to providing a pedestal 139 as previously illustrated in FIG. 6. Referring once again to FIG. 24N, one can see a dashed line 401 that separates the gold braze in the slot 140s from the perimeter gold braze 140. The inventors have found that when one attempts to gold braze both the slot and the full perimeter of the hermetic seal at the same time that gold may flow out of the slot area to where it gets too thin. Accordingly, a two-step process may be used wherein, a pure gold or a higher temperature gold braze is first formed 140 and then in a subsequent gold brazing operation, a lower temperature gold braze or even a lower temperature braze of other materials, like CuSil or TiCuSil, can be placed into the slot area 140f. These materials need not be biocompatible since they are on the device side not the body fluid side. The important thing is that they be highly conductive and resistant to oxides.

Figure 24O:
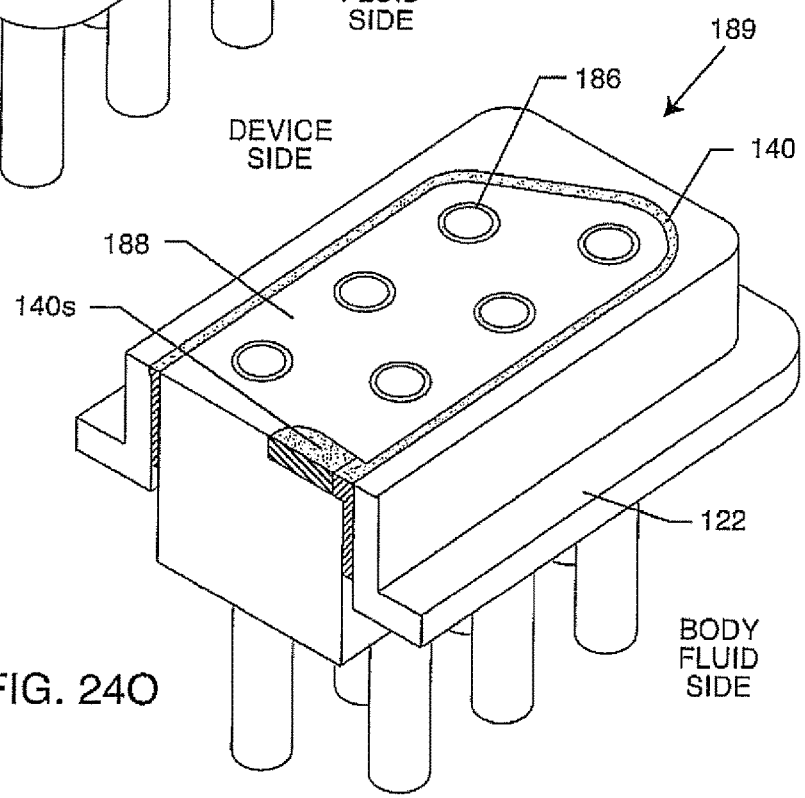
FIG. 24O is a sectional view taken from section 24O-24O from FIG. 24N illustrating the novel grounding slot in cross-section.

FIG. 24O is a sectional view taken from section 24O-24O from FIG. 24N illustrating the novel grounding slot 140s in cross-section.

Figure 24P:
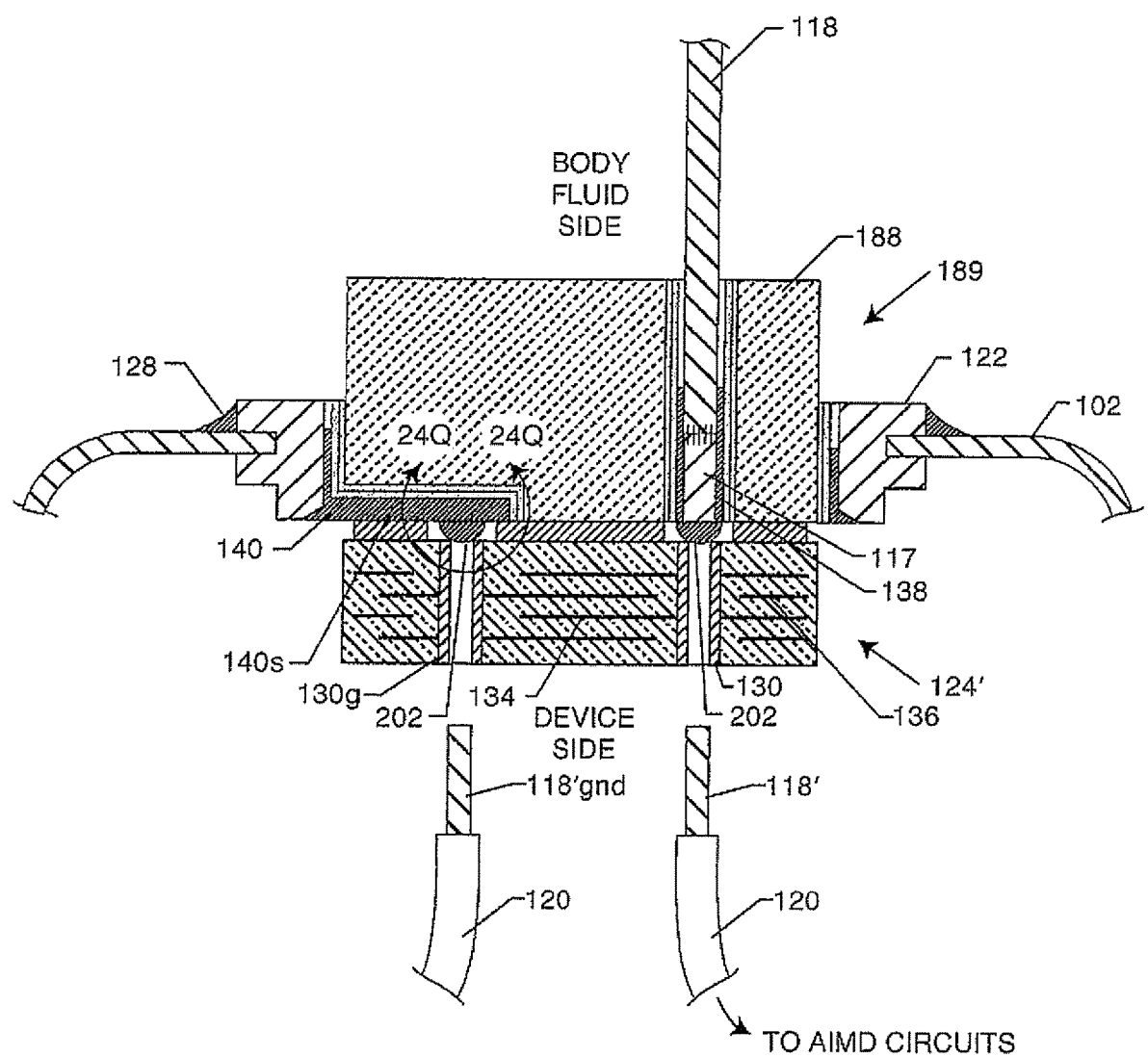
FIG. 24P illustrates an internally grounded capacitor mounted to the hermetic seal subassembly previously illustrated in FIGS. 24N and 24O.

FIG. 24P illustrates an internally grounded capacitor 124' mounted to the hermetic seal subassembly previously illustrated in FIGS. 24N and 24O. The active electrode plates 124 of the internally grounded capacitor 124' are connected to the via hole metallization 130. The ground electrode plates 136 are connected to the ground via hole metallization 130G which is electrically connected to the internally grounded capacitor's ground electrode plate set 136. It is important to note that the ground electrode plate set for internally grounded capacitor does not extend to the outside perimeter or diameter of the capacitor 124'. Instead, the internal grounding is by a BGA, solder or thermal-setting conductive adhesive connection 202 directly to the gold braze slot 140s as shown. The gold braze slot 140s makes a very mechanically robust, but more importantly, a very low resistance connection to the titanium ferrule 122. As previously mentioned, it is important to have connection to a non-oxidized surface. Titanium, such as the titanium of ferrule 122, can form oxides, which can be resistive or semi-conductive. The gold braze 140 burns through these oxides accomplishing a very low impedance electrical connection to the capacitor's ground electrode plates 136. As previously described, depending on the number of active pins and their spacing, a number of novel gold braze slots 140s could be provided, including 'n' number slots as provided as previously illustrated in FIG. 24K elements 403. It should be noted that FIG. 24P is a cross-section taken generally through the insulator of FIG. 24N cutting generally along the line 24O-24O, except that in this case, the section has been altered such that, both the slot 140s and one of the active pins has been picked up. It will be noted that the internally grounded feedthrough capacitor 124' was not illustrated in FIG. 24N, but has been added in cross-section to FIG. 24P.

Referring once again to FIG. 24P, one can see that a device side, very low cost leadwire 118'gnd can be co-connected or co-soldered at the same time that the electrical connection 202 is made. The same is true on the active lead 118,118'. In accordance with the present invention, there is a two-part pin consisting of 118 and 117. In this case, the novel co-brazed or co-welded short pin 117 (platinum, palladium or nickel or the like) is shown flush with the insulator surface, such that an electrical connection 202 can be made, as previously described for the ground connection side including attachment of a device side ground leadwire 118'gnd. In the case of the active pins or active leadwires 118', which will be routed to AIMD electronic circuits or circuit boards, not illustrated. On the body fluid side, in general, there is not a need for a ground pin. So on the body fluid side, as previously described in FIG. 24N, there is a telemetry pin T along with active pins 117a through 117k. Each of these active pins are associated with its own active electrode plates, as previously described in FIG. 5. Referring once again to FIG. 24P, one can see that the hermetic seal subassembly, including the internally grounded feedthrough capacitor 124' has been laser welded 128 into the housing 102 of an active implantable medical device. One can see from the curvature of the housing 102, that in general, the feedthrough capacitor 124 is disposed on the device side, which means that it is contained within the hermetically sealed and overall electromagnetically sealed AIMD housing 102.

Referring now back to FIG. 8 and comparing it to FIG. 24P, one can see some very important advantages of the internally grounded capacitor 124'. In FIG. 8, the conventional feedthrough capacitor 124 has an external metallization or perimeter metallization 132 and a corresponding electrical connection 148. Both of these elements 132 and 148 have been eliminated in FIG. 24P. Elimination of these connections has many advantages, including protection of the relatively sensitive feedthrough capacitor 124' from thermal shocks imposed by laser welding 128 of the completed assembly of the housing of an AIMD.

Figure 24Q:
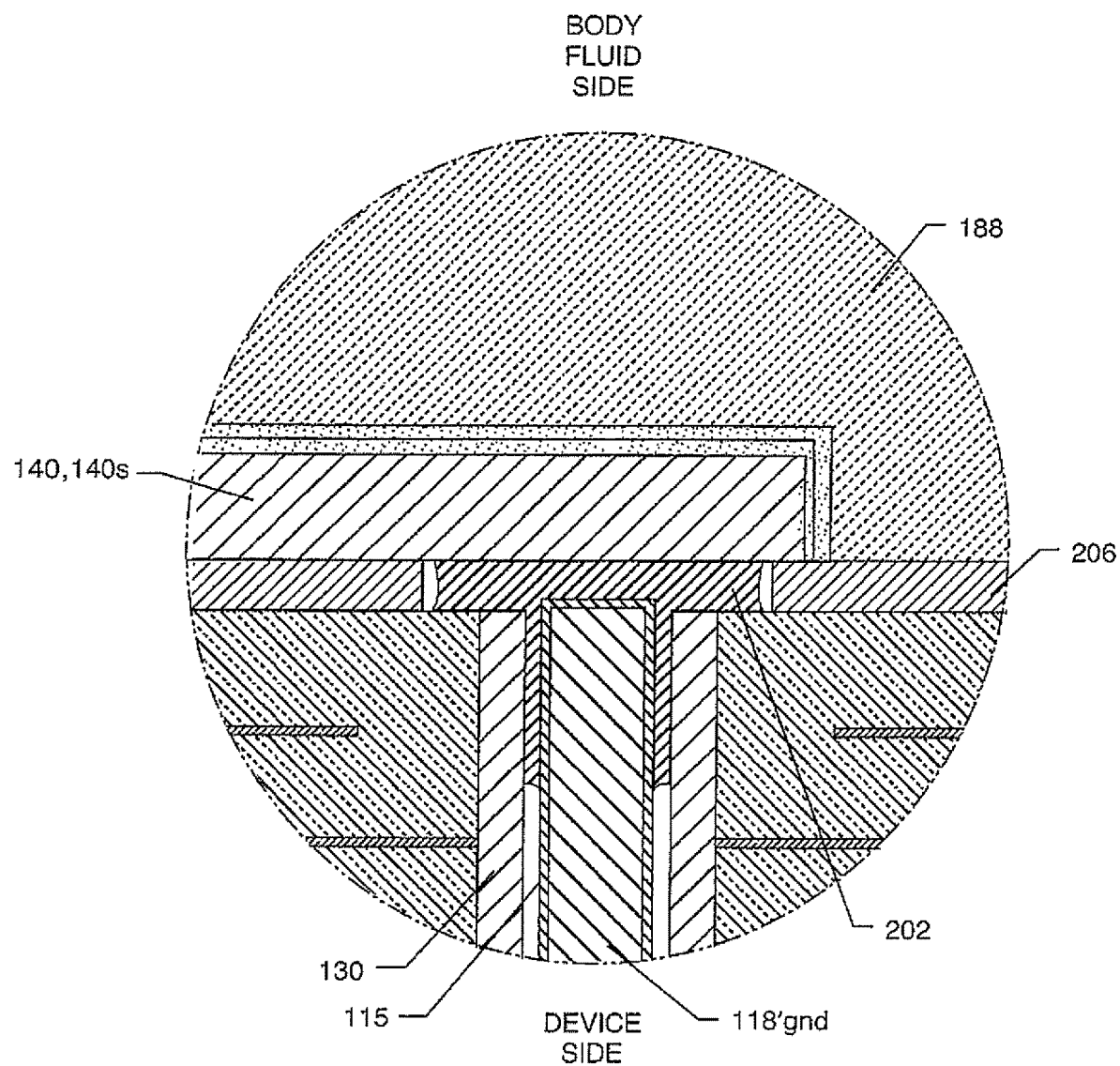
FIG. 24Q is taken from section 24Q-24Q from FIG. 24P illustrating an enlarged view of the internally grounded capacitor's ground connection to the gold braze grounding slot.

FIG. 24Q is taken from section 24Q-24Q from FIG. 24P illustrating a blow-up of the internally grounded capacitor's ground connection to the gold braze grounding slot 140s. One can see that the BGA material, which can be, of course, of solder or of thermal-setting conductive material, has been reflowed such that it makes a strong mechanical and electrical connection both to the gold braze slot 140s and to the device side ground leadwire 118'gnd. Importantly, there is also an electrical connection made at the same time to the capacitor's through hole metallization 130 as shown. As previously described, the low cost leadwire on the device side 118'gnd, will have a very high pull strength since much of the electrical connection material 202 is in shear both to the lead 118'gnd and to metallization surface 130. Also, in this section one can see that the ground leadwire 118'gnd has a tinned surface 115, which helps material 202 flow thereby increasing pull strength and reliability.

Figure 24R:
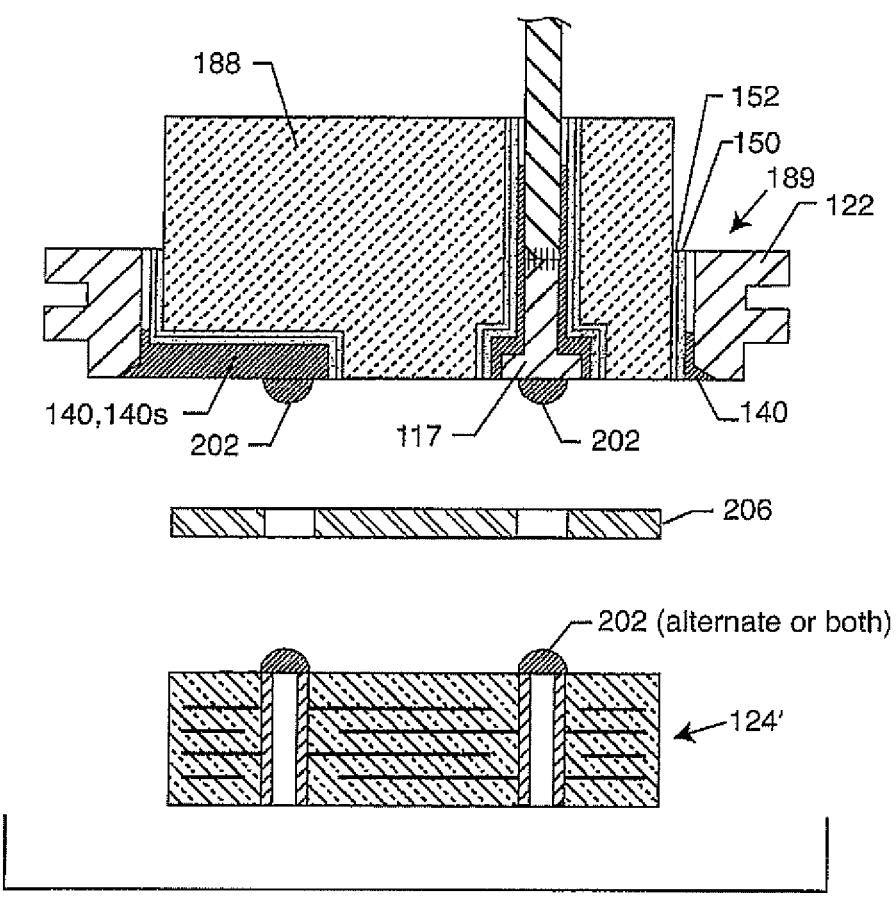
FIG. 24R is an exploded view taken from FIG. 24P illustrating that the BGA connection may be dispensed by a robot.

FIG. 24R is an exploded view taken from FIG. 24P illustrating that the BGA connection 202 may be dispensed by a robot or by human hand on the hermetically sealed insulator 189 or alternatively to the internally grounded feedthrough capacitor 124' or in some embodiments, to both. Shown is an adhesive insulating washer 206. It will be appreciated that these elements will be brought together and co-attached in a high temperature process which bonds in the adhesive of washer 206 and either subsequently or at the same time, reflows solder BGA connection 202 or thermal-setting conductive adhesive or cures thermal-setting conductive adhesive 202.

Figure 24S:
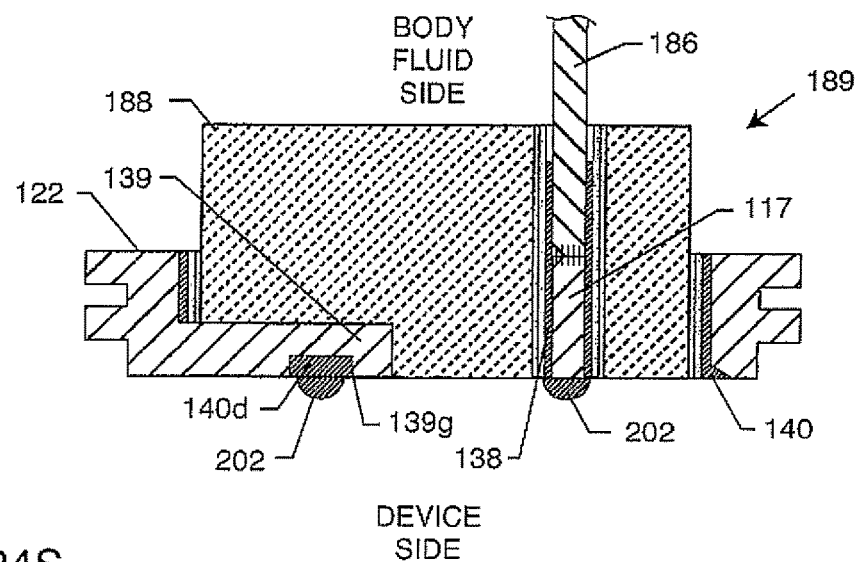
FIG. 24S is similar to FIGS. 24P and 24R, except in this case, instead of a gold braze slot, a peninsula structure, which is very similar to that described in FIG. 6, is shown.
Figure 24T:
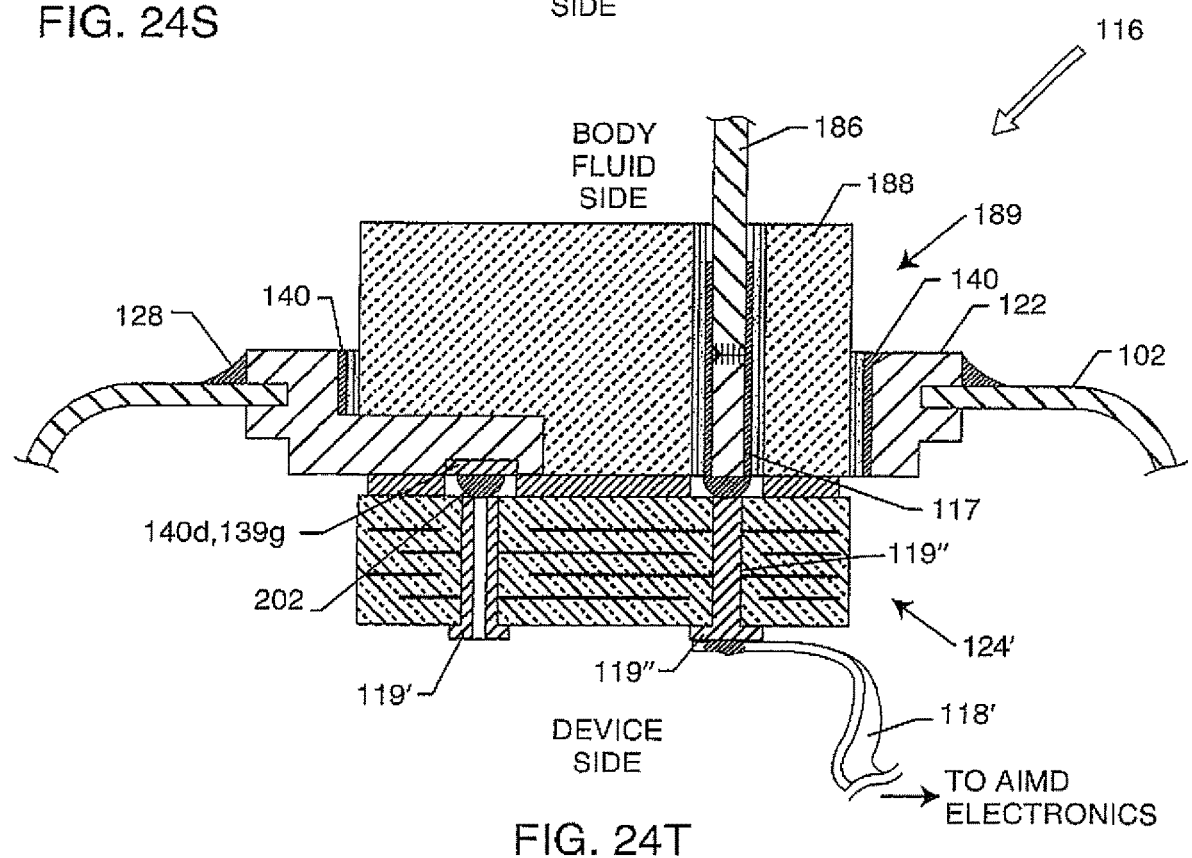
FIG. 24T is similar to FIG. 24S, except now the ferrule is connected to the housing of the active implantable medical device and the capacitor is being mounted to the ferrule and insulator surfaces.

FIG. 24S and FIG. 24T are very similar to FIGS. 24P and 24R, except in this case, instead of a gold braze slot 140s, a peninsula structure 139 is very similar to that described in FIG. 6, is shown. This peninsula structure 139 would generally be machined out of the same block of titanium that also forms the ferrule 122. As had been previously described, titanium can form oxides or even tri-oxides, which can be very resistive. Connecting to titanium could preclude the proper insertion loss (filter performance) of the feedthrough capacitor 124'. Referring once again to FIG. 24S, one can see that there is a novel counter-bore 139g into which a gold braze preform 180d is placed. In general, gold brazed preform 140d would comprise a small dot, a rectangle, a slot or any other shape. Gold braze preform 140d would generally be reflowed in a gold braze furnace at the same time that the insulator 188 gold braze to ferrule 140 is formed and also gold braze 138, which hermetically seals and co-joins device side leadwire 186 to pin 117. Importantly, bold braze 140d provides a non-oxidized surface to which the ground electrical material 202 can be attached.

Referring to FIG. 24T, one can see on the device side of the internally grounded feedthrough capacitor 124', that the capacitor metallization, on the left side, has been extended onto a portion of the top of the device side of the feedthrough capacitor 119'. This is also known as a white-wall tire effect and when a leadwire (not shown) is added, this greatly increases the pull strength. On the right side of the feedthrough capacitor 124' of FIG. 24T, one can see that the capacitor via hole has been completely filled with metallization, including a metallization area on the device side of the feedthrough capacitor 119". This provides a convenient location for soldering, for wire bonding of a ribbon or a round lead 118' that will be routed to AIMD electronics (not shown).

Figure 24U:
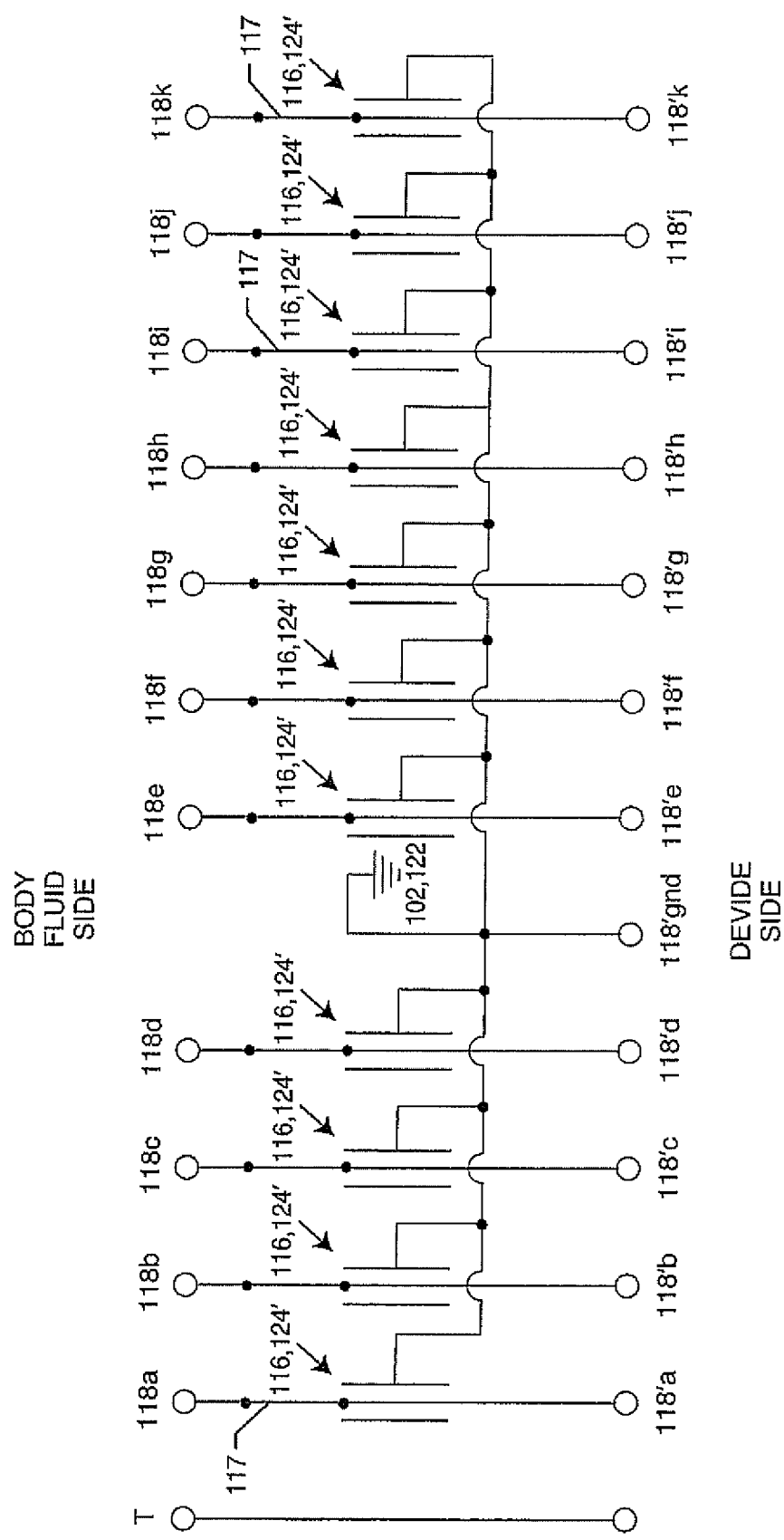
FIG. 24U is the schematic diagram of the internally grounded capacitor which was taught in FIG. 24C to FIG. 24T.

FIG. 24U is the schematic diagram of the internally grounded capacitor which was developed all the way from FIG. 24C all the way inclusive to FIG. 24T.

Figure 25:
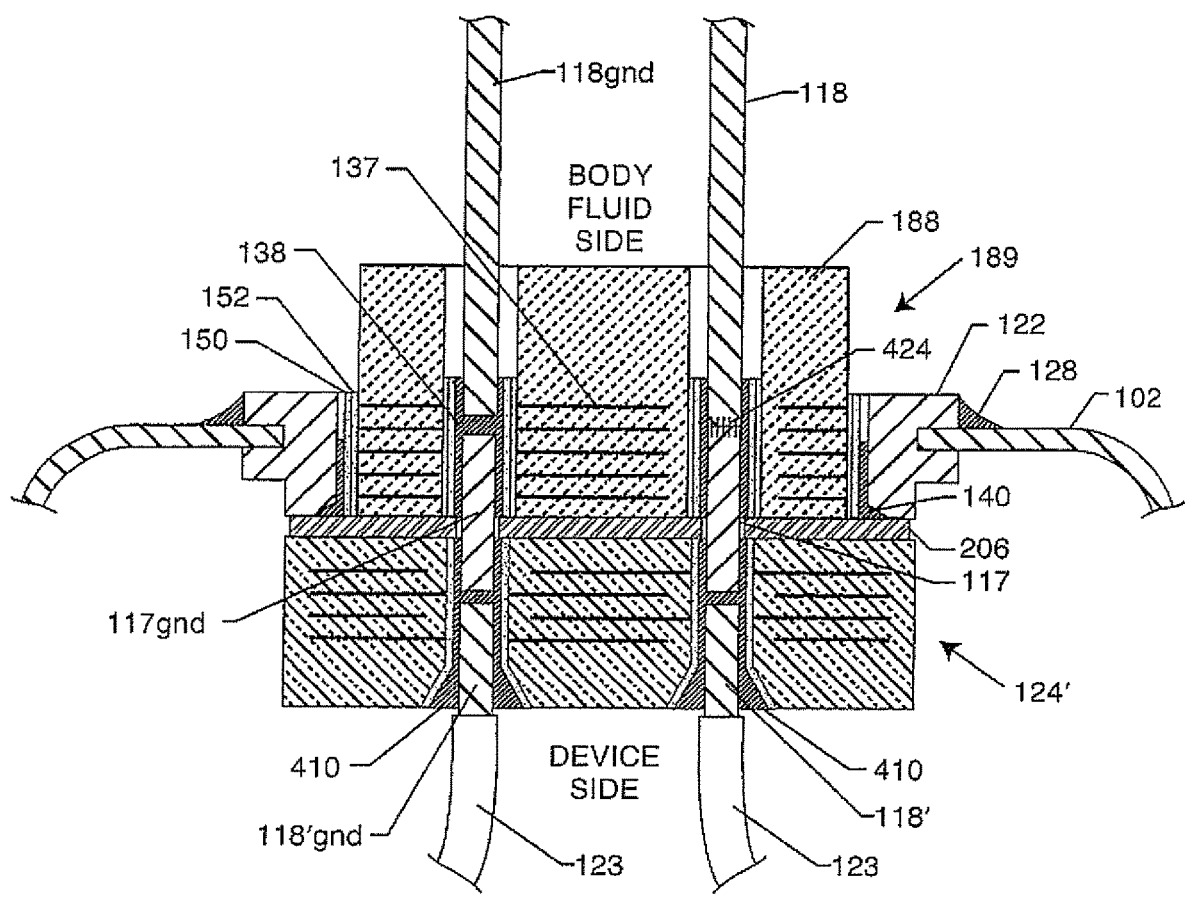
FIG. 25 illustrates an internally grounded feedthrough capacitor as previously described in FIG. 24, except that the gold braze moat has been replaced by internal ground plates that are embedded within a multilayer and co-fired insulator.

FIG. 25 illustrates an internally grounded feedthrough capacitor 124' as previously described in FIG. 24, except that the gold braze moat 138, 140, 408 has been eliminated and instead replaced by internal ground plates 137 that are embedded within a multilayer and co-fired alumina ceramic insulator 188. Sputtering of the adhesion 152 and wetting layers 150 electrically connects these embedded ground plates 137 in parallel. Subsequent gold brazing operation 140 electrically connects the ferrule 122 by way of this sputtering 150, 152 to the ground plates 137. Embedded ground plates within a hermetic insulator are described by U.S. Pat. No. 7,035,076, the contents of which are incorporated herein by reference. Accordingly, the internally grounded structure illustrated in FIG. 25 has all of the advantages previously described for FIG. 24.

Figure 26:
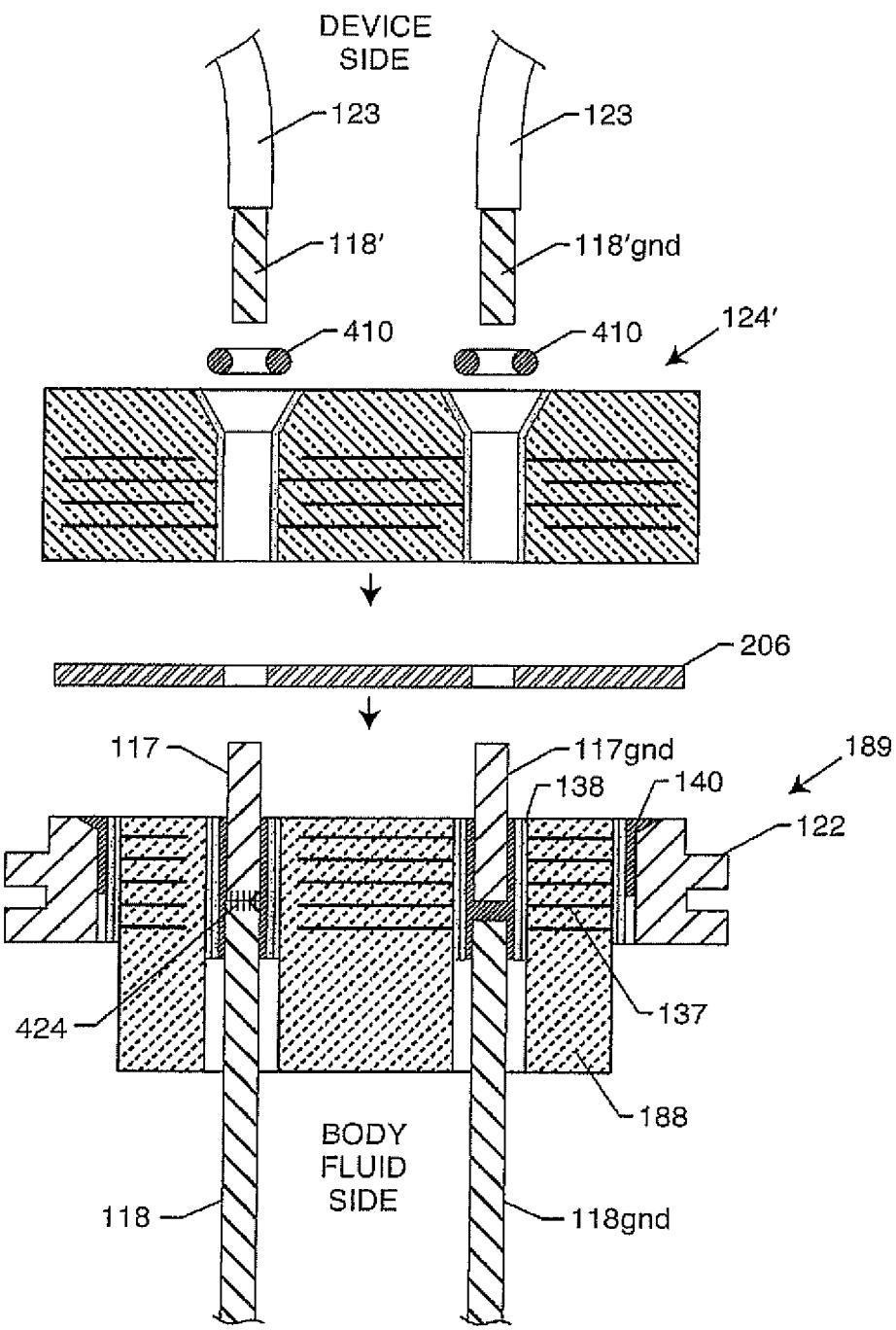
FIG. 26 illustrates the assembly steps for the structure of FIG. 25 in a manner very similar to that previously described in FIG. 9.

FIG. 26 illustrates the assembly steps for the structure of FIG. 25 in a manner very similar to that previously described in FIG. 24R. A major advantage is the elimination of the capacitor outside diameter or perimeter metallization 132 and electrical attachment 148 to the ferrule (reference FIG. 8 electrical attachment material 148). Accordingly, FIG. 26 is completely designed for automation.

FIG. 26 is the assembly of FIG. 25 showing it exploded into its various subcomponents. Shown is the internally grounded hermetic insulator subassembly 189 and the internally grounded feedthrough capacitor 124' ready to be disposed on top of the adhesive washer 206 and on top of the hermetic seal insulator 188. As previously described, this assembly can be automated and can be reflowed in a conveyor belt, furnace process or in a bulk process, such as a DAP sealer.

Figure 27:
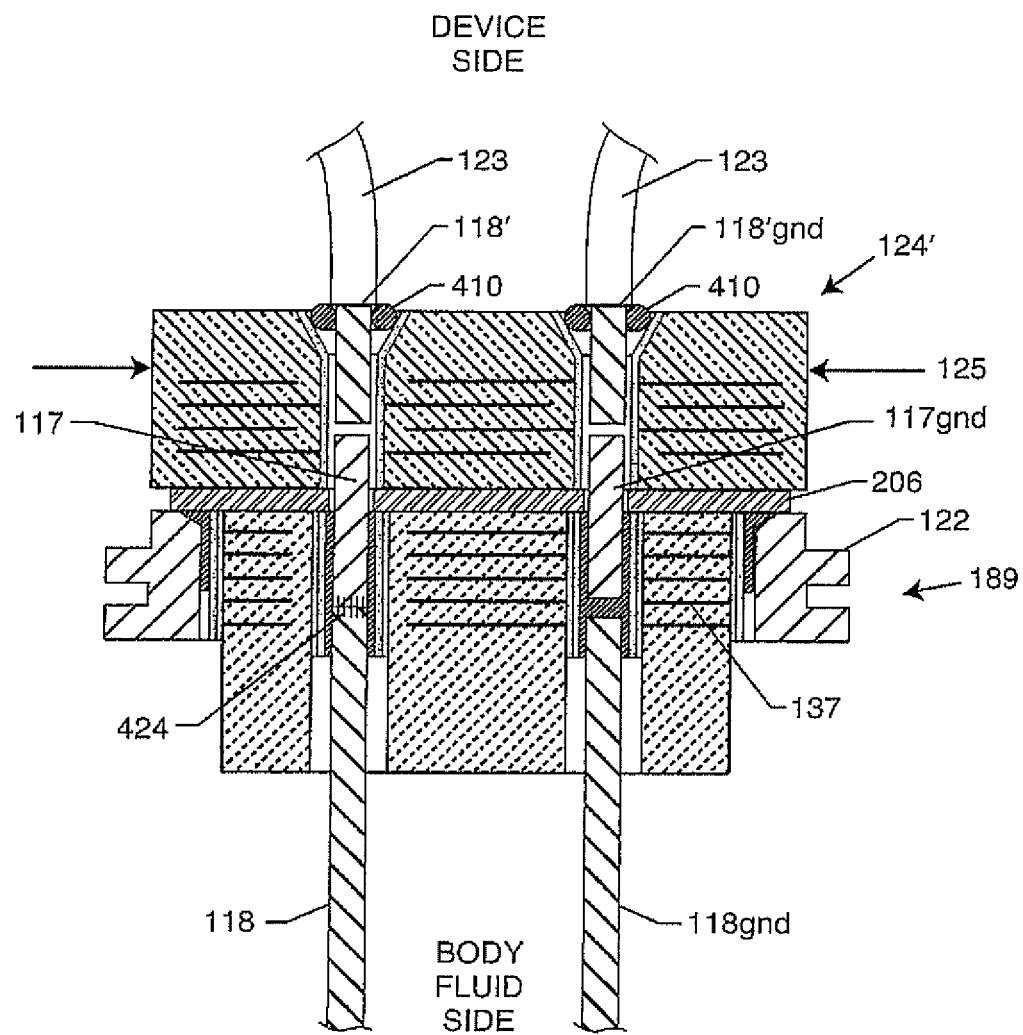
FIG. 27 illustrates the exploded components of FIG. 26 after the capacitor has been adhesively bonded to the hermetic seal insulator and ferrule.

FIG. 27 illustrates the exploded components of FIG. 26 after the capacitor 124' has been adhesively bonded 206 to the hermetic seal insulator 189 and ferrule 122, Solder preform 410 is in place and ready to be reflowed. Attention should be drawn to another very important advantage of the present invention. This can be seen in FIG. 27 as the diameter or the dimension of a rectangle 125. By elimination of any electrical connection between the capacitor outside diameter or perimeter to the ferrule 122, the capacitor 124' can actually be made larger in diameter or in a rectangular dimension. This adds enormously to the capacitor's effective capacitance area (ECA). It should be noted that this ECA is a square law. For example, if one were to double the outside diameter or double the length and width, one would multiply the effective capacitance area by a factor of four. So even a 10% addition, or 20% addition to the capacitor diameter, greatly increases its volumetric efficiency. It will be appreciated that instead of a solder preform 410, one could also use a robotic or hand dispenser of a thermal-setting conductive adhesive, which would be flowed down and make a similar connection.

Figure 28:
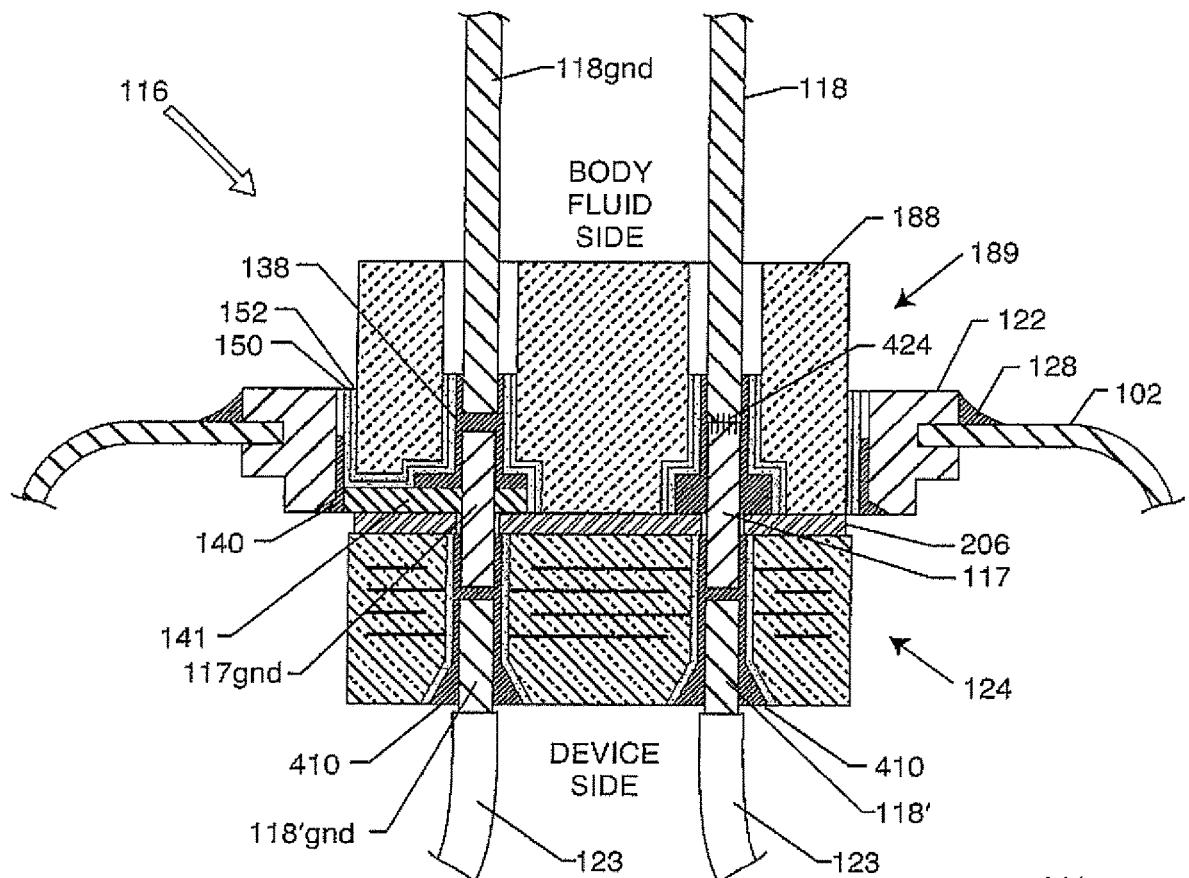
FIG. 28 is another internally grounded capacitor similar to those previously described in FIG. 24 and FIG. 25 where now the gold braze moat of FIG. 24 has been largely replaced with a metallic piece.
Figure 29:
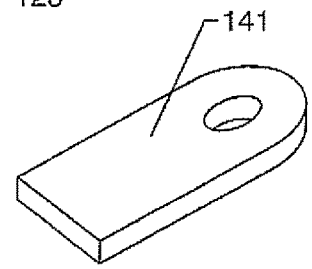
FIG. 29 is a perspective view of the metallic piece from FIG. 28.

FIG. 28 is another internally grounded capacitor 124 similar to those previously described in FIG. 24 and FIG. 25, The advantage of FIG. 28 is that the gold braze moat 138, 140s, 408 of FIG. 24 has been largely replaced with a metallic piece 141 illustrated isometrically in FIG. 29. This metallic piece 141 would typically be of titanium so that it will readily accept gold brazes 138 and 140s. The advantage of using a titanium metallic piece 141 is that less gold is required and of course, gold is very expensive. It will be noted in FIG. 28 that in the area where the metal piece 141 is located, sputter layers 150 and 152 cover this peninsula area of the hermetic insulator 188. This means that in actual production that the gold braze layer 138 would merge with the gold braze layer 140 as a very thin line of gold above the metal piece 141. This is desirable since it enhances the mechanical, structural and hermetic stability of the entire package. It will be understood that this thin layer of gold will typically be present, but is not shown for simplicity. It is also likely or even probable that the thin layer of gold will partially or totally cover both the top and bottom of the metal piece 141.

FIG. 29 is a perspective view of the metallic piece from FIG. 28. Referring once again to FIG. 29, one can see that this appears to be a machined piece of material, which would typically be of titanium. It will be appreciated that the metallic piece 141 could also be a very thin stamped titanium metal which would make it much less expensive to manufacture. The stamped or machined metal piece 141 of FIG. 29 offers many advantages over the gold brazed slot 140s illustrated in FIG. 24P. It is very difficult to maintain gold braze is it will want to wet or flow to other areas, for example, around the outside diameter or perimeter of insulator 188. The metal piece 141 prevents the gold from flowing to areas where it is not desired, achieving the result shown in FIG. 28.

Figure 30:
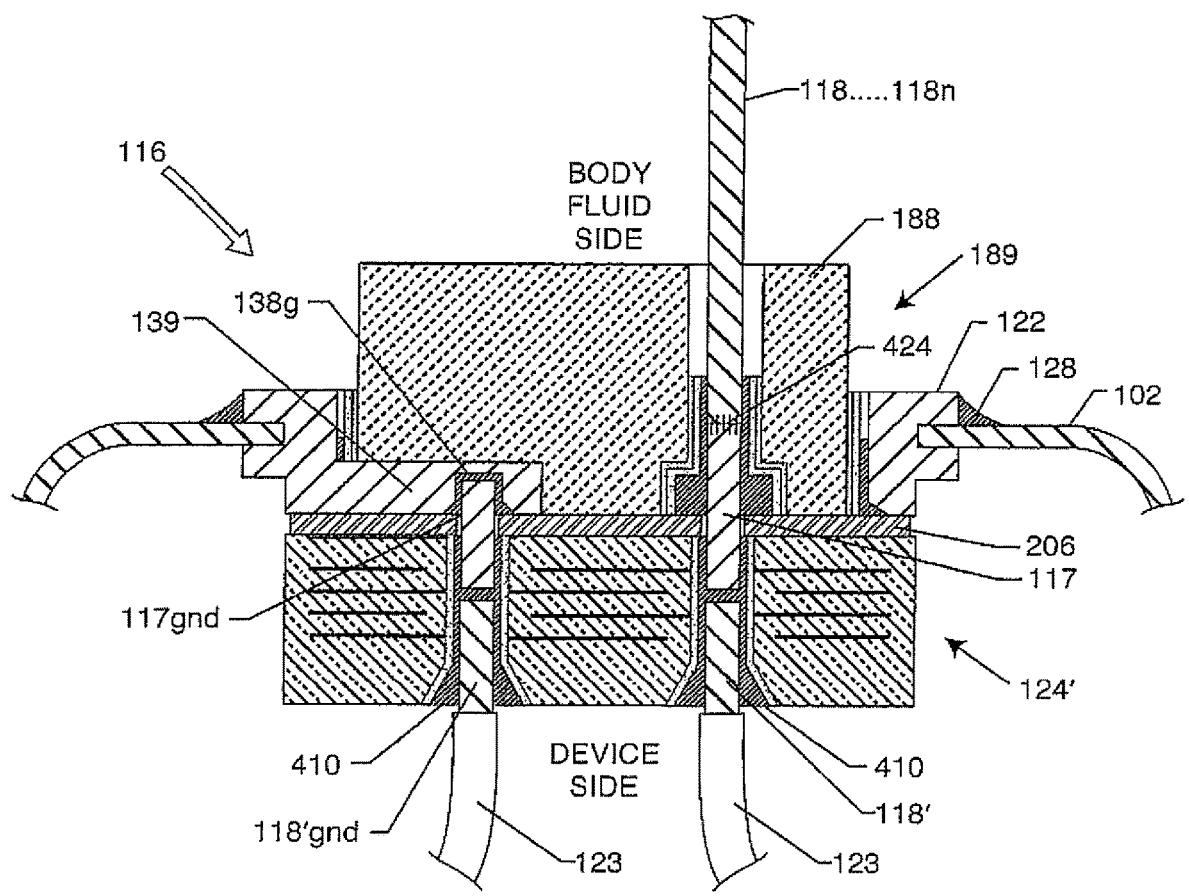
FIG. 30 is another internally grounded capacitor version similar to FIGS. 25 and 28 where now the ferrule has been extended into a peninsula and electrically coupled to the ground lead.

FIG. 30 is another internally grounded capacitor version. In this case, the ferrule 122 has been extended into a peninsula 139 as shown. The ferrule 122 would be machined such that, the peninsula 139 is formed. This is best understood by referring back to prior art FIG. 6 where one can see peninsula 139. The peninsula 139 could be very similar in shape. As previously noted, there could even be multiple peninsulas and multiple ground leads. Referring once again to FIG. 30, one can see that there is a short ground pin in accordance with the present invention 117gnd that has been gold brazed 138 into the peninsula 139. This provides a convenient grounding pin for contact to the internally grounded feedthrough capacitor 124 and to ground electrode plates 136. The device side of the internally grounded feedthrough capacitor 124' has been provided with convenient counter-sinks for placement of solder preform or thermal-setting conductive adhesives 410. It will be appreciated that one could machine, in one piece, the ferrule 122, the pedestal 139 and the ground pin 117gnd. This would eliminate the ground pin 117gnd and the gold braze 138g. However, now we'd be faced with a problem when the ground pin 117gnd would comprise titanium because it would oxidize. This would require a supplemental plating or sputtering operations, such that one could make a good electrical connection 410 to ground pin 117gnd.

Figure 30A:
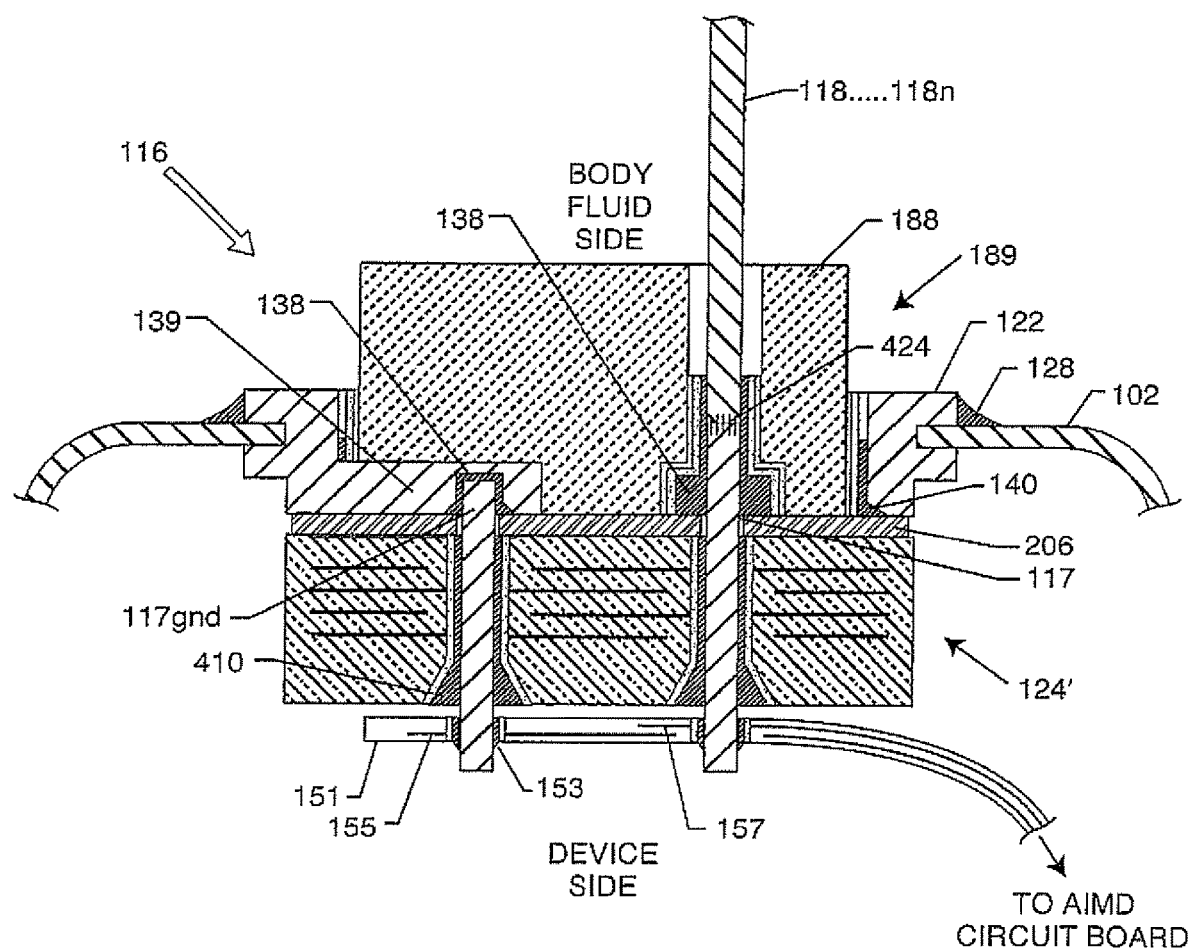
FIG. 30A is similar to FIG. 40, except that the device side leads have been extended below the surface of an internally grounded feedthrough capacitor such that a flex cable can be attached.

FIG. 30A is similar to FIG. 40, except that the device side leads 117 and 117gnd have been extended below the surface of an internally grounded feedthrough capacitor 124', such that a flex cable 151 can be attached. This would normally be done in two steps where a higher temperature solder 410 makes the electrical connection between the feedthrough capacitor metallization and the relatively short pins 117 and 117gnd of the present invention, Flex cable 151 is attached, usually by a secondary soldering operation 153 at a lower temperature. The flex cable 151 can have many different circuit traces. In this case, only two are illustrated for simplicity. These are circuit traces 155 and 157. Each of the flex cable 151, circuit traces 155 and 157 is associated with a via hole for placement over pins 117 and 117gnd and subsequent soldering 153. Of course, flex cables, as is known in the art, can be multilayer or quite wide and have many different circuit traces embedded within them. Flex cables are commonly used in AIMDs for connection to an AIMD circuit board (not shown). Flex cables are also advantageous since their installation can be automated and that they are inherently resistant to shock and vibration stresses.

Figure 30B:
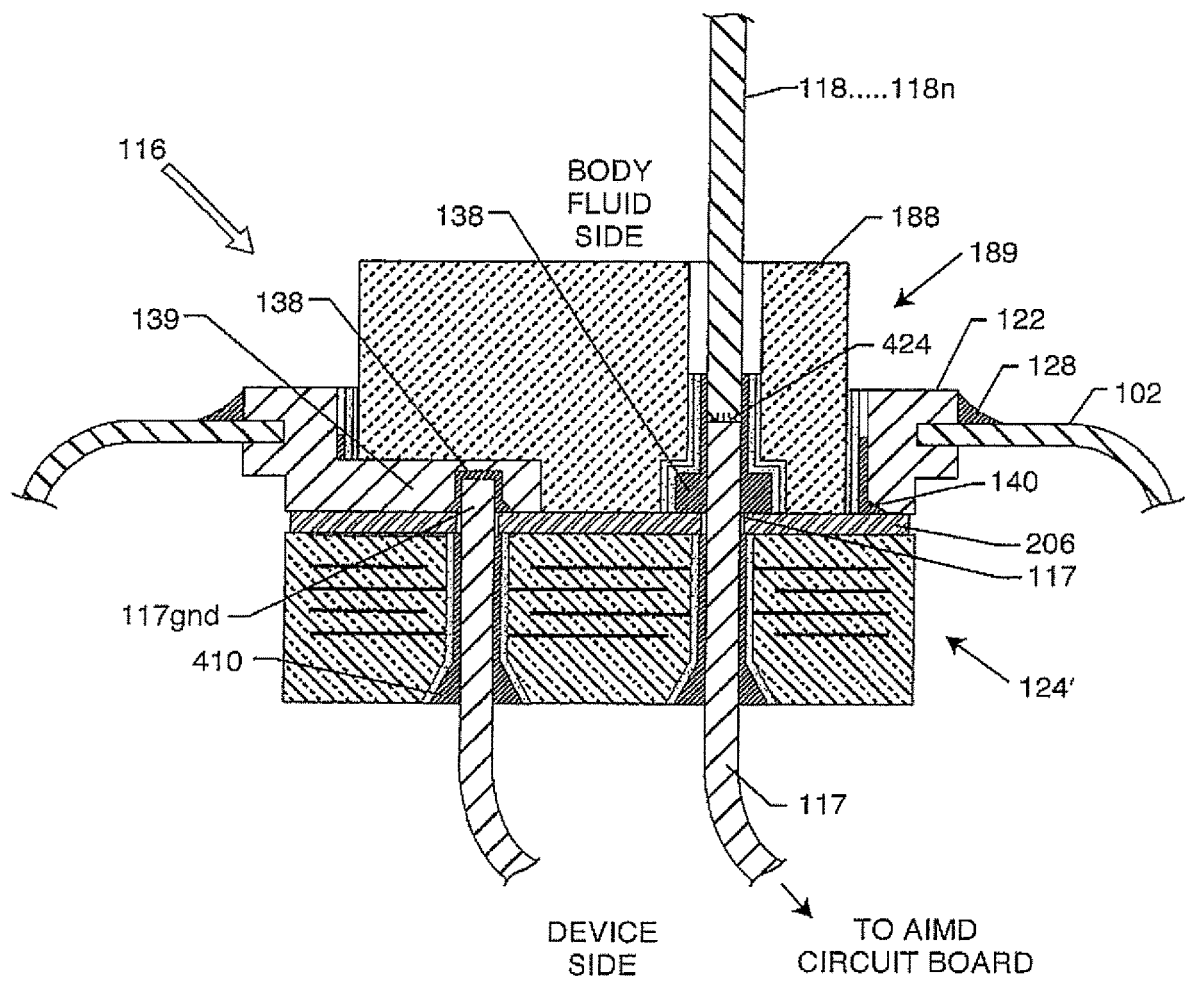
FIG. 30B is similar to FIG. 30A, except that in this case the leadwires have been elongated such that they can be routed all the way to an AIMD circuit board.

FIG. 30B is similar to FIG. 30A, except that in this case, leadwires 117gnd and 117 have been elongated such that they can be routed all the way to an AIMD circuit board (not shown). As previously described, since the leadwires 117 of the present invention are generally co-brazed 138 or co-welded 424 to a device side lead 118, they must be capable of withstanding these high temperature operations. In other words, referring once again to FIG. 30B, it would not be possible to use a low cost device side leadwire 117 comprised of a low melting material, such as copper or the like. In this case, a suitable material would be nickel, which would probably require a supplemental tin dipping, solder coating or plating operation.

Figure 31:
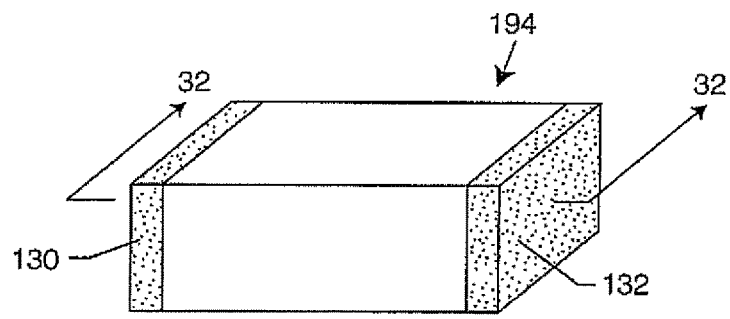
FIG. 31 illustrates a prior art monolithic ceramic capacitor.

FIG. 31 illustrates a prior art monolithic ceramic capacitor 194. These are otherwise known as MLCCs. Monolithic ceramic capacitors are very well known in the prior art and are produced daily in the hundreds of millions. It will be appreciated that MLCCs are also commonly referred to as multilayer ceramic capacitors. MLCCs are common components in every electronic device, including computers, modern smart phones and the like. It should be noted here that not all rectangular 2-terminal capacitors, as illustrated in FIG. 31, must be ceramic. As used herein, MLCC or monolithic ceramic capacitors shall also include all kinds of stacked tantalum, stacked film and other dielectric type capacitors that form 2-terminal rectangular shapes. It will also be appreciated that any of the 2-terminal capacitors in the art, including ceramic, film and tantalum could also have other shapes other than rectangular, including cylindrical and the like.

Figure 32:
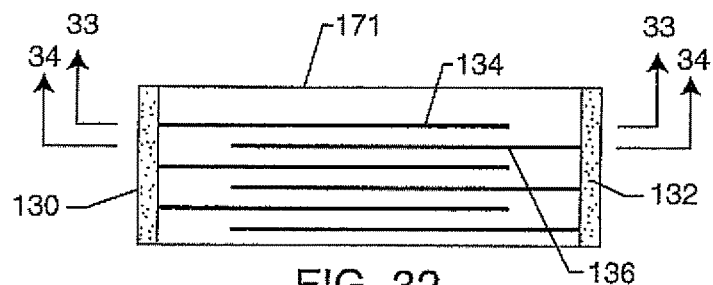
FIG. 32 illustrates a cross-section of an MLCC capacitor of FIG. 31 taken along lines 32-32.
Figure 33:
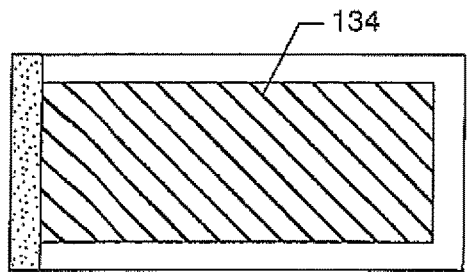
FIG. 33 illustrates a cross-section of the MLCC capacitor of FIG. 32 taken along lines 33-33.
Figure 34:
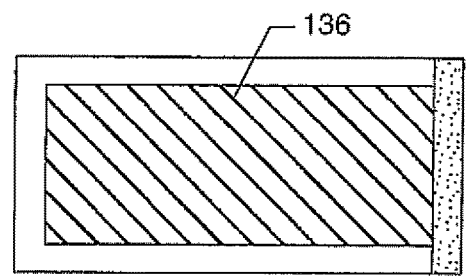
FIG. 34 illustrates a cross-section of the MLCC capacitor of FIG. 32 taken along lines 34-34.

FIG. 32 taken from section 32-32 from FIG. 31, illustrates a cross-section of an MLCC capacitor. As can be seen, the prior art MLCC is a two-terminal device having a metallization on the left 130 and a metallization on the right 132. It has overlapping electrodes as illustrated in FIGS. 33 and 34. It has an effective capacitance area ECA created by the overlap of the left-hand electrodes 134 with the right-hand electrodes 136.

Figure 35:
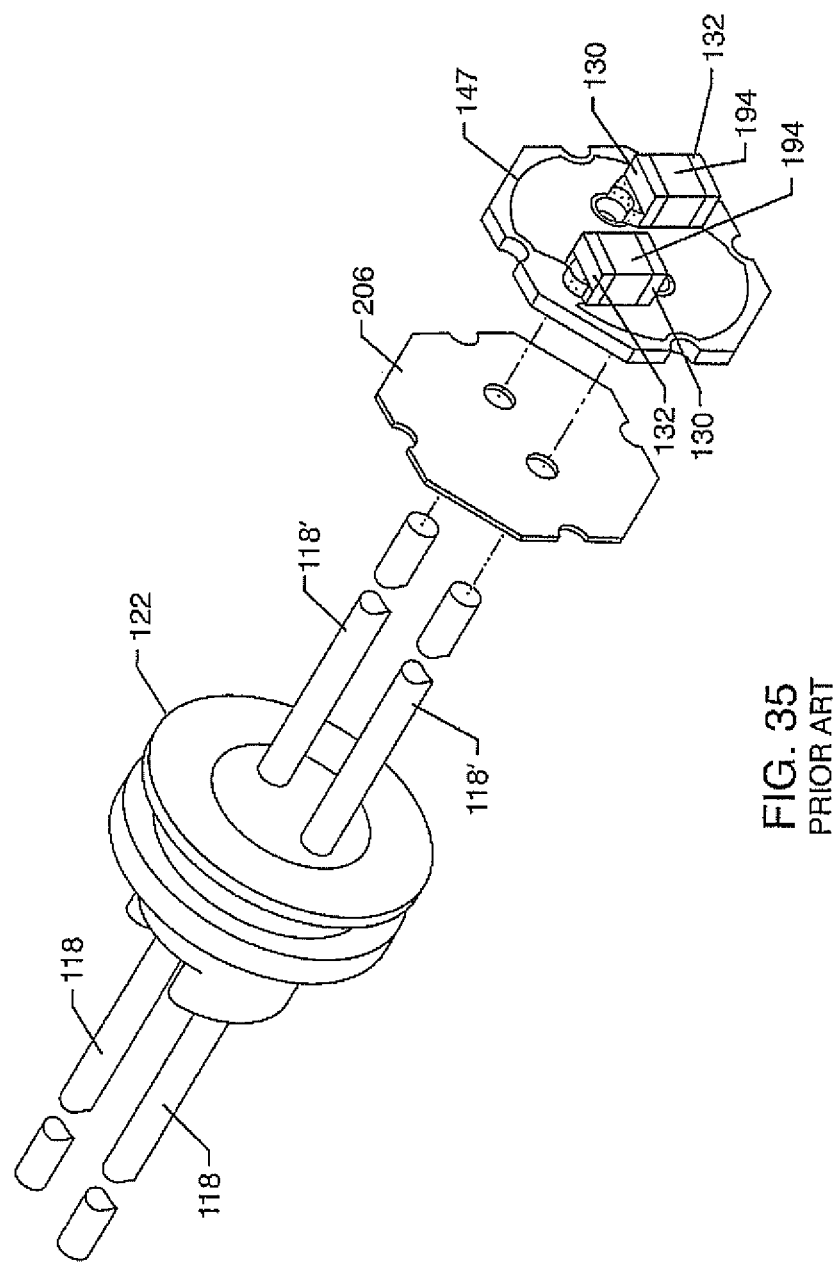
FIG. 35 illustrates a bipolar prior art applications of MLCC capacitors to active implantable medical device applications.
Figure 35A:
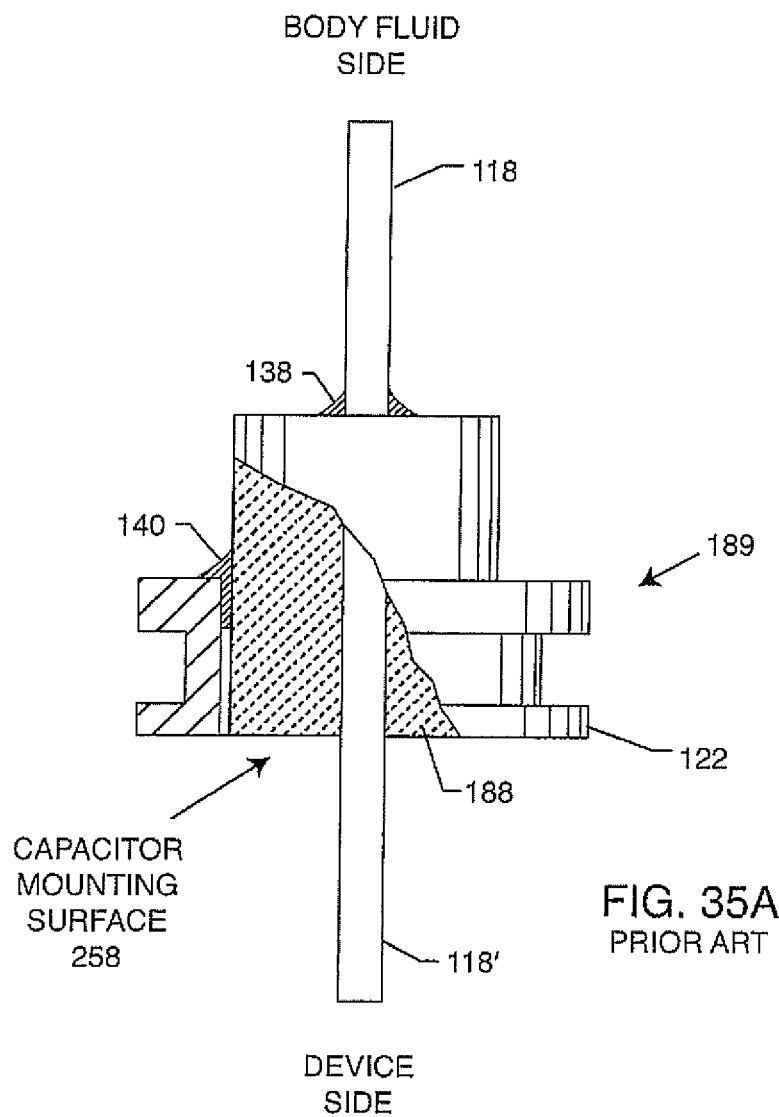
FIG. 35A illustrates a unipolar prior art applications of MLCC capacitors to active implantable medical device applications.
Figure 35B:
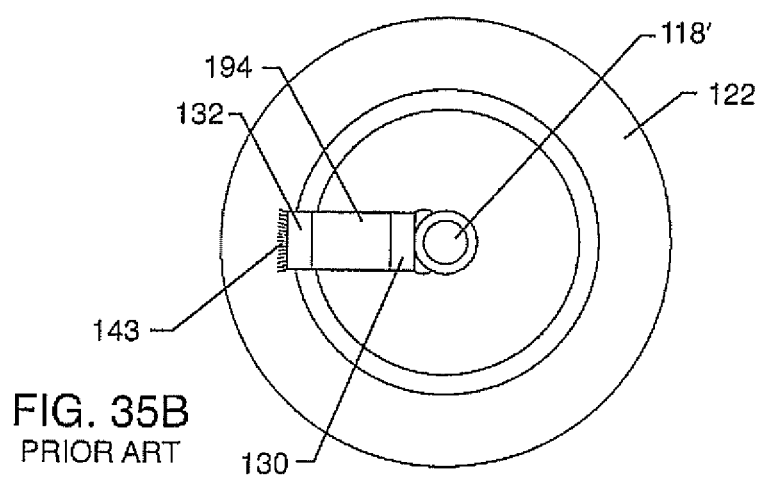
FIG. 35B illustrates a top view of the structure of FIG. 35A.

FIGS. 35, 35A and 35B illustrate prior applications of MLCC capacitors 194 to hermetic seal subassemblies of active implantable medical devices. These patents include: U.S. Pat. Nos. 5,650,759; 5,896,267; 5,959,829 and 5,973,906, the contents of which are incorporated herein by reference.

Figure 35C:
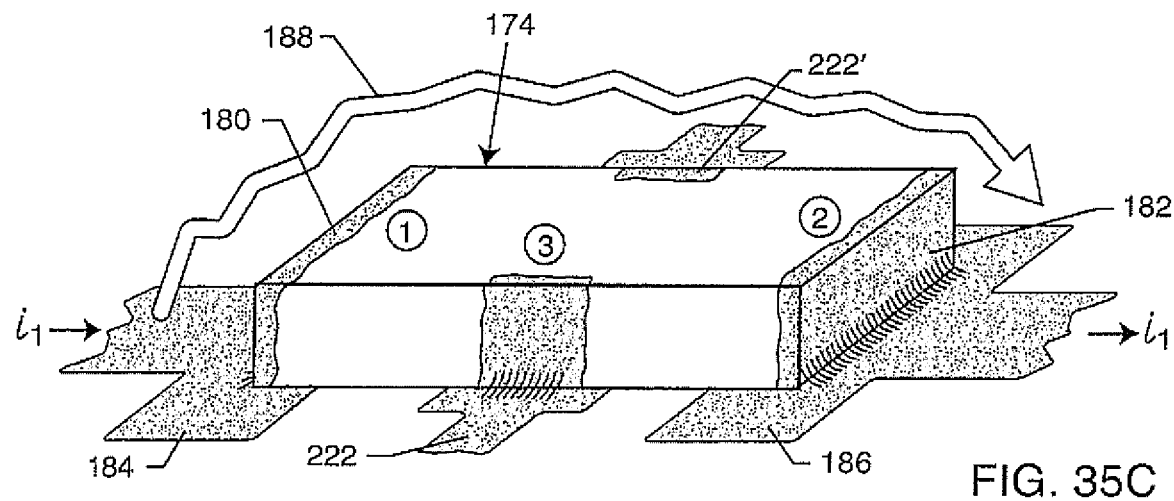
FIG. 35C illustrates a prior art flat-thru capacitor.
Figure 35D:
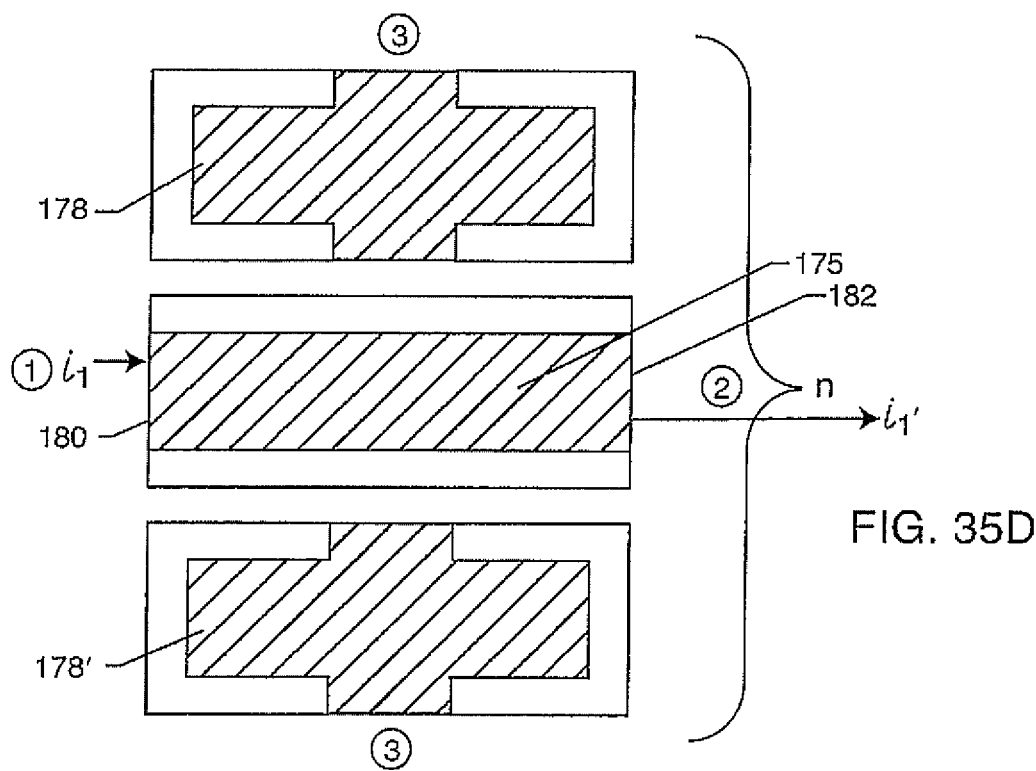
FIG. 35D illustrates the electrode plates of the flat-thru capacitor of FIG. 35C.

FIG. 35C illustrates a prior art flat-thru capacitor. This is better understood by referring to its internal electrode plates as illustrated in FIG. 35D. This is also known as a three-terminal capacitor because there is a circuit current $i_1$ that passes through its electrode plate 175 from the first terminal 180. If there is a high frequency electromagnetic interference signal being conducted along this electrode plate, then it comes out the other side at a second terminal 182. Referring back to FIG. 35C, there is a general disadvantage to such capacitors in that, at very high frequency EMI 188 can cross-couple from the left side of the MLCC capacitor to the right side.

Figure 35E:
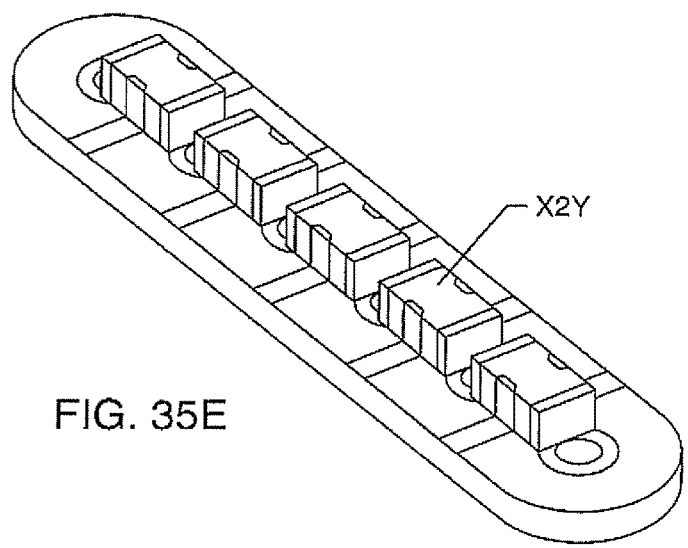
FIG. 35E illustrate a perspective view of a three-terminal capacitor that is also known in the industry as X2Y attenuator.
Figure 35F:
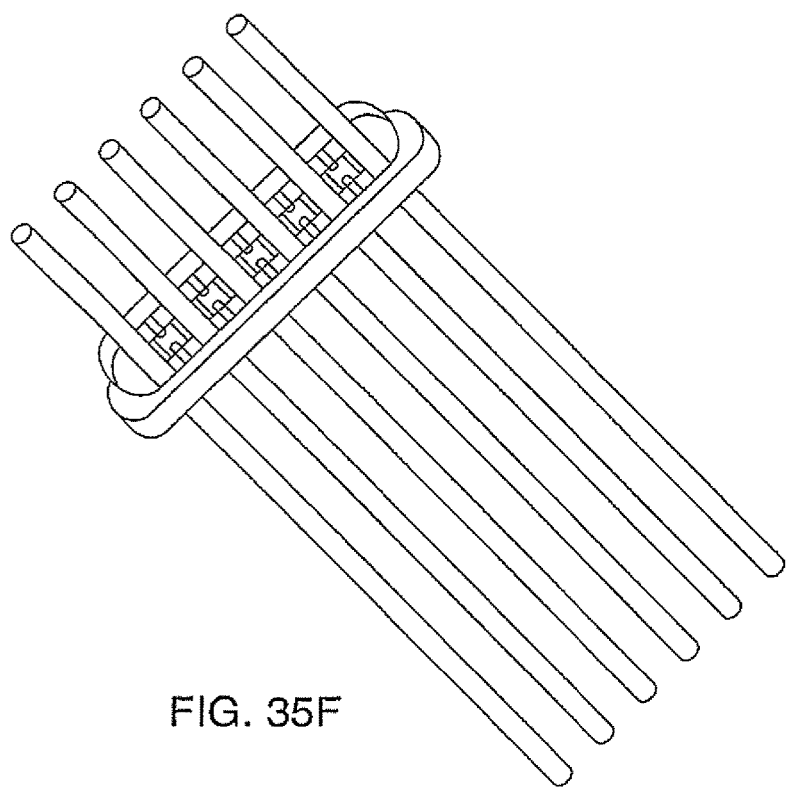
FIG. 35F is another perspective view of the structure of FIG. 35E.
Figure 35G:
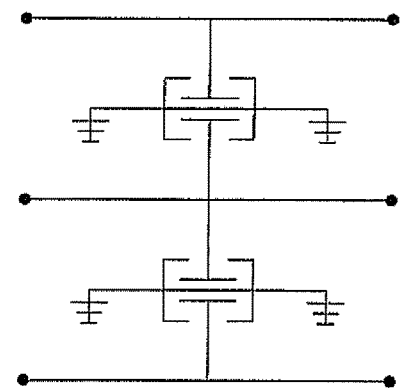
FIG. 35G is the electrical schematic for FIGS. 35E and 35F.

FIGS. 35E, 35F and 35G illustrate a three-terminal capacitor that is also known in the industry as X2Y attenuator. These are well known in the prior art. It will be appreciated by one skilled in the art, that any of these flat-thru or X2Y attenuators can be applied to the present invention.

Figure 36:
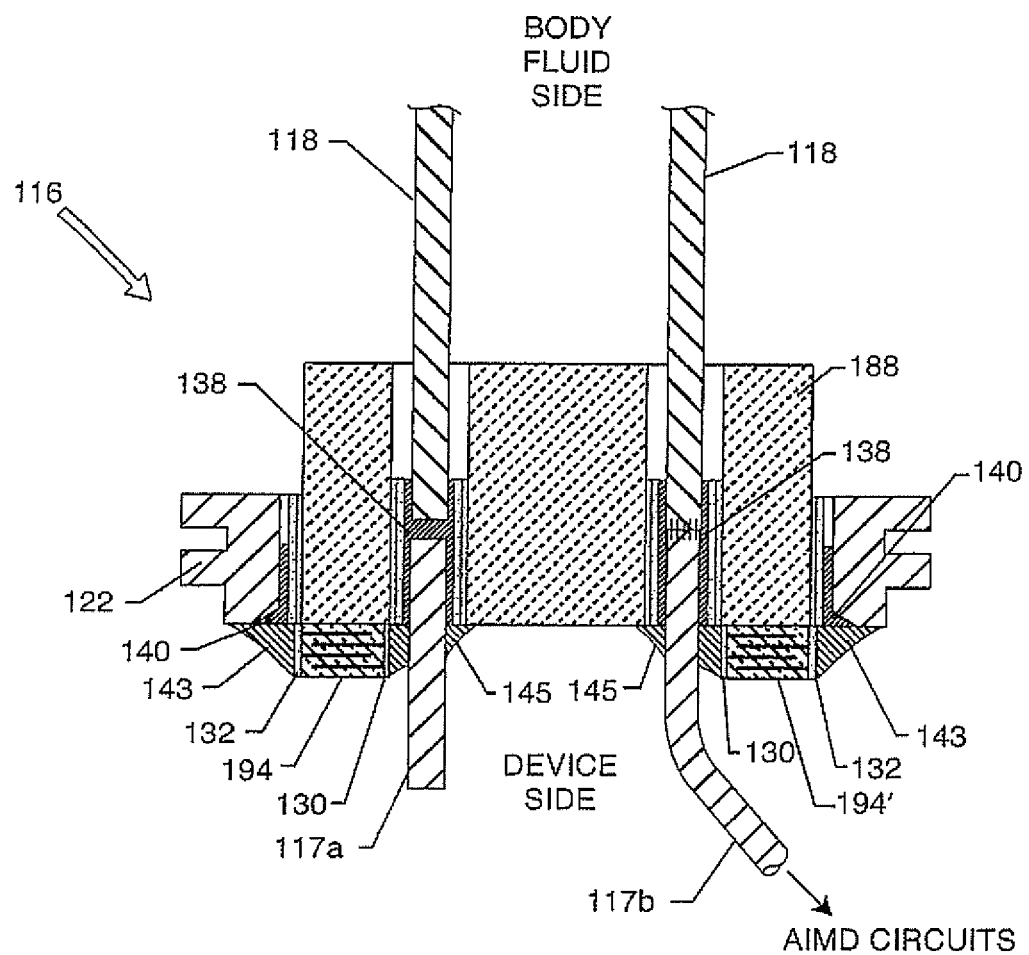
FIG. 36 is a sectional view and illustrates the application of MLCC capacitors to the present invention.

FIG. 36 illustrates the application of MLCC capacitors 194 and 194' to the present invention. It will be noted that the left-hand device side pin 117a is relatively short to accommodate placement of flex cable (not shown) or a circuit board adjacent the hermetic seal insulator 188 and ferrule 122 on the device side. Referring once again to FIG. 36, one can see that the right-hand device-side leadwire 117b has been elongated so that it can be directly connected to an AIMD circuit board 126 (not shown). An optional insulating sleeve (not shown) could be placed over the right-hand leadwire 117b. A disadvantage of MLCC chip capacitors is that they are two terminal devices and have substantial series inductance. This causes them to self-resonate at lower frequencies than a feedthrough capacitor. Above resonance, MLCC capacitors become increasingly less effective as a filtering element. Accordingly, it is preferable that MLCC chip capacitors be relatively small in size. Reverse geometry is a popular technique, where the terminations are placed along the long sides instead of the short sides. Reverse geometry reduces the internal inductance of the MLCC capacitors 194. The advantage of reverse geometry MLCCs for higher frequency filtering is further explained in U.S. Patent Publication 2014/0168917 (look at FIGS. 16 through 18) the contents of which are incorporated in full herein by this reference.

It is also very important that in an AIMD application that the MLCCs be placed in such a way that the electrical connections do not substantially increase this undesirable series inductance. Accordingly, the capacitors 194, 194' of FIG. 36, have been placed immediately adjacent leadwires 117a and 117b at the point of entry of the AIMD housing. MLCC capacitors do not have a polarity; therefore, they can be oriented in any direction. For the purposes of the present invention, the capacitor termination 132 will also be known as the ground termination. This is because there is an electrical connection 143 between the capacitor ground termination 132 and the ferrule 122 and its corresponding gold braze 140. Connection to the gold braze is important such that a very low impedance, non-oxidized connection is made. The active side of the MLCC chip capacitors is denoted by termination material 130. There is an electrical connection 145 that is made between the active termination 130 and the corresponding leadwires 117a and 117b. Referring once again back to FIG. 36, electrical connection materials 143 and 145 can include a wide range of thermal-setting conductive adhesives, including conductive epoxies and conductive polyimides. There is also a wide range of solders and low temperature brazes that also could function as these electrical connections.

Figure 37:
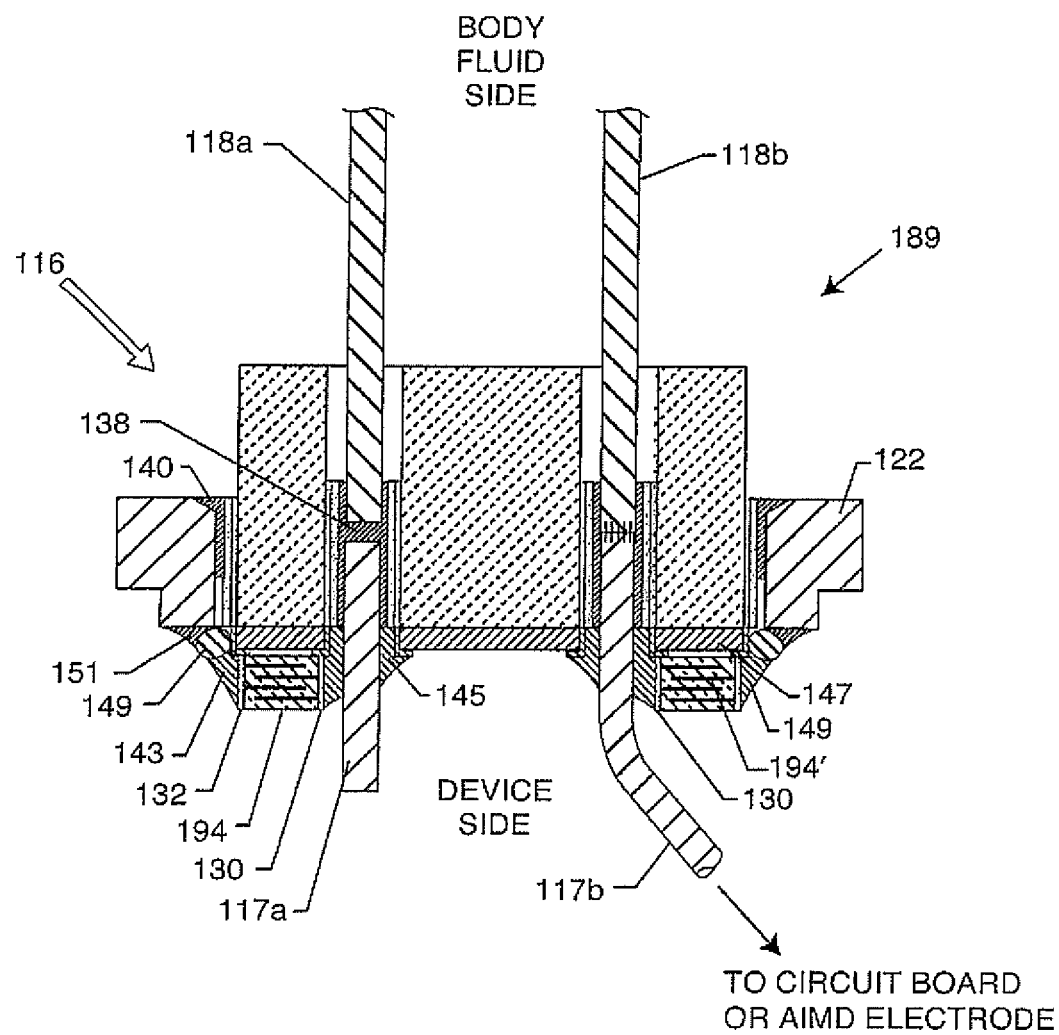
FIG. 37 illustrates a modified hermetic terminal similar to FIG. 36 where now the gold braze is disposed towards the body fluid side instead of towards the device side and therefore an oxide-resistant metal addition is used.

FIG. 37 illustrates a modified hermetic terminal. In this context, modified means that the gold braze 140 is disposed towards the body fluid side instead of towards the device side. This makes it difficult to perform an oxide-free electrical attachment 143 to the gold braze 138. Accordingly, an oxide-free metal addition 149 has been added. Typically, this metal addition is laser welded 151 to the ferrule 122. It could also be brazed to the ferrule 122. Importantly, the oxide-free metal addition 149 is a high temperature non-oxidizing material that will readily accept the electrical connection material 143 that makes contact to the capacitor ground metallization 132. Oxide-free additions to AIMD ferrules have been described in U.S. Pat. Nos. 9,108,066 and 9,427,596 and U.S. Patent Publication 2014/0168917, the contents of all of which are incorporated in full herein by these references.

Figure 38:
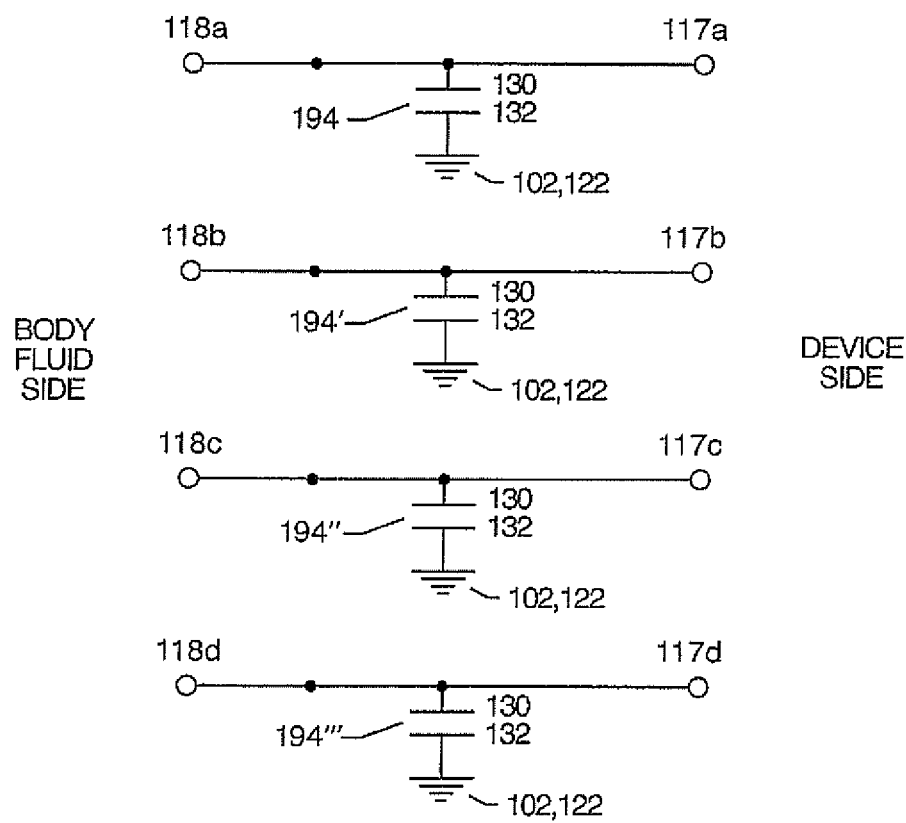
FIG. 38 is one exemplary possible electrical schematic of the overall filtered feedthrough assembly previously illustrated in FIG. 37.

FIG. 38 is one exemplary possible electrical schematic of the overall filtered feedthrough assembly 116 previously illustrated in FIG. 37. FIG. 37 is a cross-sectional view showing only two leads 117. If this part was long and rectangular, it could have 8, 9, 10, 12 or any number of leads. If it was round, it could also have any number of leads. FIG. 38 illustrates that the filtered feedthrough assembly 116 of FIG. 37, could be quadpolar. In other words, having four MLCC chip capacitors 194 through 194'''.

Referring once again to FIG. 38, one will see that the electrical schematic for the MLCC capacitors 194 is different indicating that they are two-terminal devices. In other words, the leadwire 118, 117 does not pass through the capacitor. A schematic for three-terminal or feedthrough capacitors is shown in FIG. 24U where one can see that the active leadwires consist of segment 118, 117 and 118'a and these pass right through the feedthrough capacitor. The thing that really distinguishes feedthrough capacitors as three-terminal devices is that they generally have a through hole compared to MLCC capacitors which do not.

Figure 39:
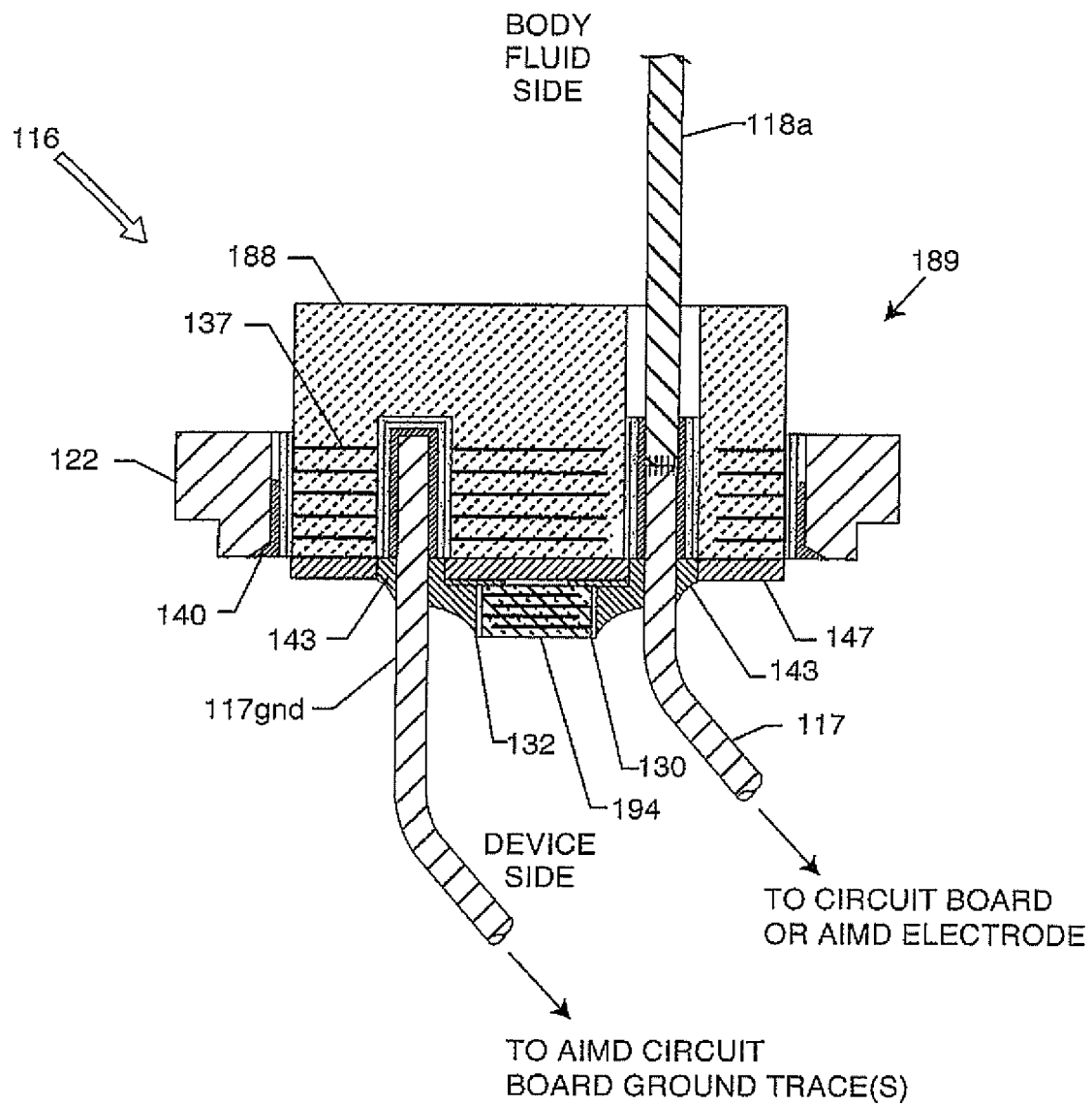
FIG. 39 is a cross-sectional drawing of a filtered feedthrough hermetic assembly wherein a single MLCC chip capacitor is used, connected between an internal ground pin and an active pin.

FIG. 39 is a cross-sectional drawing of a filtered feedthrough hermetic assembly 116 wherein, a single MLCC chip capacitor 194 is used, connected between an internal ground pin 117gnd and an active pin 117 (both on the device side). The cross-section of FIG. 39 is unipolar meaning that there is only one active lead 118a, 117. There is also a ground lead 117gnd. This lead 117gnd is grounded through embedded ground plates 137 in the hermetic insulator, as previously described in FIG. 27. As can be seen, the capacitor ground metallization 132 is connected to the grounded leadwire 117gnd with electrical connection material 143. The MLCC capacitor active termination 130 is also connected using electrical connection material 143 to active lead 117.

Figure 39A:
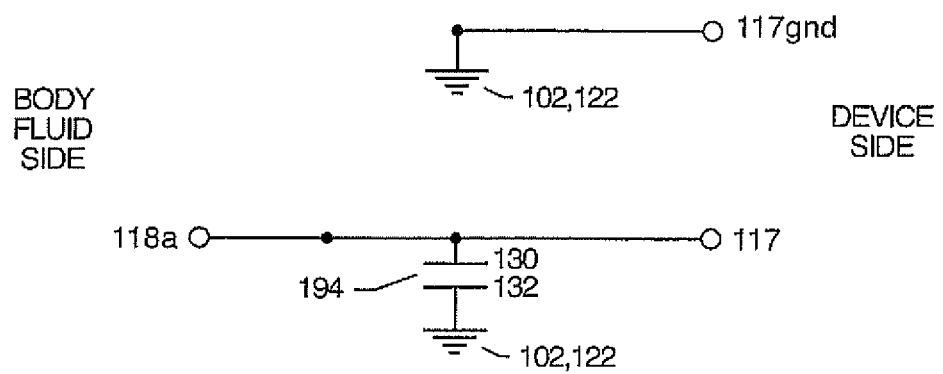
FIG. 39A is the electrical schematic of the filter feedthrough assembly of FIG. 39.

FIG. 39A is the electrical schematic of the filter feedthrough assembly 116 of FIG. 39. Illustrated on the device side is the ground lead 117gnd and also the single (unipolar), active leadwire labeled 118a on the body fluid side and 117 on the device side. Also shown is the unipolar or single MLCC capacitor 194. Referring once again to FIG. 39, one can see that the MLCC capacitor 194 is first mounted to a circuit board 147.

Figure 40:
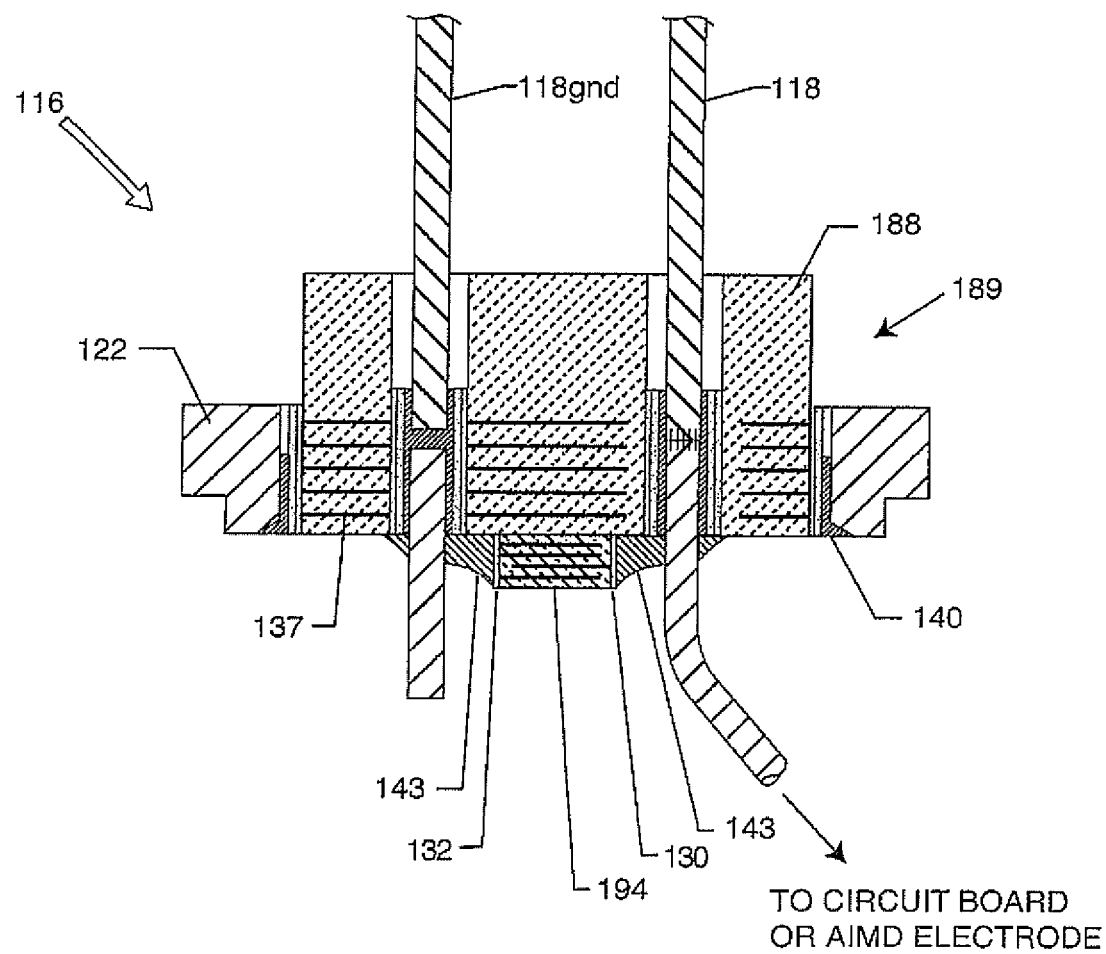
FIG. 40 is very similar to FIG. 39, except that the circuit board has been eliminated and the MLCC capacitor has been directly mounted to the insulator of the hermetic seal subassembly.

FIG. 40 is very similar to FIG. 39, except that the circuit board 147 has been eliminated and the MLCC capacitor 194 has been directly mounted to the insulator 188 of the hermetic seal subassembly 189.

Figure 41:
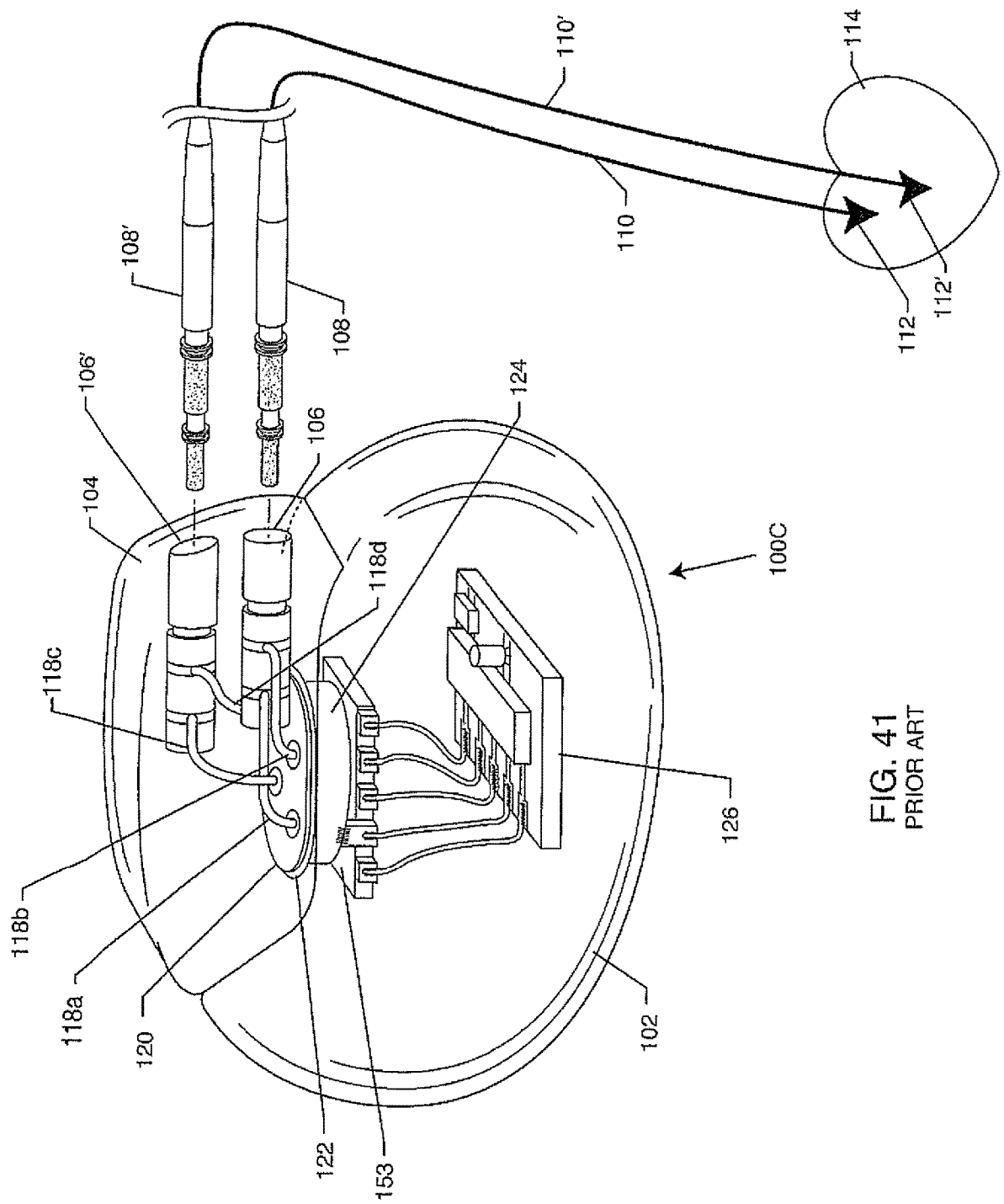
FIG. 41 is very similar to FIG. 2 in that it shows the interior of an active implantable medical device.
Figure 42:
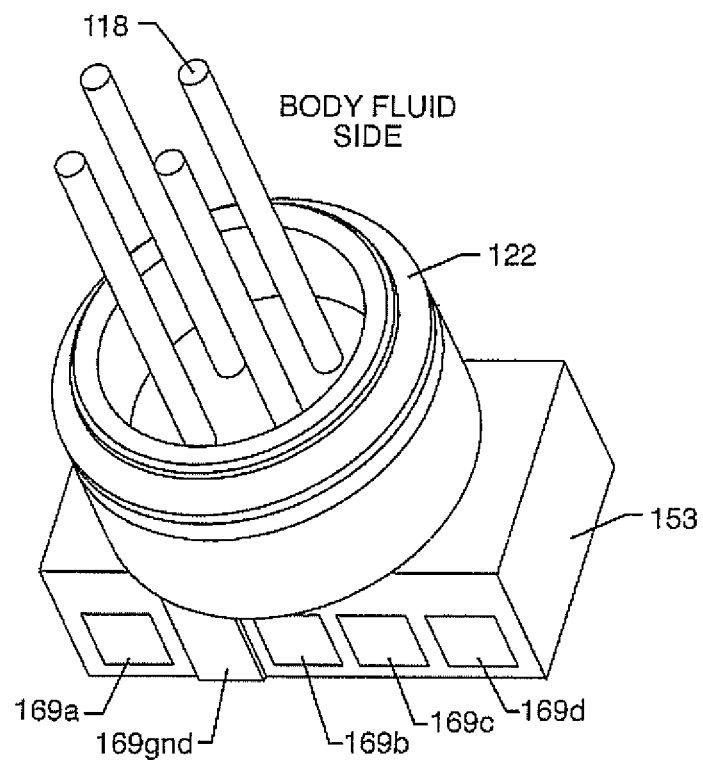
FIG. 42 illustrates a perspective view quadpolar filtered feedthrough similar to a prior art design.
Figure 43:
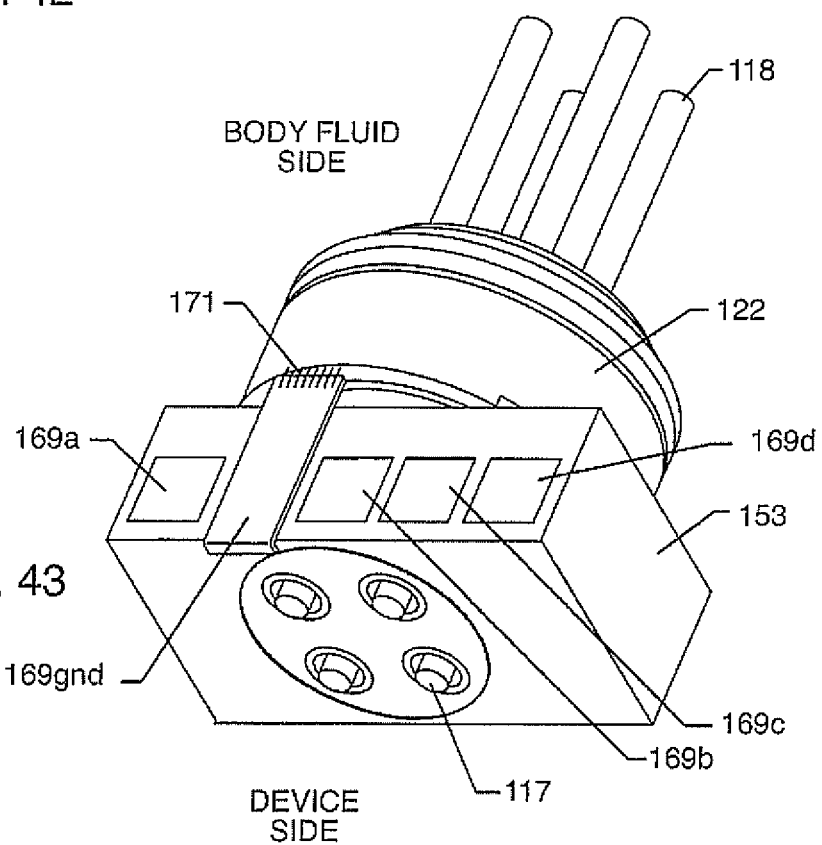
FIG. 43 illustrates another perspective view of the structure of FIG. 42.
Figure 44:
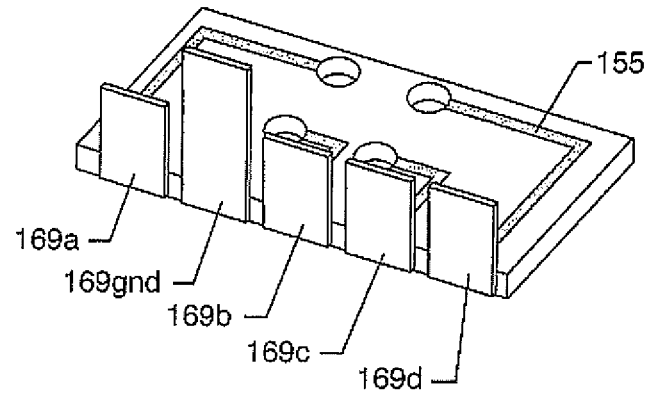
FIG. 44 illustrates the first layer of the multilayer board shown in FIGS. 42 and 43.
Figure 45:
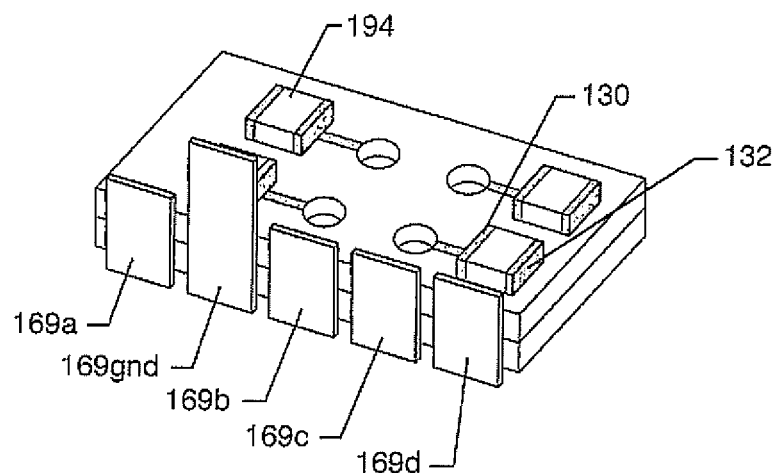
FIG. 45 illustrates the second layer of the multilayer board shown in FIGS. 42 and 43.
Figure 46:
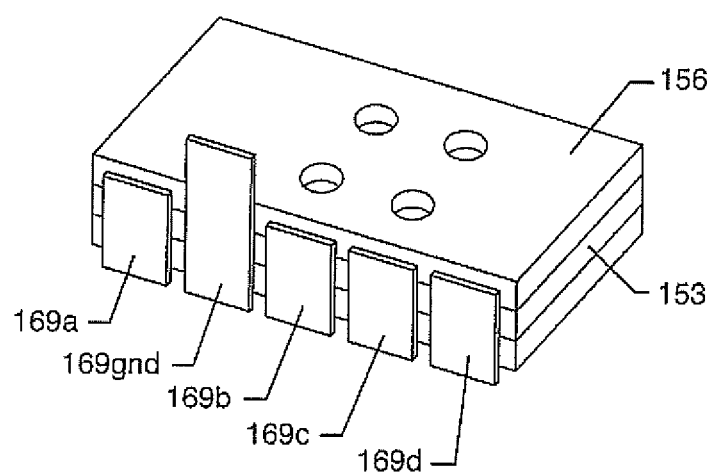
FIG. 46 illustrates the third layer of the multilayer board shown in FIGS. 42 and 43.

FIG. 41 is very similar to FIG. 2 in that, it shows the interior of an active implantable medical device 100C. In this case, it would be typically a cardiac pacemaker. It will be known to those skilled in the art that this prior art figure could apply to any type of AIMD. A wire bond board 153 is shown attached adjacent to a feedthrough capacitor 124 which is in turn, attached to the ferrule 122 of a hermetic seal feedthrough assembly. One is referred to U.S. Pat. No. 7,038,900, FIGS. 75 to 77 for a more complete description of the wire bond board 153. The contents of the U.S. Pat. No. 7,038,900 patent are incorporated herein by reference. One is also referred to U.S. Patent Publication 2014/0168917, the contents of which are incorporated herein and are known as the '917 Publication. FIGS. 42 through 46 herein are similar with FIGS. 21 to 25 of the '917 patent Publication. FIGS. 21 to 25 of the '917 patent Publication do differ from FIGS. 41 through 46 herein, in that, in the present invention, there are four (quadpolar) active wire bond pads 169a through 169d and a ground wire bond pad 169gnd. The ground wire bond pad 169gnd is at the same electrical potential as the ferrule 122. One can see that the wire bond board 153 is generally adjacent to the hermetic seal ferrule 122 and is disposed on the device side. FIGS. 44 through 46 illustrate that the wire bond pad board 153 of FIGS. 42 and 43 may be multilayer. FIG. 44 illustrates that there may be internal circuit traces 155 that are built up in sandwiched layers. FIG. 45 illustrates that an internal layer may contain embedded MLCC chip capacitors 194, which connect 130 from each of the active quadpolar leads to ground 132, 122 and thereby act as filters. It will be appreciated that these chip capacitors 194 have been previously described in FIG. 37 and generally connect from the active (quadpolar) leadwires or pins at MLCC capacitor termination surface 130. It will also be appreciated, in FIG. 45, that the opposite termination or metallization 132 of the MLCC capacitor 194 is connected to ground 122 (through an internal circuit trace via that electrically connects to the ferrule potential that is not shown). Referring back to FIG. 43, one will appreciate that on the body fluid side, the leadwires are labeled 118 and in accordance with the present invention inside of a hermetic insulator 122, leadwire 118 is co-joined by welding or co-brazing to the device side leadwire 117. Once again, referring to FIG. 45, one will see that the embedded MLCC capacitors 194 could be discrete components, but could also be laid out in discrete layers with active and ground electrode plates as the multilayer board itself is filled up. FIG. 46 illustrates that one or more cover sheets 156 may be added on top of the multilayer board of FIGS. 44 and 45, thereby embedding the MLCC chip capacitors 194 entirely within the board. This embedded technology is generally known in the prior art. It will also be appreciated and shown in subsequent drawings that the MLCC chip capacitors 194 need not be embedded in the board, but could be surface mounted on its device side. It will be appreciated that any of the wire bond boards described in FIGS. 41 through 46 can be applied to any of the embodiments of the present invention.

Referring once again to FIG. 43, one can see that the leadwire 118 on the body fluid side, is labeled 117 on the device side. This is in accordance with the present invention. It will be appreciated that the leadwire in accordance with the present invention, could be co-welded or co-brazed within the hermetic seal insulator (not shown). It could also be co-joined within the wire bond block 153. In another embodiment, the body fluid side leadwire 118 could be co-joined in the insulator to a short pin segment 117 as shown. In general, the body fluid side leadwire 118 would be of a different material than the device side leadwire 117. It will also be appreciated that wires would be attached to pads 169a through 169d either through wire bonding or the like and these wires would be routed to AIMD circuits (not shown).

Figure 47:
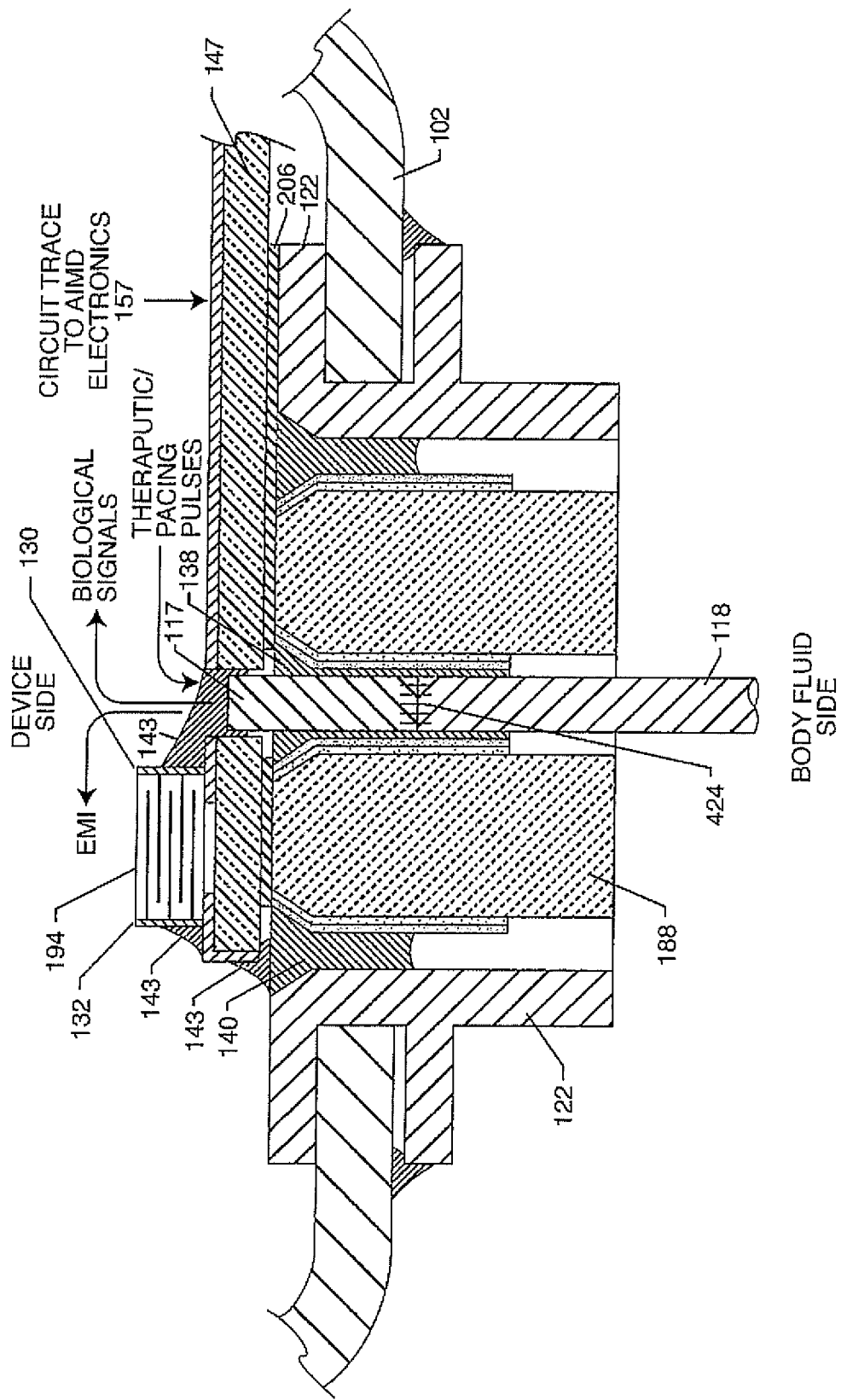
FIG. 47 illustrates a sectional view and includes a circuit board which is adjacent the hermetic ferrule and hermetic insulator.

FIG. 47 includes a circuit board 147 which is adjacent the hermetic ferrule 122 and hermetic insulator 188. FIG. 47 is taken from FIG. 35 of the '917 U.S. patent Publication. FIG. 47 does incorporate the present invention in that, the body fluid side lead 118 has been co-brazed 138 with the device side lead 117. One will note that these two have been welded 424 together prior to the brazing operation in accordance with the present invention. As can be seen, the circuit board 147 is co-bonded to the ferrule 122 and insulator 188 with an adhesive washer 206, which is considered optional. It will be appreciated that there are a wide variety of ferrules and hermetic insulators that are used in the AIMD industry. It is not in all cases that the insulator 188 is adjacent or is aligned at the top of the ferrule. In this case, it is appreciated that the circuit board may be bonded to the ferrule, the insulator or both. The circuit board 147 includes one or more circuit traces 157 to AIMD electronics. Referring once again to FIG. 47, it will be appreciated that board 147 may be single layer, as shown, with circuit traces 157 on its top (device side). It will be further appreciated that board 147 could be multilayer and the circuit traces 157 could be embedded within the board. In the case where there are a number of leadwires 118, for example, 10 or 12 leads, then it would be preferable that the board 147 be wide and multilayer thereby incorporating a number of circuit traces on its top surface and on multiple layers (not shown).

Figure 48:
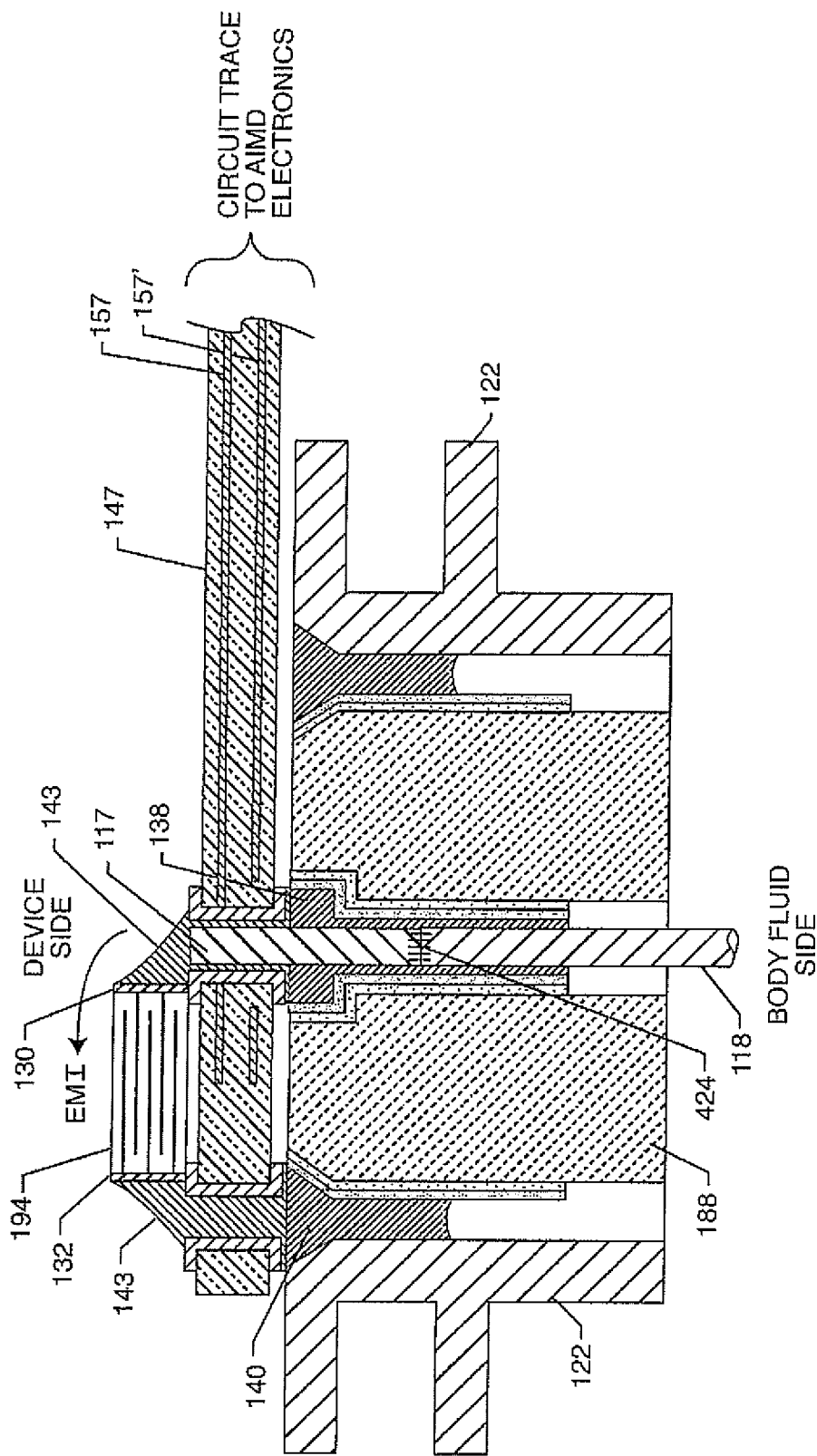
FIG. 48 is similar to FIG. 47 but now illustrates two embedded circuit traces.
Figure 55:
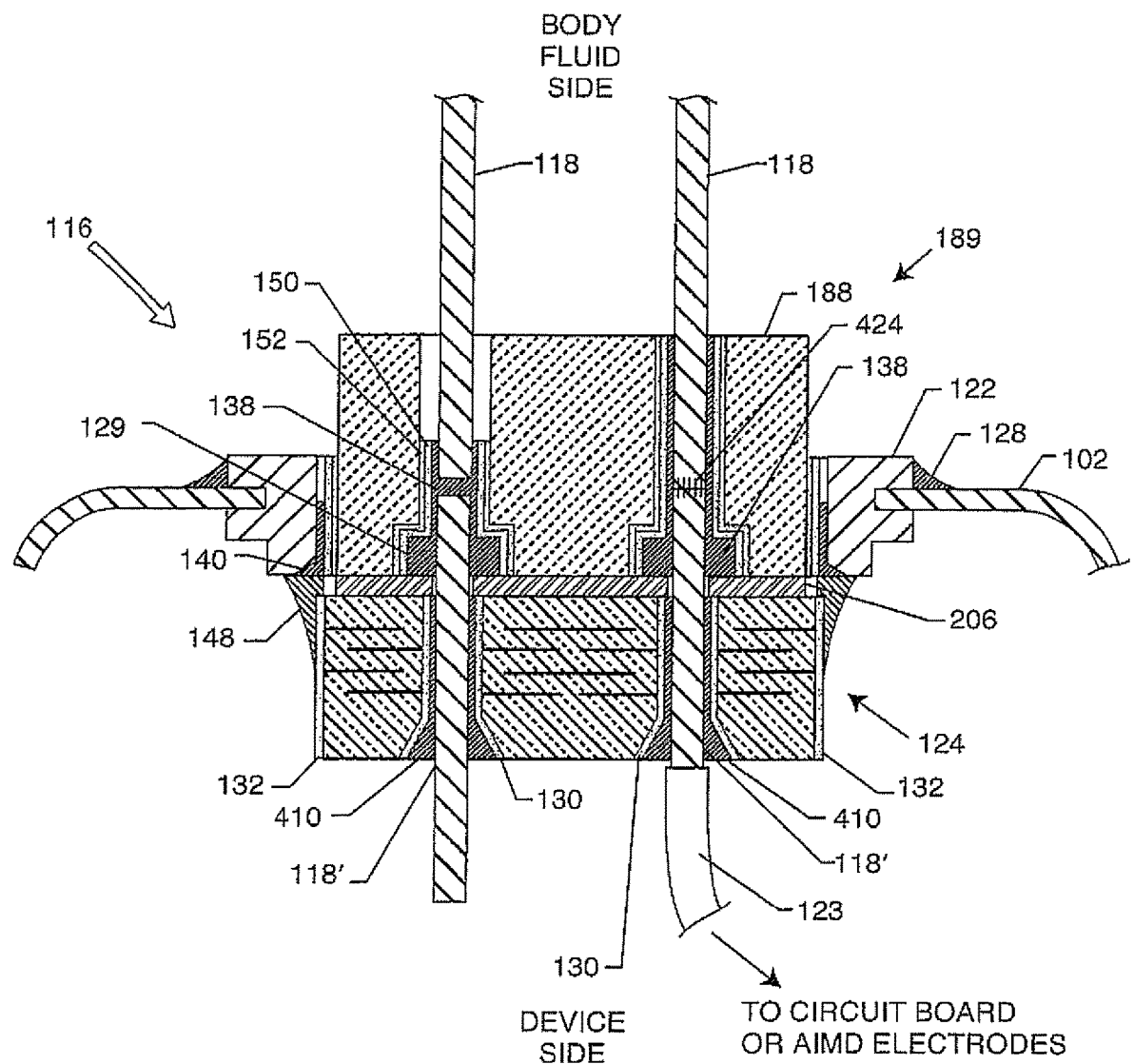
FIG. 55 is very similar to FIG. 8, except that the short lead or pin of FIG. 8 has been eliminated.

FIG. 48 is taken from FIG. 55 of the '917 U.S. patent Publication. In this case, there are two embedded circuit traces 157 and 157'. There is also a surface mounted MLCC chip capacitor 194, as was previously shown in FIG. 47. The MLCC capacitor 194 decouples undesirable electromagnetic interference (EMI) signals from lead 118, 117 and diverts it to the ferrule 122 and in turn, to the AIMD housing 102 (not shown). The sectional view shown in FIG. 48 again, embodies the present invention, including body fluid side biocompatible leadwire 118, which is co-brazed 138 to the device side leadwire 117. Again, in this case, they are pre-joined (optionally) by welding 424 in accordance with the present invention. Referring once again to FIG. 48, one can see that this hermetically sealed filter assembly appears to be unipolar. However, it can be multipolar, such as bipolar, tripolar, quadpolar or the like (all the way to "n"-polar). Embedded circuit traces within the circuit board may be both routed to a unipolar pin or preferably multiple circuit traces that are embedded in the circuit board could be routed each to multipolar pins, such that the multipolar pins are each associated with an MLCC capacitor $194 \ldots 194_n$ and are associated with individual circuit traces $157 \ldots 157_n$. Circuit board 147 could be a rigid circuit board, such as FR4 board, alumina ceramic or the like. Circuit board 147 could also be a flex cable, which is well known in the art.

Figure 49:
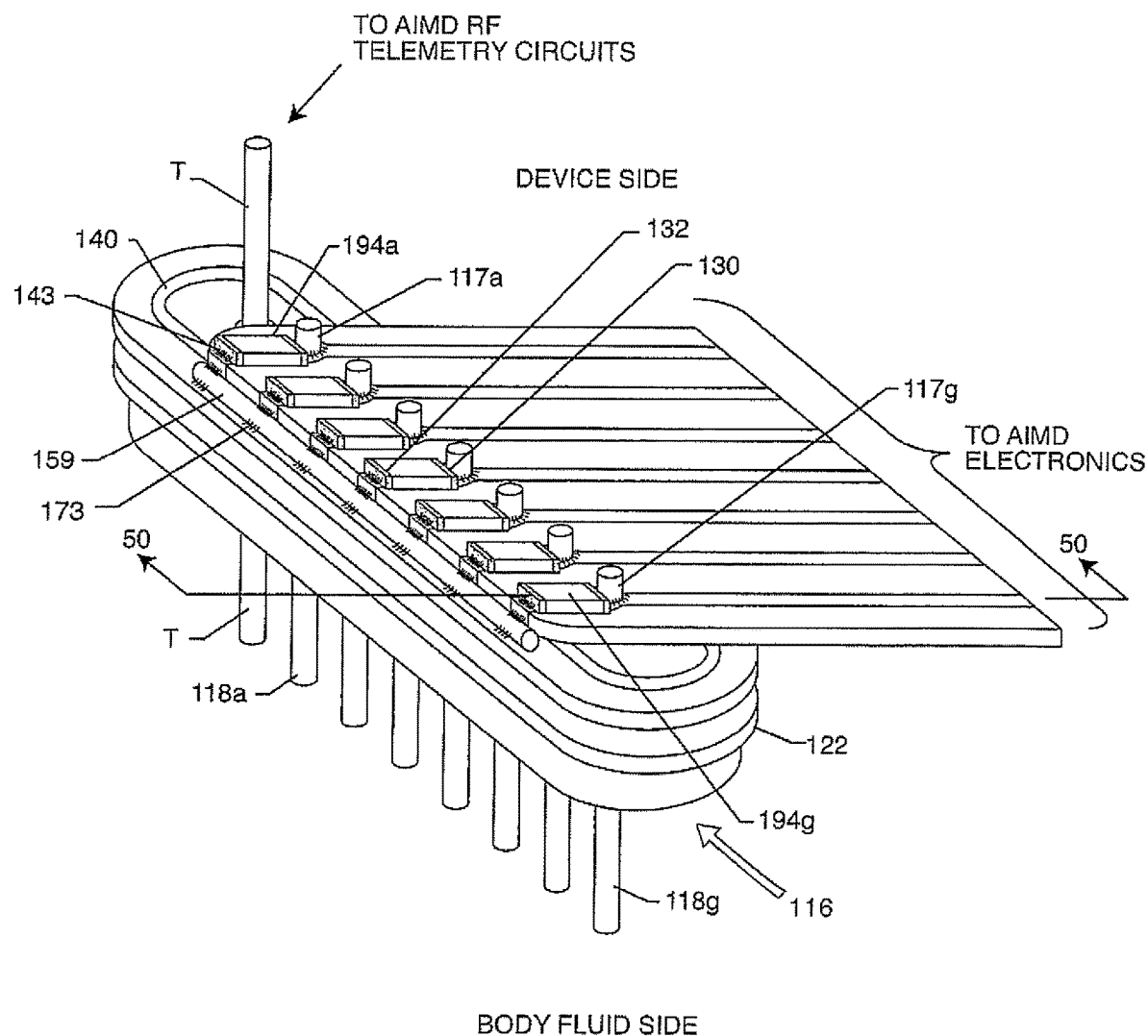
FIG. 49 illustrates a perspective view of an octapolar filtered feedthrough utilizing a circuit board with MLCCs.

FIG. 49 is taken from the '917 patent Publication, FIG. 37. The hermetic seal assembly 116 is octapolar, meaning that it has 8 pins. Seven of these pins are active and one is a telemetry pin T, which as previously described, has to be unfiltered. Each one of the active pins 117a through 117g are each associated with an MLCC chip capacitor 194a through 194g, which act as EMI low pass filters, which can also be called RF diverter elements. Capacitors are grounded to an oxide-free metal addition 159, which is in turn is laser welded 173 to the ferrule 122. FIG. 49 is very similar to FIG. 48 of U.S. Patent Publication 2014/0168917. The function of the metal addition 159 in performing an oxide-resistant low impedance ground connection from the ferrule 122 to the MLCC capacitor ground terminations 132, is more fully described in the '917 patent publication. Typically, this metal addition 159 could be of platinum or palladium or the like. This facilitates easy welding to the ferrule 122 while at the same time, has excellent solderability. Accordingly, an electrical attachment material 143 can comprise of solder, a thermal-setting conductive adhesive or the like. It will also be appreciated that the metal addition 159 can be eliminated if the capacitor ground terminations are electrically connected 143 directly to the gold braze area 140. The importance of grounding a feedthrough capacitor or MLCC chip capacitor to an oxide-free connection is more thoroughly described in U.S. Pat. No. 6,765,779, the contents of which are incorporated herein by reference.

Referring once again to FIG. 49, one can see that the body fluid side pins are labeled 118a through 118g and are generally biocompatible and non-toxic. The leadwire segments are drawn on the device side as 118'a through 118'g and in accordance with the present invention, embody a different material than the body fluid side leads. Referring once again to FIG. 49, it will be appreciated that the ground side 132 of the MLCC capacitors 194 could embody a circuit trace running all along the left side of the board with one or more attachments either directly to the gold braze 140 and ferrule 122 or through a metal addition 159, as previously described.

Figure 50:
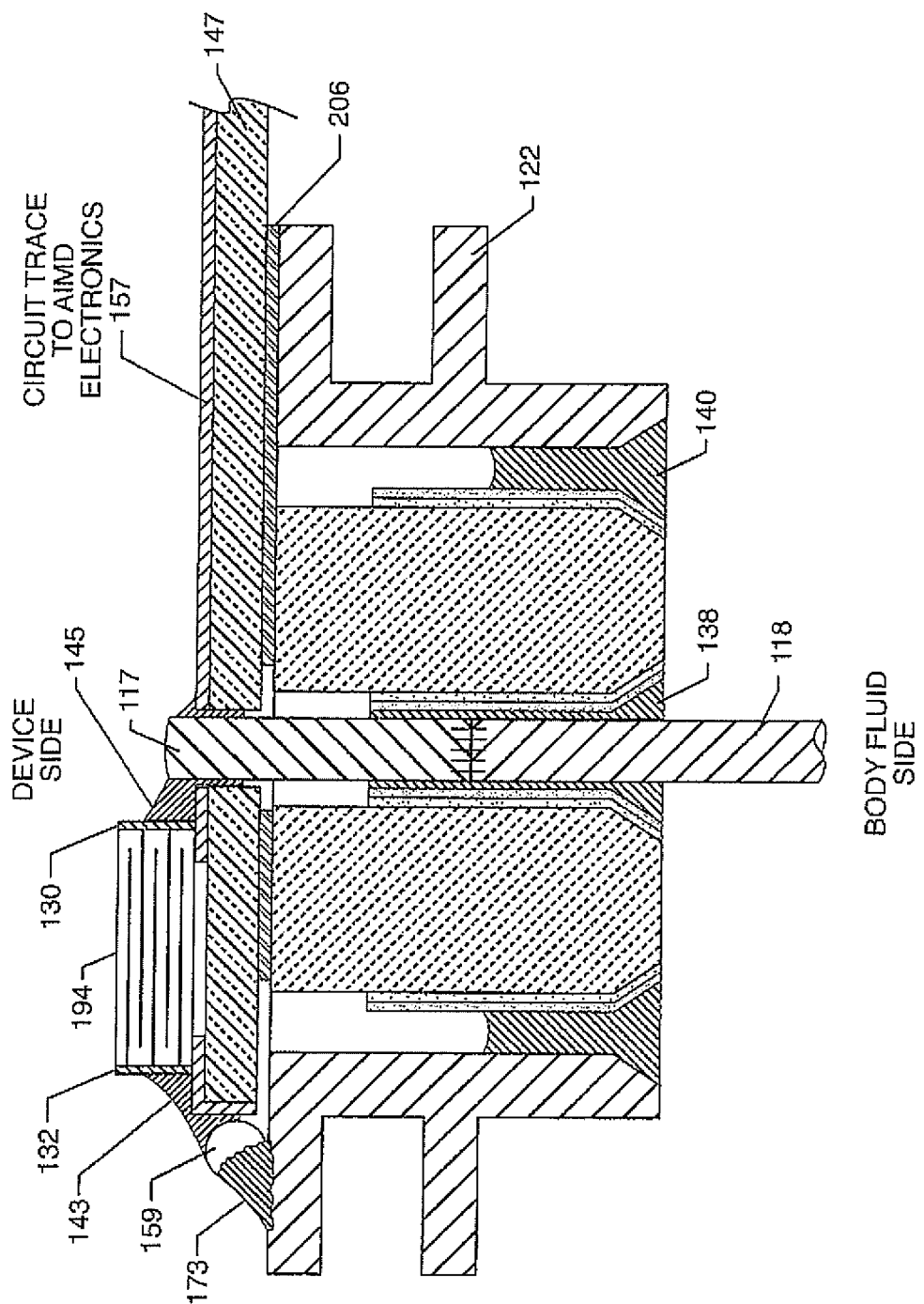
FIG. 50 is a sectional view taken from section 50-50 from FIG. 49.

FIG. 50 is taken from section 50-50 from FIG. 49. Another difference between FIG. 50 and FIGS. 47 and 49 are that the gold brazes 140 and 138 are now disposed to the body fluid side instead of to the device side. Importantly, the gold braze 138 flows around both the body fluid side pin 118 and the device side pin 117, thereby effecting a mechanically strong hermetic seal connection. Having gold braze 138 surround both pins or leadwires 118 and 117 is important such that a strong sheer connection is created. This makes for a relatively high pull strength for both the body side lead/pin 118 and the device side lead/pin 117. It should be noted throughout this patent, in general, when referring to the pin in a hermetic seal or in a feedthrough capacitor that this pin can also be referred to as a lead or a leadwire. In accordance with the present invention, these terms can be used interchangeably. The term "conductive pathway" could also be applied; for example, to the conductive pathway created by body fluid side pin 118 to device side pin 117 of FIG. 50. Again, the circuit board 147 could be rigid or flexible and incorporate at least one circuit trace 157 routed to AIMD electronics. Furthermore, the electrical FIG. 51 describes a hexapolar (6) hermetically sealed filtered terminal in accordance with the present invention. Shown are 6 MLCC capacitors 194a through 194f that are mounted onto circuit board 147. The circuit board is shown in cross-section in FIG. 52, which is taken from section 52-52 from FIG. 51.

Figure 51:
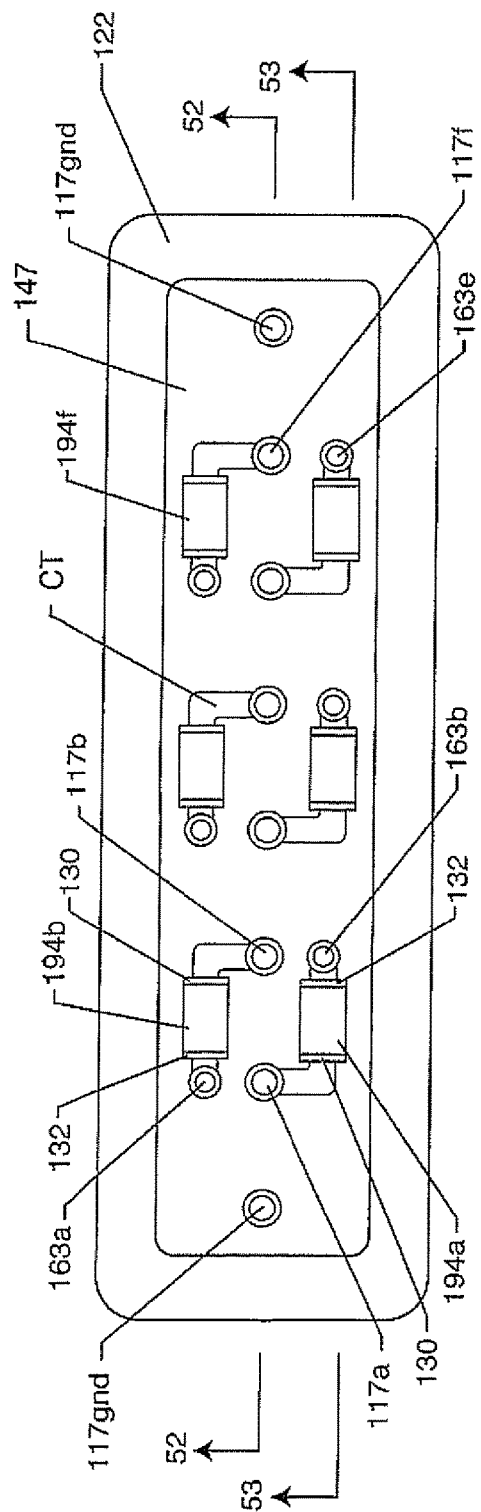
FIG. 51 is a top view of a hexapolar filtered feedthrough of the present invention.
Figure 52:
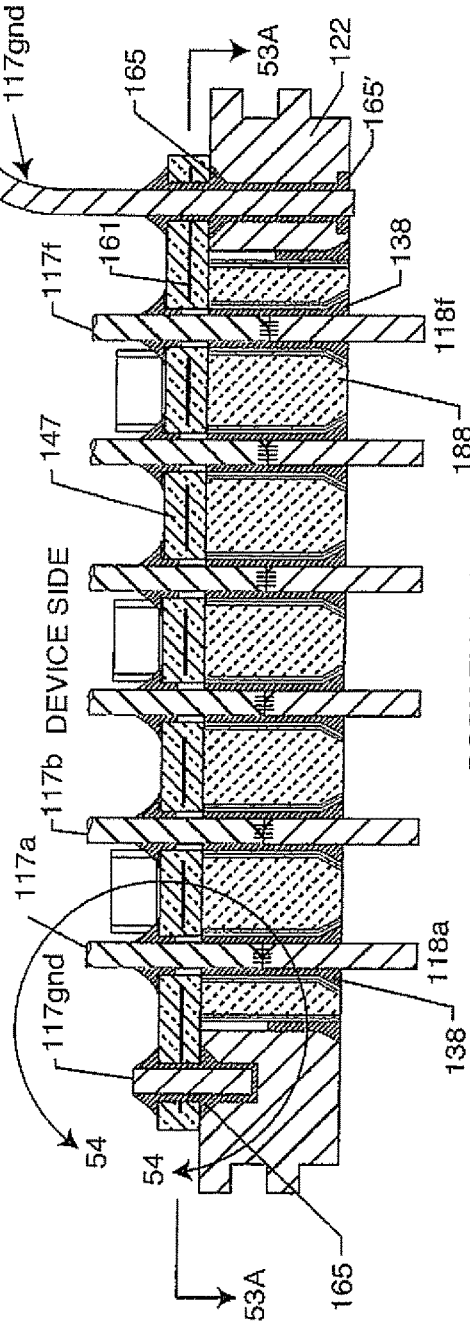
FIG. 52 is a sectional view taken along lines 52-52 from FIG. 51.

FIG. 53 is a second sectional view taken from section 53-53 from FIG. 51. As best shown in FIG. 52, there are two ground pins (or ground leadwires) 117gnd that are directly co-brazed 165 into the ferrule 122 as shown. One of these ground pins 118'gnd is on the far left of circuit board 147 and the other is on the far right of the circuit board 147.

Referring once again to FIG. 52, one can see that the left side ground pin 117gnd does not go all the way from the body fluid side to the device side of the ferrule 122. An alternative ground pin 117gnd is shown on the right side. This pin 117gnd goes all the way through the ferrule 122 as shown. This pin shows both an optional counter-sink 165 and a counter-bore 165' on the body fluid side. It will be appreciated that counter-sink 165 could also be a counter-bore and counter-bore 165' could also be a counter-sink. It will be further appreciated that the pin could be gold brazed in without a counter-bore or counter-sink on either side. Referring once again to the right hand side ground lead 117gnd, one appreciates that it can be gold brazed to the ferrule at location 165 or at location 165' on the body fluid side.

Embedded within circuit board 147 is a ground circuit trace 161. It will be appreciated that a plurality of internal ground circuit traces 161 can be incorporated, which would further reduce the impedance between the ground pins 117gnd across the ground plane 161. In one preferred embodiment, there would be two internal ground plates 161 and an external ground plate disposed at or near the bottom of the circuit board where it is adjacent to either the ferrule 122, the insulator 188 or both. The active hexapolar leadwires on the device side are labeled 118'a through 118'f. Each one of these are associated with an MLCC capacitor which acts as an EMI low pass filter or diverter. Referring to MLCC capacitor 194a in FIG. 51, one can see that on its ground metallization side 132, it is electrically connected to ground via hole 163b. On the active termination side 130 of MLCC capacitor 194a, you can see a circuit trace (CT) and an electrical connection to via hole about leadwire pin 117'a. Referring to FIG. 52, one can see the active device side pin 117'a running through the via hole of the circuit board 147 and being co-gold brazed 138 with the hermetic insulator 188 to the body fluid side leadwire 117a. This is in accordance with the present invention. Referring once again to FIG. 51, MLCC capacitor 194a on its ground metallization side 132 is connected through a short circuit trace or directly through soldering or thermal-setting conductive adhesives to ground via hole 163b. It will be appreciated that on either the active or ground side of the MLCC capacitors 194, there could be a direct connection to either the via holes or pins or elongated circuit traces could be used on one or both sides, as illustrated. It will also be appreciated that these circuit traces could embody a second via hole and the circuit trace itself could be internal to the circuit board, as is known in the art. Referring to FIG. 53, one can see in cross-section, the grounded via hole 163b, which is electrically connected to the embedded ground plane or ground circuit trace 161 within the circuit board 147. It will be appreciated by those in the art that the ground circuit trace 161 could take on many different shapes or dimensions or even be multilayer. For simplicity, a single layer is shown. The circuit board 147 could be of a flex board or what's known in the art as a flex cable. It could also be a rigid board as shown. Materials for a rigid board would include ceramic, such as an alumina ceramic circuit board or fiberglass, otherwise known as FR4 boards.

FIG. 53A is taken generally from section 53A-53A from FIG. 52. This shows the top view of the ground plane 161. Referring to FIG. 53A, one can see that the ground plane 151 is connected to the left ground pin 117gnd and the right ground pin 117gnd, which is previously shown in FIG. 52, are gold brazed or welded directly to the ferrule structure 122. One ground pin, instead of two, could be used; however, this would increase the impedance across the ground plane and would lead to reduced filtering effectiveness, also known as insertion loss of the most distant pins. It will be appreciated that any number of ground planes 117gnd as required for proper ground plane performance can be used. Referring once again to FIG. 52, one can see that the left-hand ground pin 117gnd is quite short and only extends a little ways above the circuit board 137. It is typical in an AIMD applications that an internal circuit board be properly grounded. Accordingly, on the right-hand side of FIG. 52, the ground pin 117gnd on the device side, has been elongated so that it can extend and connect to the ground trace of an AIMD circuit board (not shown). In accordance with the present invention, it would be desirable that these pins on the device side be of non-oxidizable material, such as palladium or platinum. Other materials or alloys, such as platinum-iridium or palladium-iridium, can also be used. On the device side, these leadwires 117' are generally long so that they can be routed to a distant circuit board 126 having AIMD electronic circuits. Referring once again to FIG. 51, one can see the second MLCC capacitor labeled 194b. It is connected at its active termination 130 to via hole 117b, which is also illustrated in FIG. 52. Referring once again to MLCC capacitor 194b, its ground termination 132 is dielectrically connected to ground via hole 163a. Referring back to FIG. 51, one can see that the MLCC capacitors 194a, 194b all the way to 194f, alternate their active connections back and forth along with their ground connection, which also alternate as shown in FIG. 53A. It will be appreciated that the hexpolar (6) filter hermetic terminal of FIGS. 51 through 53 can be of any number of terminals, including "n" active terminals, which would embody "n" MLCC capacitors. It will also be appreciated that non-filtered telemetry pins T (not shown) could be added.

The ground pins 117gnd are also known as metal additions in accordance with U.S. Patent Publication 2014/0168917, the contents of which are incorporated herein fully by reference. For example, one is referred to FIG. 36 of the '917 U.S. patent Publication as showing metal addition 220.

Figure 54:
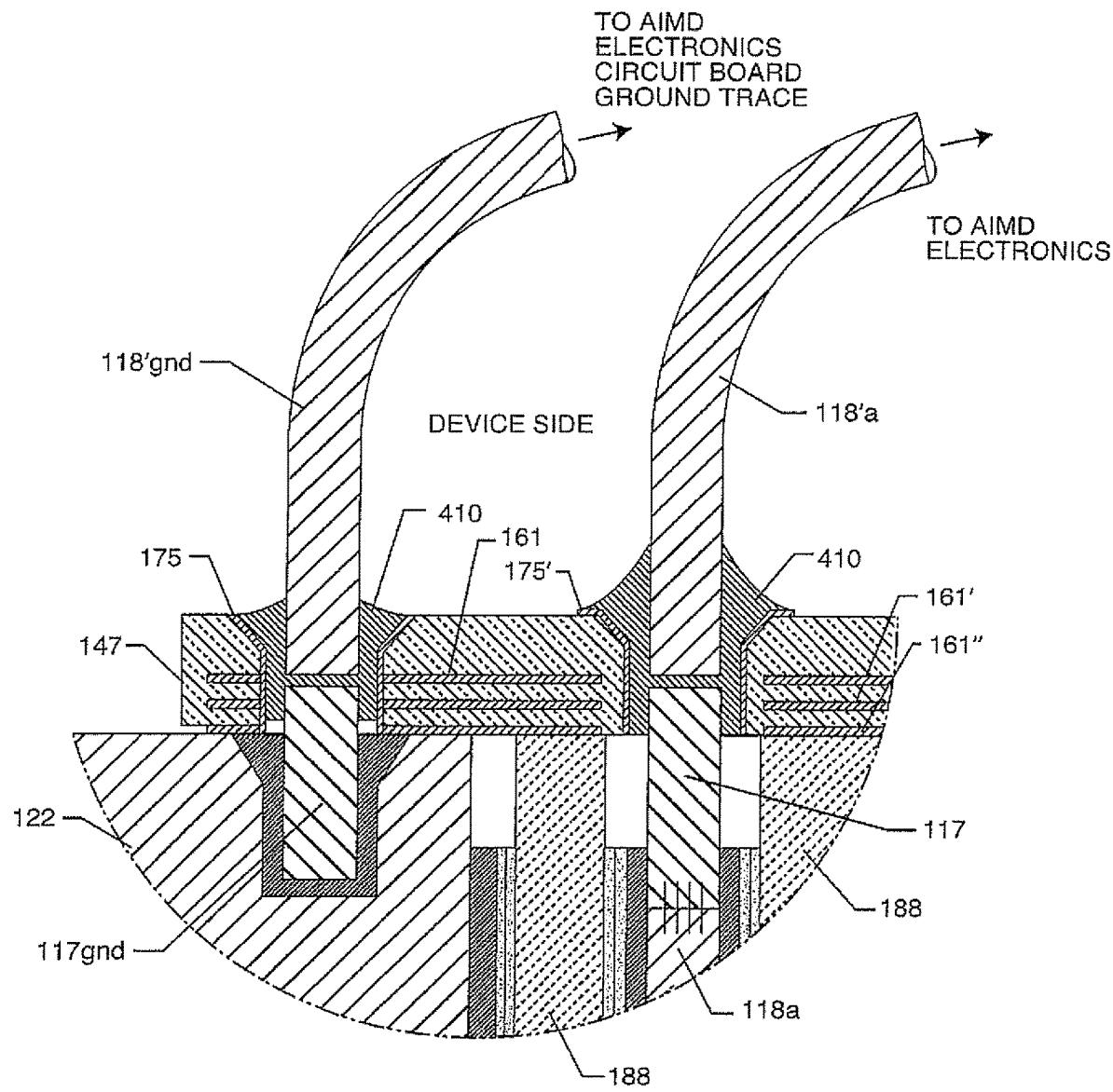
FIG. 54 is an enlarged view taken along lines 54-54 from FIG. 52 but is now showing a new embodiment.

FIG. 54 is a sectional view generally taken from section 54-54 from FIG. 52. This shows an important low cost alternative to running the leadwires 118' all the way to AIMD electronic circuits. It needs to be remembered that as illustrated in FIGS. 51 through 53, that these leadwires 118' are generally of platinum, palladium or various alloys involving iridium, Shown in FIG. 54, one can have a short leadwire segment 117 of platinum or palladium and then co-join a low cost leadwire 118'a. In some cases, at least one of the ground pins 118'gnd would also be long in order to connect the AIMD housing ground to the AIMD electronic circuit board ground trace. As taught in FIG. 8, these low cost leadwires 118' can be of extremely low cost materials, such as tin-copper wire. These low cost leadwires 118'gnd and 118'a may also embody an insulative material 123 as illustrated in FIG. 8, or an insulation sleeve which can be subsequently added. Comparing FIG. 54 to FIG. 8, one can see that the connection of low cost leadwire 118' to the short pin 117 can be accomplished either inside the feedthrough capacitor of FIG. 8 or within a circuit board 147, as illustrated in FIG. 54. Referring back to FIG. 54, one can see that one ideal way to co-connect the short lead pin 117gnd to the low cost leadwire extension 118'gnd, would be the use of a solder or a thermal-setting conductive adhesive 410. As taught in FIG. 8, the solder 410 would preferably be of a high temperature solder and it would create a shear connection around both leadwires, lead pin 117gnd and low cost leadwire extension 118'gnd and at the same time, also form a shear connection on the inside diameter point of ing 175 of the circuit board 147 via holes. Referring once again to FIG. 54, one can see that there are three ground plates 161, 161' and 161". Two of the ground plates 161 and 161' are embedded within circuit board 147. Ground plane 161" is disposed on the bottom surface of the circuit board 147 and is immediately adjacent the ferrule and the insulator 188. This external ground plate 161" is important as it acts to prevent the direct radiation of a closely held emitter into the interior of the AIMD housing. This is known as direct radiated interference as opposed to conductive interference. Conductive interference would be picked up on the body fluid side of the leads and it is the purpose of the diverter capacitors 194, to divert this unwanted high frequency conductive interference away from the active leadwires to the ferrule 122. Direct radiated interference could penetrate through the edges of the circuit board 147 and undesirably couple to sensitive electronic circuits. Accordingly, the ground plates, especially the external ground plate 161", has a dual purpose. That is, it acts as a shield to such direct radiated interference. It also desirably decreases the impedance along the ground planes such that the active pins are more effectively filtered.

FIG. 55 is very similar to FIG. 8, except that the short lead or pin of FIG. 8 has been eliminated. In this case, there is still a co-brazed joint 138, which may also embody a weld 424, as shown in both FIGS. 55 and 8. In this case, there is a continuous leadwire 118', which runs to AIMD electronics generally mounted on a circuit board (not shown).

Figure 56:
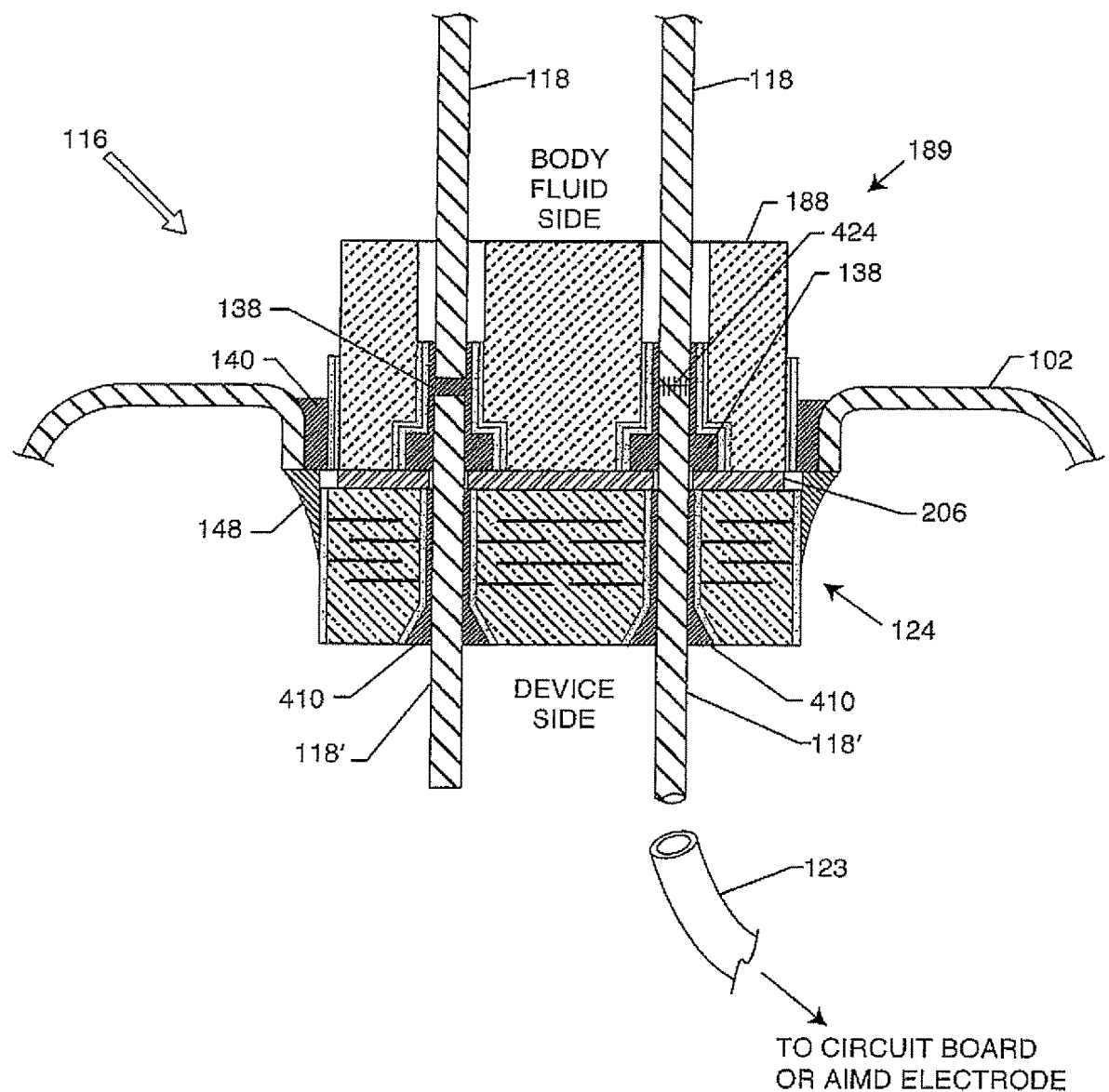
FIG. 56 is very similar to FIG. 55, except that the insulation material on the wire can be added as separate tubing or even a heat-shrink tubing and in addition the structure of FIG. 56 has no ferrule.

FIG. 56 is very similar to FIG. 55, except that the insulation material 123 on the wire can be added as separate tubing or even a heat-shrink tubing. In addition the structure of FIG. 56 has no ferrule 122 as described in FIG. 55. In FIG. 56, the AIMD housing 102 has been bent down forming an aperture, which enables the hermetic seal insulator 188 to be co-brazed 140 to the AIMD housing 102. The advantage is that the relatively high cost ferrule 122 has been completely eliminated.

Figure 57:
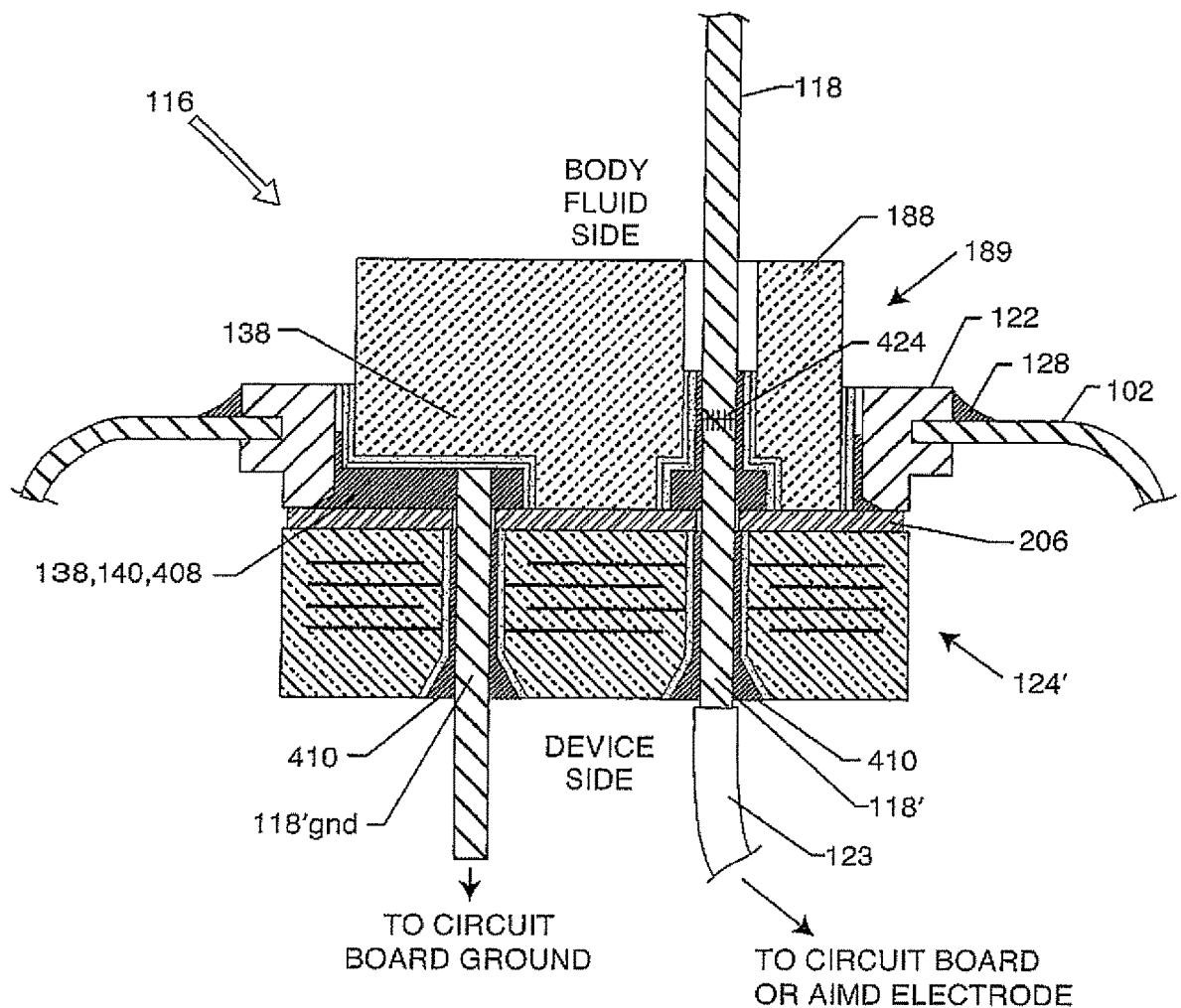
FIG. 57 is very similar to FIG. 54, except the short leadwire pin or stub has been eliminated and the length of the leadwire has been lengthened to effect a co-braze joint in accordance with the present invention in the hermetic insulator, furthermore the ground lead wire is electrically coupled to the ferrule through a gold braze moat.

FIG. 57 is very similar to FIG. 54, except the short leadwire pin or stub 117 has been eliminated and the length of the leadwire 118' has been lengthened to effect a co-braze joint in accordance with the present invention in the hermetic insulator 188. There is a gold braze moat 138,140,408, which grounds the left-hand pin 118'gnd. An internally grounded feedthrough capacitor 124' is illustrated. Importantly, there is no need for an external perimeter or diameter metallization 132 on the feedthrough capacitor nor is there a need for a capacitor ground connection 148 from the capacitor outside diameter or perimeter to the ferrule 122. Optional leadwire insulation 123 is shown, as has been previously described in FIG. 56. As one can see in FIG. 57, there is at least one ground pin 118'gnd that is connected to the capacitors internal ground electrode plate set. In this case, the ground pin is co-brazed into a gold brazed moat 138, 140, 108. The gold braze moat provides a very low impedance and oxide-free electrical connection to both the ferrule and to ground pin 118'gnd.

Figure 58:
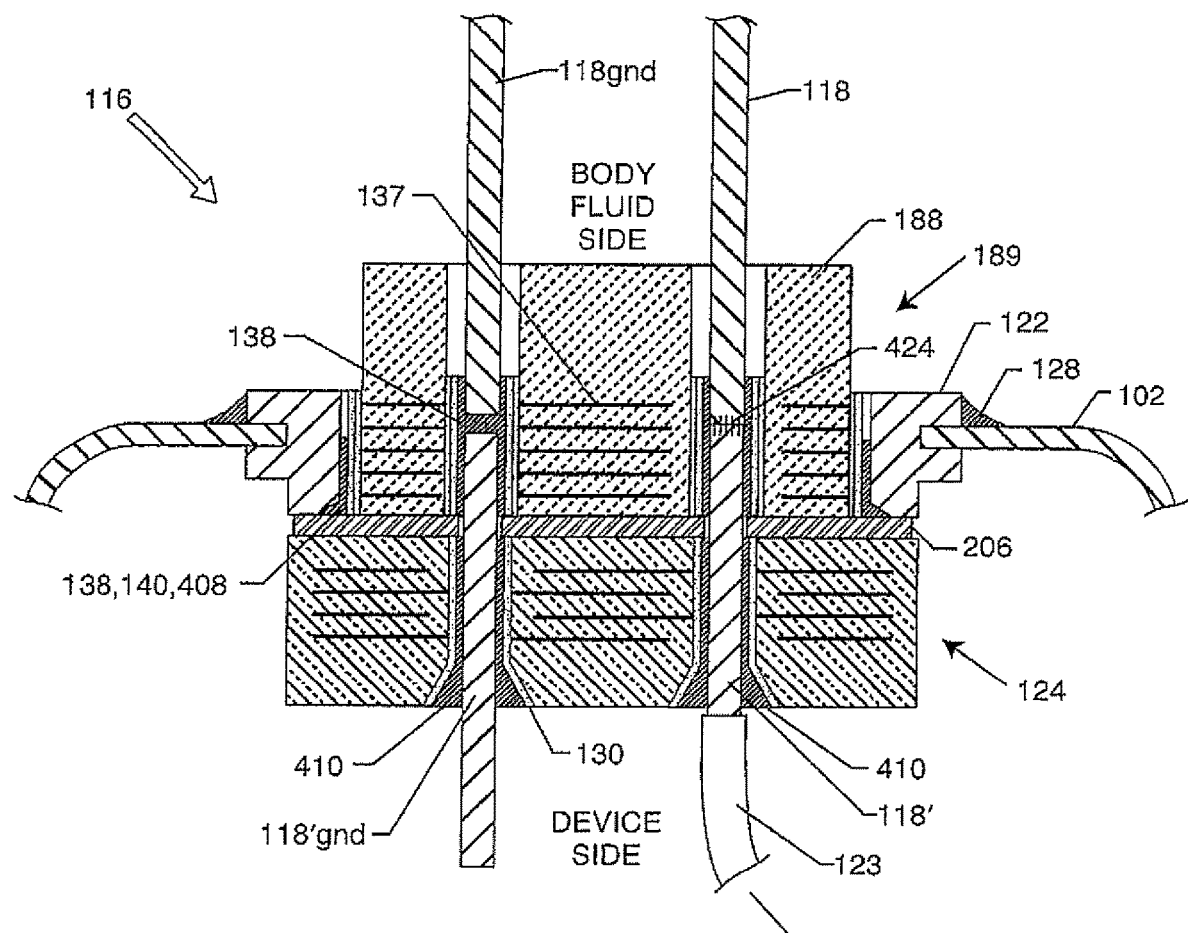
FIG. 58 is very similar to FIG. 57 and now FIG. 25 in that, the left-hand ground pin is grounded through a gold braze joint to embedded ground electrode plates within the hermetic seal insulator.

FIG. 58 is very similar to FIG. 25 in that, the left-hand ground pin 118gnd is grounded through a gold braze joint 138 to embedded ground electrode plates 137 within the hermetic seal insulator 188. Again, in FIG. 58, the short pin or 117 has been eliminated, as previously described in FIGS. 56 and 57. In this case, the ground pin 118'gnd extends all the way through the insulator 188 to the body fluid side. This is normally not the case in prior art applications, but could be important for MRI applications, especially where a grounded port or surrogate pacemaker was also incorporated.

Figure 59:
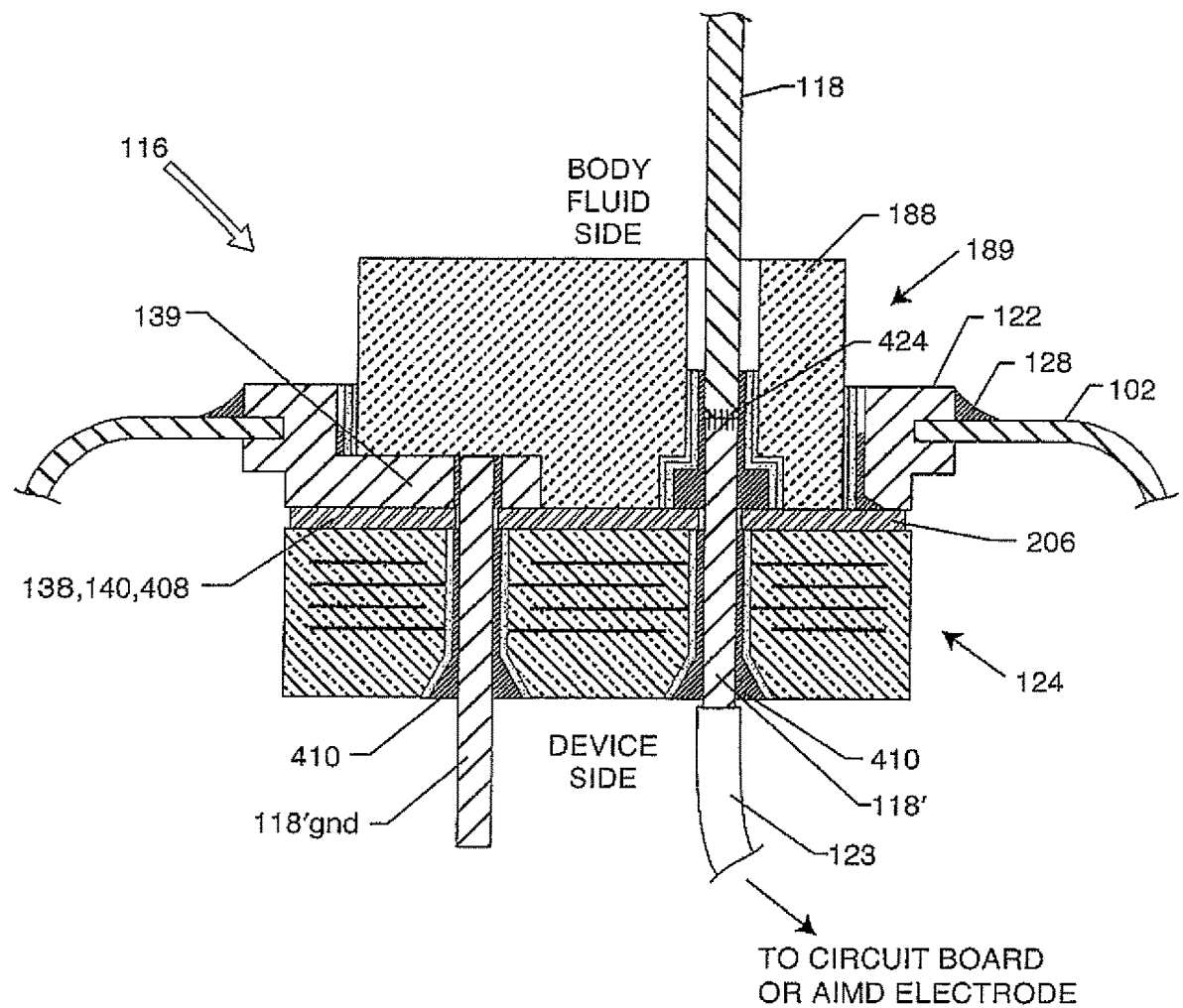
FIG. 59 is very similar to FIG. 58 and now FIG. 30 in that, the ferrule has one or more peninsulas which facilitates the grounding of the left-hand pin.

FIG. 59 is very similar to FIG. 30 in that, the ferrule 122 has one or more peninsulas 139 which facilitates the grounding of the left-hand pin 118'gnd. Again, as previously described in FIG. 57, the short ground pin 117 of FIG. 30 has been eliminated. One will appreciate, referring to FIG. 59, that the peninsula 139 could be replaced with a metal piece 141, as previously described in FIGS. 28 and 29.

Figure 60:
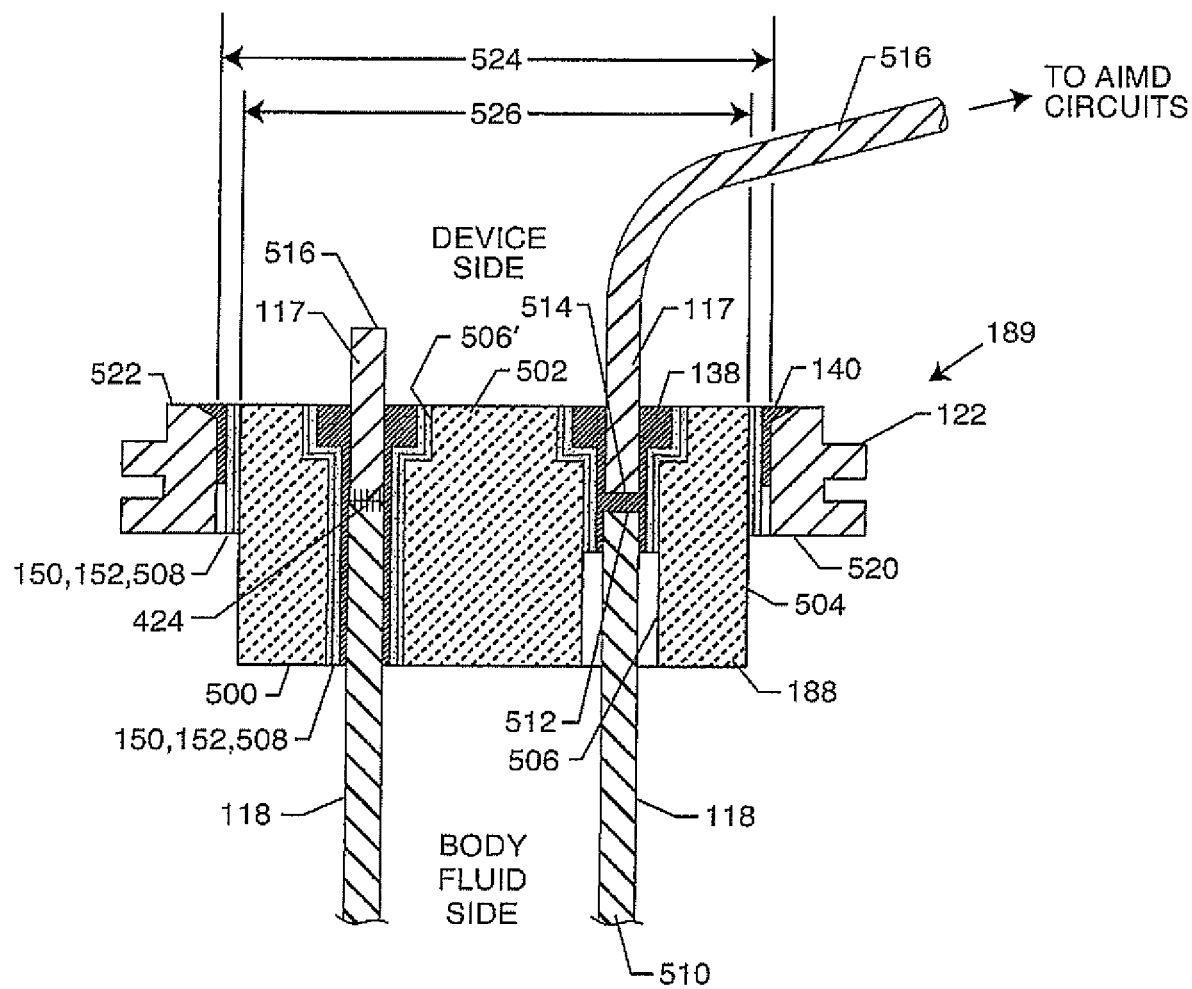
FIG. 60 is taken from the bottom portion of the exploded view previously illustrated in FIG. 9.

FIG. 60 is taken from the bottom portion of the exploded view previously illustrated in FIG. 9. It is noted that the feedthrough capacitor 124 has been removed. FIG. 60 is known in the art as an unfiltered hermetic feedthrough terminal. These are also known as UFTs (unfiltered terminals). It can be seen that there is a joining by co-brazing 138 of two different materials for the pins 117 and 118 within the hermetic seal insulator body 188. The pins can be short, as shown on the left 117 or it can be elongated and directed to AIMD circuits, as shown on the right 117. Importantly, not all AIMDs require filtering. For example, there are neurostimulators that have no sense circuits and are inherently immune to EMI. For example, a cardiac pacemaker or an implantable defibrillator have very sensitive circuits that monitor cardiac activity and other biologic signals. These sensing circuits make them relatively sensitive to emitters, such as cellular telephones that may embody modulation at biologic frequencies. On the other hand, a spinal cord stimulator that only produces a regular pulse, which is adjustable by the patient, is relatively insensitive to EMI and may not require EMI filtering at the point of ingress to pins 117 into the AIMD housing. This is because, in general, spinal cord stimulators do not have any biological sensing circuits that would be sensitive. Throughout this patent, when labeled "device side", this means that this is the side that is generally inside of the AIMD hermetically sealed housing. In summary, FIG. 60 is to emphasize that the present invention can be sold as a hermetic seal without any filtering in the marketplace. It will be appreciated that the UFT of FIG. 60 may provide for grounding to the ferrule potential 122 by means of a braze moat 138, 140, 408, as shown in FIG. 24, by ground plates 137 embedded in the insulator 188, as shown in FIG. 25, by a grounding metal piece, as shown in FIGS. 28 and 29 or by a peninsula 139 of the ferrule 122, as taught in FIG. 30. Referring back to FIG. 60, we have a hermetic seal feedthrough assembly 189, which is attachable to an opening in the housing of an active implantable medical device. Assembly 189 comprises an insulator body 188 defined as having a first insulator side 500 opposite a second insulator side 502. The first insulator side and second insulator side are separated and connected by at least one outside surface 504, 526. There is at least one via hole 506, 506' disposed through the insulator body extending from the first insulator side 500 to the second insulator side 502. It will be appreciated that any number of via holes are possible. For example, in a retinal implant, there may be several hundred via holes. The assembly 189 of FIG. 60, including an internal metallization 508, which is sputtered, deposited or otherwise adhered to the insulator 188. In the present invention, the internal metallization is characterized as comprising two sputter layers 150 and 152. However, this could be a single metallization layer, as previously described. The internal metallization 502 is formed, at least partially, on the inside of the one via hole 506, 506'. Assembly 189 includes a first conductive leadwire 118 having a first conductive leadwire first end 512, at least partially disposed within at least one via hole 506, 506' and having a first conductive leadwire second end 510 disposed past the first insulator side 500. Leadwires 118 can be routed to an AIMD connector block, an implantable lead, including lead conductors or the like (not shown). In addition, there is a second conductive leadwire 117 having a second conductive leadwire first end 514, at least partially disposed within the at least one via hole 506, 506', and having a second conductive leadwire second end 516 disposed past the second insulator side 502. Typically, the second conductive leadwire second end would be attached to a flex cable, circuit board, a feedthrough capacitor, other types of filtered capacitors and onto AIMD circuits (not shown). The first conductive leadwire first end is disposed near, at or adjacent to the second conductive leadwire first end. Optionally, the first conductive leadwire first end may be welded 424 to the second conductive leadwire first end. In accordance with the present invention, the first conductive leadwire 118 is not of the same material as the second conductive leadwire 117. As shown, there is a first braze 138 at least partially between the first conductive leadwire 118 first end 512 and the second conductive leadwire 117 first end 517 and the internal metallization 508 wherein, the first braze 138 forms a first hermetic seal separating the first insulator 500 from the second insulator side 502 and a second external metallization 518 is disposed at least partially on the at least one outside surface 504 and insulator body 188. As shown, the outside surface 504 of the insulator may be gold brazed 140 to a conductive ferrule 122 defined as having a first ferrule side 520 opposite a second ferrule side 522 and defining a ferrule opening 524 between and through the first ferrule side 520 and second ferrule side 522 wherein, the insulator body 188 is at least partially disposed within the ferrule opening 524. As shown, there is a second gold braze 140 at least partially between the external metallization of the insulator body 518 and the conductive ferrule body 122. A second braze forming a second hermetic seal hermetically sealing the ferrule opening.

Figure 61:
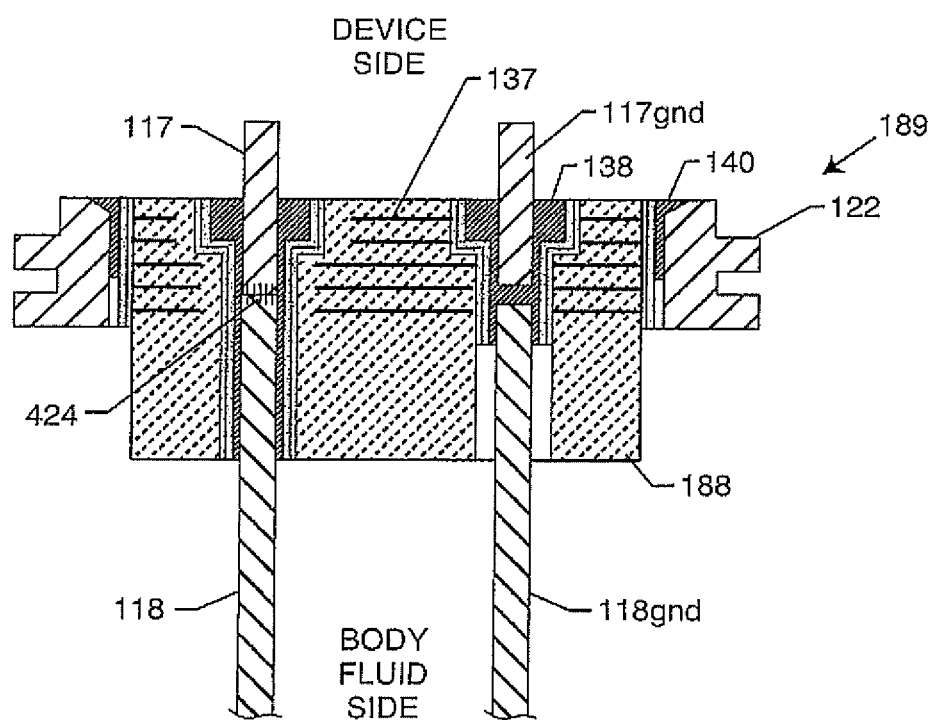
FIG. 61 is very similar to FIG. 60, except that it incorporates internal ground plates that are contained within the hermetic insulator.

FIG. 61 is very similar to FIG. 60, except that it incorporates internal ground plates 137 that are contained within the hermetic insulator 188. These internal ground plates 137 facilitate the grounding of at least one of the pins, in this case 118gnd, 117gnd on the right-hand side, which provides a convenient way for grounding of an AIMD circuit board ground trace.

Figure 62:
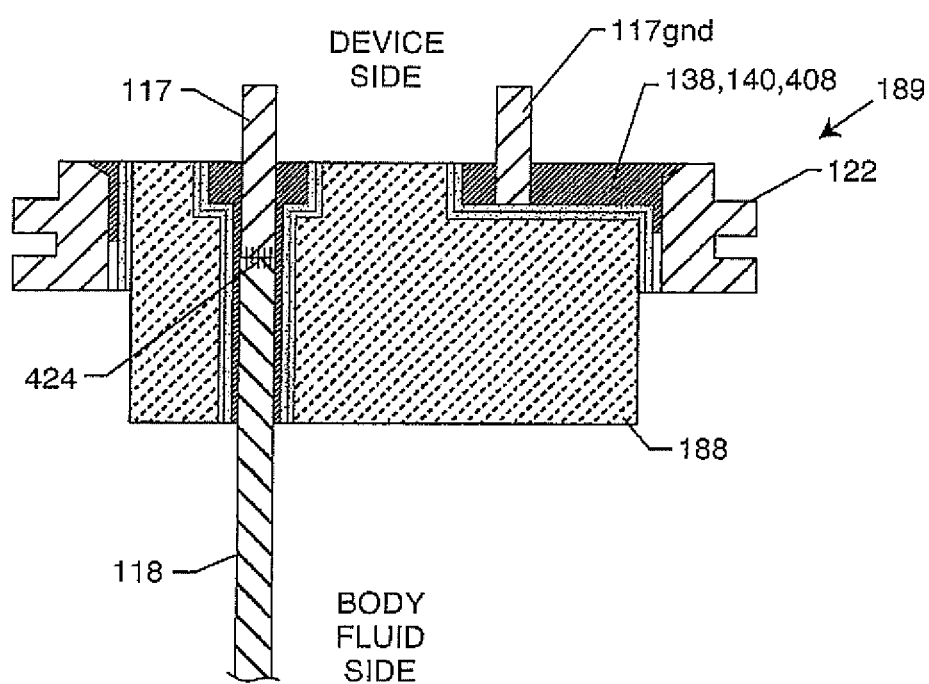
FIG. 62 shows an alternative method of FIG. 61 now using a gold braze moat.

FIG. 62 shows an alternative method using a gold braze moat 138, 140, 408 for ground pin 117gnd.

Figure 63:
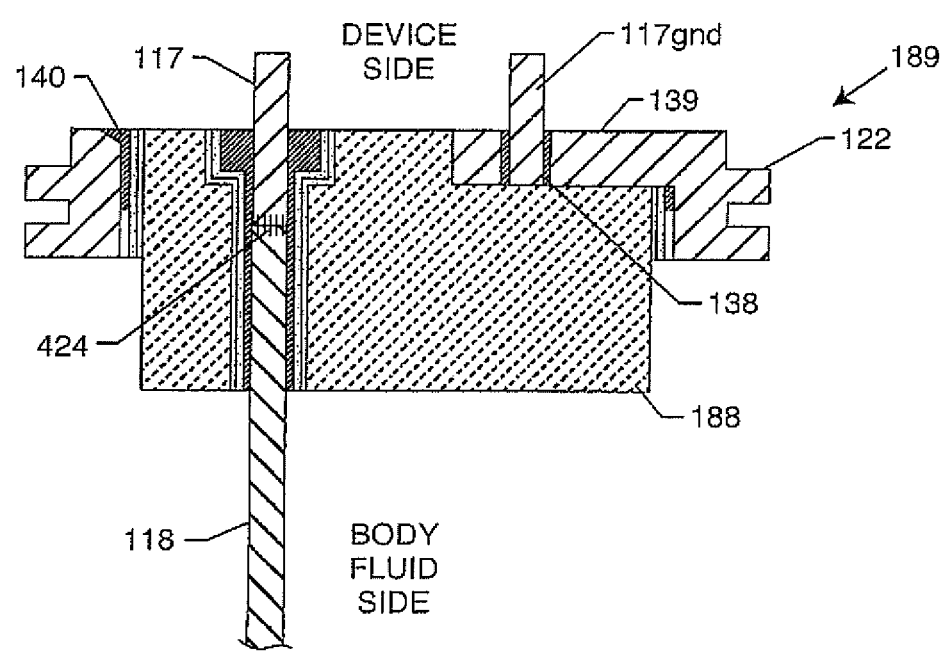
FIG. 63 illustrates that the right-hand ground pin can also be grounded by a co-machined peninsula of the hermetic seal insulator.

FIG. 63 illustrates that the right-hand ground pin 118gnd can also be grounded by a co-machined peninsula 139 of the hermetic seal insulator 122, as previously described in FIG. 6. Referring once again to FIGS. 60, 61, 62 and 63, it shall be noted that on the device side, the pins or 117 may be short or may be elongated and directed to AIMD circuits. When short, it would be convenient to make electrical attachment inside the AIMD with a circuit board (not shown), a flex cable (not shown), or individual wires (not shown).

Figure 64:
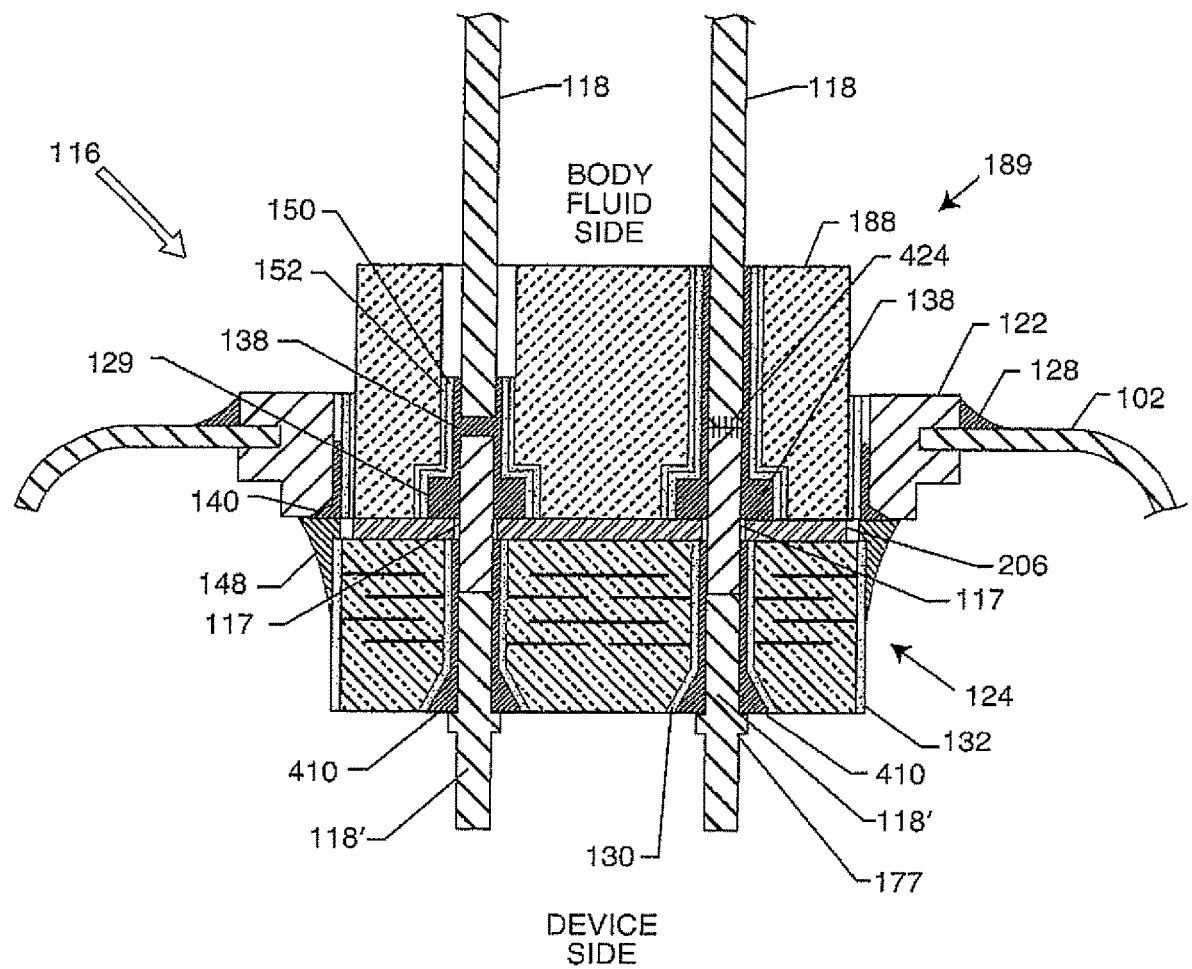
FIG. 64 is very similar to FIG. 8, except that the pin has been formed into a wire wrapped terminal.

FIG. 64 is very similar to FIG. 8, except that the pin 118' has been formed into a wire wrapped terminal 177. This wire wrapped terminal 177 is shown proud of the device side surface of the feedthrough capacitor 124.

Figure 65:
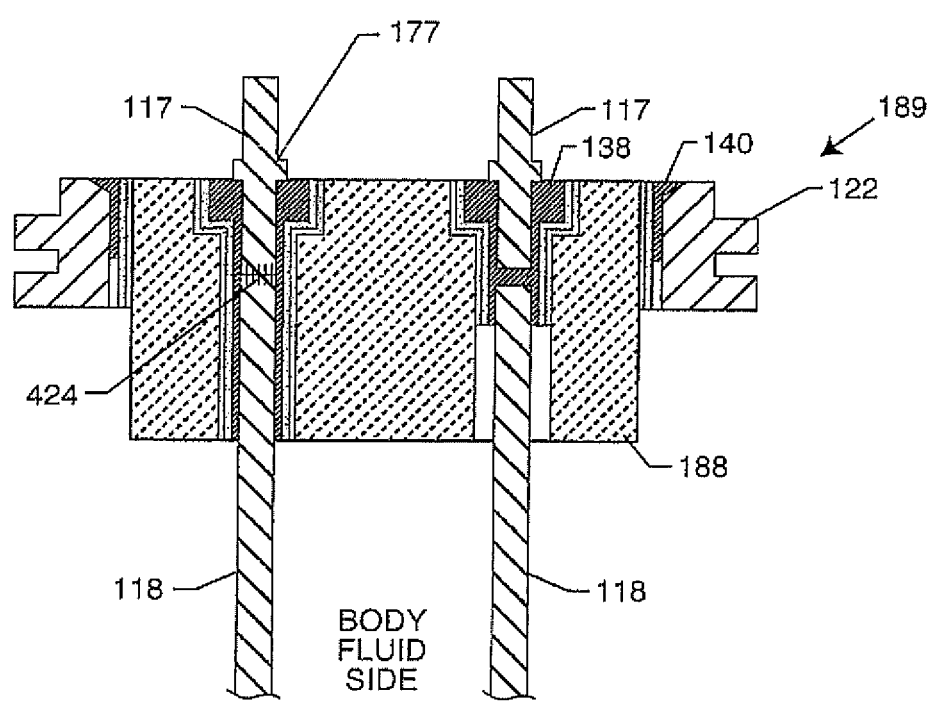
FIG. 65 is very similar to FIG. 64, except that it shows the hermetic terminal subassembly inverted and the feedthrough capacitor has been eliminated.
Figure 66A:
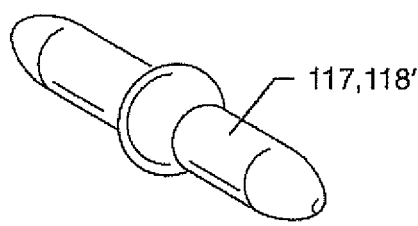
FIG. 66A is a perspective view of new embodiment of pin used in the present invention.
Figure 66B:
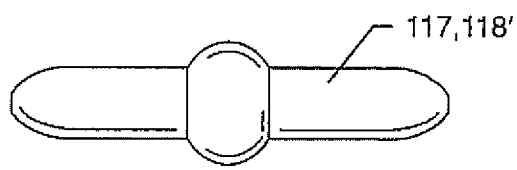
FIG. 66B is the side view of the structure of FIG. 66A.
Figure 67A:
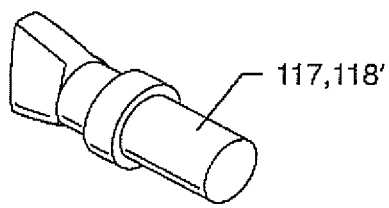
FIG. 67A is a perspective view of new embodiment of pin used in the present invention.
Figure 67B:
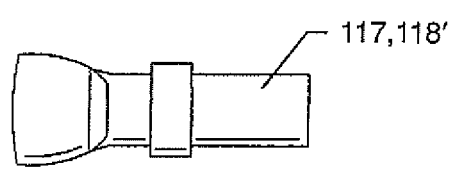
FIG. 67B is the side view of the structure of FIG. 67A.
Figure 68A:
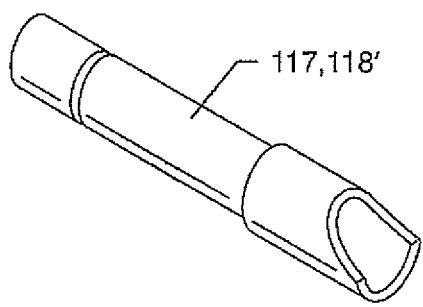
FIG. 68A is a perspective view of new embodiment of pin used in the present invention.
Figure 68B:
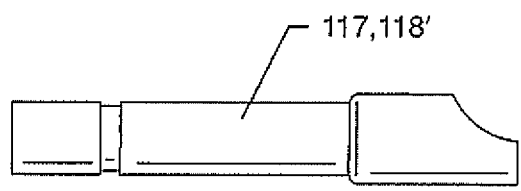
FIG. 68B is the side view of the structure of FIG. 68A.
Figure 69A:
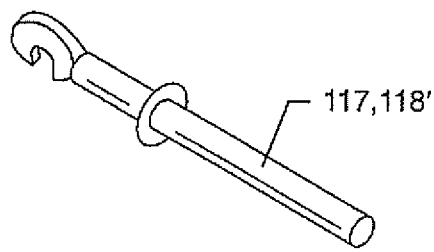
FIG. 69A is a perspective view of new embodiment of pin used in the present invention.
Figure 69B:
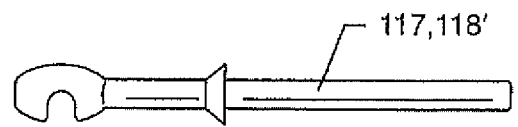
FIG. 69B is the side view of the structure of FIG. 69A.
Figure 70A:
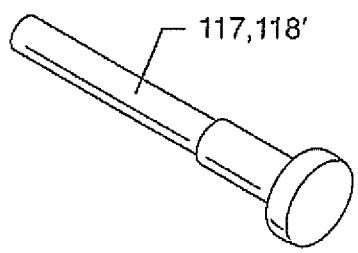
Figure 70B:
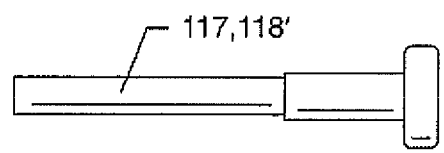
Figure 71A:
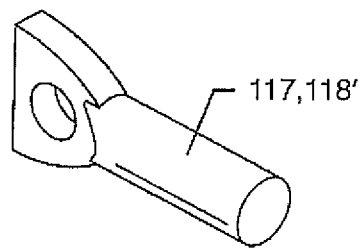
Figure 71B:
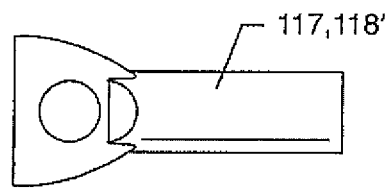
Figure 72A:
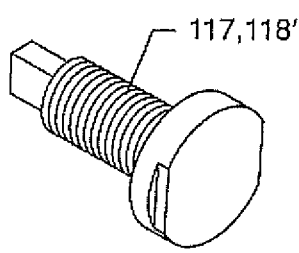
Figure 72B:
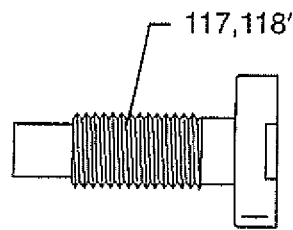

FIG. 65 is very similar to FIG. 64, except that it shows the hermetic terminal subassembly 189 inverted and the feedthrough capacitor 124 has been eliminated. This means that FIG. 65 is very similar to FIG. 61, except that the device side pin 117 has been replaced by a formed wire wrapped pin 117, 177, as illustrated in FIG. 65.

One is now directed to FIGS. 66A through 72B, which illustrate that the wire wrapped pins 118' of both FIG. 64 and FIG. 65, may be replaced by any of these shapes to facilitate a connection to device side leadwires or circuit boards (not shown).

Figure 73:
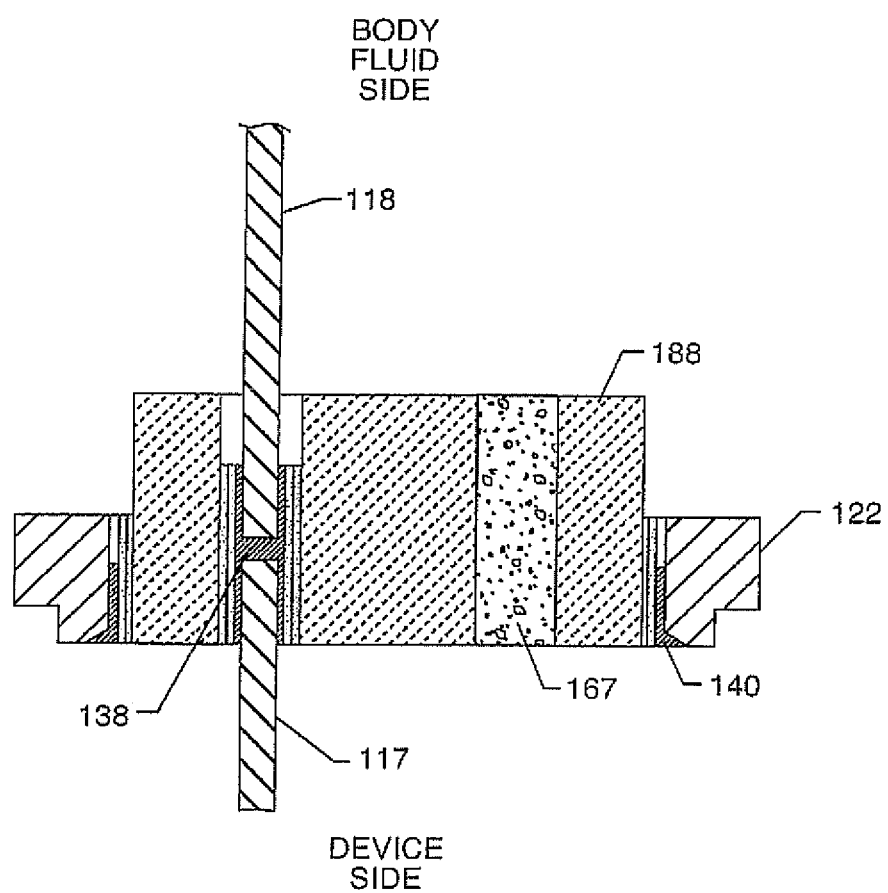

FIG. 73 illustrates that the present invention, shown on the left side embodying body fluid side pin or leadwire 118 and device side 117 were co-joined or co-brazed 138, may comprise a hybrid structure wherein, one or more of the conductive pathways or conductive vias through the hermetic seal insulator, has been co-fired forming a conductive via 167. Conductive vias are well known in the prior art and may comprise substantially pure platinum, CERMET materials, various combinations of metal binders and metal paste and the like. One is referred to U.S. Pat. Nos. 8,653,384; 8,938,309; 9,233,253, the contents all of which are incorporated herein by reference. Referring once again to FIG. 73, it will be appreciated that the left side pin 117, shown on the device side, may be replaced by any of the wire wrapped terminals or shapes previously illustrated in FIGS. 65 and 66A through 72B. Referring once again to FIG. 73, it will be appreciated that the co-firing of the conductive via 167 and the alumina insulator would be typically formed as a first step at a very high temperature. In a secondary manufacturing operation, gold brazes 138 and 140 would be performed in a gold braze furnace thereby, co-joining 118 and 117 while at the same time, creating a mechanical and hermetic seal 140 to the ferrule 122 and the insulator 188. Referring back to the drawing description for FIG. 88, it will be appreciated that in FIG. 73, that the sintered paste 167 could comprise any of the material combinations previously described for FIG. 8B.

Figure 74:
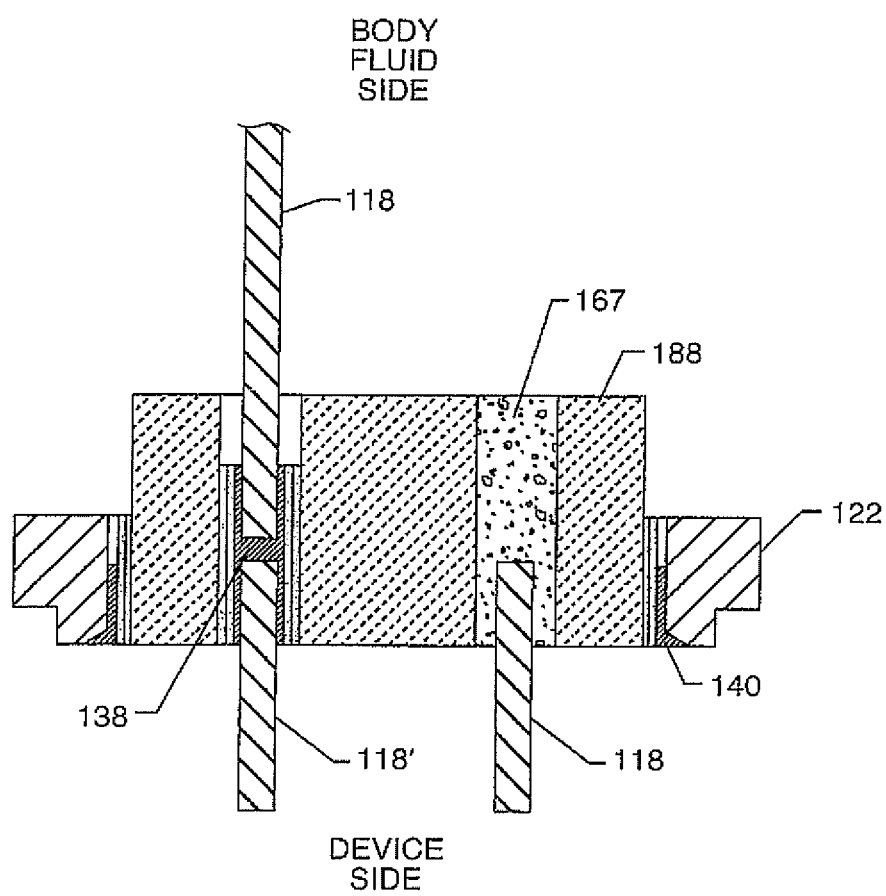

As illustrated in FIG. 74 any of the embodiments of these referenced patents can be combined with the present invention, including a co-fired or co-sintered pin 118 that is co-fired with via fill material 167. Again, it will be appreciated that referenced U.S. Pat. Nos. 8,653,384; 8,938,309 and 9,233,253 have many embodiments and any of the embodiments of these references can be combined in other conductive pathways; for example, as illustrated in FIG. 8, FIG. 15 and FIG. 11 herein.

Figure 75:
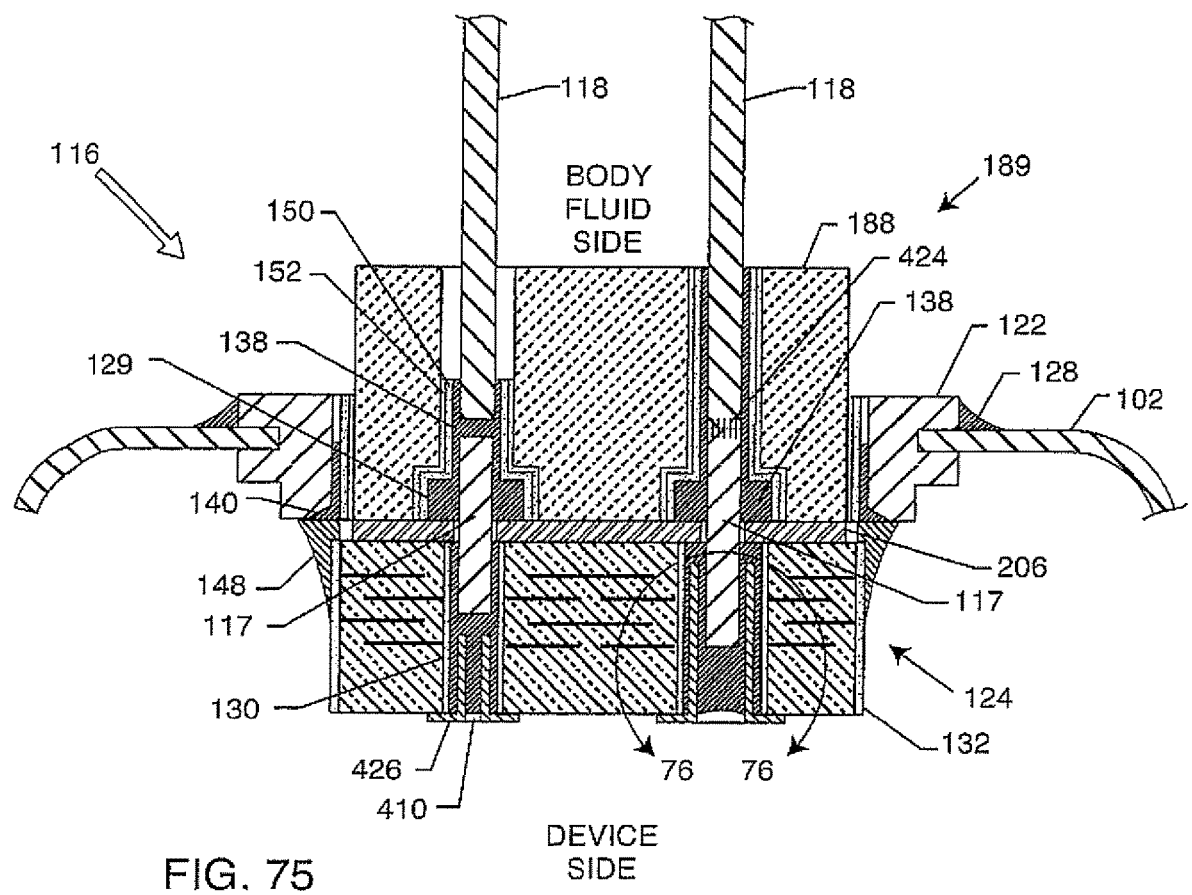

FIG. 75 is very similar to FIG. 12, except that an eyelet 426 is used in place of leadwire 118' and its insulation 123. This eyelet can abut pin 117 as shown. In both cases, the solder 410 will flow down around both the inside and outside diameters of the eyelet and also around the outside diameter and end of pin 117 thereby, making a very mechanically strong connection. As shown on the right-hand side of FIG. 75, the eyelet 426 can overlap pin 117, which would provide even more strength due to the solder that is in sheer between the inside diameter of the eyelet and the outside diameter of pin 117. The eyelet is designed to facilitate convenient wire bonding by a customer. Wire bonding is well known in the art and could involve a round or a flat ribbon wire that would be electrically and mechanically connected to the device side of the eyelet 426 and then connect to a circuit board or internal AND electronics (not shown).

Figure 76:
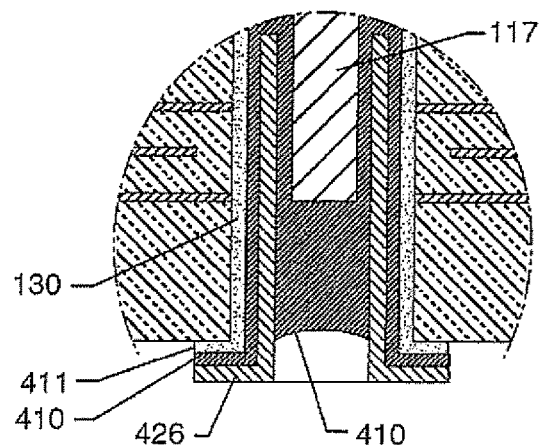

FIG. 76 is taken generally from section 76-76 of FIG. 75 and illustrates that the capacitor inside diameter or via hole metallization 130 may extend onto the device side of the feedthrough capacitor forming a white-wall tire configuration 411, as previously described in FIG. 12. This would allow solder 410 (or a thermal-setting conductive adhesive) to not only flow down around the inside diameter (or via hole) of the feedthrough capacitor, but it would also flow all around the eyelet and also form a solder joint between the bottom surface of the top of the eyelet and the white-wall tire metallization 411. As mentioned in FIG. 12, this would greatly increase the mechanical strength of a connection between the eyelet 426 and the feedthrough capacitor 124. Importantly, this also provides an even lower electrical resistivity between the eyelet and the capacitor metallization, and corresponding active electrode plates. It will be appreciated that the white-wall tire structure 411, as illustrated in FIG. 76, could be applied to any of the feedthrough capacitors previously described herein.

Figure 77:
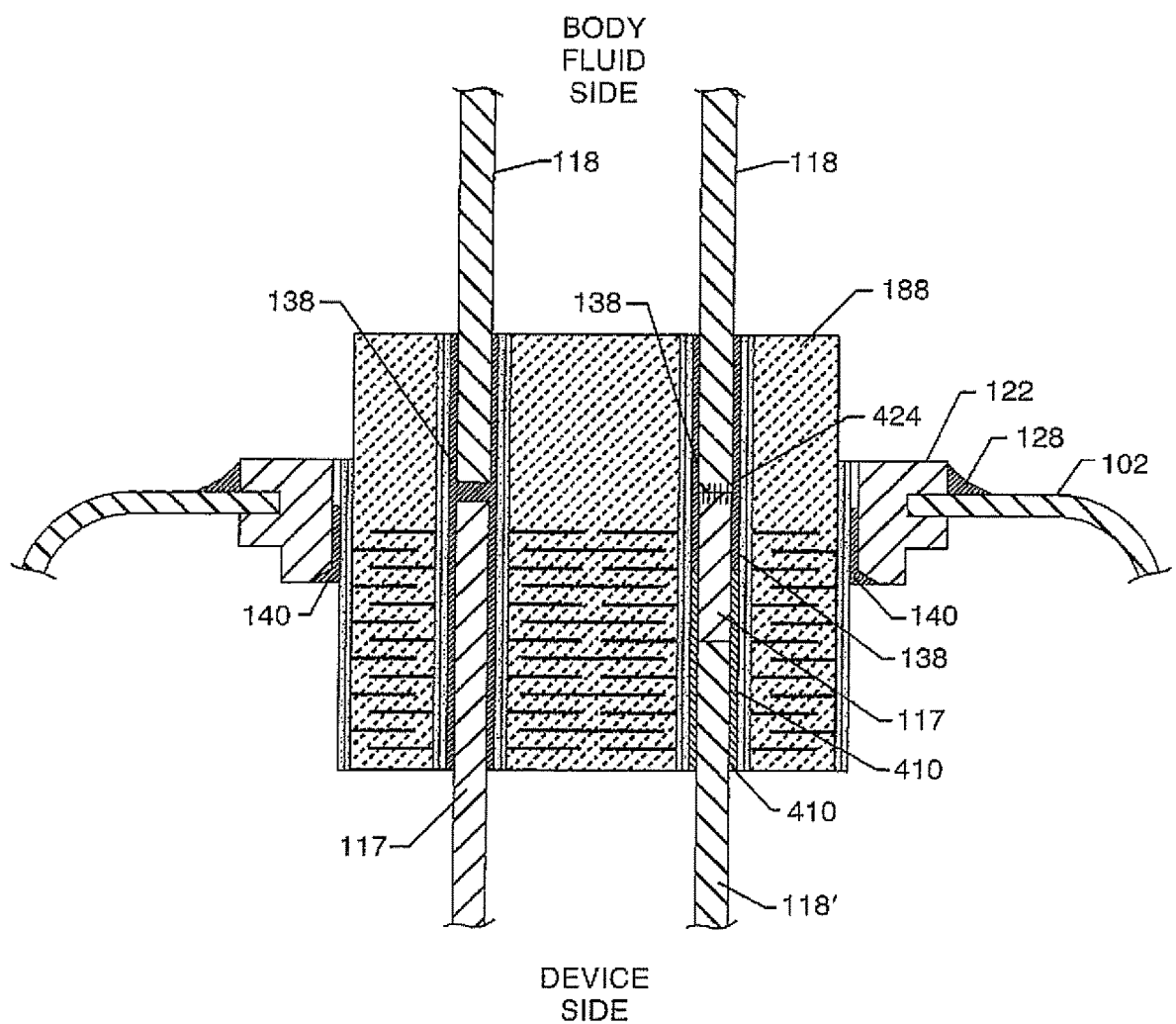

FIG. 77 is generally taken from FIG. 3 of U.S. Pat. No. 6,008,980, the contents of which are incorporated herein fully by reference. FIG. 77 shows two and three part pins in accordance with the present invention. As previously taught in the present invention, on the left side, the body fluid side leadwire 118 is co-brazed 138 to device side leadwire 117. At the same time, the gold braze 140, between the ferrule 122 and the hermetic seal insulator, would be formed. Referring once again to FIG. 77, the right-hand side illustrates another alternative of the present invention wherein, there is body fluid side leadwire 118 of a different material than short pin 117 and then on the device side, there is a relatively low cost leadwire 118'. On the right-hand side, in a gold brazing operation, pins 118 and 117 are co-brazed within the hermetic seal insulator 188. In accordance with the present invention, these two lead segments 117 and 118 could be pre-welded 424 as shown. In this case, the low cost leadwire 118 is then inserted into the device side along with solder or thermal-setting conductive adhesive 410, which forms a mechanical and electrical connection between the lead segment 117 and leadwire 118'. In general, in accordance with the present invention, leadwire 118 could be of biocompatible low cost material on the body fluid side, such as tantalum, niobium or the like. The short pin 117 would generally be of platinum or palladium. Leadwire 118' would generally be of a tinned copper or other low cost leadwire as previously described.

Referring once again to FIG. 77, it will be appreciated that the dielectric body 188 is the same throughout. The inventors have discovered through extensive research and development, that it is not possible to build the assembly illustrated in FIG. 77 with high k dielectric (ceramics having a dielectric constant of above approximately 2000). The reason for this is such dielectrics are mechanically weak and the gold brazing 140 always induced fractures within the insulator structure 188. One could easily build this structure, as shown in FIG. 77, with an alumina ceramic, which has a very low k. The problem with this is the resulting capacitance value, from the electrode plates, as shown, would be relatively low (too low for effective EMI filtering of pacemakers and implantable defibrillators). The inventors contemplate that a medium k dielectric could be developed with a k between 200 and 1000 that would allow for the co-brazing 140 and still provide a high enough dielectric constant to achieve the required capacitance value. Accordingly, the teachings of U.S. Pat. No. 6,008,980 may be realizable in accordance with the present invention. The use of primary ceramic capacitor EMI filters having a k less than 1000, is more thoroughly described in U.S. Patent Publication 2015/0217111, the contents of which are fully incorporated herein.

Although several embodiments have been described in detail for purposes of illustration, various modifications may be made to each without departing from the scope and spirit of the invention. Additionally, it is to be understood that any of the features taught herein could be applied to any of the embodiments taught herein. Accordingly, the invention is not to be limited, except as by the appended claims.

What is claimed is:

1. A circuit board mounted filtered feedthrough assembly having a composite conductive lead for an active implantable medical device (AIMD), the circuit board mounted filtered feedthrough assembly comprising:
   a) a ferrule comprising a ferrule opening, wherein the ferrule is configured to be attachable to an opening in a housing of an AIMD;
   b) an insulator at least partially residing in the ferrule opening where a first gold braze hermetically seals the insulator to the ferrule, wherein at least one insulator passageway extends through the insulator to an insulator first end surface and an insulator second end surface, and wherein an internal metallization is disposed on an inner surface of the at least one insulator passageway;
   c) a first leadwire comprising a first leadwire first end spaced from a first leadwire second end, wherein the first leadwire first end resides in the at least one insulator passageway;

d) a second leadwire which is not of the same material as the first leadwire, the second leadwire comprising a second leadwire first end spaced from a second leadwire second end, wherein the second leadwire first end resides in the at least one insulator passageway and is positioned at or adjacent to the first leadwire first end, and wherein the second leadwire second end extends outwardly beyond the insulator second end surface;

e) a second gold braze contacting the first leadwire first end, the second leadwire first end and the internal metallization in the at least one insulator passageway, the first braze forming a hermetic seal separating the insulator first end surface from the insulator second end surface in the at least one insulator passageway; and f) a circuit board comprising spaced apart circuit board first and second sides, wherein the circuit board first side is adjacent to the insulator second end surface;

g) a circuit board active via hole extending through the circuit board, wherein at least a portion of the second leadwire second end extending outwardly beyond the insulator second end surface resides in the circuit board active via hole, and wherein the circuit board comprises at least one circuit board active circuit trace that is electrically connectable to electronic circuits housed in the AIMD, and wherein the circuit board comprises a circuit board ground metallization that is spaced from the at least one active circuit trace; and h) at least one two-terminal MLCC chip capacitor comprising a chip capacitor dielectric supporting at least one active electrode plate interleaved in a capacitive relationship with at least one ground electrode plate, wherein an active metallization is electrically connected to the at least one active electrode plate, and a ground metallization is electrically connected to the at least one ground electrode plate of the at least one two-terminal MLCC chip capacitor, i) wherein an active electrical path extends from the first leadwire to the second leadwire and then to the active metallization of the at least one two-terminal MLCC chip capacitor and to the circuit board active circuit trace, and j) wherein a ground electrical path extends from the ground metallization of the at least one two-terminal MLCC chip capacitor to the circuit board ground metallization and then to the ferrule.

2. The circuit board mounted filtered feedthrough assembly of claim 1, wherein the circuit board ground metallization extends from a circuit board ground metallization first portion that is electrically connected to the ground metallization of the at least one two-terminal MLCC chip capacitor to a circuit board ground metallization second portion that is electrically connected to the ferrule or to the first gold braze hermetically sealing the insulator to the ferrule.

3. The circuit board mounted filtered feedthrough assembly of claim 1, wherein the circuit board active via hole extending through the circuit board is electrically isolated from the at least one circuit board ground metallization.

4. The circuit board mounted filtered feedthrough assembly of claim 3, wherein the active electrical path comprises a first electrically conductive material that electrically connects the capacitor active metallization to the second leadwire and to the circuit board active circuit trace, and wherein the ground electrical path comprises a second electrically conductive material that electrically connects the capacitor ground metallization to at least one of the ferrule and the first gold braze.

5. The circuit board mounted filtered feedthrough assembly of claim 4, wherein the first and second electrically conductive materials are selected from the group consisting of a solder, a solder BGA, a solder paste, an epoxy, and a polyimide.

6. The circuit board mounted filtered feedthrough assembly of claim 1, wherein the at least one two-terminal MLCC chip capacitor is attached to the circuit board, and wherein the circuit board is attached to the insulator.

7. The circuit board mounted filtered feedthrough assembly of claim 1, further including an oxide-resistant metal addition, wherein:
a) a second electrically conductive material electrically connects the ground metallization of the at least one two-terminal MLCC chip capacitor to the oxide resistant metal addition, and
b) a third electrically conductive material electrically connects the oxide-resistant metal addition to the ferrule, wherein the second and third electrically conductive materials and the oxide-resistant metal addition comprise the ground electrical path, or
c) the oxide-resistant metal addition is welded to the ferrule, and wherein a fourth electrically conductive material electrically connects the oxide-resistant metal addition to the ground metallization of the at least one two-terminal MLCC chip capacitor, the fourth electrically conductive material and the oxide-resistant metal addition comprising the ground electrical path.

8. The circuit board mounted filtered feedthrough assembly of claim 1, wherein the second leadwire comprises platinum or palladium.

9. The circuit board mounted filtered feedthrough assembly of claim 1, wherein the first leadwire is not biocompatible.

10. The circuit board mounted filtered feedthrough assembly of claim 9, wherein the first leadwire comprises niobium or tantalum.

11. The circuit board mounted filtered feedthrough assembly of claim 1, wherein the first gold braze hermetically sealing the insulator to the ferrule is disposed at or adjacent to the insulator second end surface but does not extend to the insulator first end surface.

12. The circuit board mounted filtered feedthrough assembly of claim 1, wherein the first and second hermetic seals each have a leak rate that is not greater than $1 \times 10^{-7}$ std cc He/sec.

13. The circuit board mounted filtered feedthrough assembly of claim 1, wherein an adhesion metallization is disposed at least partially on an outer surface of the insulator and a wetting metallization is disposed on the adhesion metallization, and wherein the first gold braze hermetically seals the ferrule to the wetting metallization.

14. The circuit board mounted filtered feedthrough assembly of claim 1, wherein an insulative washer is disposed between the insulator and the circuit board.

15. The circuit board mounted filtered feedthrough assembly of claim 1, wherein the ferrule is configured to be joined to a housing for the AIMD by a laser weld or braze.

16. The circuit board mounted filtered feedthrough assembly of claim 1, wherein, when the filtered feedthrough assembly is attached to a housing of an AIMD, the insulator first end surface is a body fluid side that resides outside the AIMD and the insulator second end surface is a device side that resides inside the AIMD.

17. The circuit board mounted filtered feedthrough assembly of claim 1, wherein the second leadwire second end extends outwardly beyond the circuit board.

18. The circuit board mounted filtered feedthrough assembly of claim 1, wherein the second leadwire second end is recessed inwardly from the circuit board second side opposite the insulator second end surface.

19. The circuit board mounted filtered feedthrough assembly of claim 1, wherein the first leadwire first end is soldered or welded to the second leadwire first end.

20. The circuit board mounted filtered feedthrough assembly of claim 1, wherein the circuit board active circuit trace is embedded in the circuit board.

21. The circuit board mounted filtered feedthrough assembly of claim 1, wherein a ground pin is conductively and mechanically connected to the ferrule, and wherein there is at least one internal circuit board ground circuit trace that is electrically connected to the ground pin and to the ground metallization of the at least one two-terminal MLCC chip capacitor.

22. The circuit board mounted filtered feedthrough assembly of claim 21, wherein there are at least two internal circuit board ground circuit traces and an external circuit board ground circuit trace disposed adjacent to either the ferrule, the insulator, or both, and wherein the at least two internal circuit board ground circuit traces and the external circuit board ground circuit trace are electrically connected to the ground pin and to the ground metallization of the at least one two-terminal MLCC chip capacitor.

23. The circuit board mounted filtered feedthrough assembly of claim 21, wherein the ground pin is conductively and mechanically connected to the ferrule by one of the group consisting of a third gold braze, a laser weld, and being integral with the ferrule.

24. The circuit board mounted filtered feedthrough assembly of claim 21, wherein the ground pin resides in a countersink in the ferrule.

25. The circuit board mounted filtered feedthrough assembly of claim 21, wherein the ground pin extends through a ferrule via hole extending to a ferrule first side and a ferrule second side.

26. The circuit board mounted filtered feedthrough assembly of claim 1, the first leadwire second end extends outwardly beyond the insulator first end surface.

27. A circuit board mounted filtered feedthrough assembly having a composite conductive lead for an active implantable medical device (AIMD), the circuit board mounted filtered feedthrough assembly comprising:
a) a ferrule comprising a ferrule opening, wherein the ferrule is configured to be attachable to an opening in a housing of an AIMD;
b) an insulator at least partially residing in the ferrule opening where a first gold braze hermetically seals the insulator to the ferrule, wherein a plurality of insulator passageways extend through the insulator to an insulator first end surface and an insulator second end surface, and wherein an internal metallization is disposed on an inner surface of each of the plurality of insulator passageways;
c) a plurality of first leadwires, each comprising a first leadwire first end spaced from a first leadwire second end, wherein a first leadwire first end resides in each of the plurality of insulator passageways;
d) a plurality of second leadwires which are not of the same material as the first leadwires, the plurality of second leadwires each comprising a second leadwire first end spaced from a second leadwire second end, wherein a second leadwire first end resides in each of the plurality of insulator passageways and is positioned at or adjacent to a respective first leadwire first end, and wherein the plurality of second leadwire second ends extend outwardly beyond the insulator second end surface;
e) a plurality of second gold brazes, a respective second gold braze contacting the first leadwire first end, the second leadwire first end and the internal metallization to thereby form a hermetic seal separating the insulator first end surface from the insulator second end surface in each of the plurality of insulator passageways; and
f) a circuit board comprising spaced apart circuit board first and second sides, wherein the circuit board first side is adjacent to the insulator second end surface;
g) a plurality of circuit board active via holes extending through the circuit board, wherein at least a portion of a respective one of the plurality of second leadwire second ends extending outwardly beyond the insulator second end surface resides in one of the circuit board active via holes, and wherein the circuit board comprises a plurality of circuit board active circuit traces that are electrically connectable to electronic circuits housed in the AIMD; and
h) a plurality of two-terminal MLCC chip capacitors, each comprising a chip capacitor dielectric supporting at least one active electrode plate interleaved in a capacitive relationship with at least one ground electrode plate, wherein an active metallization is electrically connected to the at least one active electrode plate, and a ground metallization is electrically connected to the at least one ground electrode plate of each of the plurality of two-terminal MLCC chip capacitors,
i) wherein an active electrical path extends from each of the first leadwires to a respective one the second leadwires and then to the active metallization of a respective one of the plurality of two-terminal MLCC chip capacitors and to a respective one of the circuit board active circuit traces, and
j) wherein a ground electrical path extends from the ground metallization of a respective one of the plurality of two-terminal MLCC chip capacitors to the circuit board ground metallization and then to the ferrule.

28. The circuit board mounted filtered feedthrough assembly of claim 27, wherein the plurality of first leadwire second ends extend outwardly beyond the insulator first end surface.

29. A circuit board mounted filtered feedthrough assembly having a composite conductive lead for an active implantable medical device (AIMD), the circuit board mounted filtered feedthrough assembly comprising:
a) a ferrule comprising a ferrule opening, wherein the ferrule is configured to be attachable to an opening in a housing of an AIMD, and wherein a ground pin is conductively and mechanically connected to the ferrule;
b) an insulator at least partially residing in the ferrule opening where a first gold braze hermetically seals the insulator to the ferrule, wherein a plurality of insulator passageways extend through the insulator to an insulator first end surface and an insulator second end surface, and wherein an internal metallization is disposed on an inner surface of each of the plurality of insulator passageways;
c) a plurality of first leadwires, each comprising a first leadwire first end spaced from a first leadwire second end, wherein a first leadwire first end resides in each of the plurality of insulator passageways;
d) a plurality of second leadwires which are not of the same material as the first leadwires, the plurality of second leadwires each comprising a second leadwire first end spaced from a second leadwire second end, wherein a second leadwire first end resides in each of the plurality of insulator passageways and is positioned at or adjacent to a respective first leadwire first end, and wherein the plurality of second leadwire second ends extend outwardly beyond the insulator second end surface;

e) a plurality of second gold brazes, a respective second gold braze contacting the first leadwire first end, the second leadwire first end and the internal metallization to thereby form a hermetic seal separating the insulator first end surface from the insulator second end surface in each of the plurality of insulator passageways;

f) a plurality of two-terminal MLCC chip capacitors, each comprising a chip capacitor dielectric supporting at least one active electrode plate interleaved in a capacitive relationship with at least one ground electrode plate, wherein an active metallization is electrically connected to the at least one active electrode plate, and a ground metallization is electrically connected to the at least one ground electrode plate of each of the plurality of two-terminal MLCC chip capacitors;

g) a circuit board comprising spaced apart circuit board first and second sides, wherein the circuit board first side is adjacent to the insulator second end surface, and wherein there is at least one internal circuit board ground circuit trace;

h) a plurality of circuit board active via holes extending through the circuit board, wherein at least a portion of a respective one of the second leadwire second ends extending outwardly beyond the insulator second end surface resides in one of the circuit board active via holes, and wherein the circuit board comprises a plurality of circuit board active circuit traces that are electrically connectable to electronic circuits housed in the AIMD; and i) a plurality of circuit board ground via holes extending through the circuit board, wherein a ground metallization resides on an inner surface of each of the plurality of ground via holes in the circuit board, and wherein the at least one internal circuit board ground circuit trace is electrically connected to the ground pin and to the plurality of circuit board ground metallizations, j) wherein an active electrical path extends from each of the first leadwires to a respective one the second leadwires and then to the active metallization of a respective one of the plurality of two-terminal MLCC chip capacitors and to a respective one of the circuit board active circuit traces, and k) wherein a ground electrical path extends from the ground metallization of a respective one of the plurality of two-terminal MLCC chip capacitors to the ground metallization residing in a respective one of the plurality of ground via holes in the circuit board, the ground metallization being electrically connected to the internal circuit board ground circuit trace electrically connected to the ground pin and to the ferrule.

30. The circuit board mounted filtered feedthrough assembly of claim 29, wherein at least two ground pins are conductively and mechanically connected to the ferrule, and wherein the plurality of two-terminal MLCC chip capacitors reside between the two ground pins.

31. The circuit board mounted filtered feedthrough assembly of claim 29, wherein there are at least two internal circuit board ground circuit traces and an external circuit board ground circuit trace disposed adjacent to either the ferrule, the insulator, or both, and wherein the at least two internal circuit board ground circuit traces and the external circuit board ground trace are electrically connected to the ground pin and to the ground metallizations of each of the plurality of two-terminal MLCC chip capacitors.

32. The circuit board mounted filtered feedthrough assembly of claim 29, wherein the plurality of first leadwire second ends extend outwardly beyond the insulator first end surface.

* * * * *